United States Patent
Kley et al.

(10) Patent No.: US 12,351,633 B2
(45) Date of Patent: Jul. 8, 2025

(54) PD-1 AND PD-L1 BINDING AGENTS

(71) Applicants: Orionis Biosciences Inc., Waltham, MA (US); Orionis Biosciences BV, Ghent (BE)

(72) Inventors: Nikolai Kley, Newton, MA (US); Jan Tavernier, Balegem (BE); Lennart Zabeau, Zwijnaarde (BE); Erik Depla, Zwijnaarde (BE)

(73) Assignees: Orionis Biosciences, Inc., Waltham, MA (US); Orionis Biosciences BV, Ghent (BE)

( * ) Notice: Subject to any disclaimer, the term of this patent is extended or adjusted under 35 U.S.C. 154(b) by 261 days.

(21) Appl. No.: 17/938,109

(22) Filed: Oct. 5, 2022

(65) Prior Publication Data

US 2023/0295304 A1    Sep. 21, 2023

Related U.S. Application Data

(63) Continuation of application No. 16/636,501, filed as application No. PCT/US2018/045743 on Aug. 8, 2018, now Pat. No. 11,498,966.

(60) Provisional application No. 62/542,921, filed on Aug. 9, 2017.

(51) Int. Cl.
| | | |
|---|---|---|
| C07K 16/28 | (2006.01) | |
| A61K 39/00 | (2006.01) | |
| A61P 35/00 | (2006.01) | |
| C07K 14/56 | (2006.01) | |
| C07K 14/565 | (2006.01) | |

(52) U.S. Cl.
CPC .......... *C07K 16/2827* (2013.01); *A61P 35/00* (2018.01); *C07K 14/56* (2013.01); *C07K 14/565* (2013.01); *A61K 2039/505* (2013.01); *C07K 2317/21* (2013.01); *C07K 2317/565* (2013.01); *C07K 2317/569* (2013.01); *C07K 2317/76* (2013.01); *C07K 2319/02* (2013.01); *C07K 2319/30* (2013.01)

(58) Field of Classification Search
CPC ...... C07K 16/2827; C07K 14/56; A61P 35/00
See application file for complete search history.

(56) References Cited

U.S. PATENT DOCUMENTS

| | | | |
|---|---|---|---|
| 5,914,254 | A | 6/1999 | Mascarenhas et al. |
| 8,980,267 | B2 | 3/2015 | Grewal et al. |
| 9,139,634 | B2 | 9/2015 | Morrison et al. |
| 9,492,562 | B2 | 11/2016 | Tavernier et al. |
| 9,534,056 | B2 | 1/2017 | Grewal et al. |
| 9,732,135 | B2 | 8/2017 | Tavernier et al. |
| 9,878,014 | B2 | 1/2018 | Tavernier et al. |
| 9,914,759 | B2 | 3/2018 | Tavernier et al. |
| 9,932,409 | B2 | 4/2018 | Tavernier et al. |
| 10,034,919 | B2 | 7/2018 | Tavernier et al. |
| 10,035,835 | B2 | 7/2018 | Tavernier et al. |
| 10,072,059 | B2 | 9/2018 | Tavernier et al. |
| 10,407,480 | B2 | 9/2019 | Tavernier et al. |
| 10,640,542 | B2 | 5/2020 | Tavernier et al. |
| 2010/0172868 | A1 | 7/2010 | Morrison et al. |
| 2010/0297076 | A1 | 11/2010 | Morrison et al. |
| 2011/0020273 | A1 | 1/2011 | Chang et al. |
| 2011/0081341 | A1 | 4/2011 | Honjo et al. |
| 2011/0104112 | A1 | 5/2011 | Morrison et al. |
| 2011/0224407 | A1 | 9/2011 | Langer et al. |
| 2011/0274658 | A1 | 11/2011 | Silver et al. |
| 2013/0183298 | A1 | 7/2013 | Le et al. |
| 2013/0230517 | A1 | 9/2013 | Grewal et al. |
| 2014/0271462 | A1 | 9/2014 | Ho et al. |
| 2014/0348789 | A1 | 11/2014 | Tavernier et al. |
| 2015/0139951 | A1 | 5/2015 | Grewal et al. |
| 2015/0313965 | A1 | 11/2015 | Pogue et al. |
| 2018/0186894 | A1 | 7/2018 | Tavernier et al. |
| 2018/0333465 | A1 | 11/2018 | Tavernier et al. |
| 2018/0334488 | A1 | 11/2018 | Tavernier et al. |
| 2018/0334489 | A1 | 11/2018 | Tavernier et al. |
| 2019/0010199 | A1 | 1/2019 | Tavernier et al. |
| 2019/0071500 | A1 | 3/2019 | Kley et al. |
| 2019/0144553 | A1 | 5/2019 | Kley et al. |
| 2019/0194284 | A1 | 6/2019 | Kley et al. |
| 2019/0202934 | A1 | 7/2019 | Tavernier et al. |
| 2019/0351021 | A1 | 11/2019 | Tavernier et al. |
| 2019/0352406 | A1 | 11/2019 | Tavernier et al. |
| 2019/0367575 | A1 | 12/2019 | Tavernier et al. |
| 2019/0367604 | A1 | 12/2019 | Kley et al. |
| 2020/0071414 | A1 | 3/2020 | Kley et al. |

(Continued)

FOREIGN PATENT DOCUMENTS

| | | |
|---|---|---|
| RU | 2011127226 A | 1/2013 |
| WO | WO 91/02754 A1 | 3/1991 |
| WO | WO 03/033720 A2 | 4/2003 |

(Continued)

OTHER PUBLICATIONS

Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.

(Continued)

*Primary Examiner* — Elly-Gerald Stoica

(74) *Attorney, Agent, or Firm* — Morgan, Lewis & Bockius LLP

(57) ABSTRACT

The present invention relates, in part, to agents that bind PD-1 or PD-L1 and their use as diagnostic and therapeutic agents. The present invention further relates to pharmaceutical compositions comprising the PD-1 or PD-L1 binding agents and their use in the treatment of various diseases.

16 Claims, 14 Drawing Sheets

Specification includes a Sequence Listing.

(56) References Cited

U.S. PATENT DOCUMENTS

2020/0087411 A1   3/2020  Kley et al.

FOREIGN PATENT DOCUMENTS

| | | |
|---|---|---|
| WO | WO 2006/053883 A1 | 4/2003 |
| WO | WO 2006/115800 A2 | 11/2006 |
| WO | WO 2008/014612 A1 | 2/2008 |
| WO | WO 2008/124086 A2 | 10/2008 |
| WO | WO 2009/003145 A1 | 12/2008 |
| WO | WO 2009/013484 A1 | 1/2009 |
| WO | WO 2009/039409 A1 | 3/2009 |
| WO | WO 2010/036918 A2 | 4/2010 |
| WO | WO 2010/066740 A1 | 6/2010 |
| WO | WO 2011/020783 A2 | 2/2011 |
| WO | WO 2011/029870 A1 | 3/2011 |
| WO | WO 2012/170072 A1 | 12/2012 |
| WO | WO 2013/053008 A2 | 4/2013 |
| WO | WO 2013/059885 A2 | 5/2013 |
| WO | WO 2013/107791 A1 | 7/2013 |
| WO | WO 2013/134138 A1 | 9/2013 |
| WO | WO 2015/007520 A1 | 1/2015 |
| WO | WO 2015/007536 A2 | 1/2015 |
| WO | WO 2015/007542 A1 | 1/2015 |
| WO | WO 2015/007903 A1 | 1/2015 |
| WO | WO 2015/018528 A1 | 2/2015 |
| WO | WO 2017/077382 A1 | 5/2017 |
| WO | WO 2017/134302 A2 | 8/2017 |
| WO | WO 2017/194782 A2 | 11/2017 |

OTHER PUBLICATIONS

Baba, et al., "Identification of CCR6, the Specific Receptor for a Novel Lymphocyte-Directed CC Chemokine LARC," The Journal of Biological Chemistry, vol. 272, No. 23, pp. 14893-14898, 1997.
Barbara, et al., "Dissociation of TNF-α cytotoxic and proinflammatory activities by p55 receptor-and p75 receptor-selective TNF-α mutants," EMBO Journal, vol. 13, No. 4, pp. 843-850, 1994.
Bork, et al., "Go hunting in sequence databases but watch out for the traps." Trends in Genetics, vol. 12, pp. 125-427, 1996.
Bork, "Powers and Pitfalls in Sequence Analysis: The 70% Hurdle," Genome Research, vol. 10, pp. 398-400, 2000.
Boschert, et al., "Single chain TNF derivatives with individually mutated receptor binding sites reveal differential stoichiometry of ligand receptor complex formation for TNFR1 and TNFR2," Cellular Signalling 22 (7):1088-1096, 2010.
Bremer, et al., "Superior activity of fusion protein scFvRit:sFasL over cotreatment with rituximab and Fas agonists," Cancer Res. 68: 597-604, 2008.
Camacho, et al., "Structure of an Interleukin-1β Mutant With Reduced Bioactivity Shows Multiple Subtle Changes in Conformation That Affect Protein-Protein Recognition," Biochemistry, vol. 32, No. 34, pp. 8749-8757, 1993.
Coulstock, et al., "Liver-Targeting of Interferon-Alpha with Tissue Specific Domain Antibodies," PLOS ONE, vol. 8, No. 2, pp. 1-11, 2013.
De Bruyn, et al., "Antibody-Based Fusion Proteins to Target Death Receptors in Cancer," Cancer Letters, vol. 332, pp. 175-183, 2013.
Deffar, et al., "Nanobodies—The New Concept in Antibody Engineering," African Journal of Biotechnology, vol. 8, No. 12, pp. 2645-2652, 2009.
Dijkmans, et al., "Murine Interferon-γ Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.
Dimitrov, "Engineered CH2 Domains (Nanoantibodies)," mAbs, Landes Bioscience, vol. 1, No. 1, pp. 26-28, 2009.
Frey, et al., "Antibody-Based Targeting of Interferon-Alpha to the Tumor Neovasculature: A Critical Evaluation," ntegrative Biology, vol. 3, pp. 468-478, 2011.
Garcin, et al., "High Efficiency cell-specific targeting of cytokine activity," Nature Communications, vol. 5, No. 8, 9 pages, 2014.
Garlanda, et al., "The Interleukin-1 Family: Back to the Future," Immunity, 39 (6): pp. 1003-1018, Dec. 12, 2013.
Holler, et al., "Two Adjacent Trimeric Fas Ligands are Required for Fas Signaling and Formation of a Death-Inducing Signaling Complex," Molecular and Cellular Biology, vol. 23, No. 4, pp. 1428-1440, 2003.
Huang, et al., "A Trimeric Anti-HER2/neu ScFv and Tumor Necrosis Factor-[alpha] Fusion Protein Induces HER2/Neu Signaling and Facilitates Repair of Injured Epithelia," The Journal of Pharmacology and Experimental Therapeutics, vol. 316, No. 3, pp. 983-991, 2006.
Idoyaga, et al., "Comparable T helper 1 (Th1) and CD8 T-cell immunity by targeting HIV gag p24 to CD8 dendritic cells within antibodies to Langerin, DEC205, and Clec9A," PNAS, vol. 108, No. 6, pp. 2384-2389, Jan. 24, 2011.
International Search Report & Written Opinion, PCT Application No. PCT/EP2017/052544, dated Jun. 6, 2017, 16 pages.
Kircheis, et al., "Biological activity of mutants of human tumour necrosis factor-alpha," Immunology, pp. 433-438, Jul. 1, 1992.
Krippner-Heidenreich, et al., "Single-Chain TNF, a TNF Derivative with Enhanced Stability and Antitumoral Activity," The Journal of Immunology, vol. 180, pp. 8176-8183, 2008.
Lahoud, et al., "Targeting Antigen to Mouse Dendritic Cells via Clec9A Induces Potent CD4 T Cell Responses Biased toward a Follicular Helper Phenotype," The Journal Of Immunology, vol. 187, No. 2, Jul. 15, 2011, pp. 842-850.
Loetscher, et al., "Human Tumor Necrosis Factor a (TNFα) Mutants with Exclusive Specificity for 55-kDA or 75-kDa TNF Receptors," Journal of Biological Chemistry, American Society For Biochemistry and Molecular Biology, US, vol. 268, No. 35, pp. 26350-26357, 1993.
Masci, et al., "New and Modified Interferon alfas: Preclinical and Clinical Data," Current Oncology Reports, vol. 5, pp. 108-113, 2003.
Minn, "Interferons and the Immunogenic Effects of Cancer Therapy," Trends In Immunology, vol. 36, No. 11, pp. 725-737, Nov. 1, 2015.
Ngo, et al., "Computational Complexity, Protein Structure Prediction, and the Levinthal Paradox. The Protein Folding Problem and Tertiary Structure Prediction," Edited by: Mertz et al., (Birkhauser, Boston), pp. 491-495, 1994.
Pan, et al., "Mutation of the IFNAR-1 Receptor Binding Site of Human IFN-α2 Generates Type I IFN Competitive Antagonists," Biochemistry, vol. 47, pp. 12018-12027, 2008.
Patris, et al., "Nanoimmunoassay onto a screen printed electrode for HER2 breast cancer biomarker determination," Talanta, 2014, vol. 130, pp. 164-170, 2014.
Penafuerte, et al., "The Human Ortholog of Granulocyte Macrophage Colony-Stimulating Factor and Interleukin-2 fusion Protein Induces Potent Ex Vivo Natural Killer Cell Activation and Maturation," Cancer Res, vol. 69, No. 23, pp. 9020-9028, 2009.
Picco, et al., "Targeting DNGR-1 (CLEC9A) with antibody/MUC1 peptide conjugates as a vaccine for carcinomas", European Journal Of Immunology, vol. 44, No. 7, pp. 1947-1955, Apr. 17, 2014.
Puskas, et al., "Development of an attenuated interleukin-2 fusion protein than can be activated by tumour-expressed proteases," Immunology, vol. 133, No. 2, pp. 206-220, Jun. 23, 2011.
Rafei, et al., "A MCP1 Fusokine with CCR2-Specific Tumoricidal Activity," Molecular Cancer, vol. 10, No. 121, pp. 1-11, 2011.
Rafei, et al., "An Engineered GM-CSF-CCL2 Fusokine Is A Potent Inhibitor of CCR2-Driven Inflammation as Demonstrated in a Murine Model of Inflammatory Arthritis," The Journal of Immunology, vol. 183, pp. 1759-1766, 2009.
Roisman, et al., "Structure of the Interferon-Receptor Complex Determined by Distant Constraints from Double Mutant Cycles and Flexible Docking," PNAS, vol. 98, No. 23, pp. 13231-13236, 2001.
Rovero, et al., "Insertion of the DNA for the 163-171 Peptide of IL 1 II Enables a DNA Vaccine Encoding p185[neu] to inhibit Mammary Carcinogenesis in Her-2/neu Transgenic BALB/c Mice," Gene Therapy, vol. 8, pp. 447-452, 2001.

(56) References Cited

OTHER PUBLICATIONS

Sancho, et al., "Identification of a dendritic cell receptor that couples sensing of necrosis to immunity", Nature, Nature Publishing Group, United Kingdom, vol. 458, No. 7240, pp. 899-903, Apr. 16, 2009.
Schutyser, et al., "The CC Chemokine CCL20 and its Receptor CCR6," Cytokine & Growth Factor Reviews, vol. 14, pp. 409-426, 2003.
Vaneycken, et al., "Preclinical Screening of Anti-HER2 Nanobodies for Molecular Imaging of Breast Cancer", The ASEB Journal, vol. 25, pp. 2433-2446, 2011.
Weber, et al., "Single Amino Acid Changes that Render Human IFN-α2 Biologically Active on Mouse Cells," The EMBO Journal, vol. 6, No. 3, pp. 591-598, 1987.
Wells, "Additivity of Mutational Effects in Proteins," Biochemistry, vol. 29, No. 37, pp. 8509-8517, 1990.
Wesolowski, et al., "Single Domain Antibodies: Promising Experimental and Therapeutic Tools in Infection and Immunity," Med. Microbiol. Immunol., vol. 198, pp. 157-174, 2009.
Zitvogel, et al., "Type I interferons in anticancer immunity," The Journal of Immunology, vol. 15, No. 7, pp. 405-141, Jun. 1, 2015.

PD-1 AND PD-L1 BINDING AGENTS

CROSS-REFERENCE TO RELATED APPLICATIONS

The present application is a continuation of U.S. application Ser. No. 16/636,501 (now U.S. Pat. No. 11,498,966), filed Feb. 4, 2020, which is a 371 national stage entry of International Application No. PCT/US18/45743, filed Aug. 8, 2018, which claims the benefit of and priority to U.S. Provisional Patent Application No. 62/542,921, filed Aug. 9, 2017, the contents of which are hereby incorporated by reference in its their entireties.

FIELD

The present invention relates, in part, to binding agents which bind PD-1 or PD-L1 and their use as therapeutic and diagnostic agents.

DESCRIPTION OF THE SEQUENCE LISTING SUBMITTED ELECTRONICALLY

This application contains a Sequence Listing in XML format submitted electronically herewith via Patent Center. The contents of the XML file submitted electronically herewith are incorporated herein by reference in their entirety: A XML copy of the Sequence Listing (Filename: "ORN-034C1_114384-5034.xml"; Date filed: Oct. 5, 2022; File size: 1,628,360 bytes).

BACKGROUND

Immunotherapies have been developed to re-direct the body's immune system towards cancers. Immunotherapy provides the advantage of cell specificity that other treatment modalities, such as chemotherapy and radiation, lack. As such, methods for enhancing the efficacy of immune based therapies can be clinically beneficial. For example, immune checkpoint molecules that provide costimulatory or coinhibitory signals play a central role in the regulation of T cell immune responses against tumor cells.

However, despite impressive patient responses to agents targeting the checkpoint molecules, including, for example, clinical trials that led to the approval of YERVOY, KEYTRUDA, and OPDIVO, immunotherapies such as checkpoint inhibition therapy still fails in the overwhelming majority of patients. Further still, many immunotherapies are complicated by side effects that significantly narrows a patient's therapeutic window for treatment and makes the patient more susceptible to other diseases.

Accordingly, there remains a need for improved immunotherapeutic agents that can provide targeted therapy against cancers while causing minimal side effects.

SUMMARY

In various aspects, the present invention relates to binding agents having at least one targeting moiety that specifically binds to PD-1 or PD-L1. In various embodiments, these binding agents bind to, and functionally modulate (e.g. partially or fully neutralize) PD-1 or PD-L1. In various embodiments, these binding agents bind to, but do not functionally modulate (e.g. partially or fully neutralize) PD-1 or PD-L1. Therefore, in various embodiments, the present binding agents have use in, for instance, directly or indirectly recruiting a PD-1-expressing cell or a PD-L1-expressing cell to a site of interest while still allowing the cell to signal via either PD-1 or PD-L1 (i.e. the binding of the PD-1 or PD-L1 binding agent does not reduce or eliminate PD-1 or PD-L1 signaling at the site of interest). In an embodiment, the targeting moiety is a single domain antibody (VHH).

In various embodiments, the binding agents of the invention further comprises a signaling agent, e.g., without limitation, an interferon, an interleukin, and a tumor necrosis factor, that may be modified to attenuate activity. In various embodiments, the binding agent comprises additional targeting moieties that bind to other targets (e.g. antigens, receptor) of interest. In an embodiment, the other targets (e.g. antigens, receptor) of interest are present on tumor cells. In another embodiment, the other targets (e.g. antigens, receptor) of interest are present on immune cells. In some embodiments, the present binding agent may directly or indirectly recruit an immune cell (e.g. a dendritic cell) to a site of action (such as, by way of non-limiting example, the tumor microenvironment). In some embodiments, the present binding agent facilitates the presentation of antigens (e.g., tumor antigens) by dendritic cells.

In various embodiments, the present binding agents find use in the treatment of various diseases or disorders such as cancer, infections, immune disorders, and other diseases and disorders, and the present invention encompasses various methods of treatment.

DETAILED DESCRIPTION

Figure 1:
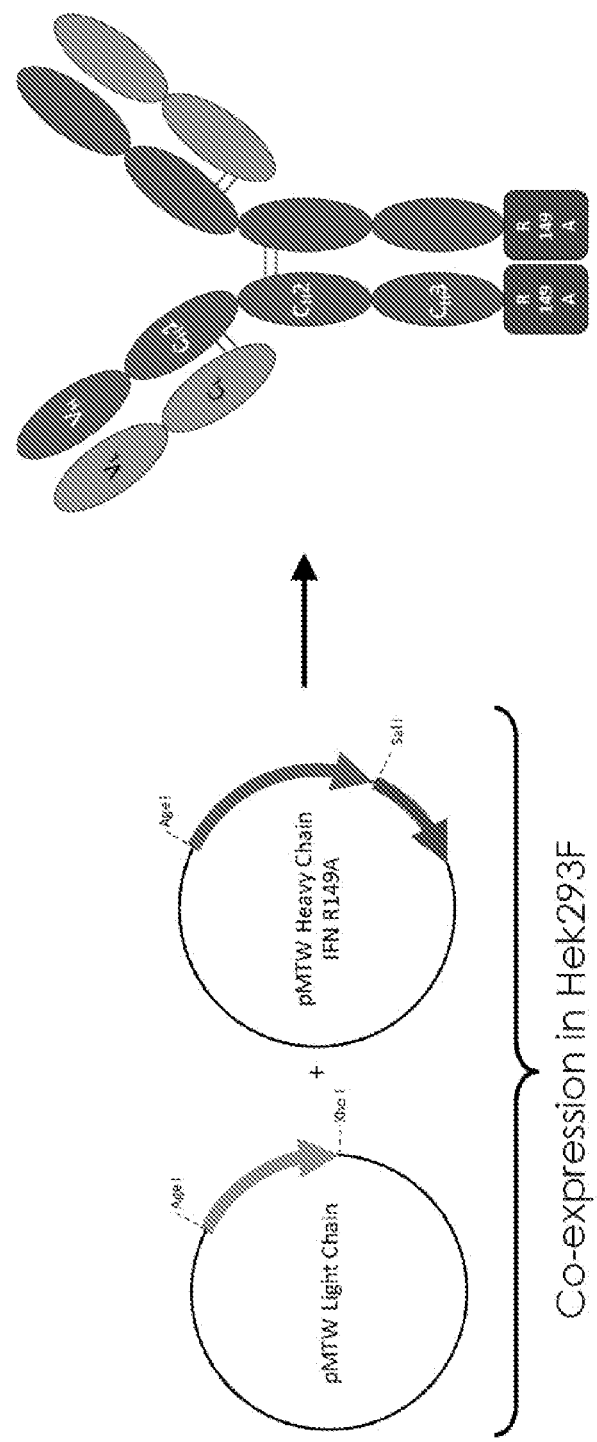
FIG. 1 provides a schematic of the cloning strategy of the PD-1 or PD-L1 Actaferons described in Example 1.
Figure 2:
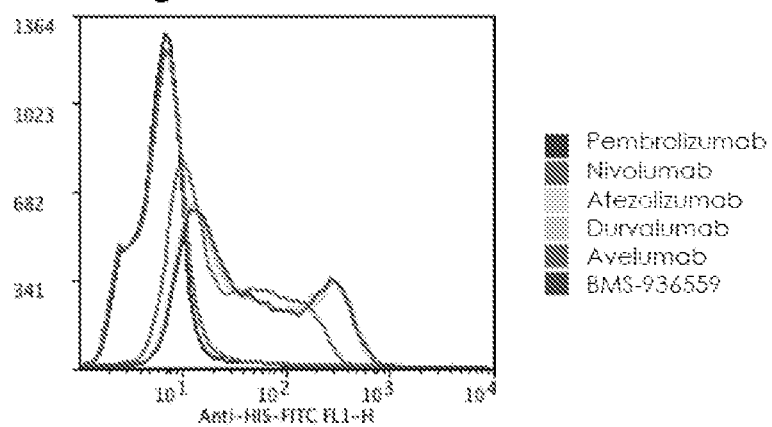
FIG. 2 shows binding of PD-L1 (top panel) or PD-1 (bottom panel) Actaferons to transfected Hek293T cells.
Figure 2:
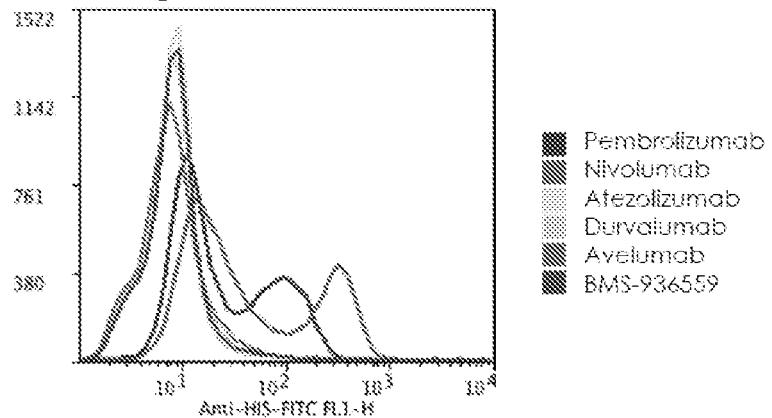

The present invention is based, in part, on the discovery of binding agents (e.g. antibodies such as, by way of non-limiting example, VHHs) that recognize and bind to PD-1 or PD-L1. In some embodiments, the present binding agents are part of a chimeric or fusion protein with one or more targeting moieties and/or one or more signaling agents. In various embodiments, these binding agents bind to, and functionally modulate (e.g. partially or fully neutralize) PD-1 or PD-L1. In some embodiments, these binding agents bind to, but do not functionally modulate PD-1 or PD-L1.

The present invention further provides pharmaceutical compositions comprising the binding agents and their use in the treatment of various diseases, including cancer, autoimmune, and/or neurodegenerative diseases.

PD-1 or PD-L1 Binding Agents

In various embodiments, the present PD-1 or PD-L1 binding agent is a protein-based agent capable of specific binding to PD-1 or PD-L1. In various embodiments, the present PD-1 or PD-L1 binding agent is a protein-based agent capable of specific binding to PD-1 or PD-L1 without functional modulation (e.g., partial or full neutralization) of PD-1 or PD-L1.

Programmed cell death protein 1, also known as PD-1 and cluster of differentiation 279 (CD279), is a cell surface receptor that is primarily expressed on activated T cells, B cells, and macrophages. PD-1 has been shown to negatively regulate antigen receptor signaling upon engagement of its ligands (i.e., PD-L1 and/or PD-L2). PD-1 plays an important role in down-regulating the immune system and promoting self tolerance by suppressing T cell inflammatory activity. PD-1 is a type I transmembrane glycoprotein containing an Ig Variable-type (V-type) domain responsible for ligand binding and a cytoplasmic tail that is responsible for the binding of signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

In various embodiments, the PD-1 binding agent of the invention comprises a targeting moiety having an antigen recognition domain that recognizes an epitope present on PD-1. In an embodiment, the antigen-recognition domain recognizes one or more linear epitopes present on PD-1. As used herein, a linear epitope refers to any continuous sequence of amino acids present on PD-1. In another embodiment, the antigen-recognition domain recognizes one or more conformational epitopes present on PD-1. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the PD-1 binding agent of the present invention may bind to the full-length and/or mature forms and/or isoforms and/or splice variants and/or fragments and/or any other naturally occurring or synthetic analogs, variants, or mutants of human PD-1. In various embodiments, the PD-1 binding agent of the invention may bind to any forms of the human PD-1. In an embodiment, the PD-1 binding agent binds to a phosphorylated form of PD-1.

In an embodiment, the present PD-1 binding agent comprises a targeting moiety with an antigen recognition domain that recognizes one or more epitopes present on human PD-1. In an embodiment, the human PD-1 comprises the amino acid sequence of SEQ ID NO: 1.

In another embodiment, the human PD-1 comprises the amino acid sequence of SEQ ID NO:1 without the amino-terminal signal peptide.

In various embodiments, the present PD-1 binding agent comprises a targeting moiety capable of specific binding. In various embodiments, the PD-1 binding agent comprises a targeting moiety having an antigen recognition domain such as an antibody or derivatives thereof. In an embodiment, the PD-1 binding agent comprises a targeting moiety which is an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the PD-1 binding agent comprises a targeting moiety which is an antibody derivative or format. In some embodiments, the present PD-1 binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a F(ab')$_2$, a peptide mimetic molecule, or a synthetic molecule, as described in US patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the PD-1 binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_HH$) and two constant domains (CH2 and CH3).

In an embodiment, the PD-1 binding agent comprises a VHH. In some embodiments, the VHH is a humanized VHH or camelized VHH.

In some embodiments, the VHH comprises a fully human V$_H$ domain, e.g. a HUMABODY (Crescendo Biologics, Cambridge, UK). In some embodiments, fully human V$_H$ domain, e.g. a HUMABODY is monovalent, bivalent, or trivalent. In some embodiments, the fully human V$_H$ domain, e.g. a HUMABODY is mono- or multi-specific such as monospecific, bispecific, or trispecific. Illustrative fully human V$_H$ domains, e.g. a HUMABODIES are described in, for example, WO2016/113555 and WO2016/113557, the entire disclosure of which is incorporated by reference.

In some embodiments, the PD-1 binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the PD-1 binding agent comprises a VHH having a variable domain comprising at least one CDR1, CDR2, and/or CDR3 sequences. In various embodiments, the PD-1 binding agent comprises a VHH having a variable region comprising at least one FR1, FR2, FR3, and FR4 sequences.

In some embodiments, the PD-1 CDR1 sequence is selected from: GFSMDYYAIA (SEQ ID NO: 2); GFSVDYYAIA (SEQ ID NO: 3); GGFNRVSYMG (SEQ ID NO: 4); GIIKSINFMG (SEQ ID NO: 5); GFILDYYGIG (SEQ ID NO: 6); GLSLDYDGVG (SEQ ID NO: 7); GRTFSSLGMG (SEQ ID NO: 8); GFAFGSYDMG (SEQ ID NO: 9); GFSFGNNDMS (SEQ ID NO: 10); IHAMG (SEQ ID NO: 11); INAMA (SEQ ID NO: 12); SGTMG (SEQ ID NO: 13); GSIASIHAM (SEQ ID NO: 14); GSIASIHAMG (SEQ ID NO: 15); FYGMG (SEQ ID NO: 16); GGTFSFYGMG (SEQ ID NO: 17); YYAIA (SEQ ID NO: 18); VSYMG (SEQ ID NO: 19); INFMG (SEQ ID NO: 20); SLGMG (SEQ ID NO: 21); SYDMG (SEQ ID NO: 22); and NNDMS (SEQ ID NO: 23).

In some embodiments, the PD-1 CDR2 sequence is selected from: CITGSDFMVDT (SEQ ID NO: 24); SVTSGGEI (SEQ ID NO: 25); STTSDGRT (SEQ ID NO: 26); CISSSDGST (SEQ ID NO: 27); AIAWNGAST (SEQ ID NO: 28); GINSGGRIT (SEQ ID NO: 29); AINSGGGST (SEQ ID NO: 30); AITWSGGITYYEDSVKG (SEQ ID NO: 31); VITWSGGITYYADSVKG (SEQ ID NO: 32); VITVSGGITYYADSVKG (SEQ ID NO: 33); AITWSGGITYYADSLKG (SEQ ID NO: 34); LISWSGGSTYYEDSVKG (SEQ ID NO: 35); SIPWSGGRIYYADSVKG (SEQ ID NO: 36); VITWSGGITY (SEQ ID NO: 37); VITVSGGITY (SEQ ID NO: 38); DIRTSAGRTYYADSVKG (SEQ ID NO: 39); DIRTSAGRTY (SEQ ID NO: 40); CITGSDFMVDTY (SEQ ID NO: 41); CITGSDFMVDTYYVASVKG (SEQ ID NO: 42); SVTSGGEIT (SEQ ID NO: 43); SVTSGGEITIADSVKG (SEQ ID NO: 44); SVTSGGEITVADSVKG (SEQ ID NO: 45); STTSDGRTT (SEQ ID NO: 46); STTSDGRTTVADSVKG (SEQ ID NO: 47); CISSSDGSTY (SEQ ID NO: 48); AIAWNGASTY (SEQ ID NO: 49); AIAWNGASTYYTESVKG (SEQ ID NO: 50); GINSGGRITD (SEQ ID NO: 51); GINSGGRITDYADSVTG (SEQ ID NO: 52); AINSGGGSTY (SEQ ID NO: 53); and AINSGGGSTYYADSVKG (SEQ ID NO: 54).

In some embodiments, the PD-1 CDR3 sequence is selected from: AVRSTANTLCPSHYSVMDY (SEQ ID NO: 55); AVRSTANTLCPSHYSIMDY (SEQ ID NO: 56); NADIWVSDARMYNY (SEQ ID NO: 57); NADIWLPSDRMYNY (SEQ ID NO: 58); ATATLCDGGIWGY (SEQ ID NO: 59); AASGLGSVWTANEYDY (SEQ ID NO: 60); AQGDRSSWHYYGMDY (SEQ ID NO: 61); ATKSDPMTNEYDL (SEQ ID NO: 62); DRAESSWYDY (SEQ ID NO: 63); DKHQSSWYDY (SEQ ID NO: 64); DKHQSSFYDY (SEQ ID NO: 65); DRAQSSWYDY (SEQ ID NO: 66); DRVDSNWYDY (SEQ ID NO: 67); KERSTGWDFAS (SEQ ID NO: 68); and EMSGISGWDY (SEQ ID NO: 69).

In various exemplary embodiments, the PD-1 binding agent comprises an amino acid sequence selected from the following sequences:

2PD23
(SEQ ID NO: 70)
QVQLQESGGGLVQPGGSLRLSCAASGFSMDYYAIAWFRQAPGKEREEIS

CITGSDFMVDTYYVASVKGRFTISRDNAENTAYLQMNNLKPEDTGVYFC

AVRSTANTLCPSHYSVMDYWGKGTQVTVSSAAAYPYDVPDYGSHHHHHH;

2PD26
(SEQ ID NO: 71)
QVQLQESGGGLVQAGGSLRLSCAASGFSMDYYAIAWFRQAPGKEREEIS

CITGSDFMVDTYYVASVKGRFTISRDNAENTAYLQMNNLKPEDTGVYFC

AVRSTANTLCPSHYSVMDYWGKGTQVTVSSAAAYPYDVPDYGSHHHHHH;

2PD90
(SEQ ID NO: 72)
QVQLQESGGGLVQPGGSLRLSCSASGFSVDYYAIAWFRQAPGKEREEIS

CITGSDFMVDTYYVASVKGRFTISRDNAKNTAYLQMNSLKPEDTGVYFC

AVRSTANTLCPSHYSIMDYWGKGTQVTVSSAAAYPYDVPDYGSHHHHHH;

2PD-106
(SEQ ID NO: 73)
QVQLQESGGGLVQPGGSLRLSCSASGFSMDYYAIAWFRQAPGKEREEIS

CITGSDFMVDTYYVASVKGRFTISRDNAKNTAHLQMNSLKPEDTGVYFC

AVRSTANTLCPSHYSVMDYWGKGTQVTVSSAAAYPYDVPDYGSHHHHHH;

2PD-16
(SEQ ID NO: 74)
QVQLQESGGGLVQAGGSLRLSCAASGGFNRVSYMGWYRQAPGTKRELVA

SVTSGGEITIADSVKGRFTVSRDNSKNTLYLQMNGLKPEDGATYWCNAD

IWVSDARMYNYWGQGTQVTVSSAAAYPYDVPDYGSHHHHHH;

2PD71
(SEQ D NO: 75)
QVQLQESGGGLVQTGESLRLSCAASGGFNRVSYMGWYRQAPGSKRELVA

SVTSGGEITVADSVKGRFTVSRDNNKNTLYLQMNGLKPEDGATYWCNAD

IWVSDARMYNYWGQGTQVTVSSAAAYPYDVPDYGSHHHHHH;

2PD-152
(SEQ ID NO: 76)
QVQLQESGGGLVQTGESLRLSCAASGIIKSINFMGWYRQPPGTKRELVA

STTSDGRTTVADSVKGRFTISRDNAKNTIYLEMSSLKPEDTATYWCNAD

IWLPSDRMYNYWGQGTQVTVSSAAAYPYDVPDYGSHHHHHH;

-continued

2PD-12

(SEQ ID NO: 77)
QVQLQESGGGLVQAGGSLRLSCAVSGFILDYYGIGWFRQAPGKEREAVS

CISSSDGSTYYADSVKGRFTISRDNALNTLYLQMNSLKPEDTAVYHCAT

ATLCDGGIWGYWGQGTQVTVSSAAAYPYDVPDYGSHHHHHH;

3PD55

(SEQ ID NO: 78)
QVQLQESGGGLAQAGGSLRLSCEGSGLSLDYDGVGWFRQAPGKEREAVS

CISSSDGSTYYADSVKGRFTISRGNALNTLYLQMNSLKPEDTAVYYCAT

ATLCDGGIWGYWGQGTQVTVSSAAAYPYDVPDYGSHHHHHH;

3PD82

(SEQ ID NO: 79)
QVQLQESGGGSVQPGGSLRLSCAVSGFILDYYGIGWFRQAPGKEREAVS

CISSSDGSTYYADSVKGRFTISRDNALNTLYLQMNSLKPEDTAVYYCAT

ATLCDGGIWGYWGQGTQVTVSSAAAYPYDVPDYGSHHHHHH;

2PD8

(SEQ ID NO: 80)
QVQLQESGGGSVQAGDSLRLSCTASGRTFSSLGMGWFRQAPGKEREFVS

AIAWNGASTYYTESVKGRFTISRDDAKNTVYLQMNSLKPTDTAVYFCAA

SGLGSVVVTANEYDYWGQGTQVTVSSAAAYPYDVPDYGSHHHHHH;

2PD27

(SEQ ID NO: 81)
QVQLQESGGGSVQPGKSLRLSCAASGRTFSSLGMGWFRQAPGKEREFVS

AIAWNGASTYYTESVKGRFTISRDDAKNTVYLQMNSLKPTDTAVYFCAA

SGLGSVVVTANEYDYWGQGTQVTVSSAAAYPYDVPDYGSHHHHHH;

2PD82

(SEQ ID NO: 82)
QVQLQESGGGLVQPGGSLRLSCTTSGFAFGSYDMGWVRQAPGKGPEWVS

GINSGGRITDYADSVTGRFTISRDNAKNTLYLQMNSLKPEDTAVYYCAQ

GDRSSWHYYGMDYWGKGTQVTVSSAAAYPYDVPDYGSHHHHHH;
or

3PD36

(SEQ ID NO: 83)
QVQLQESGGGLVQPGGSLRLSCAASGFSFGNNDMSWVRQAPGKGPEWVS

AINSGGGSTYYADSVKGRFTISRDNAKNTLYLQMNSLKPEDTAVYYCAT

KSDPMTNEYDLWGXGTQVTVSSAAAYPYDVPDYGSHHHHHH.

In various exemplary embodiments, the PD-1 binding agent comprises an amino acid sequence selected from SEQ ID NO: 70 to SEQ ID NO: 83 without the terminal histidine tag sequence (i.e., HHHHHH; SEQ ID NO: 84).

In some embodiments, the PD-1 binding agent comprises an amino acid sequence selected from SEQ ID Nos: 70-83 (provided above) without the HA tag (i.e., YPYDVPDYGS; SEQ ID NO: 85).

In some embodiments, the PD-1 binding agent comprises an amino acid sequence selected from SEQ ID Nos: 70-83 (provided above) without the AAA linker.

In some embodiments, the PD-1 binding agent comprises an amino acid sequence selected from SEQ ID Nos: 70-83 (provided above) without the AAA linker, HA tag, and terminal histidine tag sequence (i.e., AAAY-PYDVPDYGSHHHHHH; SEQ ID NO: 86).

In various exemplary embodiments, the PD-1 binding agent comprises an amino acid sequence selected from the following sequences:

102C3:

(SEQ ID NO: 1246)
QVQLQESGGGLVQAGKSLRLSCAASGSIFSIHAMGWFRQAPGKEREFV

AAITWSGGITYYEDSVKGRFTISRDNAKNTVYLQMNSLKPEDTAIYYC

AADRAESSWYDYWGQGTQVTVSS;

or

102C12:

(SEQ ID NO: 1247)
QVQLQESGGGLVQAGKSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTQVTVSS.

In various embodiments, the PD-1 binding agent comprises an amino acid sequence described in U.S. Publication No. 2017/0137517, the entire contents of which are incorporated by reference. By way of example, in some embodiments the PD-1 binding agent comprises one of the following sequences in U.S. Publication No. 2017/0137517:

(SEQ ID NO: 87)
EVQLVESGGGLVQAGGSLRLSCAASGSIASIHAMGWFRQAPGKEREFVA

VITWSGGITYYADSVKGRFTISRDNAKNTVYLQMNSLKPEDTAIYYCAG

DKHQSSWYDYWGQGTLVTVSS;

(SEQ ID NO: 88)
EVQLVESGGGLVQAGGSLRLSCAASGSIASIHAMGWFRQAPGKEREFVA

VITWSGGITYYADSVKGRFTISRDNAKNTVYLQMNSLKPEDTATYYCAG

DKHQSSWYDYWGQGTLVTVSS;

(SEQ ID NO: 89)
EVQLVESGGGLVQAGGSLRLSCAASGSIASIHAMGWFRQAPGKEREFVA

VITWSGGITYYADSVKGRFTISRDNAKNTVYLQMNSLKPEDTATYYCAG

DKHQSSWYDYWGQGTLVKVSS;

(SEQ ID NO: 90)
EVQLVESGGGVVQAGGSLRLSCAASGGTFSFYGMGWFRQAPGKEQEFVA

DIRTSAGRTYYADSVKGRFTISRDNAKNTVYLQMNSLKPEDTAVYYCAA

EMSGISGWDYWGQGTQVQVSS;

(SEQ ID NO: 91)
EVQLVESGGGVVQAGGSLRLSCAASGGTFSFYGMGWFRQAPGKEQEFVA

DIRTSAGRTYYADSVKGRFTISRDNAKNTVYLQMNSLKPEDTAVYYCAA

EMSGISGWDYWGQGTLVTVKS;

(SEQ ID NO: 92)
EVQLVESGGGVVQAGGSLRLSCAASGGTFSFYGMGWFRQAPGKEQEFVA

DIRTSAGRTYYADSVKGRFTISRDNAKNTVYLQMNSLKPEDTAVYYCAA

EMSGISGWDYWGQGTLVTVQS;

(SEQ ID NO: 93)
EVQLVESGGGLVQAGGSLRLSCAASGSIASIHAMGWFRQAPGKEREFVA

DIRTSAGRTYYADSVKGRFTISRDNAKNTVYLQMNSLKPEDTALYYCAA

EMSGISGWDYWGQGTLVKVSS;

(SEQ ID NO: 94)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVQVSS;

(SEQ ID NO: 95)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVKS;

(SEQ ID NO: 96)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVQS;

(SEQ ID NO: 97)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVSS;

(SEQ ID NO: 98)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVKVSS;

(SEQ ID NO: 99)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVQVSS;

(SEQ ID NO: 100)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVKS;

(SEQ ID NO: 101)
EVQLVESGGGVVQPGGSLRLSCAASGGTFSFYGMGWFRQAPGKEQEFVADIRTSAGRTYYADSVKGRFTISRDNSKNTVYLQMNSLRPEDTALYYCAAEMSGISGWDYWGQGTLVTVQS;

(SEQ ID NO: 102)
EVQLVESGGGVVQPGGSLRLSCAASGGTFSFYGMGWFRQAPGKEREFVADIRTSAGRTYYADSVKGRFTISRDNSKNTVYLQMNSLRPEDTALYYCAAEMSGISGWDYWGQGTLVTVSS;

(SEQ ID NO: 103)
DVQLVESGGGVVQPGGSLRLSCAASGGTFSFYGMGWFRQAPGKEQEFVADIRTSAGRTYYADSVKGRFTISRDNSKNTVYLQMNSLRPEDTALYYCAAEMSGISGWDYWGQGTLVTVSS;

(SEQ ID NO: 104)
DVQLVESGGGVVQPGGSLRLSCAASGGTFSFYGMGWFRQAPGKEREFVADIRTSAGRTYYADSVKGRFTISRDNSKNTVYLQMNSLRPEDTALYYCAAEMSGISGWDYWGQGTLVTSSA;

(SEQ ID NO: 105)
EVQLVESGGGLVQAGGSLRLSCAASGGTFSFYGMGWFRQAPGKEQEFVADIRTSAGRTYYADSVKGRFTISRDNAKNTVYLQMNSLKPEDTATYYCAAEMSGISGWDYWGQGTLVKVSSA;

(SEQ ID NO: 106)
EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVQVSSA;

(SEQ ID NO: 107)
EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVTVKSA;

(SEQ ID NO: 108)
EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVTVQSA;

(SEQ ID NO: 109)
EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVKVSSA;

(SEQ ID NO: 110)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVQVSSA;

(SEQ ID NO: 111)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVKSA;

(SEQ ID NO: 112)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVQSA;

(SEQ ID NO: 113)
EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVTVSSA;

(SEQ ID NO: 114)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVKVSSA;

(SEQ ID NO: 115)
EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTLVQVSSA;

(SEQ ID NO: 116)
EVQLVESGGGVVQAGGSLRLSCAASGGTFSFYGMGWFRQAPGKEQEFVA
DIRTSAGRTYYADSVKGRFTISRDNAKNTVYLQMNSLKPEDTALYYCAA
EMSGISGWDYWGQGTLVTVKSA;

(SEQ ID NO: 117)
EVQLVESGGGVVQAGGSLRLSCAASGGTFSFYGMGWFRQAPGKEQEFVA
DIRTSAGRTYYADSVKGRFTISRDNAKNTVYLQMNSLKPEDTALYYCAA
EMSGISGWDYWGQGTLVTVQSA;

(SEQ ID NO: 118)
EVQLVESGGGVVQAGGSLRLSCAASGGTFSFYGMGWFRQAPGKEQEFVA
DIRTSAGRTYYADSVKGRFTISRDNAKNTVYLQMNSLKPEDTALYYCAA
EMSGISGWDYWGQGTLVTVSSA;

(SEQ ID NO: 119)
EVQLVESGGGVVQPGGSLRLSCAASGGTFSFYGMGWFRQAPGKEQEFVA
DIRTSAGRTYYADSVKGRFTISRDNSKNTVYLQMNSLRPEDTALYYCAA
EMSGISGWDYWGQGTLVTVSSA;

(SEQ ID NO: 120)
DVQLVESGGGVVQPGGSLRLSCAASGSIASIHAMGWFRQAPGKEREFVA
VITWSGGITYYADSVKGRFTISRDNSKNTVYLQMNSLRPEDTALYYCAG
DKHQSSWYDYWGQGTLVTVSS;

(SEQ ID NO: 121)
EVQLVESGGGLVQPGGSLRLSCAASGSIASIHAMGWERQAPGKEREEVA
VITWSGGITYYADSVKGRFTISRDNSKNTVYLQMNSLRPEDTAIYYCAG
DKHQSSWYDYWGQGTLVTVSS;

(SEQ ID NO: 122)
EVQLVESGGGVVQPGGSLRLSCAASGSIASIHAMGWERQAPGKEREEVA
VITWSGGITYYADSVKGRFTISRDNSKNTVYLQMNSLRPEDTALYYCAG
DKHQSSWYDYWGQGTLVTVSS;

(SEQ ID NO: 123)
DVQLVESGGGVVQPGGSLRLSCAASGSIASIHAMGWERQAPGKEREEVA
VITWSGGITYYADSVKGRFTISRDNSKNTVYLQMNSLRPEDTALYYCAG
DKHQSSWYDYWGQGTLVTVSSGGGGSGGGGSGGGGSGGGGSGGGGSGGG
GSGGGGSEVQLVESGGGVVQPGNSLRLSCAASGFTFSSFGMSWVRQAPG
KGLEWVSSISGSGSDTLYADSVKGRFTISRDNAKTTLYLQMNSLRPEDT
ALYYCTIGGSLSRSSQGTLVTVSSA;

(SEQ ID NO: 124)
DVQLVESGGGVVQPGGSLRLSCAASGSIASIHAMGWERQAPGKEREEVA
VITWSGGITYYADSVKGRFTISRDNSKNTVYLQMNSLRPEDTALYYCAG
DKHQSSWYDYWGQGTLVTVSSGGGGSGGGGSGGGGSGGGGSGGGGSGGG
GSGGGGSEVQLVESGGGVVQPGGSLRLSCAASGSIASIHAMGWFRQAPG
KEREFVAVITWSGGITYYADSVKGRFTISRDNSKNTVYLQMNSLRPEDT
ALYYCAGDKHQSSWYDYWGQGTLVTVSSGGGGSGGGGSGGGGSGGGGSG
GGGSGGGGSGGGGSEVQLVESGGGVVQPGNSLRLSCAASGFTFSSFGMS
WVRQAPGKGLEWVSSISGSGSDTLYADSVKGRFTISRDNAKTTLYLQMN
SLRPEDTALYYCTIGGSLSRSSQGTLVTVSSA;

(SEQ ID NO: 125)
DVQLVESGGGVVQPGGSLRLSCAASGSIASIHAMGWERQAPGKEREEVA
VITVSGGITYYADSVKGRFTISRDNSKNTVYLQMNSLRPEDTALYYCAG
DKHQSSFYDYWGQGTLVTVSS;

(SEQ ID NO: 126)
DVQLVESGGGVVQPGGSLRLSCAASGSIASIHAMGWFRQAPGKEREFVA
VITVSGGITYYADSVKGRFTISRDQSKNTVYLQMNSLRPEDTALYYCAG
DKHQSSFYDYWGQGTLVTVSS;

(SEQ ID NO: 127)
DVQLVESGGGVVQPGGSLRLSCAASGSIASIHAMGWFRQAPGKEREFVA
VITVSGGITYYADSVKGRFTISRDPSKNTVYLQMNSLRPEDTALYYCAG
DKHQSSFYDYWGQGTLVTVSS;

(SEQ ID NO: 128)
DVQLVESGGGVVQPGGSLRLSCAASGSIASIHAMGWFRQAPGKEREFVA
VITVSGGITYYADSVKGRFTISRDPSKNTVYLQMNSLRPEDTALYYCAG
DKHQSSFYDYWGQGTLVTVSS;

(SEQ ID NO: 129)
DVQLVESGGGVVQPGGSLRLSCAASGSIASIHAMGWFRQAPGKEREFVA
VITVSGGITYYADSVKGRFTISRDQSKNTVYLQMNSLRPEDTALYYCAG
DKHQSSFYDYWGQGTLVTVSS;

(SEQ ID NO: 130)
DVQLVESGGGVVQPGGSLRLSCAASGSIASIHAMGWFRQAPGKEREFVA
VITVSGGITYYADSVKGRFTISRDSSKNTVYLQMNSLRPEDTALYYCAG
DKHQSSFYDYWGQGTLVTVSS;

(SEQ ID NO: 131)
EVQLVESGGGLVQPGGSLRLSCAASGSIASIHAMGWERQAPGKEREEVA
VITWSGGITYYADSVKGRFTISRDNSKNTVYLQMNSLRPEDTAIYYCAG
DKHQSSWYDYWGQGTLVTVSSGGGGSGGGGSGGGGSGGGGSGGGGSGGG
GSGGGGSEVQLVESGGGLVQPGGSLRLSCAASGSIASIHAMGWERQAPG
KEREEVAVITWSGGITYYADSVKGRFTISRDNSKNTVYLQMNSLRPEDT
AIYYCAGDKHQSSWYDYWGQGTLVTVSSGGGGSGGGGSGGGGSGGGGSG
GGGSGGGGSGGGGSEVQLVESGGGLVQPGNSLRLSCAASGFTFSSFGMS
WVRQAPGKGLEWVSSISGSGSDTLYADSVKGRFTISRDNAKTTLYLQMN
SLRPEDTAVYYCTIGGSLSRSSQGTLVTVSS;
and (SEQ ID NO: 132)
MQIPQAPWPVVWAVLQLGWRPGWFLDSPDRPWNPPTFSPALLVVTEGDN
ATFTCSFSNTSESFVLNWYRMSPSNQTDKLAAFPEDRSQPGQDCRFRVT
QLPNGRDFHMSVVRARRNDSGTYLCGAISLAPKAQIKESLRAELRVTER
RAEVPTAHPSPSPRPAGQFQTLVVGVVGGLLGSLVLLVWVLAVICSRAA
RGTIGARRTGQPLKEDPSAVPVFVDYGELDFQWREKTPEPPVPCVPEQT
EYATIVFPSGMGTSSPARRGSADGPRSAQPLRPEDGHCSWPL.

In some embodiments, the PD-1 binding agent comprises an amino acid sequence selected from SEQ ID NOs: 87-132 having one or more substitutions at positions 1, 11, 14, 52a, 73, 74, 83, 89, 100a, 110, and 112 (according to Kabat numbering). In some embodiments, the amino acid at position 1 is E or D. In some embodiments, the amino acid at position 11 is L or V. In some embodiments, the amino acid at position 14 is A or P. In some embodiments, the amino acid at position 52a is W or V. In some embodiments, the amino acid at position 73 is N, S, P, or Q. In some embodiments, the amino acid at position 74 is A or S. In some embodiments, the amino acid at position 83 is K or R. In some embodiments, the amino acid at position 89 is T, V, I, or L. In some embodiments, the amino acid at position 100a is W or F. In some embodiments, the amino acid at position 110 is T, K, or Q. In some embodiments, the amino acid at position 112 is S, K, or Q.

In various embodiments, the PD-1 binding agent comprises an amino acid sequence described in PCT Publication No. WO 2017/087587, the entire contents of which are incorporated by reference. By way of example, in some embodiments the PD-1 binding agent comprises one of the following sequences in PCT Publication No. WO 2017/087587:

```
                                          (SEQ ID NO: 133)
EVQLVESGGGLVQAGGSLRLSCAASGGTFSFYGMGWFRQAPGKEQEFV

ADIRTSAGRTYYADSVKGRFTISRDNAKNTVYLQMNSLKPEDTAVYYC

AAEMSGISGWDYWGQGTQVTVSS;

(SEQ ID NO: 134)
EVQLVESGGGLVQAGGSLRLSCAASGSIASIHAMGWFRQAPGKEREFV

AVITWSGGITYYADSVKGRFTISRDNAKNTVYLQMNSLKPEDTATYYC

AGDKHQSSWYDYWGQGTLVTVSS;

(SEQ ID NO: 135)
EVQLVESGGGVVQAGGSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTLVKVSS;

(SEQ ID NO: 136)
EVQLVESGGGVVQAGGSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTLVQVSS;

(SEQ ID NO: 137)
EVQLVESGGGVVQAGGSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTLVTVKS;

(SEQ ID NO: 138)
EVQLVESGGGVVQAGGSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTLVTVQS;

(SEQ ID NO: 139)
EVQLVESGGGLVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVKVSS;

(SEQ ID NO: 140)
EVQLVESGGGLVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVQVSS;

(SEQ ID NO: 141)
EVQLVESGGGLVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVTVKS;

(SEQ ID NO: 142)
EVQLVESGGGLVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVTVQS;

(SEQ ID NO: 143)
EVQLVESGGGVVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVTVSS;

(SEQ ID NO: 144)
EVQLVESGGGVVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVKVSS;

(SEQ ID NO: 145)
EVQLVESGGGVVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVQVSS;

(SEQ ID NO: 146)
EVQLVESGGGVVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVTVKS;

(SEQ ID NO: 147)
EVQLVESGGGVVQAGGSLRLSCAASGSIASIHAMGWFRQAPGKEREFV

AVITWSGGITYYADSVKGRFTISRDNAKNTVYLQMNSLKPEDTALYYC

AGDKHQSSWYDYWGQGTLVTVQS;

(SEQ ID NO: 148)
EVQLVESGGGVVQPGGSLRLSCAASGSIASIHAMGWFRQAPGKEREFV

AVITWSGGITYYADSVKGRFTISRDNSKNTVYLQMNSLRPEDTALYYC

AGDKHQSSWYDYWGQGTLVTVSS;

(SEQ ID NO: 149)
DVQLVESGGGVVQPGGSLRLSCAASGSIASIHAMGWFRQAPGKEREFV

AVITWSGGITYYADSVKGRFTISRDNSKNTVYLQMNSLRPEDTALYYC

AGDKHQSSWYDYWGQGTLVTVSS;

(SEQ ID NO: 150)
EVQLVESGGGLVQAGGSLRLSCAASGSIASIHAMGWFRQAPGKEREFV

AVITWSGGITYYADSVKGRFTISRDNAKNTVYLQMNSLKPEDTATYYC

AGDKHQSSWYDYWGQGTLVTVSSA;

(SEQ ID NO: 151)
EVQLVESGGGVVQAGGSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTLVKVSSA;
```

(SEQ ID NO: 152)
EVQLVESGGGVVQAGGSLRLSCAASGSIASIHAMGWFRQAPGKEREFV
AVITWSGGITYYADSVKGRFTISRDNAKNTVYLQMNSLKPEDTAIYYC
AGDKHQSSWYDYWGQGTLVQVSSA;

(SEQ ID NO: 153)
EVQLVESGGGVVQAGGSLRLSCAASGSIASIHAMGWFRQAPGKEREFV
AVITWSGGITYYADSVKGRFTISRDNAKNTVYLQMNSLKPEDTAIYYC
AGDKHQSSWYDYWGQGTLVTVKSA;

(SEQ ID NO: 154)
EVQLVESGGGVVQAGGSLRLSCAASGSIASIHAMCWFRQAPGKEREFV
AVITWSGGITYYADSVKGRFTISRDNAKNTVYLQMNSLKPEDTAIYYC
AGDKHQSSWYDYWGQGTLVTVQSA;

(SEQ ID NO: 155)
EVQLVESGGGLVQAGGSLRLSCAASGSIASIHAMCWFRQAPGKEREFV
AVITWSGGITYYADSVKGRFTISRDNAKNTVYLQMNSLKPEDTALYYC
AGDKHQSSWYDYWGQGTLVKVSSA;

(SEQ ID NO: 156)
EVQLVESGGGLVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVQVSSA;

(SEQ ID NO: 157)
EVQLVESGGGLVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVTVKSA;

(SEQ ID NO: 158)
EVQLVESGGGLVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVTVQSA;

(SEQ ID NO: 159)
EVQLVESGGGVVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVTVSSA;

(SEQ ID NO: 160)
EVQLVESGGGVVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVKVSSA;

(SEQ ID NO: 161)
EVQLVESGGGVVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVQVSSA;

(SEQ ID NO: 162)
EVQLVESGGGVVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVTVKSA;

(SEQ ID NO: 163)
EVQLVESGGGVVQAGGSLRLSCAASGSIASIHAMGWFRQAPGKEREFV
AVITWSGGITYYADSVKGRFTISRDNAKNTVYLQMNSLKPEDTALYYC
AGDKHQSSWYDYWGQGTLVTVQSA;

(SEQ ID NO: 164)
EVQLVESGGGVVQPGGSLRLSCAASGSIASIHAMGWFRQAPGKEREFV
AVITWSGGITYYADSVKGRFTISRDNSKNTVYLQMNSLRPEDTALYYC
AGDKHQSSWYDYWGQGTLVTVSSA;

(SEQ ID NO: 165)
DVQLVESGGGVVQPGGSLRLSCAASGSIASIHAMGWFRQAPGKEREFV
AVITWSGGITYYADSVKGRFTISRDNSKNTVYLQMNSLRPEDTALYYC
AGDKHQSSWYDYWGQGTLVTVSSA;

(SEQ ID NO: 166)
DVQLVESGGGVVQPGGSLRLSCAASGSIASIHAMGWFRQAPGKEREFV
AIITWSGGITYYADSVKGRFTISRDNSKNTVYLQMNSLRPEDTALYYC
AGDKHQSSWYDYWGQGTLVTVSS;

(SEQ ID NO: 167)
EVQLVESGGGLVQPGGSLRLSCAASGSIASIHAMGWFRQAPGKEREFV
AVITWSGGITYYADSVKGRFTISRDNSKNTVYLQMNSLRPEDTAIYYC
AGDKHQSSWYDYWGQGTLVTVSS;

(SEQ ID NO: 168)
EVQLVESGGGVVQPGGSLRLSCAASGSIASIHAMGWFRQAPGKEREFV
AVITWSGGITYYADSVKGRFTISRDNSKNTVYLQMNSLRPEDTALYYC
AGDKHQSSWYDYWGQGTLVTVSS;

(SEQ ID NO: 169)
DVQLVESGGGVVQPGGSLRLSCAASGSIASIHAMGWFRQAPGKEREFV
AVITWSGGITYYADSVKGRFTISRDNSKNTVYLQMNSLRPEDTALYYC
AGDKHQSSWYDYWGQGTLVTVSSGGGGSGGGGSGGGGSGGGGSGGGGS
GGGGSGGGGSEVQLVESGGGWVQPGNSLRLSCAASGFTFSSFGMSWVR
QAPGKGLEWVSSISGSGSDTLYADSVKGRFTISRDNAKTTLYLQMNSL
RPEDTALYYCTIGGSLSRSSQGTLVTVSSA;

(SEQ ID NO: 170)
DVQLVESGGGVVQPGGSLRLSCAASGSIASIHAMGWFRQAPGKEREFV
AVITWSGGITYYADSVKGRFTISRDNSKNTVYLQMNSLRPEDTALYYC
AGDKHQSSWYDYWGQGTLVTVSSGGGGSGGGGSGGGGSGGGGSGGGGS
GGGGSGGGGSEVQLVESGGGVVQPGSLRLSCAASGSIASIHAMWFR
QAPGKEREFVAVITWSGGITYYADSVKGRFTISRDNSKNTVYLQMNSL
RPEDTALYYCAGDKHQSSWYDYWGQGTLVTVSSGGGGSGGGGSGGGGS
GGGGSGGGGSGGGGSGGGGSEVQLVESGGGVVQPGNSLRLSCAASGFT
FSSFGMSWVRQAPGKGLEWVSSISGSGSDTLYADSVKGRFTISRDNAK
TTLYLQMNSLRPEDTALYYCTIGGSLSRSSQGTLVTVSSA;

(SEQ ID NO: 171)
DVQLVESGGGVVQPGGSLRLSCAASGSIASIHAMGWFRQAPGKEREFV
AVITVSGGITYYADSVKGRFTISRDNSKNTVYLQMNSLRPEDTALYYC
AGDKHQSSFYDYWGQGTLVTVSS;

```
                                         (SEQ ID NO: 172)
DVQLVESGGGVVQPGGSLRLSCAASGSIASIHAMGWFRQAPGKEREFV

AVITVSGGITYYADSVKGRFTISRDQSKNTVYLQMNSLRPEDTALYYC

AGDKHQSSFYDYWGQGTLVTVSS;
and (SEQ ID NO: 173)
DVQLVESGGGVVQPGGSLRLSCAASGSIASIHAMGWFRQAPGKEREFV

AVITVSGGITYYADSVKGRFTISRDPSKNTVYLQMNSLRPEDTALYYC

AGDKHQSSFYDYWGQGTLVTVSS.
```

In some embodiments, the PD-1 binding agent comprises an amino acid sequence selected from SEQ ID NOs: 133-173 having one or more substitutions at positions 1, 11, 14, 52a, 73, 74, 83, 89, 100a, 110, and 112 (according to Kabat numbering). In some embodiments, the amino acid at position 1 is E or D. In some embodiments, the amino acid at position 11 is L or V. In some embodiments, the amino acid at position 14 is A or P. In some embodiments, the amino acid at position 52a is W or V. In some embodiments, the amino acid at position 73 is N, S, P, or Q. In some embodiments, the amino acid at position 74 is A or S. In some embodiments, the amino acid at position 83 is K or R. In some embodiments, the amino acid at position 89 is T, V, I, or L. In some embodiments, the amino acid at position 100a is W or F. In some embodiments, the amino acid at position 110 is T, K, or Q. In some embodiments, the amino acid at position 112 is S, K, or Q.

In various embodiments, the present invention contemplates the use of any natural or synthetic analogs, mutants, variants, alleles, homologs and orthologs (herein collectively referred to as "analogs") of the PD-1 binding agent of the invention as described herein. In various embodiments, the amino acid sequence of the PD-1 binding agent further includes an amino acid analog, an amino acid derivative, or other non-classical amino acids.

In various embodiments, the present further provides PD-L1 binding agents. Programmed death-ligand 1 (PD-L1) also known as cluster of differentiation 274 (CD274) or B7 homolog 1 (B7-H1) is a type 1 transmembrane protein that has been speculated to play a major role in suppressing the immune system. PD-L1 is upregulated on macrophages and dendritic cells (DC) in response to LPS and GM-CSF treatment, and on T cells and B cells upon TCR and B cell receptor signaling.

In various embodiments, the PD-L1 binding agent of the invention comprises a targeting moiety having an antigen recognition domain that recognizes an epitope present on PD-L1. In an embodiment, the antigen-recognition domain recognizes one or more linear epitopes present on PD-L1. As used herein, a linear epitope refers to any continuous sequence of amino acids present on PD-L1. In another embodiment, the antigen-recognition domain recognizes one or more conformational epitopes present on PD-L1. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the PD-L1 binding agent of the present invention may bind to the full-length and/or mature forms and/or isoforms and/or splice variants and/or fragments and/or any other naturally occurring or synthetic analogs, variants, or mutants of human PD-L1. In various embodiments, the PD-L1 binding agent of the invention may bind to any forms of the human PD-L1. In an embodiment, the PD-L1 binding agent binds to a phosphorylated form of PD-L1. In an embodiment, the PD-L1 binding agent binds to an acetylated form of PD-L1.

In an embodiment, the present PD-L1 binding agent comprises a targeting moiety with an antigen recognition domain that recognizes one or more epitopes present on human PD-L1. In an embodiment, the human PD-L1 comprises the amino acid sequence of (signal peptide underlined):

```
Isoform 1:
                                         (SEQ ID NO: 174)
MRIFAVFIFMTYWHLLNAFTVTVPKDLYVVEYGSNMTIECKFPVEKQL

DLAALIVYWEMEDKNIIQFVHGEEDLKVQHSSYRQRARLLKDQLSLGN

AALQITDVKLQDAGVYRCMISYGGADYKRITVKVNAPYNKINQRILVV

DPVTSEHELTCQAEGYPKAEVIWTSSDHQVLSGKTTTTNSKREEKLFN

VTSTLRINTTTNEIFYCTFRRLDPEENHTAELVIPELPLAHPPNERTH

LVILGAILLCLGVALTFIFRLRKGRMMDVKKCGIQDTNSKKQSDTHLE

ET;

Isoform 2:
                                         (SEQ ID NO: 175)
MRIFAVFIFMTYWHLLNAPYNKINQRILVVDPVTSEHELTCQAEGYPK

AEVIWTSSDHQVLSGKTTTTNSKREEKLFNVTSTLRINTTTNEIFYCT

FRRLDPEENHTAELVIPELPLAHPPNERTHLVILGAILLCLGVALTFI

FRLRKGRMMDVKKCGIQDTNSKKQSDTHLEET;
or

Isoform 3:
                                         (SEQ ID NO: 176)
MRIFAVFIFMTYWHLLNAFTVTVPKDLYVVEYGSNMTIECKFPVEKQL

DLAALIVYWEMEDKNIIQFVHGEEDLKVQHSSYRQRARLLKDQLSLGN

AALQITDVKLQDAGVYRCMISYGGADYKRITVKVNAPYNKINQRILVV

DPVTSEHELTCQAEGYPKAEVIWTSSDHQVLSGD.
```

In various embodiments, the present PD-L1 binding agent comprises a targeting moiety capable of specific binding. In various embodiments, the PD-L1 binding agent comprises a targeting moiety having an antigen recognition domain such as an antibody or derivatives thereof. In an embodiment, the PD-L1 binding agent comprises a targeting moiety which is an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the PD-L1 binding agent comprises a targeting moiety which is an antibody derivative or format. In some embodiments, the present PD-L1 binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a F(ab')$_2$, a peptide mimetic molecule, or a synthetic molecule, as described in US patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the PD-L1 binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_HH$) and two constant domains (CH2 and CH3).

In an embodiment, the PD-L1 binding agent comprises a VHH. In some embodiments, the VHH is a humanized VHH or camelized VHH.

In some embodiments, the VHH comprises a fully human $V_H$ domain, e.g. a HUMABODY (Crescendo Biologics, Cambridge, UK). In some embodiments, fully human $V_H$ domain, e.g. a HUMABODY is monovalent, bivalent, or trivalent. In some embodiments, the fully human $V_H$ domain, e.g. a HUMABODY is mono- or multi-specific such as monospecific, bispecific, or trispecific. Illustrative fully human $V_H$ domains, e.g. a HUMABODIES are described in, for example, WO2016/113555 and WO2016/113557, the entire disclosure of which is incorporated by reference.

In some embodiments, the PD-L1 binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the PD-L1 binding agent comprises a VHH having a variable domain comprising at least one CDR1, CDR2, and/or CDR3 sequences. In various embodiments, the PD-L1 binding agent comprises a VHH having a variable region comprising at least one FR1, FR2, FR3, and FR4 sequences.

In some embodiments, the PD-L1 CDR1 sequence is selected from: GFTLDYYAIG (SEQ ID NO: 177); GTIFSINHMD (SEQ ID NO: 178); GFTFDDYGMS (SEQ ID NO: 179); GFTLDYYAIN (SEQ ID NO: 180); GTIFSINRMD (SEQ ID NO: 181); GFTFSSYGMS (SEQ ID NO: 182); GKIFSGNDMG (SEQ ID NO: 183); GFTFNDYAMS (SEQ ID NO: 184); GFNLDPYAIA (SEQ ID NO: 185); GFTFTAYAMS (SEQ ID NO: 186); GFTFDYYAIG (SEQ ID NO: 187); GFNLDPYAIG (SEQ ID NO: 188); ESIFSIEAMG (SEQ ID NO: 189); GRTFSISAMG (SEQ ID NO: 190); YYAIG (SEQ ID NO: 191); YYAKC (SEQ ID NO: 192); QYDVG (SEQ ID NO: 193); NSAMG (SEQ ID NO: 194); DSIVS (SEQ ID NO: 195); INHMD (SEQ ID NO: 196); DYGMS (SEQ ID NO: 197); YYAIN (SEQ ID NO: 198); INRMD (SEQ ID NO: 199); SYGMS (SEQ ID NO: 200); GNDMG (SEQ ID NO: 201); DYAMS (SEQ ID NO: 202); PYAIA (SEQ ID NO: 203); AYAMS (SEQ ID NO: 204); PYAIG (SEQ ID NO: 205); IEAMG (SEQ ID NO: 206); and ISAMG (SEQ ID NO: 207).

In some embodiments, the PD-L1 CDR2 sequence is selected from: ISSSDGSTY (SEQ ID NO: 208); ITSDGFPT (SEQ ID NO: 209); IRWNGGSTN (SEQ ID NO: 210); ITSDGTPT (SEQ ID NO: 211); IDSGGGSTS (SEQ ID NO: 212); ITSGGITD (SEQ ID NO: 213); ITSDGTPT (SEQ ID NO: 214); IDSGGGSTS (SEQ ID NO: 215); IRSNGGYTN (SEQ ID NO: 216); ISSSDVGTY (SEQ ID NO: 217); INSSDGSTY (SEQ ID NO: 218); ISGSDSSTY (SEQ ID NO: 219); ISSSDVGTY (SEQ ID NO: 220); ITSDGTPT (SEQ ID NO: 221); ITSDGTPA (SEQ ID NO: 222); IDSGGGSTS (SEQ ID NO: 223); ISSGDGSKY (SEQ ID NO: 224); ISSSDVGTY (SEQ ID NO: 225); IFGGGFTN (SEQ ID NO: 226); ITSGGITD (SEQ ID NO: 227); IDSGGGSTS (SEQ ID NO: 228); ITSDGTPT (SEQ ID NO: 229); IDSGGGSTS (SEQ ID NO: 230); ISSSDVGTY (SEQ ID NO: 231); ITWSGGSTS (SEQ ID NO: 232); IDSGGGSTS (SEQ ID NO: 233); IRSNGGYTN (SEQ ID NO: 234); SISSSDGSTYYADSVKG (SEQ ID NO: 235); CISSSDGSTYYADSVKG (SEQ ID NO: 236); CISGGDNSTYYADSVKG (SEQ ID NO: 237); FSSSGGRTIYPDSVKG (SEQ ID NO: 238); RITGGGLIAYTDSVKG (SEQ ID NO: 239); GISNGGTIKYAESVLG (SEQ ID NO: 240); LITSDGFPT (SEQ ID NO: 241); LITSDGFPTYADSAKG (SEQ ID NO: 242); AIRWNGGSTN (SEQ ID NO: 243); AIRWNGGSTNYADSVKG (SEQ ID NO: 244); LITSDGTPT (SEQ ID NO: 245); LITSDGTPTYADSAKG (SEQ ID NO: 246); AIDSGGGSTS (SEQ ID NO: 247); AIDSGGGSTSYADSVKG (SEQ ID NO: 248); IITSGGITD (SEQ ID NO: 249); IITSGGITDYADAVKG (SEQ ID NO: 250); GIRSNGGYTN (SEQ ID NO: 251); GIRSNGGYTNYADSVKG (SEQ ID NO: 252); CISSSDVGTY (SEQ ID NO: 253); CISSSDVGTYYADSVKG (SEQ ID NO: 254); CINSSDGSTY (SEQ ID NO: 255); CINSSDGSTYYADSVKG (SEQ ID NO: 256); CISGSDSSTY (SEQ ID NO: 257); CISGSDSSTYYADSVKG (SEQ ID NO: 258); LITSDGTPA (SEQ ID NO: 259); LITSDGTPAYADSAKG (SEQ ID NO: 260); CISSGDGSKY (SEQ ID NO: 261); CISSGDGSKYYADSVKG (SEQ ID NO: 262); AIFGGGFTN (SEQ ID NO: 263); AIFGGGFTNYADSVKG (SEQ ID NO: 264); AITWSGGSTS (SEQ ID NO: 265); and AITWSGGSTSYTDSVKG (SEQ ID NO: 266).

In some embodiments, the CDR3 sequence is selected from: DGWSSCRHGINEYLYW (SEQ ID NO: 267); SSGVYNYW (SEQ ID NO: 268); QGYYCSGYGCPR (SEQ ID NO: 269); SGWRLCRPTDEYDYSYW (SEQ ID NO: 270); QGYYCSGYGCSDYW (SEQ ID NO: 271); RDRTIWW (SEQ ID NO: 272); QGYYCSGYGCYP (SEQ ID NO: 273); DGYYYCSDYPHPLYW (SEQ ID NO: 274); DGWRDCTWSNEYAYW (SEQ ID NO: 275); TGWRTCRGLNEYDYW (SEQ ID NO: 276); DLVSGSSRLYDYW (SEQ ID NO: 277); MGRTNYGVIYDPNMYNYW (SEQ ID NO: 278); SGWRLCRPTDEYDYLYW (SEQ ID NO: 279); SQAPITIATMMKPFYDY (SEQ ID NO: 280); RHGGPLTVEYFFDY (SEQ ID NO: 281); GGWKYCSGYDPEYIY (SEQ ID NO: 282); DWYLNSY (SEQ ID NO: 283); INSRDG (SEQ ID NO: 284); and RQY (SEQ ID NO: 285).

In various exemplary embodiments, the PD-L1 binding agent comprises an amino acid sequence selected from the following sequences:

2LIG2

(SEQ ID NO: 286)
QVQLQESGGGLVQAGGSLRLSCAASGFTLDYYAIGWFRQAPGKEREEV

SCISSSDGSTYYADSVKGRFTISRDNAKNTVNLQMNSLKPEDTAVYYC

ATDGWSSCRHGIN-EYLYWGQGTQVTVSSAAAYPYDVPDYGSHHHHHH;
or

2LIG3

(SEQ ID NO: 287)
QVQLQESGGGLVQAGGSLRLSCTASGTIFSINHMDWFRQAPGKQRELV

ALITSDGFPTYADSAKGRFTISRDNTKKTVSLQMNSLKPEDTAVYYCH

VSSGVYNYWGQGTQVTVSSAAAYPYDVPDYGSHHHHHH;
or

2LIG16

(SEQ ID NO: 288)
QVQLQESGGGLVQPGGSLRLSCAASGFTFDDYGMSWVRQAPGKGLEWV

SAIRWNGGSTNYADSVKGRFTISRDNAKNTLYLQMNSLKSEDTAVYYC

A-QGYY-CSGYGCPRGQGTQVTVSSAAAYPYDVPDYGSHHHHHH;
or

2LIG22

(SEQ ID NO: 289)
QVQLQESGGGLVQPGGSLRLSCAASGFTLDYYAINWFRQAPGKEREEV

SCISSSDGSTYYADSVKGRFTISRDNAKNTVYLQMNSLKPEDTAVYYC

ATSGWRLCRPTDEYDYSYWGQGTQVTVSSAAAYPYDVPDYGSHHHHHH;
or

2LIG27

(SEQ ID NO: 290)
QVQLQESGGGVVQAGGSLRLSCTASGTIFSINRMDWFRQAPGKQRELV

ALITSDGTPTYADSAKGRFTISRDNTKKTVSLQMNSLKPEDTAVYYCH

VSSGVYNYWGQGTQVTVSSAAAYPYDVPDYGSHHHHHH;
or

2LIG29

(SEQ ID NO: 291)
QVQLQESGGGLVQTGGSLRLSCAASGFTFSSYGMSWVRQTPGKGPEWV

SAIDSGGGSTSYADSVKGRFTISRDNAKNTLYLQMNSLKPEDTAVYYC

A-QGYY-CSGYGCSDYWGQGTQVTVSSAAAYPYDVPDYGSHHHHHH;
or

2LIG30

(SEQ ID NO: 292)
QVQLQESGGGLVQPGGSLRLSCAASGKIFSGNDMGWYRQAPGKQRELV

GIITSGGITDYADAVKGRFTISRDNAKNMMYLQMNSLKPEDTAVYYCN

MRDRTIWWGQGTQVTVSSAAAYPYDVPDYGSHHHHHH;
or

2LIG34

(SEQ ID NO: 293)
QVQLQESGGGSVQAGGSLRLSCTASGTIFSINRMDWFRQAPGKQRELV

ALITSDGTPTYADSAKGRFTISRDNTKKTVSLQMNSLKPEDTAVYYCH

VSSGVYNYWGQGTQVTVSSAAAYPYDVPDYGSHHHHHH;
or

2LIG35

(SEQ ID NO: 294)
QVQLQESGGGLVQPGGSLRLSCAASGFTFSSYGMSWVRQTPGKGPEWV

SAIDSGGGSTSYADSVKGRFTTSRDNAKNTLYLQMNSLKPEDTAVYYC

A-QGYY-CSGYGCSDYWGQGTQVTVSSAAAYPYDVPDYGSHHHHHH;
or

2LIG48

(SEQ ID NO: 295)
QVQLQESGGGLVQPGGSLRLSCAASGFTFNDYAMSWVRQAPGKGLEWV

SGIRSNGGYTNYADSVKGRFTISRDNAKNTLYLQMNSLKSEDTAVYYC

A-QGYY-CSGYGCYPGQGTQVTVSSAAAYPYDVPDYGSHHHHHH;
or

2LIG65

(SEQ ID NO: 296)
QVQLQESGGGLVQAGGSLRLSCAASGFNLDPYAIAWFRQAPGKEREEV

SCISSSDVGTYYADSVKGRFTISRDNAKKTVYLQMNSLKPEDTAVYYC

ATDGYYYCSDYPHPLYWGQGTQVTVSSAAAYPYDVPDYGSHHHHHH;
or

2LIG85

(SEQ ID NO: 297)
QVQLQESGGGLVQPGGSLRLSCAASGFTFTAYAMSWFRQAPGKEREEV

SCINSSDGSTYYADSVKGRFTISRDNAKNTVYLQMNSLKPEDTAVYHC

ATDGWRDCTWSNEYAYWGQGTQVTVSSAAAYPYDVPDYGSHHHHHH;
or

2LIG86

(SEQ ID NO: 298)
QVQLQESGGGLVQPGGSLRLSCAASGFTFDYYAIGWFRQAPGKEREEV

SCISGSDSSTYYADSVKGRFTIVRDNAQNTVYLQMNSLKPEDTAIYYC

AVTGWRTCRGLNEYDYWGQGTQVTVSSAAAYPYDVPDYGSHHHHHH;
or

2LIG89

(SEQ ID NO: 299)
QVQLQESGGGLVQPGGSLRLSCAASGFNLDPYAIAWFRQAPGKEREEV

SCISSSDVGTYYADSVKGRFTISRDNTKKTVYLQMNSLKPEDTAVYYC

ATDGYYYCSDYPHPLYWGQGTQVTVSSAAAYPYDVPDYGSHHHHHH;
or

2LIG97

(SEQ ID NO: 300)
QVQLQESGGGLVQAGESLRLSCTASGTIFSINRMDWFRQAPGKQRELV

ALITSDGTPTYADSAKGRFTISRDNTKKTVSLQMNSLKPEDTAVYYCH

VSSGVYNYWGQGTQVTVSSAAAYPYDVPDYGSHHHHHH;
or

2LIG99

(SEQ ID NO: 301)
QVQLQESGGGLVQAGGSLRLSCTASGTIFSINRMDWFRQAPGKQRELV

ALITSDGTPAYADSAKGRFTISRDNTKKTVSLQMNSLKPEDTAVYYCH

VSSGVYNYWGQGTQVTVSSAAAYPYDVPDYGSHHHHHH;
or

2LIG109
(SEQ ID NO: 302)
QVQLQESGGGLVQSGGSLRLSCKTSGFTFSSYGMSWVRQTPGKGPEWS

AIDSGGGSTSYADSVKGRFTISRDNAKNTLYLQMNSLKPEDTAVYYCA

QGYY-CSGYGCSDYWGQGTQVTVSSAAAYPYDVPDYGSHHHHHH;
or

2LIG127
(SEQ ID NO: 303)
QVQLQESGGGLVQPGGSLRLSCAASGFNLDPYAIGWFRQAPGKEREEV

SCISSGDGSKYYADSVKGRFTMSRDNAKKTVYLQMNSLKPEDTAVYYC

ATDGYYYCSDYPHPLYWGQGTQVTVSSAAAYPYDVPDYGSHHHHHH;
or

2LIG139
(SEQ ID NO: 304)
QVQLQESGGGLVQPGGSLRLSCAVSGFNLDPYAIAWFRQAPGKEREEV

SCISSSDVGTYYADSVKGRFTISRDNAKKTVYLQMNSLKPEDTAVYYC

ATDGYYYCSDYPHPLYWGQGTQVTVSSAAAYPYDVPDYGSHHHHHH;
or

2LIG176
(SEQ ID NO: 305)
QVQLQESGGGLVQAGGSLRLSCAASESIFSIEAMGWYRQAPGKQRELV

AAIFGGGFTNYADSVKGRFTISRDNANRTVYLQMNSLKPEDTAVYYCN

ADLVSGSSRLYDYWGQGTQVTVSSAAAYPYDVPDYGSHHHHHH;
or

2LIG189
(SEQ ID NO: 306)
QVQLQESGGGLVQAGGSLRLSCAASGKIFSGNDMGWYRQAPGKQRELV

GIITSGGITDYADAVKGRFTISRDNAKNMMYLQMNSLKPEDTAVYYCN

MRDRTIWWGQGTQVTVSSAAAYPYDVPDYGSHHHHHH;
or

3LIG3
(SEQ ID NO: 307)
QVQLQESGGGLVQPGGSLRLSCAASGFTLDYYAIGWFRQAPGKEREEV

SCISSSDGSTYYADSVKGRFTISRDNAKNTVNLQMNSLKPEDTAVYYC

ATDGWSSCRHGINEYLYWGQGTQVTVSSAAAYPYDVPDYGSHHHHHH;
or

3LIG7
(SEQ ID NO: 308)
QVQLQESGGGLVQAGGSLRLSCAASGFTFSSYGMSWVRQTPGKGPEWV

SAIDSGGGSTSYADSVKGRFTISRDNAKNTLYLQMNSLKPEDTAVYYC

AQGYY-CSGYGCSDYWGQGTQVTVSSAAAYPYDVPDYGSHHHHHH;

or

3LIG8
(SEQ ID NO: 309)
QVQLQESGGGLVQPGGSLRLSCTASGTIFSINRMDWFRQAPGKQRELV

ALITSDGTPTYADSAKGRFTISRDNTKKTVSLQMNSLKPEDTAVYYCH

VSSGVYNYWGQGTQVTVSSAAAYPYDVPDYGSHHHHHH;
or

3LIG9
(SEQ ID NO: 310)
QVQLQESGGGLVQPGGSLRLSCAASGFTFSSYGMSWVRQTPGKGPEWV

SAIDSGGGSTSYADSVKGRFTISRDNAKNTLYLQMNSLKPEDTAVYYC

AQGYYCSGYGCSDYWGQGTQVTVSSAAAYPYDVPDYGSHHHHHH;
or

3LIG18
(SEQ ID NO: 311)
QVQLQESGGGLVQPGGSLRLSCAASGFNLDPYAIAWFRQAPGKEREEV

SCISSSDVGTYYADSVKGRFTISRDNAKKTVYLQMNSLKPEDTAVYYC

ATDGYYYCSDYPHPLYWGQGTQVTVSSAAAYPYDVPDYGSHHHHHH;
or

3LIG20
(SEQ ID NO: 312)
QVQLQESGGGLVXAGGSLRLSCAASGRTFSISAMGWFRQAPGKEREFV

AAITWSGGSTSYTDSVKGRFTISRDNAKNTLYLQMNSLKPEDTAIYYC

AAMGRTNYGVIYDPNMYNYWGQGTQVTVSSAAAYPYDVPDYGSHHHHH

H;
or

3LIG28
(SEQ ID NO: 313)
QVQLQESGGGLVQPGGSLRLSCAASGFTLDYYAINWFRQAPGKEREEV

SCISSSDGSTYYADSVKGRFTISRDNAKNTVYLQMNSLKPEDTAVYYC

ATSGWRLCRPTDEYDYLYWGQGTQVTVSSAAAYPYDVPDYGSHHHHHH;
or

3LIG29
(SEQ ID NO: 314)
QVQLQESGGGLVQAGGSMRLSCAASGFTFSSYGMSWVRQTPGKGPEWV

SAIDSGGGSTSYADSVKGRFTISRDNAKNTLYLQMNSLKPEDTAVYYC

AQGYYCSGYGCSDYWGQGTQVTVSSAAAYPYDVPDYGSHHHHHH;
or

3LIG30
(SEQ ID NO: 315)
QVQLQESGGGTVQAGGSLRLSCAASGFTFNDYAMSWVRQAPGKGLEWV

SGIRSNGGYTNYADSVKGRFTISRDNAKNTLYLQMNSLKSEDTAVYYC

AQGYYCSGYGCYPGQGTQVTVSSAAAYPYDVPDYGSHHHHHH;
or

3LIG33
(SEQ ID NO: 316)
QVQLQESGGGLVQPGTSLRLSCAASGFTLDYYAIGWFRQAPGKEREEV

SCISSSDGSTYYADSVKGRFTISRDNAKNTVNLQMNSLKPEDTAVYYC

ATDGWSSCRHGINEYLYWGQGTQVTVSSAAAYPYDVPDYGSHHHHHH.

In various exemplary embodiments, the PD-L1 binding agent comprises an amino acid sequence selected from any one of the above sequences without the terminal histidine tag sequence (i.e., HHHHHH; SEQ ID NO: 84).

In some embodiments, the PD-L1 binding agent comprises an amino acid sequence selected from SEQ ID Nos: 286-316 (provided above) without the HA tag (i.e., YPYDVPDYGS; SEQ ID NO: 85).

In some embodiments, the PD-L1 binding agent comprises an amino acid sequence selected from SEQ ID Nos: 286-316 (provided above) without the AAA linker.

In some embodiments, the PD-L1 binding agent comprises an amino acid sequence selected from SEQ ID Nos: 286-316 (provided above) without the AAA linker, HA tag, and terminal histidine tag sequence (i.e., AAAYPYDVPDYGSHHHHHH; SEQ ID NO: 86).

In various embodiments, the present invention contemplates the use of any natural or synthetic analogs, mutants, variants, alleles, homologs and orthologs (herein collectively referred to as "analogs") of the PD-L1 binding agent of the invention as described herein. In various embodiments, the amino acid sequence of the PD-L1 binding agent further includes an amino acid analog, an amino acid derivative, or other non-classical amino acids.

In various embodiments, the PD-1 or PD-L1 binding agent comprises a targeting moiety comprising a sequence that is at least 60% identical to any one of the sequences disclosed herein. For example, the PD-1 or PD-L1 binding agent may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In various embodiments, the PD-1 or PD-L1 binding agent comprises a targeting moiety comprising an amino acid sequence having one or more amino acid mutations with respect to any one of the sequences disclosed herein. In various embodiments, the PD-1 or PD-L1 binding agent comprises a targeting moiety comprising an amino acid sequence having one, or two, or three, or four, or five, or six, or seen, or eight, or nine, or ten, or fifteen, or twenty amino acid mutations with respect to any one of the sequences disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids. Exemplary non-classical amino acids include, but are not limited to, selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general.

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the present PD-1 or PD-L1 binding agent's capability to specifically bind to PD-1 or PD-L1. In various embodiments, the mutations do not substantially reduce the present PD-1 or PD-L1 binding agent's capability to specifically bind to PD-1 or PD-L1 and without functionally modulating (e.g., partially or fully neutralizing) PD-1 or PD-L1.

In various embodiments, the binding affinity of the PD-1 or PD-L1 binding agent of the invention for the full-length and/or mature forms and/or isoforms and/or splice variants and/or fragments and/or monomeric and/or dimeric forms and/or any other naturally occurring or synthetic analogs, variants, or mutants (including monomeric and/or dimeric forms) of human PD-1 or PD-L1 may be described by the equilibrium dissociation constant ($K_D$). In various embodiments, the PD-1 or PD-L1 binding agent comprises a targeting moiety that binds to the full-length and/or mature forms and/or isoforms and/or splice variants and/or fragments and/or any other naturally occurring or synthetic analogs, variants, or mutants (including monomeric and/or dimeric forms) of human PD-1 or PD-L1 with a $K_D$ of less than about 1 uM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In various embodiments, the PD-1 or PD-L1 binding agent comprises a targeting moiety that binds but does not functionally modulate (e.g., partially or fully neutralize) the antigen of interest, i.e., PD-1 or PD-L1. For instance, in various embodiments, the targeting moiety of the PD-1 or PD-L1 binding agent simply targets the antigen but does not substantially functionally modulate (e.g. partially or fully inhibit, reduce or neutralize) a biological effect that the antigen has. In various embodiments, the targeting moiety of the PD-1 or PD-L1 binding agent binds an epitope that is physically separate from an antigen site that is important for its biological activity (e.g. an antigen's active site).

In various embodiments, these binding agents bind to, and functionally modulate (e.g. partially or fully neutralize) PD-1 or PD-L1.

Therapeutic Agents Comprising the Present PD-1 or PD-L1 Binding Agents

Chimeras and Fusions with Signaling Agents

In various embodiments, the PD-1 or PD-L1 binding agent of the invention is part of a chimera or fusion with one or more signaling agents. Accordingly, the present invention provides for chimeric or fusion proteins that include, for example, a targeting moiety against PD-1 or PD-L1 and one or more signaling agents.

In various embodiments, the signaling agent is modified to have reduced affinity or activity for one or more of its receptors, which allows for attenuation of activity (inclusive of agonism or antagonism) and/or prevents non-specific signaling or undesirable sequestration of the chimeric or fusion protein. In various embodiments, the signaling agent is antagonistic in its wild type form and bears one or more mutations that attenuate its antagonistic activity.

In various embodiments, the signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

Accordingly, in various embodiments, the signaling agent is a modified (e.g. mutant) form of the signaling agent having one or more modifications (e.g. mutations). In various embodiments, the mutations allow for the modified signaling agent to have one or more of attenuated activity such as one or more of reduced binding affinity, reduced endogenous activity, and reduced specific bioactivity relative to unmutated, i.e. the wild type form of the signaling agent (e.g. comparing the same signaling agent in a wild type form versus a modified (e.g. mutant) form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to have improved safety, e.g. reduced systemic toxicity, reduced side effects, and reduced off-target effects relative to unmutated, i.e. wild type, signaling agent (e.g. comparing the same signaling agent in a wild type form versus a modified (e.g. mutant) form).

As described herein, the agent may have improved safety due to one of more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In various embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or mutations that reduce its binding affinity or activity for one or more of its receptors or that substantially reduce or ablate binding affinity or activity for one or more of its receptors.

In some embodiments, the reduced affinity or activity at the receptor is restorable by attachment with one or more of the targeting moieties as described herein (e.g., targeting moiety against PD-1 or PD-L1). In other embodiments, the reduced affinity or activity at the receptor is not substantially restorable by the activity of one or more of the targeting moieties.

In various embodiments, the chimeric proteins of the present invention reduce off-target effects because their signaling agents have mutations that weaken or ablate binding affinity or activity at a receptor. In various embodiments, this reduction in side effects is observed relative with, for example, the wild type signaling agents. In various embodiments, the signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety (e.g., a targeting moiety against PD-1 or PD-L1 or any other targeting moiety described herein). In some embodiments, the substantial reduction or ablation of binding or activity is restorable with a targeting moiety. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In various embodiments, the modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the immumodulating agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the modified signaling agent has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent.

In some embodiments, the modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the signaling agent is an immune-modulating agent, e.g. one or more of an interleukin, interferon, and tumor necrosis factor.

In some embodiments, the signaling agent is an interleukin or a modified interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferens: A Practical Approach*, Clemens et al., eds, IRL Press, Washington, D.C. 1987, pp. 221-225; and Orencole & Dinarello (1989) Cytokine 1, 14-20.

In some embodiments, the signaling agent is an interferon or a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In some embodiments, the signaling agent is a tumor necrosis factor (TNF) or a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

The amino acid sequences of the wild type signaling agents described herein are well known in the art. Accordingly, in various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions, as described elsewhere herein. In various embodiments, the substitutions may also include non-classical amino acids as described elsewhere herein.

As described herein, the modified signaling agents bear mutations that affect affinity and/or activity at one or more receptors. In various embodiments, there is reduced affinity and/or activity at a therapeutic receptor, e.g. a receptor through which a desired therapeutic effect is mediated (e.g. agonism or antagonism). In various embodiments, the modified signaling agents bear mutations that substantially reduce or ablate affinity and/or activity at a receptor, e.g. a receptor through which a desired therapeutic effect is not mediated (e.g. as the result of promiscuity of binding). The receptors of any modified signaling agents, e.g. one of the cytokines, growth factors, and hormones as described herein, are known in the art.

Illustrative mutations which provide reduced affinity and/or activity (e.g. agonistic) at a receptor are found in WO 2013/107791 and PCT/EP2017/061544 (e.g. with regard to interferons), WO 2015/007542 (e.g. with regard to interleukins), and WO 2015/007903 (e.g. with regard to TNF), the entire contents of each of which are hereby incorporated by reference. Illustrative mutations which provide reduced affinity and/or activity (e.g. antagonistic) at a therapeutic receptor are found in WO 2015/007520, the entire contents of which are hereby incorporated by reference.

In some embodiments, the modified signaling agent comprises one or more mutations that cause the signaling agent to have reduced affinity and/or activity for a type I cytokine receptor, a type II cytokine receptor, a chemokine receptor, a receptor in the Tumor Necrosis Factor Receptor (TNFR) superfamily, TGF-beta Receptors, a receptor in the immunoglobulin (Ig) superfamily, and/or a receptor in the tyrosine kinase superfamily.

In various embodiments, the receptor for the signaling agent is a Type I cytokine receptor. Type I cytokine receptors are known in the art and include, but are not limited to receptors for IL2 (beta-subunit), IL3, IL4, IL5, IL6, IL7, IL9, IL11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In various embodiments, the receptor for the signaling agent is a Type II cytokine receptor. Type II cytokine receptors are multimeric receptors composed of heterologous subunits, and are receptors mainly for interferons. This family of receptors includes, but is not limited to, receptors for interferon-α, interferon-β and interferon-γ, IL10, IL22, and tissue factor. Illustrative type II cytokine receptors include, but are not limited to, IFN-α receptor (e.g. IFNAR1 and IFNAR2), IFN-β receptor, IFN-γ receptor (e.g. IFNGR1 and IFNGR2), and type II IL receptors.

In various embodiments, the receptor for the signaling agent is a G protein-coupled receptor. Chemokine receptors are G protein-coupled receptors with seven transmembrane structure and coupled to G-protein for signal transduction. Chemokine receptors include, but are not limited to, CC chemokine receptors, CXC chemokine receptors, CX3C chemokine receptors, and XC chemokine receptor (XCR1). Exemplary chemokine receptors include, but are not limited to, CCR1, CCR2, CCR3, CCR4, CCR5, CCR6, CCR7, CCR8, CCR9, CCR10, CXCR1, CXCR2, CXCR3, CXCR3B, CXCR4, CXCR5, CSCR6, CXCR7, XCR1, and CX3CR1.

In various embodiments, the receptor for the signaling agent is a TNFR family member. Tumor necrosis factor receptor (TN FR) family members share a cysteine-rich domain (CRD) formed of three disulfide bonds surrounding a core motif of CXXCXXC creating an elongated molecule. Exemplary tumor necrosis factor receptor family members include: CDI 20a (TNFRSFIA), CD 120b (TNFRSFIB), Lymphotoxin beta receptor (LTBR, TNFRSF3), CD 134 (TNFRSF4), CD40 (CD40, TNFRSF5), FAS (FAS, TNFRSF6), TNFRSF6B (TNFRSF6B), CD27 (CD27, TNFRSF7), CD30 (TNFRSF8), CD137 (TNFRSF9), TNFRSF10A (TNFRSF10A), TNFRSF10B, (TNFRSF10B), TNFRSF10C (TNFRSF10C), TNFRSF10D (TNFRSF10D), RANK (TNFRSF11A), Osteoprotegerin (TNFRSF11B), TNFRSF12A (TNFRSF12A), TNFRSF13B (TNFRSF13B), TNFRSF13C (TNFRSF13C), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25). In an embodiment, the TNFR family member is CD120a (TNFRSF1A) or TNF-R1. In another embodiment, the TNFR family member is CD 120b (TNFRSFIB) or TNF-R2.

In various embodiments, the receptor for the signaling agent is a TGF-beta receptor. TGF-beta receptors are single pass serine/threonine kinase receptors. TGF-beta receptors include, but are not limited to, TGFBR1, TGFBR2, and TGFBR3.

In various embodiments, the receptor for the signaling agent is an Ig superfamily receptor. Receptors in the immunoglobulin (Ig) superfamily share structural homology with immunoglobulins. Receptors in the Ig superfamily include, but are not limited to, interleukin-1 receptors, CSF-1R, PDGFR (e.g. PDGFRA and PDGFRB), and SCFR.

In various embodiments, the receptor for the signaling agent is a tyrosine kinase superfamily receptor. Receptors in the tyrosine kinase superfamily are well known in the art. There are about 58 known receptor tyrosine kinases (RTKs), grouped into 20 subfamilies. Receptors in the tyrosine kinase superfamily include, but are not limited to, FGF receptors and their various isoforms such as FGFR1, FGFR2, FGFR3, FGFR4, and FGFR5.

In an embodiment, the modified signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon α are known to the person skilled in the art. In an illustrative embodiment, the modified signaling agent is the allelic form IFN-α2a having the amino acid sequence of SEQ ID NO: 317.

In an illustrative embodiment, the modified signaling agent is the allelic form IFN-α2b having the amino acid sequence of (which differs from IFN-α2a at amino acid position 23) SEQ ID NO: 318.

In some embodiments, said IFN-α2 mutant (IFN-α2a or IFN-α2b) is mutated at one or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/ 107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wild type IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885.

In an embodiment, the modified signaling agent is interferon β. In such embodiments, the modified interferon 3 agent has reduced affinity and/or activity for the IFN-α/β receptor (IFNAR), i.e., IFNAR1 and/or IFNAR2 chains. In some embodiments, the modified interferon 3 agent has substantially reduced or ablated affinity and/or activity for the IFN-α/β receptor (IFNAR), i.e., IFNAR1 and/or IFNAR2 chains.

In an illustrative embodiment, the modified signaling agent is IFN-β. In various embodiments, the IFN-β encompasses functional derivatives, analogs, precursors, isoforms, splice variants, or fragments of IFN-β. In various embodiments, the IFN-β encompasses IFN-β derived from any species. In an embodiment, the chimeric protein comprises a modified version of mouse IFN-β. In another embodiment, the chimeric protein comprises a modified version of human IFN-β. Human IFN-β is a polypeptide with a molecular weight of about 22 kDa comprising 166 amino acid residues. The amino acid sequence of human IFN-β is SEQ ID NO: 319.

In some embodiments, the human IFN-β is IFN-β-1a which is a glycosylated form of human IFN-β. In some embodiments, the human IFN-β is IFN-β-1b which is a non-glycosylated form of human IFN-β that has a Met-1 deletion and a Cys-17 to Ser mutation.

In various embodiments, the modified IFN-β has one or more mutations that reduce its binding to or its affinity for the IFNAR1 subunit of IFNAR. In one embodiment, the modified IFN-β has reduced affinity and/or activity at IFNAR1. In various embodiments, the modified IFN-β is human IFN-β and has one or more mutations at positions F67, R71, L88, Y92, I95, N96, K123, and R124. In some embodiments, the one or more mutations are substitutions selected from F67G, F67S, R71A, L88G, L88S, Y92G, Y92S, I95A, N96G, K123G, and R124G. In an embodiment, the modified IFN-β comprises the F67G mutation. In an embodiment, the modified IFN-β comprises the K123G mutation. In an embodiment, the modified IFN-β comprises the F67G and R71A mutations. In an embodiment, the modified IFN-β comprises the L88G and Y92G mutations. In an embodiment, the modified IFN-β comprises the Y92G, I95A, and N96G mutations. In an embodiment, the modified IFN-β comprises the K123G and R124G mutations. In an embodiment, the modified IFN-β comprises the F67G, L88G, and Y92G mutations. In an embodiment, the modified IFN-β comprises the F67S, L88S, and Y92S mutations.

In some embodiments, the modified IFN-β has one or more mutations that reduce its binding to or its affinity for the IFNAR2 subunit of IFNAR. In one embodiment, the modified IFN-β has reduced affinity and/or activity at IFNAR2. In various embodiments, the modified IFN-β is human IFN-β and has one or more mutations at positions W22, R27, L32, R35, V148, L151, R152, and Y155. In some embodiments, the one or more mutations are substitutions selected from W22G, R27G, L32A, L32G, R35A, R35G, V148G, L151G, R152A, R152G, and Y155G. In an embodiment, the modified IFN-β comprises the W22G mutation. In an embodiment, the modified IFN-β comprises the L32A mutation. In an embodiment, the modified IFN-β comprises the L32G mutation. In an embodiment, the modified IFN-β comprises the R35A mutation. In an embodiment, the modified IFN-β comprises the R35G mutation. In an embodiment, the modified IFN-β comprises the V148G mutation. In an embodiment, the modified IFN-β comprises the R152A mutation. In an embodiment, the modified IFN-β comprises the R152G mutation. In an embodiment, the modified IFN-β comprises the Y155G mutation. In an embodiment, the modified IFN-β comprises the W22G and R27G mutations. In an embodiment, the modified IFN-β comprises the L32A and R35A mutation. In an embodiment, the modified IFN-β comprises the L151G and R152A mutations. In an embodiment, the modified IFN-β comprises the V148G and R152A mutations.

In some embodiments, the modified IFN-β has one or more of the following mutations: R35A, R35T, E42K, M62I, G78S, A141Y, A142T, E149K, and R152H. In some embodiments, the modified IFN-β has one or more of the following mutations: R35A, R35T, E42K, M62I, G78S, A141Y, A142T, E149K, and R152H in combination with C17S or C17A.

In some embodiments, the modified IFN-β has one or more of the following mutations: R35A, R35T, E42K, M62I, G78S, A141Y, A142T, E149K, and R152H in combination with any of the other IFN-β mutations described herein.

The crystal structure of human IFN-β is known and is described in Karpusas et al., (1998) PNAS, 94(22): 11813-11818. Specifically, the structure of human IFN-β has been shown to include five α-helices (i.e., A, B, C, D, and E) and four loop regions that connect these helices (i.e., AB, BC, CD, and DE loops). In various embodiments, the modified IFN-β has one or more mutations in the A, B, C, D, E helices and/or the AB, BC, CD, and DE loops which reduce its binding affinity or activity at a therapeutic receptor such as IFNAR. Exemplary mutations are described in WO2000/023114 and US20150011732, the entire contents of which are hereby incorporated by reference. In an exemplary embodiment, the modified IFN-β is human IFN-β comprising alanine substitutions at amino acid positions 15, 16, 18, 19, 22, and/or 23. In an exemplary embodiment, the modified IFN-β is human IFN-β comprising alanine substitutions at amino acid positions 28-30, 32, and 33. In an exemplary embodiment, the modified IFN-β is human IFN-β comprising alanine substitutions at amino acid positions 36, 37, 39, and 42. In an exemplary embodiment, the modified IFN-β is human IFN-β comprising alanine substitutions at amino acid positions 64 and 67 and a serine substitution at position 68. In an exemplary embodiment, the modified IFN-β is human IFN-β comprising alanine substitutions at amino acid positions 71-73. In an exemplary embodiment, the modified IFN-β is human IFN-β comprising alanine substitutions at amino acid positions 92, 96, 99, and 100. In an exemplary embodiment, the modified IFN-β is human IFN-β comprising alanine substitutions at amino acid positions 128, 130, 131, and 134. In an exemplary embodiment, the modified IFN-β is human IFN-β comprising alanine substitutions at amino acid positions 149, 153, 156, and 159. In some embodiments, the mutant IFN-β comprises SEQ ID NO: 319 and a mutation at W22, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at R27, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at W22, the mutation being an aliphatic hydrophobic residue selected from glycine (G), alanine (A), leucine (L), isoleucine (I), methionine (M), and valine (V) and a mutation at R27, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L32, the mutation being an aliphatic hydrophobic residue selected from glycine (G), alanine (A), isoleucine (I), methionine (M), and valine (V).

In some embodiments, the mutant IFN-β comprises SEQ ID NO: 319 and a mutation at R35, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L32, the mutation being an aliphatic hydrophobic residue selected from glycine (G), alanine (A), isoleucine (I), methionine (M), and valine (V) and a mutation at R35, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at F67, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at R71, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at F67, the mutation being an aliphatic hydrophobic residue selected from glycine (G), alanine (A), leucine (L), isoleucine (I), methionine (M), and valine (V) and a mutation at R71, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L88, the mutation being an aliphatic hydrophobic residue selected from glycine (G), alanine (A), isoleucine (I), methionine (M), and valine (V).

In some embodiments, the mutant IFN-β comprises SEQ ID NO: 319 and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at F67, the mutation being an aliphatic hydrophobic residue selected from glycine (G), alanine (A), leucine (L), isoleucine (I), methionine (M), and valine (V) and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at 195, the mutation being an aliphatic hydrophobic residue selected from glycine (G), alanine (A), leucine (L), methionine (M), and valine (V) and a mutation at Y92, the mutation being an aliphatic hydrophobic residue selected from glycine (G), alanine (A), leucine (L), isoleucine (1), methionine (M), and valine (V).

In some embodiments, the mutant IFN-β comprises SEQ ID NO: 319 and a mutation at N96, the mutation being an aliphatic hydrophobic residue selected from glycine (G), alanine (A), leucine (L), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at Y92, the mutation being an aliphatic hydrophobic residue selected from glycine (G), alanine (A), leucine (L), isoleucine (I), methionine (M), and valine (V) and a mutation at 195, the mutation being an aliphatic hydrophobic residue selected from glycine (G), alanine (A), leucine (L), methionine (M), and valine (V) and a mutation at N96, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at K123, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at R124, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 188 and a mutation at K123, the mutation being an aliphatic hydrophobic residue selected from glycine (G), alanine (A), leucine (L), isoleucine (I), methionine (M), and valine (V) and a mutation at R124, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L151, the mutation being an aliphatic hydrophobic residue selected from glycine (G), alanine (A), isoleucine (I), methionine (M), and valine (V).

In some embodiments, the mutant IFN-β comprises SEQ ID NO: 319 and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at L151, the mutation being an aliphatic hydrophobic residue selected from glycine (G), alanine (A), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at V148, the mutation being an aliphatic hydrophobic residue selected from glycine (G), alanine (A), leucine (L), isoleucine (I), and methionine (M).

In some embodiments, the mutant IFN-β comprises SEQ ID NO: 319 and a mutation at V148, the mutation being an aliphatic hydrophobic residue selected from glycine (G), alanine (A), leucine (L), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 319 and a mutation at Y155, the mutation being an aliphatic hydrophobic residue selected from glycine (G), alanine (A), leucine (L), isoleucine (I), methionine (M), and valine (V).

In some embodiments, the present invention relates to a chimeric protein comprising: (a) a modified IFN-β, having the amino acid sequence of SEQ ID NO: 319 and a mutation at position W22, wherein the mutation is an aliphatic hydrophobic residue; and (b) one or more targeting moieties, said targeting moieties comprising recognition domains which specifically bind to antigens or receptors of interest (e.g., PD-1 or PD-L1), the modified IFN-β and the one or more targeting moieties are optionally connected with one or more linkers. In various embodiments the mutation at position W22 is aliphatic hydrophobic residue is selected from G, A, L, I, M, and V. In various embodiments the mutation at position W22 is G.

Additional exemplary IFN-β mutants are provided in PCT/EP2017/061544, the entire disclosure of which is incorporated by reference herein.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

IFN-γ is the only member of the type II class of interferons. IFN-γ is produced predominantly by natural killer (NK) and natural killer T (NKT) cells as part of the innate immune response. IFN-γ is also produced by CD4 Th1 and CD8 cytotoxic T lymphocyte (CTL) effector T cells, macrophages, dendritic cells, and B cells. Activated IFN-γ forms a dimer which acts through a heterodimeric receptor (i.e., IFN-γ receptor or IFN-γR) composed of IFN-γ receptor 1 and IFN-γ receptor 2 subunits. IFN-γ receptor 1 is the major ligand-binding subunit, while IFN-γ receptor 2 is necessary for signal transduction and also increases the affinity of IFN-γ receptor 1 for its ligand. Binding of the IFN-γ dimer to the receptor activates the JAK-STAT signaling pathway to elicit various biological effects.

In various embodiments, the modified signaling agent comprises a modified version of IFN-γ as a signaling agent. In various embodiments, the IFN-γ encompasses functional derivatives, analogs, precursors, isoforms, splice variants, or fragments of IFN-γ. In various embodiments, the IFN-γ encompasses IFN-γ derived from any species. In an embodiment, the modified signaling agent comprises a modified version of mouse IFN-γ. In another embodiment, the modified signaling agent comprises a modified version of human IFN-γ.

Human IFN-γ is a polypeptide comprising 166 amino acid residues. In an embodiment, the human IFN-γ has the amino acid sequence of SEQ ID NO: 320.

As used herein, human IFN-γ may also refer to mature human IFN-γ without the N-terminal signal peptide. In this embodiment, the mature human IFN-γ comprises 143 amino acids and has the amino acid sequence of SEQ ID NO: 321.

In some embodiments, the human IFN-γ is a glycosylated form of human IFN-γ. In some embodiments, the human IFN-γ is a non-glycosylated form of human IFN-γ.

The sequences of IFN-γ are known in the art. In various embodiments the modified IFN-γ comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of IFN-γ (e.g., about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In some embodiments the modified IFN-γ comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with human IFN-γ having an amino acid sequence of SEQ ID NO: 320 (e.g., about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In some embodiments the modified IFN-γ comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with human IFN-γ having an amino acid sequence of SEQ ID NO: 321 (e.g., about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified IFN-γ comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, 3-alanine, fluoro-amino acids, designer amino acids such as 13 methyl amino acids, C α-methyl amino acids, N α-methyl amino acids, and amino acid analogs in general).

In various embodiments, the IFN-γ is modified to have one or more mutations. In some embodiments, the mutations allow for the modified IFN-γ to have one or more of attenuated activity such as one or more of reduced binding affinity, reduced endogenous activity, and reduced specific bioactivity relative to unmutated, e.g., the wild type form of IFN-γ. For instance, the one or more of attenuated activity such as reduced binding affinity, reduced endogenous activity, and reduced specific bioactivity relative to unmutated, e.g., the wild type form of IFN-γ may be at a therapeutic receptor such as the IFN-γ receptor. Consequentially, in various embodiments, the mutations allow for the modified soluble agent to have reduced systemic toxicity, reduced side effects, and reduced off-target effects relative to unmutated, e.g., the wild type form of IFN-γ.

In various embodiments, the IFN-γ is modified to have a mutation that reduces its binding affinity and/or activity at a therapeutic receptor such as the IFN-γ receptor comprising the IFN-γ receptor 1 and IFN-γ receptor 2 subunits. In some embodiments, the activity provided by the wild type IFN-γ is agonism at the therapeutic receptor (e.g., activation of a cellular effect at a site of therapy). For example, the wild type IFN-γ may activate the therapeutic receptor. In such embodiments, the mutation results in the modified IFN-γ to have reduced activating activity at the therapeutic receptor.

In some embodiments, the reduced affinity and/or activity at the therapeutic receptor (e.g., IFN-γ receptor) is restorable by attachment with a targeting moiety. In other embodiments, the reduced affinity and/or activity at the therapeutic receptor is not substantially restorable by attachment with the targeting moiety. In various embodiments, the therapeutic chimeric proteins of the present invention reduce off-target effects because the IFN-γ has mutations that weaken binding affinity and/or activity at a therapeutic receptor. In various embodiments, this reduces side effects observed with, for example, the wild type IFN-γ. In various embodiments, the modified IFN-γ is substantially inactive en route to the site of therapeutic activity and has its effect substantially on specifically targeted cell types which greatly reduces undesired side effects.

In various embodiments, the modified IFN-γ has one or more mutations that cause the IFN-γ to have attenuated or reduced affinity and/or activity, e.g., binding (e.g., KD) and/or activation (measurable as, for example, KA and/or EC50) for one or more therapeutic receptors (e.g., IFN-γ receptor). In various embodiments, the reduced affinity and/or activity at the therapeutic receptor allows for attenuation of activity and/or signaling from the therapeutic receptor.

In various embodiments, the modified IFN-γ has one or more mutations that reduce its binding to or its affinity for and/or biological activity for the IFN-γ receptor 1 subunit. In one embodiment, the modified IFN-γ has reduced affinity and/or activity at the IFN-γ receptor 1 subunit. In various embodiments, the modified IFN-γ is human IFN-γ that has one or more mutations at amino acid residues involved with binding to the IFN-γ receptor 1 subunit. In some embodiments, the modified IFN-γ is human IFN-γ that has one or more mutations at amino acids located at the interface with the IFN-γ receptor 1 subunit. In various embodiments, the one or more mutations are at amino acids selected from, but not limited to Q1, V5, E9, K12, H19, S20, V22, A23, D24, N25, G26, T27, L30, K108, H111, E112, I114, Q115, A118, E119, and K125 (each with respect SEQ ID NO: 321, which is a wild type human IFN-γ and which lacks its N-terminal signal sequence). In some embodiments, the one or more mutations are substitutions selected from V5E, S20E, V22A, A23G, A23F, D24G, G26Q, H111A, H111D, I114A, Q115A, and A118G (each with respect SEQ ID NO: 321). In embodiments, the one or more mutations are substitutions selected from V22A, A23G, D24G, H111A, H111D, I114A, Q115A, and A118G.

In an embodiment, the modified IFN-γ comprises the mutations A23G and D24G. In another embodiment, the modified IFN-γ comprises the mutations I114A and A118G. In a further embodiment, the modified IFN-γ comprises the mutations V5E, S20E, A23F, and G26Q.

In various embodiments, the modified IFN-γ has one or more of the following mutations: deletion of residue A23, deletion of residue D24, an S201 substitution, an A23V substitution, a D21K substitution and a D24A substitution.

In some embodiments, the modified IFN-γ has one or more mutations that reduce its binding to or its affinity and/or biological activity for the IFN-γ receptor 2 subunit.

In some embodiments, the modified IFN-γ has one or more mutations that reduce its binding to or its affinity and/or biological activity for both IFN-γ receptor 1 and IFN-γ receptor 2 subunits.

In some embodiments, the modified IFN-γ has one or more mutations that reduce its binding to or its affinity and/or biological activity for IFN-γ receptor 1 and one or more mutations that substantially reduce or ablate binding to or its affinity and/or biological activity for IFN-γ receptor 2. In some embodiments, chimeric proteins with such modified IFN-γ can provide target-selective IFN-γ receptor 1 activity (e.g., IFN-γ receptor 1 activity is restorable via targeting through the targeting moiety).

In some embodiments, the modified IFN-γ has one or more mutations that reduce its binding to or its affinity and/or biological activity for IFN-γ receptor 1 and one or more mutations that reduce its binding to or its affinity and/or biological activity for IFN-γ receptor 1. In some embodiments, chimeric proteins with such modified IFN-γ can provide target-selective IFN-γ receptor 1 and/or IFN-γ receptor 1 activity (e.g., IFN-γ receptor 1 and IFN-γ receptor 2 activities are restorable via targeting through the targeting moiety).

In various embodiments, the modified IFN-γ is truncated at the C-terminus. In some embodiments, the modified IFN-γ is mature IFN-γ comprising the amino acid sequence of SEQ ID NO: 321 with deletions of the C-terminal terminus. In such embodiments, the mature IFN-γ may comprise a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In an embodiment, the modified IFN-γ is mature IFN-γ comprising the amino acid sequence of SEQ ID NO: 321 with C-terminal deletions of 5 amino acids. In an embodiment, the modified IFN-γ is mature IFN-γ comprising the amino acid sequence of SEQ ID NO: 321 with C-terminal deletions of 7 amino acids. In an embodiment, the modified IFN-γ is mature IFN-γ comprising the amino acid sequence of SEQ ID NO: 321 with C-terminal deletions of 14 amino acids. In an embodiment, the modified IFN-γ is mature IFN-γ comprising the amino acid sequence of SEQ ID NO: 321 with C-terminal deletions of 15 amino acids. In an embodiment, the modified IFN-γ is mature IFN-γ comprising the amino acid sequence of SEQ ID NO: 321 with C-terminal deletions of 16 amino acids. Additional modified IFN-γ with C-terminal truncations that may be utilized in the present invention is described in Haelewyn et al., Biochem. J. (1997), 324:591-595 and Lundell et al., Protein Eng. (1991) 4:335-341, the entire contents are hereby incorporated by reference In various embodiments, the modified IFN-γ is a single chain IFN-γ as described, for example, in Randal et al. (2001) Structure 9:155-163 and Randal et al. (1998) Protein Sci. 7:1057-1060, the entire contents are hereby incorporated by reference. In some embodiments, the single chain IFN-γ comprises a first IFN-γ chain linked at its C-terminus to the N-terminus of a second IFN-γ chain. In various embodiments, the first and second IFN-γ chains are linked by a linker, as described elsewhere herein.

In some embodiments, the first IFN-γ chain comprises a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In an embodiment, the first IFN-γ chain comprises a C-terminal truncation of about 24 amino acid residues. In some embodiments, the second IFN-γ chain comprises an N-terminal truncation of at least about 1, about 2, about 3, about 4, or about 5 amino acid residues. In an embodiment, the second IFN-γ chain comprises an N-terminal truncation of about 3 amino acid residues. In some embodiments, the second IFN-γ chain comprises a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In various embodiments, the first and/or second IFN-γ chains comprise one or more amino acid mutations at Q1, V5, E9, K12, H19, S20, V22, A23, D24, N25, G26, T27, L30, K108, H111, E112, I114, Q115, A118, E119, and K125, as described elsewhere herein. In various embodiments, the first and/or second IFN-γ chains comprise one or more substitutions selected from VSE, S20E, V22A, A23G, A23F, D24G, G26Q, H111A, H111D, I114A, Q115A, and A118G. In various embodiments, the first and/or second IFN-γ chains comprise one or more substitutions selected from V22A, A23G, D24G, H111A, H111D, I114A, Q115A, and A118G. In various embodiments, the first and/or second IFN-γ chains comprise the A23G and the D24G substitution. In various embodiments, the first and/or second IFN-γ chains comprise the I114A and the A118G substitution. In another embodiment, the mutations are VSE, S20E, A23F, and G26Q.

In various embodiments, a first and/or second IFN-γ chain comprises one or more substitutions as disclosed herein and the first and/or second IFN-γ chain comprises a C-terminal truncation as disclosed herein.

In various embodiments, a first and/or second IFN-γ chain comprises one or more substitutions as disclosed herein and a C-terminal truncation as disclosed herein.

The crystal structure of human IFN-γ is known and is described in, for example, Ealick et al., (1991) Science, 252: 698-702. Specifically, the structure of human IFN-γ has been shown to include a core of six α-helices and an extended unfolded sequence in the C-terminal region. In various embodiments, the modified IFN-γ has one or more mutations in the one or more helices which reduce its binding affinity and/or biological activity at a therapeutic receptor (e.g., IFN-γ receptor).

In various embodiments, the modified IFN-γ has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity and/or biological activity for the therapeutic receptor (e.g., IFN-γ receptor or any one of its IFN-γ receptor 1 and IFN-γ receptor 2 subunits) relative to the wild type IFN-γ. In some embodiments, the binding affinity and/or biological activity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type IFN-γ.

In various embodiments, the modified IFN-γ comprises one or more mutations that reduce the endogenous activity of the IFN-γ to about 75%, or about 70%, or about 60%, or about 50%, or about 40%, or about 30%, or about 25%, or about 20%, or about 10%, or about 5%, or about 3%, or about 1%, e.g., relative to the wild type IFN-γ.

In some embodiments, the modified IFN-γ comprises one or more mutations that cause the modified IFN-γ to have reduced affinity and/or biological activity for a receptor. In some embodiments, the modified IFN-γ's binding affinity and/or biological activity for a receptor is lower than the binding affinity and/or biological activity of the targeting moiety for its receptor. In some embodiments, this binding affinity and/or biological activity differential is between the modified IFN-γ/receptor and targeting moiety/receptor on the same cell. In some embodiments, this binding affinity and/or biological activity, differential allows for the modified IFN-γ to have localized, on-target effects and to minimize off-target effects that underlie side effects that are observed with wild type IFN-γ. In some embodiments, this binding affinity and/or biological activity is at least about 2-fold, or at least about 5-fold, or at least about 10-fold, or at least about 15-fold lower, or at least about 25-fold, or at least about 50-fold lower, or at least about 100-fold, or at least about 150-fold less.

Receptor binding activity may be measured using methods known in the art. For example, affinity and/or binding activity may be assessed by Scatchard plot analysis and computer-fitting of binding data (e.g., Scatchard, 1949) or by reflectometric interference spectroscopy under flow through conditions, as described by Brecht et al. (1993), the entire contents of all of which are hereby incorporated by reference.

In some embodiments, the modified signaling agent is a consensus interferon. The consensus interferon is generated by scanning the sequences of several human non-allelic IFN-α subtypes and assigning the most frequently observed amino acid in each corresponding position. The consensus interferon differs from IFN-α2b at 20 out of 166 amino acids (88% homology), and comparison with IFN-β shows identity at over 30% of the amino acid positions. In various embodiments, the consensus interferon comprises the amino acid sequence of SEQ ID NO: 322.

In some embodiments, the consensus interferon comprises the amino acid sequence of SEQ ID NO: 323, which differs from the amino acid sequence of SEQ ID NO: 322 by one amino acid, i.e., SEQ ID NO: 323 lacks the initial methionine residue of SEQ ID NO: 322.

In various embodiments, the consensus interferon comprises a modified version of the consensus interferon, i.e., a consensus interferon variant, as a signaling agent. In various embodiments, the consensus interferon variant encompasses functional derivatives, analogs, precursors, isoforms, splice variants, or fragments of the consensus interferon.

In an embodiment, the consensus interferon variants are selected form the consensus interferon variants disclosed in U.S. Pat. Nos. 4,695,623, 4,897,471, 5,541,293, and 8,496,921, the entire contents of all of which are hereby incorporated by reference. For example, the consensus interferon variant may comprise the amino acid sequence of IFN-CON2 or IFN-CON3 as disclosed in U.S. Pat. Nos. 4,695,623, 4,897,471, and 5,541,293. In an embodiment, the consensus interferon variant comprises the amino acid sequence of IFN-CON2, SEQ ID NO: 324.

In an embodiment, the consensus interferon variant comprises the amino acid sequence of IFN-CONS, SEQ ID NO: 325.

In an embodiment, the consensus interferon variant comprises the amino acid sequence of any one of the variants disclosed in U.S. Pat. No. 8,496,921. For example, the consensus variant may comprise the amino acid sequence of SEQ ID NO: 326.

In another embodiment, the consensus interferon variant may comprise the amino acid sequence of SEQ ID NO: 327.

In some embodiments, the consensus interferon variant may be PEGylated, i.e., comprises a PEG moiety. In an embodiment, the consensus interferon variant may comprise a PEG moiety attached at the S156C position of SEQ ID NO: 327.

In some embodiments, the engineered interferon is a variant of human IFN-α2a, with an insertion of Asp at approximately position 41 in the sequence SEQ ID NO: 328 to yield SEQ ID NO: 329 (which resulted in a renumbering of the sequence relative to IFN-α2a sequence) and the following mutations of Arg23Lys, Leu26Pro, Glu53Gln, Thr54Ala, Pro56Ser, Asp86Glu, Ile104Thr, Gly106Glu, Thr110Glu, Lys117Asn, Arg125Lys, and Lys136Thr. All embodiments herein that describe consensus interferons apply equally to this engineered interferon.

In various embodiments, the consensus interferon variant comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, 3-alanine, fluoro-amino acids, designer amino acids such as 3 methyl amino acids, C α-methyl amino acids, N α-methyl amino acids, and amino acid analogs in general).

In various embodiments, the consensus interferon is modified to have one or more mutations. In some embodiments, the mutations allow for the consensus interferon variant to have one or more of attenuated activity such as one or more of reduced binding affinity, reduced endogenous activity, and reduced specific bioactivity relative to unmutated, e.g., the wild type form of the consensus interferon (e.g., the consensus interferon having an amino acid sequence of SEQ ID NO: 325 or 326). For instance, the one or more of attenuated activity such as reduced binding affinity, reduced endogenous activity, and reduced specific bioactivity relative to unmutated, e.g. the wild type form of the consensus interferon, may be at a therapeutic receptor such as IFNAR. Consequentially, in various embodiments, the mutations allow for the consensus interferon variant to have reduced systemic toxicity, reduced side effects, and reduced off-target effects relative to unmutated, e.g. the wild type form of the consensus interferon.

In various embodiments, the consensus interferon is modified to have a mutation that reduces its binding affinity or activity at a therapeutic receptor such as IFNAR. In some embodiments, the activity provided by the consensus interferon is agonism at the therapeutic receptor (e.g. activation of a cellular effect at a site of therapy). For example, the consensus interferon may activate the therapeutic receptor.

In such embodiments, the mutation results in the consensus interferon variant to have reduced activating activity at the therapeutic receptor.

In some embodiments, the reduced affinity or activity at the therapeutic receptor is restorable by attachment with a targeting moiety. In other embodiments, the reduced affinity or activity at the therapeutic receptor is not substantially restorable by attachment with the targeting moiety. In various embodiments, the therapeutic Fc-based chimeric proteins of the present invention reduce off-target effects because the consensus interferon variant has mutations that weaken binding affinity or activity at a therapeutic receptor. In various embodiments, this reduces side effects observed with, for example, the wild type consensus interferon. In various embodiments, the consensus interferon variant is substantially inactive en route to the site of therapeutic activity and has its effect substantially on specifically targeted cell types which greatly reduces undesired side effects.

In various embodiments, the consensus interferon variant has one or more mutations that cause the consensus interferon variant to have attenuated or reduced affinity, e.g. binding (e.g. KD) and/or activation (measurable as, for example, KA and/or EC50) for one or more therapeutic receptors. In various embodiments, the reduced affinity at the therapeutic receptor allows for attenuation of activity and/or signaling from the therapeutic receptor.

In various embodiments, the consensus interferon variant has one or more mutations that reduce its binding to or its affinity for the IFNAR1 subunit of IFNAR. In one embodiment, the consensus interferon variant has reduced affinity and/or activity at IFNAR1. In some embodiments, the consensus interferon variant has one or more mutations that reduce its binding to or its affinity for the IFNAR2 subunit of IFNAR. In some embodiments, the consensus interferon variant has one or more mutations that reduce its binding to or its affinity for both IFNAR1 and IFNAR2 subunits.

In some embodiments, the consensus interferon variant has one or more mutations that reduce its binding to or its affinity for IFNAR1 and one or more mutations that substantially reduce or ablate binding to or its affinity for IFNAR2. In some embodiments, Fc-based chimeric proteins with such consensus interferon variant can provide target-selective IFNAR1 activity (e.g. IFNAR1 activity is restorable via targeting through the targeting moiety, e.g., SIRPα).

In some embodiments, the consensus interferon variant has one or more mutations that reduce its binding to or its affinity for IFNAR2 and one or more mutations that substantially reduce or ablate binding to or its affinity for IFNAR1. In some embodiments, Fc-based chimeric proteins with such consensus interferon variant can provide target-selective IFNAR2 activity (e.g. IFNAR2 activity is restorable via targeting through the targeting moiety, e.g., SIRPα).

In some embodiments, the consensus interferon variant has one or more mutations that reduce its binding to or its affinity for IFNAR1 and one or more mutations that reduce its binding to or its affinity for IFNAR2. In some embodiments, Fc-based chimeric proteins with such consensus interferon variant can provide target-selective IFNAR1 and/or IFNAR2 activity (e.g. IFNAR1 and/IFNAR2 activity is restorable via targeting through the targeting moiety, e.g., SIRPα).

In some embodiments, the consensus interferon is modified to have a mutation at one or more amino acids at positions 145-155, such as amino acid positions 149, 150 and/or 154, with reference to SEQ ID NO: 326. In some embodiments, the consensus interferon is modified to have a mutation at one or more amino acids at positions 145-155, such as amino acid positions 149, 150 and/or 154, with reference to SEQ ID NO: 326, the substitutions optionally being hydrophobic and selected from alanine, valine, leucine, and isoleucine. In some embodiments, the consensus interferon mutant comprises one or more mutations selected from M149A, R150A, and L154A, and, with reference to SEQ ID NO: 323.

In an embodiment, the consensus interferon is modified to have a mutation at amino acid position 121 (i.e., K121), with reference to SEQ ID NO: 323. In an embodiment, the consensus interferon comprises a K121E mutation, with reference to SEQ ID NO: 323.

In some embodiments, the modified signaling agent is vascular endothelial growth factor (VEGF). VEGF is a potent growth factor that plays major roles in physiological but also pathological angiogenesis, regulates vascular permeability and can act as a growth factor on cells expressing VEGF receptors. Additional functions include, among others, stimulation of cell migration in macrophage lineage and endothelial cells. Several members of the VEGF family of growth factors exist, as well as at least three receptors (VEGFR-1, VEGFR-2, and VEGFR-3). Members of the VEGF family can bind and activate more than one VEGFR type. For example, VEGF-A binds VEGFR-1 and -2, while VEGF-C can bind VEGFR-2 and -3. VEGFR-1 and -2 activation regulates angiogenesis while VEGFR-3 activation is associated with lymphangiogenesis. The major pro-angiogenic signal is generated from activation of VEGFR-2. VEGFR-1 activation has been reported to be possibly associated with negative role in angiogenesis. It has also been reported that VEGFR-1 signaling is important for progression of tumors in vivo via bone marrow-derived VEGFR-1 positive cells (contributing to formation of premetastatic niche in the bone). Several therapies based on VEGF-A directed/neutralizing therapeutic antibodies have been developed, primarily for use in treatment of various human tumors relying on angiogenesis. These are not without side effects though. This may not be surprising considering that these operate as general, non-cell/tissue specific VEGF/VEGFR interaction inhibitors. Hence, it would be desirable to restrict VEGF (e.g. VEGF-A)/VEGFR-2 inhibition to specific target cells (e.g. tumor vasculature endothelial cells).

In some embodiments, the VEGF is VEGF-A, VEGF-B, VEFG-C, VEGF-D, or VEGF-E and isoforms thereof including the various isoforms of VEGF-A such as $VEGF_{121}$, $VEGF_{121}b$, $VEGF_{145}$, $VEGF_{165}$, $VEGF_{165}b$, $VEGF_{189}$, and $VEGF_{206}$. In some embodiments, the modified signaling agent has reduced affinity and/or activity for VEGFR-1 (Flt-1) and/or VEGFR-2 (KDR/Flk-1). In some embodiments, the modified signaling agent has substantially reduced or ablated affinity and/or activity for VEGFR-1 (Flt-1) and/or VEGFR-2 (KDR/Flk-1). In an embodiment, the modified signaling agent has reduced affinity and/or activity for VEGFR-2 (KDR/Flk-1) and/or substantially reduced or ablated affinity and/or activity for VEGFR-1 (Flt-1). Such an embodiment finds use, for example, in wound healing methods or treatment of ischmia-related diseases (without wishing to be bound by theory, mediated by VEGFR-2's effects on endothelial cell function and angiogenesis). In various embodiments, binding to VEGFR-1 (Flt-1), which is linked to cancers and pro-inflammatory activities, is avoided. In various embodiments, VEGFR-1 (Flt-1) acts a decoy receptor and therefore substantially reduces or ablates affinity at this receptor avoids sequestration of the therapeutic agent. In an embodiment, the modified signaling agent has substantially reduced or ablated affinity and/or activity for VEGFR-1 (Flt-1) and/or substantially reduced or ablated affinity and/or activity for VEGFR-2 (KDR/Flk-1). In some embodiments, the VEGF is VEGF-C or VEGF-D. In such embodiments, the modified signaling agent has reduced affinity and/or activity for VEGFR-3. Alternatively, the modified signaling agent has substantially reduced or ablated affinity and/or activity for VEGFR-3.

Proangiogenic therapies are also important in various diseases (e.g. ischemic heart disease, bleeding etc.), and include VEGF-based therapeutics. Activation of VEGFR-2 is proangiogenic (acting on endothelial cells). Activation of VEFGR-1 can cause stimulation of migration of inflammatory cells (including, for example, macrophages) and lead to inflammation associated hypervascular permeability. Activation of VEFGR-1 can also promote bone marrow associated tumor niche formation. Thus, VEGF based therapeutic selective for VEGFR-2 activation would be desirable in this case. In addition, cell specific targeting, e.g. to endothelial cells, would be desirable.

In some embodiments, the modified signaling agent has reduced affinity and/or activity (e.g. antagonistic) for VEGFR-2 and/or has substantially reduced or ablated affinity and/or activity for VEGFR-1. When targeted to tumor vasculature endothelial cells via a targeting moiety that binds to a tumor endothelial cell marker (e.g. PSMA and others), such construct inhibits VEGFR-2 activation specifically on such marker-positive cells, while not activating VEGFR-1 en route and on target cells (if activity ablated), thus eliminating induction of inflammatory responses, for example. This would provide a more selective and safe anti-angiogenic therapy for many tumor types as compared to VEGF-A neutralizing therapies.

In some embodiments, the modified signaling agent has reduced affinity and/or activity (e.g. agonistic) for VEGFR-2 and/or has substantially reduced or ablated affinity and/or activity for VEGFR-1. Through targeting to vascular endothelial cells, such construct, in some embodiments, promotes angiogenesis without causing VEGFR-1 associated induction of inflammatory responses. Hence, such a construct would have targeted proangiogenic effects with substantially reduced risk of side effects caused by systemic activation of VEGFR-2 as well as VEGR-1.

In an illustrative embodiment, the modified signaling agent is $VEGF_{165}$, which has the amino acid sequence of SEQ ID NO: 330.

In another illustrative embodiment, the modified signaling agent is $VEGF_{165b}$, which has the amino acid sequence of SEQ ID NO: 331.

In these embodiments, the modified signaling agent has a mutation at amino acid 183 (e.g., a substitution mutation at 183, e.g., 183K, 183R, or 183H). Without wishing to be bound by theory, it is believed that such mutations may result in reduced receptor binding affinity. See, for example, U.S. Pat. No. 9,078,860, the entire contents of which are hereby incorporated by reference.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of Treg cells via TNFR2, for example, thus further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes Treg cell activation and indirect suppression of cytotoxic T cells.

In some embodiments, the chimera causes the death of auto-reactive T cells, e.g. by activation of TNFR2 and/or avoidance of TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFkB pathway activity/signaling alterations. In some embodiments, the chimera causes the death of autoreactive T cells having lesions or modifications in the NFkB pathway, which underlie an imbalance of their cell death (apoptosis)/survival signaling properties and, optionally, altered susceptibility to certain death-inducing signals (e.g., TNFR2 activation).

In some embodiments, a TNFR2 based chimera has additional therapeutic applications in diseases, including various autoimmune diseases, heart disease, de-myelinating and neurodegenerative disorders, and infectious disease, among others.

In an embodiment, the wild type TNF-α has the amino acid sequence of SEQ ID NO: 332.

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified human TNF-α moiety has mutations at one or more amino acid positions R32, N34, Q67, H73, L75, T77, S86, Y87, V91, I97, T105, P106, A109, P113, Y115, E127, N137, D143, A145, and E146 as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from L29S, R32G, R32W, N34G, Q67G, H73G, L75G, L75A, L75S, T77A, S86G, S86T, Y87Q, Y87L, Y87A, Y87F, Y87H, V91G, V91A, I97A, I97Q, I97S, T105G, P106G, A109Y, P113G, Y115G, Y115A, E127G, N137G, D143N, A145G, A145R, A145T, E146D, E146K, and S147D. In an embodiment, the human TNF-α moiety has a mutation selected from Y87Q, Y87L, Y87A, Y87F, and Y87H. In another embodiment, the human TNF-α moiety has a mutation selected from I97A, I97Q, and I97S. In a further embodiment, the human TNF-α moiety has a mutation selected from Y115A and Y115G. In an embodiment, the human TNF-α moiety has an E146K mutation. In an embodiment, the human TNF-α moiety has an Y87H and an E146K mutation. In an embodiment, the human TNF-α moiety has an Y87H and an A145R mutation. In an embodiment, the human TNF-α moiety has a R32W and a S86T mutation. In an embodiment, the human TNF-α moiety has a R32W and an E146K mutation. In an embodiment, the human TNF-α moiety has a L29S and a R32W mutation. In an embodiment, the human TNF-α moiety has a D143N and an A145R mutation. In an embodiment, the human TNF-α moiety has a D143N and an A145R mutation. In an embodiment, the human TNF-α moiety has an A145T, an E146D, and a S147D mutation. In an embodiment, the human TNF-α moiety has an A145T and a S147D mutation.

In some embodiments, the modified TNF-α agent has one or more mutations selected from N39Y, S147Y, and Y87H, as described in WO2008/124086, the entire contents of which is hereby incorporated by reference.

In some embodiments, the modified human TNF-α moiety has mutations that provide receptor selectivity as described in PCT/IB2016/001668, the entire contents of which are hereby incorporated by reference. In some embodiments, the mutations to TNF are TNF-R1 selective. In some embodiments, the mutations to TNF which are TNF-R1 selective are at one or more of positions R32, S86, and E146. In some embodiments, the mutations to TNF which are TNF-R1 selective are one or more of R32W, S86T, and E146K. In some embodiments, the mutations to TNF which are TNF-R1 selective are one or more of R32W, R32W/S86T, R32W/E146K and E146K. In some embodiments, the mutations to TNF are TNF-R2 selective. In some embodiments, the mutations to TNF which are TNF-R2 selective are at one or more of positions A145, E146, and S147. In some embodiments, the mutations to TNF which are TNF-R2 selective are one or more of A145T, A145R, E146D, and S147D. In some embodiments, the mutations to TNF which are TNF-R2 selective are one or more of A145R, A145T/S147D, and A145T/E146D/S147D.

In an embodiment, the modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of SEQ ID NO: 333.

In such embodiments, the modified soluble agent may comprise mutations at one or more amino acids at positions 106-113, which produce a modified TNF-β with reduced receptor binding affinity to TNFR2. In an embodiment, the modified soluble agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified soluble agent has an insertion of about 1 to about 3 amino acids at positions 106-113.

In some embodiments, the modified agent is a TNF family member (e.g. TNF-alpha, TNF-beta) which can be a single chain trimeric version as described in WO 2015/007903, the entire contents of which are incorporated by reference.

In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of SEQ ID NO: 334.

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In some embodiments, the modified TRAIL agent may comprise one or more mutations that substantially reduce its affinity and/or activity for TRAIL-R1. In such embodiments, the modified TRAIL agent may specifically bind to TRIL-R2. Exemplary mutations include mutations at one or more amino acid positions Y189, R191, Q193, H264, I266, and D267. For example, the mutations may be one or more of Y189Q, R191K, Q193R, H264R, I266L and D267Q. In an embodiment, the modified TRAIL agent comprises the mutations Y189Q, R191K, Q193R, H264R, I266L and D267Q.

In some embodiments, the modified TRAIL agent may comprise one or more mutations that substantially reduce its affinity and/or activity for TRAIL-R2. In such embodiments, the modified TRAIL agent may specifically bind to TRIL-R1. Exemplary mutations include mutations at one or more amino acid positions G131, R149, S159, N199, K201, and S215. For example, the mutations may be one or more of G131R, R149I, S159R, N199R, K201H, and S215D. In an embodiment, the modified TRAIL agent comprises the mutations G131R, R149I, S159R, N199R, K201H, and S215D. Additional TRAIL mutations are described in, for example, Trebing et al., (2014) Cell Death and Disease, 5:e1035, the entire disclosure of which is hereby incorporated by reference.

In an embodiment, the modified signaling agent is TGFα. In such embodiments, the modified TGFα agent has reduced affinity and/or activity for the epidermal growth factor receptor (EGFR). In some embodiments, the modified TGFα agent has substantially reduced or ablated affinity and/or activity for the epidermal growth factor receptor (EGFR).

In an embodiment, the modified signaling agent is TGFβ. In such embodiments, the modified signaling agent has reduced affinity and/or activity for TGFBR1 and/or TGFBR2. In some embodiments, the modified signaling agent has substantially reduced or ablated affinity and/or activity for TGFBR1 and/or TGFBR2. In some embodiments, the modified signaling agent optionally has reduced or substantially reduced or ablated affinity and/or activity for TGFBR3 which, without wishing to be bound by theory, may act as a reservoir of ligand for TGF-beta receptors. In some embodiments, the TGFβ may favor TGFBR1 over TGFBR2 or TGFBR2 over TGFBR1. Similarly, LAP, without wishing to be bound by theory, may act as a reservoir of ligand for TGF-beta receptors. In some embodiments, the modified signaling agent has reduced affinity and/or activity for TGFBR1 and/or TGFBR2 and/or substantially reduced or ablated affinity and/or activity for Latency Associated Peptide (LAP). In some embodiments, such chimeras find use in Camurati-Engelmann disease, or other diseases associated with inappropriate TGFβ signaling.

In some embodiments, the modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at one or more of TGFBR1, TGFBR2, TGFBR3. In these embodiments, the modified agent is a TGF family member (e.g. TGFα, TGFβ) which also, optionally, has substantially reduced or ablated affinity and/or activity at one or more of TGFBR1, TGFBR2, TGFBR3.

In some embodiments, the modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TGFBR1 and/or TGFBR2. In these embodiments, the modified agent is a TGF family member (e.g. TGFα, TGFβ) which also, optionally, has substantially reduced or ablated affinity and/or activity at TGFBR3.

In an embodiment, the modified signaling agent is an interleukin. In an embodiment, the modified signaling agent is IL-1. In an embodiment, the modified signaling agent is IL-1α or IL-1β. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1β has the amino acid sequence of SEQ ID NO: 335.

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of CD8+ T cells, enhancing antigen-specific CD8+ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, I172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1 β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1β comprises the mutations R120G and H146E. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In an embodiment, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of CD8⁺ T cells (which can provide an anti-tumor effect), which have IL2 receptors β and γ and disfavor Tregs (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of autoimmune diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of CD8⁺ T cells (and therefore dampen the immune response), which have IL2 receptors β and γ and disfavor Tregs which have IL2 receptors α, β, and γ. Alternatively, in some embodiments, the chimeras bearing IL-2 favor the activation of Tregs, and therefore immune suppression, and activation of disfavor of CD8⁺ T cells. For instance, these constructs find use in the treatment of diseases or diseases that would benefit from immune suppression, e.g. autoimmune disorders.

In some embodiments, the chimeric protein has targeting moieties as described herein directed to CD8⁺ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted CD8⁺ T cell activity and are generally inactive (or have substantially reduced activity) towards Treg cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of SEQ ID NO: 336.

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In some embodiments, the modified IL-2 agent has one or more mutations at amino acids R38, F42, Y45, and E62. For example, the modified IL-2 agent may comprise one or more of R38A, F42A, Y45A, and E62A. In some embodiments, the modified IL-2 agent may comprise a mutation at C125. For example, the mutation may be C125S. In such embodiments, the modified IL-2 agent may have substantially reduced affinity and/or activity for IL-2Rα, as described in, for example, Carmenate et al. (2013) The Journal of Immunology, 190:6230-6238, the entire disclosure of which is hereby incorporated by reference. In some embodiments, the modified IL-2 agent with mutations at R38, F42, Y45, and/or E62 is able to induce an expansion of effector cells including CD8+ T cells and NK cells but not Treg cells. In some embodiments, the modified IL-2 agent with mutations at R38, F42, Y45, and/or E62 is less toxic than wildtype IL-2 agents. A chimeric protein comprising the modified IL-2 agent with substantially reduced affinity and/or activity for IL-2Rα may find application in oncology for example.

In other embodiments, the modified IL-2 agent may have substantially reduced affinity and/or activity for IL-2R3, as described in, for example, WO2016/025385, the entire disclosure of which is hereby incorporated by reference. In such embodiments, the modified IL-2 agent may induce an expansion of Treg cells but not effector cells such as CD8+

T cells and NK cells. A chimeric protein comprising the modified IL-2 agent with substantially reduced affinity and/or activity for IL-2Rβ may find application in the treatment of autoimmune disease for example. In some embodiments, the modified IL-2 agent may comprise one or more mutations at amino acids N88, D20, and/r A126. For example, the modified IL-2 agent may comprise one or more of N88R, N88I, N88G, D20H, Q126L, and Q126F.

In various embodiments, the modified IL-2 agent may comprise a mutation at D109 or C125. For example, the mutation may be D109C or C125S. In some embodiments, the modified IL-2 with a mutation at D109 or C125 may be utilized for attachment to a PEG moiety.

In an embodiment, the modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of SEQ ID NO: 337.

In such embodiments, the modified IL-4 agent has one or more mutations at amino acids R121 (R121A, R121D, R121E, R121F, R121H, R121I, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of IL-6 (mature form, wild type) (SEQ ID NO: 338).

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the modified signaling agent is IL-10. In such an embodiment, the modified signaling agent has reduced affinity and/or activity for IL-10 receptor-1 and IL-10 receptor-2. In some embodiments, the modified signaling agent has substantially reduced or ablated affinity and/or activity for IL-10 receptor-1 and IL-10 receptor-2

In an embodiment, the modified signaling agent is IL-11. In such an embodiment, the modified signaling agent has reduced affinity and/or activity for IL-11Rα and/or IL-11Rβ and/or gp130. In such an embodiment, the modified signaling agent has substantially reduced or ablated affinity and/or activity for IL-11Rα and/or IL-11Rβ and/or gp130.

In an embodiment, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-1β has the amino acid sequence of IL-1β (mature form, wild type) (SEQ ID NO: 339).

In such embodiments, the modified IL-1β agent has one or more mutations at amino acids 13, 16, 17, 66, 69, 99, 102, 104, 105, 106, 107, 108, 109, 112, 113 and 114. Without wishing to be bound by theory, it is believed that these modified IL-1β agents exhibit reduced biological activity. See, for example, WO 2002/018422, the entire contents of which are hereby incorporated by reference.

In an embodiment, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of IL-18 (wild type) (SEQ ID NO: 340).

In such embodiments, the modified IL-18 agent may comprise one or more mutations in amino acids or amino acid regions selected from Y37-K44, R49-Q54, D59-R63, E67-C74, R80, M87-A97, N127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of SEQ ID NO: 341.

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

In an embodiment, the modified signaling agent is epidermal growth factor (EGF). EGF is a member of a family of potent growth factors. Members include EGF, HB-EGF, and others such as TGFalpha, amphiregulin, neuregulins, epiregulin, betacellulin. EGF family receptors include EGFR (ErbB1), ErbB2, ErbB3 and ErbB4. These may function as homodimeric and/or heterodimeric receptor subtypes. The different EGF family members exhibit differential selectivity for the various receptor subtypes. For example, EGF associates with ErbB1/ErbB1, ErbB1/ErbB2, ErbB4/ErbB2 and some other heterodimeric subtypes. HB-EGF has a similar pattern, although it also associates with ErbB4/4. Modulation of EGF (EGF-like) growth factor signaling, positively or negatively, is of considerable therapeutic interest. For example, inhibition of EGFRs signaling is of interest in the treatment of various cancers where EGFR signaling constitutes a major growth promoting signal. Alternatively, stimulation of EGFRs signaling is of therapeutic interest in, for example, promoting wound healing (acute and chronic), oral mucositis (a major side-effect of various cancer therapies, including, without limitation radiation therapy).

In some embodiments, the modified signaling agent has reduced affinity and/or activity for ErbB1, ErbB2, ErbB3, and/or ErbB4. Such embodiments find use, for example, in methods of treating wounds. In some embodiments, the modified signaling agent binds to one or more ErbB1, ErbB2, ErbB3, and ErbB4 and antagonizes the activity of the receptor. In such embodiments, the modified signaling agent has reduced affinity and/or activity for ErbB1, ErbB2, ErbB3, and/or ErbB4 which allows for the activity of the receptor to be antagonized in an attenuated fashion. Such embodiments find use in, for example, treatments of cancer. In an embodiment, the modified signaling agent has reduced affinity and/or activity for ErbB1. ErbB1 is the therapeutic target of kinase inhibitors—most have side effects because they are not very selective (e.g., gefitinib, erlotinib, afatinib, brigatinib and icotinib). In some embodiments, attenuated antagonistic ErbB1 signaling is more on-target and has less side effects than other agents targeting receptors for EGF.

In some embodiments, the modified signaling agent has reduced affinity and/or activity (e.g. antagonistic e.g. natural antagonistic activity or antagonistic activity that is the result of one or more mutations, see, e.g., WO 2015/007520, the entire contents of which are hereby incorporated by reference) for ErbB1 and/or substantially reduced or ablated affinity and/or activity for ErbB4 or other subtypes it may interact with. Through specific targeting via the targeting moiety, cell-selective suppression (antagonism e.g. natural antagonistic activity or antagonistic activity that is the result of one or more mutations, see, e.g., WO 2015/007520, the entire contents of which are hereby incorporated by reference) of ErbB1/ErbB1 receptor activation would be achieved—while not engaging other receptor subtypes potentially associated with inhibition-associated side effects. Hence, in contrast to EGFR kinase inhibitors, which inhibit EGFR activity in all cell types in the body, such a construct would provide a cell-selective (e.g., tumor cell with activated EGFR signaling due to amplification of receptor, overexpression etc.) anti-EGFR (ErbB1) drug effect with reduced side effects.

In some embodiments, the modified signaling agent has reduced affinity and/or activity (e.g. agonistic) for ErbB4 and/or other subtypes it may interact with. Through targeting to specific target cells through the targeting moiety, a selective activation of ErbB1 signaling is achieved (e.g. epithelial cells). Such a construct finds use, in some embodiments, in the treatment of wounds (promoting would healing) with reduced side effects, especially for treatment of chronic conditions and application other than topical application of a therapeutic (e.g. systemic wound healing).

In an embodiment, the modified signaling agent is insulin or insulin analogs. In some embodiments, the modified insulin or insulin analog has reduced affinity and/or activity for the insulin receptor and/or IGF1 or IGF2 receptor. In some embodiments, the modified insulin or insulin analog has substantially reduced or ablated affinity and/or activity for the insulin receptor and/or IGF1 or IGF2 receptor. Attenuated response at the insulin receptor allows for the control of diabetes, obesity, metabolic disorders and the like while directing away from IGF1 or IGF2 receptor avoids pro-cancer effects.

In an embodiment, the modified signaling agent is insulin-like growth factor-1 or insulin-like growth factor-11 (IGF-1 or IGF-2). In an embodiment, the modified signaling agent is IGF-1. In such an embodiment, the modified signaling agent has reduced affinity and/or activity for the insulin receptor and/or IGF1 receptor. In an embodiment, the modified signaling agent may bind to the IGF1 receptor and antagonize the activity of the receptor. In such an embodiment, the modified signaling agent has reduced affinity and/or activity for IGF1 receptor which allows for the activity of the receptor to be antagonized in an attenuated fashion. In some embodiments, the modified signaling agent has substantially reduced or ablated affinity and/or activity for the insulin receptor and/or IGF1 receptor. In some embodiments, the modified signaling agent has reduced affinity and/or activity for IGF2 receptor which allows for the activity of the receptor to be antagonized in an attenuated fashion. In an embodiment, the modified signaling agent has substantially reduced or ablated affinity and/or activity for the insulin receptor and accordingly does not interfere with insulin signaling. In various embodiments, this applies to cancer treatment. In various embodiments, the present agents may prevent IR isoform A from causing resistance to cancer treatments.

In one embodiment, the present chimeric protein has (i) a targeting moiety against PD-1 or PD-L1 and (ii) a targeting moiety which is directed against a tumor cell, along with any of the modified or mutant signaling agents described herein.

In one embodiment, the present chimeric protein has (i) a targeting moiety against PD-1 or PD-L1 and (ii) a targeting moiety which is directed against a checkpoint inhibitor marker, along with any of the modified or mutant interferons described herein.

In various embodiments, the signaling agent is a toxin or toxic enzyme. In some embodiments, the toxin or toxic enzyme is derived from plants and bacteria. Illustrative toxins or toxic enzymes include, but are not limited to, the diphtheria toxin, *Pseudomonas* toxin, anthrax toxin, ribosome-inactivating proteins (RIPs) such as ricin and saporin, modeccin, abrin, gelonin, and poke weed antiviral protein. Additional toxins include those disclosed in Mathew et al., (2009) Cancer Sci 100(8): 1359-65, the entire disclosures are hereby incorporated by reference. In such embodiments, the chimeric proteins of the invention may be utilized to induce cell death in cell-type specific manner. In such embodiments, the toxin may be modified, e.g. mutated, to reduce affinity and/or activity of the toxin for an attenuated effect, as described with other signaling agents herein.

Multi-Specific Chimeras and Fusions with Signaling Agents

In various embodiments, the PD-1 or PD-L1 binding agent of the invention is part of a chimera or fusion with one or more signaling agents as described herein and/or one or more additional targeting moieties. Accordingly, the present invention provides for chimeric or fusion proteins that include one or more signaling agents and a targeting moiety against PD-1 or PD-L1 and/or one or more additional targeting moieties.

In various embodiments, the PD-1 or PD-L1 binding agent of the invention is multispecific, i.e., the PD-1 or PD-L1 binding agent comprises two or more targeting moieties having recognition domains that recognize and bind two or more targets, e.g. antigens, or receptors, or epitopes. In such embodiments, the PD-1 or PD-L1 binding agent of the invention may comprise two more targeting moieties having recognition domains that recognize and bind two or more epitopes on the same antigen or on different antigens. In various embodiments, such multi-specific PD-1 or PD-L1 binding agents exhibit advantageous properties such as increased avidity and/or improved selectivity. In an embodiment, the PD-1 or PD-L1 binding agent of the invention comprises two targeting moieties and is bispecific, i.e., binds and recognizes two epitopes on the same antigen or on different antigens.

In various embodiments, the multispecific PD-1 or PD-L1 binding agent of the invention comprises two or more targeting moieties with each targeting moiety being an antibody or an antibody derivative as described herein. In an embodiment, the multispecific PD-1 or PD-L1 binding agent of the invention comprises at least one VHH comprising an antigen recognition domain against PD-1 or PD-L1 and one antibody or antibody derivative comprising an antigen recognition domain against a tumor antigen.

In various embodiments, the present multispecific PD-1 or PD-L1 binding agents have two or more targeting moieties that target different antigens or receptors, and one targeting moiety may be attenuated for its antigen or receptor, e.g. the targeting moiety binds its antigen or receptor with a low affinity or avidity (including, for example, at an affinity or avidity that is less than the affinity or avidity the other targeting moiety has for its for its antigen or receptor, for instance the difference between the binding affinities may be about 10-fold, or 25-fold, or 50-fold, or 100-fold, or 300-fold, or 500-fold, or 1000-fold, or 5000-fold; for instance the lower affinity or avidity targeting moiety may bind its antigen or receptor at a $K_D$ in the mid- to high-nM or low- to mid-µM range while the higher affinity or avidity targeting moiety may bind its antigen or receptor at a $K_D$ in the mid- to high-µM or low- to mid-nM range). For instance, in some embodiments, the present multispecific PD-1 or PD-L1 binding agents comprises an attenuated targeting moiety that is directed against a promiscuous antigen or receptor, which may improve targeting to a cell of interest (e.g. via the other targeting moiety) and prevent effects across multiple types of cells, including those not being targeted for therapy (e.g. by binding promiscuous antigen or receptor at a higher affinity than what is provided in these embodiments).

The multispecific PD-1 or PD-L1 binding agent of the invention may be constructed using methods known in the art, see for example, U.S. Pat. No. 9,067,991, U.S. Patent Publication No. 20110262348 and WO 2004/041862, the entire contents of which are hereby incorporated by reference. In an illustrative embodiment, the multispecific PD-1 or PD-L1 binding agent of the invention comprising two or more targeting moieties may be constructed by chemical crosslinking, for example, by reacting amino acid residues with an organic derivatizing agent as described by Blattler et al., Biochemistry 24, 1517-1524 and EP294703, the entire contents of which are hereby incorporated by reference. In another illustrative embodiment, the multispecific PD-1 or PD-L1 binding agent comprising two or more targeting moieties is constructed by genetic fusion, i.e., constructing a single polypeptide which includes the polypeptides of the individual targeting moieties. For example, a single polypeptide construct may be formed which encodes a first VHH with an antigen recognition domain against PD-1 or PD-L1 and a second antibody or antibody derivative with an antigen recognition domain against a tumor antigen. A method for producing bivalent or multivalent VHH polypeptide constructs is disclosed in PCT patent application WO 96/34103, the entire contents of which is hereby incorporated by reference. In a further illustrative embodiment, the multispecific PD-1 or PD-L1 binding agent of the invention may be constructed by using linkers. For example, the carboxy-terminus of a first VHH with an antigen recognition domain against PD-1 or PD-L1 may be linked to the amino-terminus of a second antibody or antibody derivative with an antigen recognition domain against a tumor antigen (or vice versa). Exemplary linkers that may be used are described herein. In some embodiments, the components of the multispecific PD-1 or PD-L1 binding agent of the invention are directly linked to each other without the use of linkers.

In various embodiments, the multi-specific PD-1 or PD-L1 binding agent of the invention recognizes and binds to PD-1 or PD-L1 and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the PD-1 or PD-L1 binding agent specifically binds to an antigen of interest and effectively directly or indirectly recruits one of more immune cells.

In various embodiments, the multi-specific PD-1 or PD-L1 binding agent of the invention recognizes and binds to PD-1 or PD-L1 and one or more antigens found on tumor cells. In these embodiments, the present PD-1 or PD-L1 binding agents may directly or indirectly recruit an immune cell to a tumor cell or the tumor microenvironment. In some embodiments, the present PD-1 or PD-L1 binding agents may directly or indirectly recruit an immune cell, e.g. an immune cell that can kill and/or suppress a tumor cell (e.g., a CTL), to a site of action (such as, by way of non-limiting example, the tumor microenvironment).

In some embodiments, the present PD-1 or PD-L1 binding agents are capable of, or find use in methods involving, shifting the balance of immune cells in favor of immune attack of a tumor. For instance, the present PD-1 or PD-L1 binding agents can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), neutrophils, B cells, dendritic cells or subsets thereof and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present PD-1 or PD-L1 binding agent is capable of increasing a ratio of effector T cells to regulatory T cells.

In some embodiments, the multi-specific PD-1 or PD-L1 binding agent of the invention comprises a targeting moiety having an antigen recognition domain that specifically binds to an antigen associated with tumor cells. In some embodiments, the targeting moiety directly or indirectly recruits tumor cells. For instance, in some embodiments, the recruitment of the tumor cell is to one or more effector cell (e.g. an immune cell as described herein) that can kill and/or suppress the tumor cell. In some embodiments, the targeting moiety directly or indirectly recruits T cells to a tumor cell, for example, by virtue of the two targeting moieties interacting with their respective antigens on a tumor and CD8-positive immune cell (e.g. T cell).

Tumor cells, or cancer cells refer to an uncontrolled growth of cells or tissues and/or an abnormal increased in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative tumor antigens include, but are not limited to, MART-1/Melan-A, gp100, Dipeptidyl peptidase IV (DP-PIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, PMSA, and BCMA (TNFRSF17). In various embodiments, the PD-1 or PD-L1 binding agent comprises a targeting moiety that binds one or more of these tumor antigens.

In some embodiments, the present multi-specific PD-1 or PD-L1 binding agent recognizes and binds to PD-1 or PD-L1 as well as an antigen on a tumor cell.

In various embodiments, the present multi-specific PD-1 or PD-L1 binding agent has targeting moieties which target two different cells (e.g. to make a synapse) or the same cell (e.g. to get a more concentrated signaling agent effect).

In some embodiments, the multi-specific PD-1 or PD-L1 binding agent of the invention comprises a targeting moiety having an antigen recognition domain that specifically binds to a target (e.g. antigen, receptor) associated with T cells. In some embodiments, the targeting moiety directly or indirectly recruits T cells. In an embodiment, the antigen recognition domains specifically bind to effector T cells. In some embodiments, the antigen recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβ TCR, CD3$^+$, CD8$^+$, CD45RO$^+$); CD4$^+$ effector T cells (e.g. αβ TCR, CD3$^+$, CD4$^+$, CCR7$^+$, CD62Lhi, IL-7R/CD127$^+$); CD8$^+$ effector T cells (e.g. αβ TCR, CD3$^+$, CD8$^+$, CCR7$^+$, CD62Lhi, IL-7R/CD127$^+$); effector memory T cells (e.g. CD62Llow, CD44$^+$, TCR, CD3$^+$, IL-7R/CD127$^+$, IL-15R$^+$, CCR7low); central memory T cells (e.g. CCR7$^+$, CD62L$^+$, CD27$^+$; or CCR7hi, CD44$^+$, CD62Lhi, TCR, CD3$^+$, IL-7R/CD127$^+$, IL-15R$^+$); CD62L$^+$ effector T cells; CD8$^+$ effector memory T cells (TEM) including early effector memory T cells (CD27⁺CD62L⁻) and late effector memory T cells (CD27⁻ CD62L⁻) (TemE and TemL, respectively); CD127 (⁺)CD25(low/−) effector T cells; CD127(⁻)CD25(⁻) effector T cells; CD8⁺ stem cell memory effector cells (TSCM) (e.g. CD44(low)CD62L(high)CD122(high)sca(⁺)); TH1 effector T-cells (e.g. CXCR3⁺, CXCR6⁺ and CCR5⁺; or αβ TCR, CD3⁺, CD4⁺, IL-12R⁺, IFNγR⁺, CXCR3⁺), TH2 effector T cells (e.g. CCR3⁺, CCR4⁺ and CCR8⁺; or αβ TCR, CD3⁺, CD4⁺, IL-4R⁺, IL-33R⁺, CCR4⁺, IL-17RB⁺, CRTH2⁺); TH9 effector T cells (e.g. αβ TCR, CD3⁺, CD4⁺); TH17 effector T cells (e.g. αβ TCR, CD3⁺, CD4⁺, IL-23R⁺, CCR6⁺, IL-1R⁺); CD4⁺CD45RO⁺CCR7⁺ effector T cells, ICOS⁺ effector T cells; CD4⁺CD45RO⁺CCR7(⁻) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2 R β, ALCAM, B7-1, IL-4 R, B7-H3, BLAME/SLAMF5, CEACAM1, IL-6 R, CCR3, IL-7 Ra, CCR4, CXCRI/IL-S RA, CCR5, CCR6, IL-10R α, CCR 7, IL-I 0 R β, CCR5, IL-12 R β 1, CCR9, IL-12 R β 2, CD2, IL-1β R α 1, IL-13, CD3, CD4, ILT2/CDS5j, ILT3/CDS5k, ILT4/CDS5d, ILT5/CDS5a, Integrin α 4/CD49d, CDS, Integrin α E/CD103, CD6, Integrin α M/CD 11 b, CDS, Integrin α X/CD11c, Integrin β 2/CDIS, KIR/CD15S, CD27/TNFRSF7, KIR2DL1, CD2S, KIR2DL3, CD30/TNFRSF5, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSF10A, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R. In various embodiments, the PD-1 or PD-L1 binding agent comprises a targeting moiety that binds one or more of these illustrative T cell antigens.

In some embodiments, the multi-specific PD-1 or PD-L1 binding agent of the invention comprises a targeting moiety against CD8 which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the multi-specific PD-1 or PD-L1 binding agent of the invention comprises a VHH against CD8 having a variable domain comprising at least one CDR1, CDR2, and/or CDR3 sequences.

In some embodiments, the CDR1 sequence is selected from SEQ ID NO: 342 or SEQ ID NO: 343.

In some embodiments, the CDR2 sequence is selected from SEQ ID NO: 344 or SEQ ID NO: 345.

In some embodiments, the CDR3 sequence is selected from SEQ ID NO: 346 or SEQ ID NO: 347 or SEQ ID NO: 348.

In various embodiments, the CD8 targeting moiety comprises an amino acid sequence selected from the following sequences: R3HCD27 (SEQ ID NO: 349) or R3HCD129 (SEQ ID NO: 350) or R2HCD26 (SEQ ID NO: 351).

In various embodiments, the CD8 targeting moiety comprises a VHH having a variable domain comprising at least one CDR1, CDR2, and/or CDR3 sequences as described below.

In some embodiments, the CDR1 sequence is selected from SEQ ID NO: 352 to SEQ ID NO: 420.

In some embodiments, the CDR2 sequence is selected from SEQ ID NO: 421 to SEQ ID NO: 489.

In some embodiments, the CDR3 sequence is selected from SEQ ID NO: 490 to SEQ ID NO: 558.

In various embodiments, the CD8 targeting moiety comprises an amino acid sequence selected from the following sequences: 1CDA 7 (SEQ ID NO: 559) or 1CDA 12 (SEQ ID NO: 560) or 1CDA 14 (SEQ ID NO: 561) or 1CDA 15 (SEQ ID NO: 562) or 1CDA 17 (SEQ ID NO: 563) or 1CDA 18 (SEQ ID NO: 564) or 1CDA 19 (SEQ ID NO: 565) or 1CDA 24 (SEQ ID NO: 566) or 1CDA 26 (SEQ ID NO: 567) or 1CDA 28 (SEQ ID NO: 568) or 1CDA 37 (SEQ ID NO: 569) or 1CDA 43 (SEQ ID NO: 570) or 1CDA 45 (SEQ ID NO: 571) or 1CDA 47 (SEQ ID NO: 572) or 1CDA 48 (SEQ ID NO: 573) or 1CDA 58 (SEQ ID NO: 574) or 1CDA 65 (SEQ ID NO: 575) or 1CDA 68 (SEQ ID NO: 576) or 1CDA 73 (SEQ ID NO: 577) or 1CDA 75 (SEQ ID NO: 578) or 1CDA 86 (SEQ ID NO: 579) or 1CDA 87 (SEQ ID NO: 580) or 1CDA 88 (SEQ ID NO: 581) or 1CDA 89 (SEQ ID NO: 582) or 1CDA 92 (SEQ ID NO: 583) or 1CDA 93 (SEQ ID NO: 584) or 2CDA 1 (SEQ ID NO: 585) or 2CDA 5 (SEQ ID NO: 586) or 2CDA 22 (SEQ ID NO: 587) or 2CDA 28 (SEQ ID NO: 588) or 2CDA 62 (SEQ ID NO: 589) or 2CDA 68 (SEQ ID NO: 590) or 2CDA 73 (SEQ ID NO: 591) or 2CDA 74 (SEQ ID NO: 592) or 2CDA 75 (SEQ ID NO: 593) or 2CDA 77 (SEQ ID NO: 594) or 2CDA 81 (SEQ ID NO: 595) or 2CDA 87 (SEQ ID NO: 596) or 2CDA 88 (SEQ ID NO: 597) or 2CDA 89 (SEQ ID NO: 598) or 2CDA 91 (SEQ ID NO: 599) or 2CDA 92 (SEQ ID NO: 600) or 2CDA 93 (SEQ ID NO: 601) or 2CDA 94 (SEQ ID NO: 602) or 2CDA 95 (SEQ ID NO: 603) or 3CDA 3 (SEQ ID NO: 604) or 3CDA 8 (SEQ ID NO: 605) or 3CDA 11 (SEQ ID NO: 606) or 3CDA 18 (SEQ ID NO: 607) or 3CDA 19 (SEQ ID NO: 608) or 3CDA 21 (SEQ ID NO: 609) or 3CDA 24 (SEQ ID NO: 610) or 3CDA 28 (SEQ ID NO: 611) or 3CDA 29 (SEQ ID NO: 612) or 3CDA 31 (SEQ ID NO: 613) or 3CDA 32 (SEQ ID NO: 614) or 3CDA 33 (SEQ ID NO: 615) or 3CDA 37 (SEQ ID NO: 616) or 3CDA 40 (SEQ ID NO: 617) or 3CDA 41 (SEQ ID NO: 618) or 3CDA 48 (SEQ ID NO: 619) or 3CDA 57 (SEQ ID NO: 620) or 3CDA 65 (SEQ ID NO: 621) or 3CDA 70 (SEQ ID NO: 622) or 3CDA 73 (SEQ ID NO: 623) or 3CDA 83 (SEQ ID NO: 624) or 3CDA 86 (SEQ ID NO: 625) or 3CDA 88 (SEQ ID NO: 626) or 3CDA 90 (SEQ ID NO: 627).

In various exemplary embodiments, the CD8 targeting moiety comprises an amino acid sequence selected from any one of the above sequences without the terminal histidine tag sequence (i.e., HHHHHH; SEQ ID NO: 84).

In some embodiments, the CD8 targeting moiety comprises an amino acid sequence selected from SEQ ID Nos: 559-627 (provided above) without the HA tag (i.e., YPYDVPDYGS; SEQ ID NO: 85).

In some embodiments, the CD8 targeting moiety comprises an amino acid sequence selected from SEQ ID Nos: 559-627 (provided above) without the AAA linker.

In some embodiments, the CD8 targeting moiety comprises an amino acid sequence selected from SEQ ID Nos:

559-627 (provided above) without the AAA linker, HA tag, and terminal histidine tag sequence (i.e., AAAY-PYDVPDYGSHHHHHH; SEQ ID NO: 86). In various embodiments, the CD8 targeting moiety comprises an amino acid sequence described in US Patent Publication No. 2014/0271462, the entire contents of which are incorporated by reference. In various embodiments, the CD8 targeting moiety comprises an amino acid sequence described in Table 0.1, Table 0.2, Table 0.3, and/or FIGS. 1A-12I of US Patent Publication No. 2014/0271462, the entire contents of which are incorporated by reference. In various embodiments, the CD8 targeting moiety comprises a HCDR1 of a HCDR1 of SEQ ID NO: 22 or 23 and/or a HCDR2 of HCDR1 of SEQ ID NO: 22 or 23 and/or a HCDR3 of HCDR1 of SEQ ID NO: 22 or 23 and/or a LCDR1 of LCDR1 of SEQ ID NO: 24 and/or a LCDR2 of LCDR1 of SEQ ID NO: 24 and/or a LCDR3 of LCDR1 of SEQ ID NO: 24, as provided in SEQ ID NO: 628, SEQ ID NO: 629, or SEQ ID NO: 630.

In various embodiments, the present invention contemplates the use of any natural or synthetic analogs, mutants, variants, alleles, homologs and orthologs (herein collectively referred to as "analogs") of the targeting moiety directed against CD8 as described herein. In various embodiments, the amino acid sequence of the targeting moiety directed against CD8 further includes an amino acid analog, an amino acid derivative, or other non-classical amino acids.

In some embodiments, the multi-specific PD-1 or PD-L1 binding agent of the invention comprises a targeting moiety having an antigen recognition domain that specifically binds to a target (e.g. antigen, receptor) associated with B cells. In some embodiments, the targeting moiety directly or indirectly recruits B cells, e.g., in some embodiments, to a therapeutic site (e.g. a locus with one or more disease cell or cell to be modulated for a therapeutic effect). Illustrative B cell antigens of interest include, for example, CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, and B-cell maturation antigen (BCMA). In various embodiments, the PD-1 or PD-L1 binding agent comprises a targeting moiety that binds one or more of these illustrative B cell antigens.

In some embodiments, the multi-specific PD-1 or PD-L1 binding agent of the invention comprises a targeting moiety having an antigen recognition domain that specifically bind to a target (e.g. antigen, receptor) associated with Natural Killer cells. In some embodiments, the targeting moiety directly or indirectly recruits Natural Killer cells, e.g., in some embodiments, to a therapeutic site (e.g. a locus with one or more disease cell or cell to be modulated for a therapeutic effect). Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, Kidalpha, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1 α, Rae-1 β, Rae-1 delta, H60, Rae-1 epsilon, ILT2/CD85j, Rae-1 γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In various embodiments, the PD-1 or PD-L1 binding agent comprises a targeting moiety that binds one or more of these illustrative NK cell antigens.

In some embodiments, the multi-specific PD-1 or PD-L1 binding agent of the invention comprises a targeting moiety having an antigen recognition domain that specifically binds to a target (e.g. antigen, receptor) associated with macrophages/monocytes. In some embodiments, the targeting moiety directly or indirectly recruits macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common 3 Chain, Integrin α 4/CD49d, BLAME/SLAMF8, Integrin α X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R α, TCCR/WSX-1, ICAM-2/CD102, TLR3, IFN-γ RI, TLR4, IFN-gamma R2, TREM-I, IL-I RII, TREM-2, ILT2/CD85j, TREM-3, ILT3/CD85k, TREML1/TLT-1, 2B4/SLAMF 4, IL-10 R α, ALCAM, IL-10 R β, AminopeptidaseN/ANPEP, ILT2/CD85j, Common β Chain, ILT3/CD85k, Clq R1/CD93, ILT4/CD85d, CCR1, ILT5/CD85a, CCR2, CD206, Integrin α 4/CD49d, CCR5, Integrin α M/CDII b, CCR8, Integrin α X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R α, Siglec-3/CD33, HVEM/TNFRSF14, SLAM, ICAM-1/CD54, TCCR/WSX-1, ICAM-2/CD102, TREM-I, IL-6 R, TREM-2, CXCRI/IL-8 RA, TREM-3 and TREMLI/TLT-1. In various embodiments, the PD-1 or PD-L1 binding agent comprises a targeting moiety that binds one or more of these illustrative macrophage/monocyte antigens.

In some embodiments, the multi-specific PD-1 or PD-L1 binding agent of the invention comprises a targeting moiety having an antigen recognition domain that specifically binds to a target (e.g. antigen, receptor) associated with dendritic cells. In some embodiments, the targeting moiety directly or indirectly recruits dendritic cells, e.g., in some embodiments, to a therapeutic site (e.g. a locus with one or more disease cell or cell to be modulated for a therapeutic effect). Illustrative dendritic cell antigens of interest include, for example, Clec9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin a 4/CD49d, Aag, Integrin β 2/CD18, AMICA, Langerin, B7-2/ CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, DEC-205, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RIII/CD16, TREML1/TLT-1, ICAM-2/CD102, DEC205, and Vanilloid R1. In various embodiments, the PD-1 or PD-L1 binding agent comprises a targeting moiety that binds one or more of these illustrative DC antigens.

In some embodiments, the multi-specific PD-1 or PD-L1 binding agent of the invention comprises a targeting moiety against Clec9A which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the multi-specific PD-1 or PD-L1 binding agent of the invention comprises a VHH against Clec9A having a variable domain comprising at least one CDR1, CDR2, and/or CDR3 sequences.

In exemplary embodiments, the CDR1 sequence is selected from SEQ ID NO: 631 to SEQ ID NO: 650.

In exemplary embodiments, the CDR2 sequence is selected from SEQ ID NO: 651 to SEQ ID NO: 672.

In exemplary embodiments, the CDR3 sequence is selected from SEQ ID NO: 673 to SEQ ID NO: 687; or LGR; or VIK.

In various embodiments, the Clec9A targeting moiety comprises an amino acid sequence selected from the following sequences: R2CHCL8 (SEQ ID NO: 688); R1CHCL50 (SEQ ID NO: 689); R1CHCL21 (SEQ ID NO: 690); R2CHCL87 (SEQ ID NO: 691); R2CHCL24 (SEQ ID NO: 692); R2CHCL38 (SEQ ID NO: 693); R1CHCL16 (SEQ ID NO: 694); R2CHCL10 (SEQ ID NO: 695); R1CHCL34 (SEQ ID NO: 696); R1CHCL82 (SEQ ID NO: 697); R2CHCL3 (SEQ ID NO: 698); R2CHCL69 (SEQ ID NO: 699); R1CHCL56 (SEQ ID NO: 700); R2CHCL32 (SEQ ID NO: 701); R2CHCL49 (SEQ ID NO: 702); R2CHCL53 (SEQ ID NO: 703); R2CHCL22 (SEQ ID NO: 704); R2CHCL25 (SEQ ID NO: 705); R2CHCL18 (SEQ ID NO: 706); R1CHCL23 (SEQ ID NO: 707); R1CHCL27 (SEQ ID NO: 708); R2CHCL13 (SEQ ID NO: 709); R2CHCL14 (SEQ ID NO: 710); R2CHCL42 (SEQ ID NO: 711); R2CHCL41 (SEQ ID NO: 712); R2CHCL94 (SEQ ID NO: 713); or R2CHCL27 (SEQ ID NO: 714).

In various embodiments, the Clec9A targeting moiety comprises a VHH having a variable domain comprising at least one CDR1, CDR2, and/or CDR3 sequences as described below.

In some embodiments, the CDR1 sequence is selected from: SEQ ID NO: 715 to SEQ ID NO: 780.

In some embodiments, the CDR2 sequence is selected from: SEQ ID NO: 781 to SEQ ID NO: 846.

In some embodiments, the CDR3 sequence is selected from: SEQ ID NO: 847 to SEQ ID NO: 912.

In various exemplary embodiments, the Clec9A targeting moiety comprises an amino acid sequence selected from the following sequences: 1LEC 7 (SEQ ID NO: 913).

In various exemplary embodiments, the Clec9A targeting moiety comprises an amino acid sequence selected from any one of the sequences above without the terminal histidine tag sequence (i.e., HHHHHH; SEQ ID NO: 84).

In some embodiments, the Clec9A targeting moiety comprises an amino acid sequence selected from SEQ ID Nos: 913-978 (provided above) without the HA tag (i.e., YPYDVPDYGS; SEQ ID NO: 85).

In some embodiments, the Clec9A targeting moiety comprises an amino acid sequence selected from SEQ ID Nos: 913-978 (provided above) without the AAA linker.

In some embodiments, the Clec9A targeting moiety comprises an amino acid sequence selected from SEQ ID Nos: 913-978 (provided above) without the AAA linker, HA tag, and terminal histidine tag sequence (i.e., AAAY-PYDVPDYGSHHHHHH; SEQ ID NO: 86).

In an embodiment, the targeting moiety comprises the anti-Clec9A antibody as disclosed in Tullett et al., JCI Insight. 2016; 1(7):e87102, the entire disclosures of which are hereby incorporated by reference.

In various embodiments, the present invention contemplates the use of any natural or synthetic analogs, mutants, variants, alleles, homologs and orthologs (herein collectively referred to as "analogs") of the targeting moiety directed against Clec9A as described herein. In various embodiments, the amino acid sequence of the targeting moiety directed against Clec9A further includes an amino acid analog, an amino acid derivative, or other non-classical amino acids In various embodiments, the present chimeric protein comprises a targeting moiety comprising an amino acid sequence that is at least 60% identical to any one of the sequences disclosed herein. For example, the chimeric protein may comprise a targeting moiety comprising an amino acid sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any one of the sequences discloses herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In some embodiments, the multi-specific PD-1 or PD-L1 binding agent of the invention comprises a targeting moiety having an antigen recognition domain that specifically binds a target (e.g. antigen, receptor) on immune cells selected from, but not limited to, megakaryocytes, thrombocytes, erythrocytes, mast cells, basophils, neutrophils, and eosinophils. In some embodiments, the antigen recognition domains directly or indirectly recruit megakaryocytes, thrombocytes, erythrocytes, mast cells, basophils, neutrophils, and eosinophil, e.g., in some embodiments, to a therapeutic site (e.g. a locus with one or more disease cell or cell to be modulated for a therapeutic effect).

In some embodiments, the multi-specific PD-1 or PD-L1 binding agent of the invention comprises a targeting moiety having an antigen recognition domain that specifically binds to a target (e.g. antigen, receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, the PD-1 or PD-L1 binding agent comprises a targeting moiety that binds one or more of these illustrative megakaryocyte and/or thrombocyte antigens.

In some embodiments, the multi-specific PD-1 or PD-L1 binding agent of the invention comprises a targeting moiety having an antigen recognition domain that specifically binds to a target (e.g. antigen, receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, the PD-1 or PD-L1 binding agent comprises a targeting moiety that binds one or more of these illustrative erythrocyte antigens.

In some embodiments, the multi-specific PD-1 or PD-L1 binding agent of the invention comprises a targeting moiety having an antigen recognition domain that specifically binds to a target (e.g. antigen, receptor) associated with mast cells. Illustrative mast cells antigens of interest include, for example, SCFR/CD117, Fc$_\varepsilon$RI, CD2, CD25, CD35, CD88, CD203c, C5R1, CMAI, FCERIA, FCER2, TPSABI. In various embodiments, the PD-1 or PD-L1 binding agent comprises a targeting moiety that binds one or more of these mast cell antigens.

In some embodiments, the multi-specific PD-1 or PD-L1 binding agent of the invention comprises a targeting moiety having an antigen recognition domain that specifically binds to a target (e.g. antigen, receptor) associated with basophils. Illustrative basophils antigens of interest include, for example, Fc$_\varepsilon$RI, CD203c, CD123, CD13, CD107a, CD107b, and CD164. In various embodiments, the PD-1 or PD-L1 binding agent comprises a targeting moiety that binds one or more of these basophil antigens.

In some embodiments, the multi-specific PD-1 or PD-L1 binding agent of the invention comprises a targeting moiety having an antigen recognition domain that specifically binds to a target (e.g. antigen, receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, the PD-1 or PD-L1 binding agent comprises a targeting moiety that binds one or more of these neutrophil antigens.

In some embodiments, the multi-specific PD-1 or PD-L1 binding agent of the invention comprises a targeting moiety having an antigen recognition domain that specifically binds to a target (e.g. antigen, receptor) associated with eosinophils. Illustrative eosinophils antigens of interest include, for example, CD35, CD44 and CD69. In various embodiments, the PD-1 or PD-L1 binding agent comprises a targeting moiety that binds one or more of these eosinophil antigens.

In various embodiments, the multi-specific PD-1 or PD-L1 binding agent of the invention comprises a targeting moiety having an antigen recognition domain that specifically binds to any appropriate antigen or receptor or cell surface markers known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K61RS2, KRTIO, KRT13, KRT17, KRT18, KRT19, KRT4, KRT5, KRT8, MUCI, TACSTDI; neovasculature markers such as CD13, TFNA, Alpha-v beta-3 ($\alpha_v\beta_3$), E-selectin; and adipocyte surface markers such as ADIPOQ, FABP4, and RETN. In various embodiments, the PD-1 or PD-L1 binding agent comprises a targeting moiety that binds one or more of these antigens.

In various embodiments, the multi-specific PD-1 or PD-L1 binding agent of the invention comprises a targeting moiety having an antigen recognition domain that specifically binds to a checkpoint marker expressed on a T cell, e.g. one or more of PD-1, CD28, CTLA4, ICOS, BTLA, KIR, LAG3, CD137, OX40, CD27, CD40L, TIM3, and A2aR.

In various embodiments, the multi-specific PD-1 or PD-L1 binding agent of the invention comprises a targeting moiety having an antigen recognition domain that specifically binds to a checkpoint marker, e.g. one or more of PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/OX40L, CD27, CD40L, TIM3/Gal9, and A2aR.

By way of non-limiting example, in various embodiments, the present multispecific PD-1 or PD-L1 binding agent comprises a targeting moiety directed against (i) CD8; (ii) a checkpoint marker expressed on a T cell, e.g. one or more of PD-1, CD28, CTLA4, ICOS, BTLA, KIR, LAG3, CD137, OX40, Cd27, CD40L, TIM3, and A2aR and/or (iii) a targeting moiety is directed against a tumor cell, along with any of the modified (e.g. mutant) signaling agents described herein.

In various embodiments, the present multi-specific PD-1 or PD-L1 binding agent comprises one or more targeting moieties directed against PD-1 in addition to the PD-1 binding VHHs disclosed elsewhere herein. In some embodiments, the PD-1 or PD-L1 binding agent has one or more targeting moieties which selectively bind a PD-1 polypeptide. In some embodiments, the PD-1 or PD-L1 binding agent comprises one or more antibodies, antibody derivatives or formats, peptides or polypeptides, or fusion proteins that selectively bind a PD-1 polypeptide. In some embodiments, the PD-1 binding agent comprises one or more of the PD-1 binding agents disclosed below along with one or more signaling agents disclosed herein.

In an embodiment, the targeting moiety comprises the anti-PD-1 antibody pembrolizumab (aka MK-3475, KEYTRUDA), or fragments thereof. Pembrolizumab and other humanized anti-PD-1 antibodies are disclosed in Hamid, et al. (2013) New England Journal of Medicine 369 (2): 134-44, U.S. Pat. No. 8,354,509, and WO 2009/114335, the entire disclosures of which are hereby incorporated by reference. In illustrative embodiments, pembrolizumab or an antigen-binding fragment thereof for use in the methods provided herein comprises a heavy chain comprising the amino acid sequence of SEQ ID NO: 979; and/or a light chain comprising the amino acid sequence of SEQ ID NO: 980.

In an embodiment, the targeting moiety comprises the anti-PD-1 antibody, nivolumab (aka BMS-936558, MDX-1106, ONO-4538, OPDIVO), or fragments thereof. Nivolumab (clone 5C4) and other human monoclonal antibodies that specifically bind to PD-1 are disclosed in U.S. Pat. No. 8,008,449 and WO 2006/121168, the entire disclosures of which are hereby incorporated by reference. In illustrative embodiments, nivolumab or an antigen-binding fragment thereof comprises a heavy chain comprising the In an embodiment, the targeting moiety comprises a light chain comprising SEQ ID NO:18 of US 2008/0025980 and a heavy chain comprising SEQ ID NO:22 of US 2008/0025980.

In an embodiment, the targeting moiety comprises AMP-514 (aka MEDI-0680).

In an embodiment, the targeting moiety comprises the PD-L2-Fc fusion protein AMP-224, which is disclosed in WO2010/027827 and WO 2011/066342, the entire disclosures of which are hereby incorporated by reference. In such an embodiment, the targeting moiety may include a targeting domain which comprises SEQ ID NO:4 of WO2010/027827 (SEQ ID NO: 992); and/or the B7-DC fusion protein which comprises SEQ ID NO:83 of WO2010/027827 (SEQ ID NO: 993).

In an embodiment, the targeting moiety comprises the peptide AUNP 12 or any of the other peptides disclosed in US 2011/0318373 or 8,907,053. For example, the targeting moiety may comprise AUNP 12 (i.e., Compound 8 or SEQ ID NO:49 of US 2011/0318373) which has the sequence of SEQ ID NO: 994:

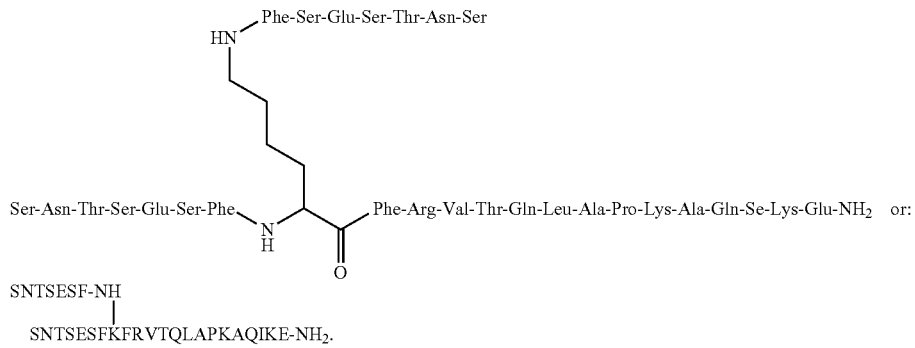

amino acid sequence of SEQ ID NO: 981; and/or a light chain comprising the amino acid sequence of SEQ ID NO: 982.

In an embodiment, the targeting moiety comprises the anti-PD-1 antibody pidilizumab (aka CT-011, hBAT or hBAT-1), or fragments thereof. Pidilizumab and other humanized anti-PD-I monoclonal antibodies are disclosed in US 2008/0025980 and WO 2009/101611, the entire disclosures of which are hereby incorporated by reference. In illustrative embodiments, the anti-PD-1 antibody or an antigen-binding fragment thereof for use in the methods provided herein comprises a light chain variable regions comprising an amino acid sequence selected from SEQ ID NOS: 15-18 of US 2008/0025980: SEQ ID No: 15 of US 2008/0025980 (SEQ ID NO: 983); SEQ ID No: 16 of US 2008/0025980 (SEQ ID NO: 984); SEQ ID No: 17 of US 2008/0025980 (SEQ ID NO: 985); SEQ ID No: 18 of US 2008/0025980 (SEQ ID NO: 986); and/or a heavy chain comprising an amino acid sequence selected from SEQ ID NOS: 20-24 of US 2008/0025980: SEQ ID No: 20 of US 2008/0025980 (SEQ ID NO: 987); SEQ ID No: 21 of US 2008/0025980 (SEQ ID NO: 988); SEQ ID No: 22 of US 2008/0025980 (SEQ ID NO: 989); SEQ ID No: 23 of US 2008/0025980 (SEQ ID NO: 990); or SEQ ID No: 24 of US 2008/0025980 (SEQ ID NO: 991).

In an embodiment, the targeting moiety comprises the anti-PD-1 antibody 1E3, or fragments thereof, as disclosed in US 2014/0044738, the entire disclosures of which are hereby incorporated by reference. In illustrative embodiments, 1E3 or an antigen-binding fragment thereof for use in the methods provided herein comprises a heavy chain variable region comprising the amino acid sequence of SEQ ID NO: 995; and/or a light chain variable region comprising the amino acid sequence of SEQ ID NO: 996.

In an embodiment, the targeting moiety comprises the anti-PD-1 antibody 1E8, or fragments thereof, as disclosed in US 2014/0044738, the entire disclosures of which are hereby incorporated by reference. In illustrative embodiments, 1E8 or an antigen-binding fragment thereof for use in the methods provided herein comprises a heavy chain variable region comprising the amino acid sequence of SEQ ID NO: 997; and/or a light chain variable region comprising the amino acid sequence of SEQ ID NO: 998.

In an embodiment, the targeting moiety comprises the anti-PD-1 antibody 1H3, or fragments thereof, as disclosed in US 2014/0044738, the entire disclosures of which are hereby incorporated by reference. In illustrative embodiments, 1H3 or an antigen-binding fragment thereof for use in the methods provided herein comprises a heavy chain variable region comprising the amino acid sequence of SEQ ID NO: 999; and/or light chain variable region comprising the amino acid sequence of SEQ ID NO: 1000.

In an embodiment, the targeting moiety comprises a VHH directed against PD-1 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOS: 347-351 of U.S. Pat. No. 8,907,065: SEQ ID No: 347 of U.S. Pat. No. 8,907,065 (SEQ ID NO: 1001); SEQ ID No: 348 of U.S. Pat. No. 8,907,065 (SEQ ID NO: 1002); SEQ ID No: 349 of U.S. Pat. No. 8,907,065 (SEQ ID NO: 1003); SEQ ID No: 350 of U.S. Pat. No. 8,907,065 (SEQ ID NO: 1004); or SEQ ID No: 351 of U.S. Pat. No. 8,907,065 (SEQ ID NO: 1005).

In some embodiments, the PD-1 targeting moiety comprising an amino acid sequence selected from SEQ ID NOs: 1001-1005 having one or more substitutions at positions 11, 37, 44, 45, 47, 83, 84, 103, 104, and 108 (according to Kabat numbering). In some embodiments, the amino acid at position 11 is L, M, S, V, or W. In some embodiments, the amino acid at position 37 is F, Y, H, I, L, or V. In some embodiments, the amino acid at position 44 is G, E, A, D, Q, R, S, or L. In some embodiments, the amino acid at position 45 is L, R, C, I, L, P, Q, or V. In some embodiments, the amino acid at position 47 is W, L, F, A, G, I, M, R, S, V or Y. In some embodiments, the amino acid at position 83 is R, K, N, E, G, I, M, Q or T. In some embodiments, the amino acid at position 84 is P, A, L, R, S, T, D, or V. In some embodiments, the amino acid at position 103 is W, P, R, or S; 104-G or D. In some embodiments, the amino acid at position 108 is Q, L, or R.

In an embodiment, the targeting moiety comprises any one of the anti-PD-1 antibodies, or fragments thereof, as disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOS: 25-29 of US2011/0271358: SEQ ID No: 25 of US2011/0271358 (SEQ ID NO: 1006); SEQ ID No: 26 of US2011/0271358 (SEQ ID NO: 1007); SEQ ID No: 27 of US2011/0271358 (SEQ ID NO: 1008); SEQ ID No: 28 of US2011/0271358 (SEQ ID NO: 1009); SEQ ID No: 29 of US2011/0271358 (SEQ ID NO: 1010); and/or a light chain comprising an amino acid sequence selected from SEQ ID NOS: 30-33 of US2011/0271358: SEQ ID No: 30 of US2011/0271358 (SEQ ID NO: 1011); SEQ ID No: 31 of US2011/0271358 (SEQ ID NO: 1012); SEQ ID No: 32 of US2011/0271358 (SEQ ID NO: 1013); or SEQ ID No: 33 of US2011/0271358 (SEQ ID NO: 1014).

In various embodiments, the present multi-specific PD-1 or PD-L1 binding agent comprises one or more antibodies directed against PD-1, or antibody fragments thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.)

In various embodiments, the present multi-specific PD-1 or PD-L1 binding agent has one or more targeting moieties directed against PD-L1. In some embodiments, the PD-1 or PD-L1 binding agent has one or more targeting moieties which selectively bind a PD-L1 polypeptide. In some embodiments, the PD-1 or PD-L1 binding agent comprises one or more antibodies, antibody derivatives or formats, peptides or polypeptides, or fusion proteins that selectively bind a PD-L1 polypeptide. In some embodiments, the PD-L1 binding agent comprises one or more of the PD-1 binding agents disclosed below along with one or more signaling agents disclosed herein.

In an embodiment, the targeting moiety comprises the anti-PD-L1 antibody MED14736 (aka durvalumab), or fragments thereof. MED14736 is selective for PD-L1 and blocks the binding of PD-L1 to the PD-1 and CD80 receptors. MED14736 and antigen-binding fragments thereof for use in the methods provided herein comprises a heavy chain and a light chain or a heavy chain variable region and a light chain variable region. The sequence of MED14736 is disclosed in WO/2016/06272, the entire contents of which are hereby incorporated by reference. In illustrative embodiments, MED14736 or an antigen-binding fragment thereof for use in the methods provided herein comprises a heavy chain comprising the amino acid sequence of SEQ ID NO: 1015; and/or a light chain comprising the amino acid sequence of SEQ ID NO: 1016.

In illustrative embodiments, the MED14736 or an antigen-binding fragment thereof for use in the methods provided herein comprises a heavy chain variable region comprising the amino acid sequence of SEQ ID NO:4 of WO/2016/06272 (SEQ ID NO: 1017); and/or a light chain variable region comprising the amino acid sequence of SEQ ID NO:3 of WO/2016/06272 (SEQ ID NO: 1018).

In an embodiment, the targeting moiety comprises the anti-PD-L1 antibody atezolizumab (aka MPDL3280A, RG7446), or fragments thereof. In illustrative embodiments, atezolizumab or an antigen-binding fragment thereof for use in the methods provided herein comprises a heavy chain comprising the amino acid sequence of SEQ ID NO: 1019; and/or a light chain comprising the amino acid sequence of SEQ ID NO: 1020.

In an embodiment, the targeting moiety comprises the anti-PD-L1 antibody avelumab (aka MSB0010718C), or fragments thereof. In illustrative embodiments, avelumab or an antigen-binding fragment thereof for use in the methods provided herein comprises a heavy chain comprising the amino acid sequence of SEQ ID NO: 1021; and/or a light chain comprising the amino acid sequence of SEQ ID NO: 1022.

In an embodiment, the targeting moiety comprises the anti-PD-L1 antibody BMS-936559 (aka 12A4, MDX-1105), or fragments thereof, as disclosed in US 2013/0309250 and WO2007/005874, the entire disclosures of which are hereby incorporated by reference. In illustrative embodiments, BMS-936559 or an antigen-binding fragment thereof for use in the methods provided herein comprises a heavy chain variable region comprising the amino acid sequence of SEQ ID NO: 1023; and/or a light chain variable region comprising the amino acid sequence of SEQ ID NO: 1024.

In an embodiment, the targeting moiety comprises the anti-PD-L1 antibody 3G10, or fragments thereof, as disclosed in US 2013/0309250 and WO2007/005874, the entire disclosures of which are hereby incorporated by reference. In illustrative embodiments, 3G10 or an antigen-binding fragment thereof for use in the methods provided herein comprises a heavy chain variable region comprising the amino acid sequence of SEQ ID NO: 1025; and/or a light chain variable region comprising the amino acid sequence of SEQ ID NO: 1026.

In an embodiment, the targeting moiety comprises the anti-PD-L1 antibody 10A5, or fragments thereof, as disclosed in US 2013/0309250 and WO2007/005874, the entire disclosures of which are hereby incorporated by reference. In illustrative embodiments, 10A5 or an antigen-binding fragment thereof for use in the methods provided herein comprises a heavy chain variable region comprising the amino acid sequence of SEQ ID NO: 1027; and/or a light chain variable region comprising the amino acid sequence of SEQ ID NO: 1028.

In an embodiment, the targeting moiety comprises the anti-PD-L1 antibody 5F8, or fragments thereof, as disclosed in US 2013/0309250 and WO2007/005874, the entire disclosures of which are hereby incorporated by reference. In illustrative embodiments, 5F8 or an antigen-binding fragment thereof for use in the methods provided herein comprises a heavy chain variable region comprising the amino acid sequence of SEQ ID NO: 1029; and/or a light chain variable region comprising the amino acid sequence of SEQ ID NO: 1030.

In an embodiment, the targeting moiety comprises the anti-PD-L1 antibody 10H10, or fragments thereof, as disclosed in US 2013/0309250 and WO2007/005874, the entire disclosures of which are hereby incorporated by reference. In illustrative embodiments, 10H10 or an antigen-binding fragment thereof for use in the methods provided herein comprises a heavy chain variable region comprising the amino acid sequence of SEQ ID NO: 1031; and/or a light chain variable region comprising the amino acid sequence of SEQ ID NO: 1032.

In an embodiment, the targeting moiety comprises the anti-PD-L1 antibody 1B12, or fragments thereof, as disclosed in US 2013/0309250 and WO2007/005874, the entire disclosures of which are hereby incorporated by reference. In illustrative embodiments, 1B12 or an antigen-binding fragment thereof for use in the methods provided herein comprises a heavy chain variable region comprising the amino acid sequence of SEQ ID NO: 1033; and/or a light chain variable region comprising the amino acid sequence of SEQ ID NO: 1034.

In an embodiment, the targeting moiety comprises the anti-PD-L1 antibody 7H1, or fragments thereof, as disclosed in US 2013/0309250 and WO2007/005874, the entire disclosures of which are hereby incorporated by reference. In illustrative embodiments, 7H1 or an antigen-binding fragment thereof for use in the methods provided herein comprises a heavy chain variable region comprising the amino acid sequence of SEQ ID NO: 1035; and/or a light chain variable region comprising the amino acid sequence of SEQ ID NO: 1036.

In an embodiment, the targeting moiety comprises the anti-PD-L1 antibody 11E6, or fragments thereof, as disclosed in US 2013/0309250 and WO2007/005874, the entire disclosures of which are hereby incorporated by reference. In illustrative embodiments, 11E6 or an antigen-binding fragment thereof for use in the methods provided herein comprises a heavy chain variable region comprising the amino acid sequence of SEQ ID NO: 1037; and/or a light chain variable region comprising the amino acid sequence of SEQ ID NO: 1038.

In an embodiment, the targeting moiety comprises the anti-PD-L1 antibody 12B7, or fragments thereof, as disclosed in US 2013/0309250 and WO2007/005874, the entire disclosures of which are hereby incorporated by reference. In illustrative embodiments, 12B7 or an antigen-binding fragment thereof for use in the methods provided herein comprises a heavy chain variable region comprising the amino acid sequence of SEQ ID NO: 1039; and/or a light chain variable region comprising the amino acid sequence of SEQ ID NO: 1040.

In an embodiment, the targeting moiety comprises the anti-PD-L1 antibody 13G4, or fragments thereof, as disclosed in US 2013/0309250 and WO2007/005874, the entire disclosures of which are hereby incorporated by reference.

In illustrative embodiments, 13G4 or an antigen-binding fragment thereof for use in the methods provided herein comprises a heavy chain variable region comprising the amino acid sequence of SEQ ID NO: 1041; and/or a light chain variable region comprising the amino acid sequence of SEQ ID NO: 1042.

In an embodiment, the targeting moiety comprises the anti-PD-L1 antibody 1E12, or fragments thereof, as disclosed in US 2014/0044738, the entire disclosures of which are hereby incorporated by reference. In illustrative embodiments, 1E12 or an antigen-binding fragment thereof for use in the methods provided herein comprises a heavy chain variable region comprising the amino acid sequence of SEQ ID NO: 1043; and/or a light chain variable region comprising the amino acid sequence of SEQ ID NO: 1044.

In an embodiment, the targeting moiety comprises the anti-PD-L1 antibody 1F4, or fragments thereof, as disclosed in US 2014/0044738, the entire disclosures of which are hereby incorporated by reference. In illustrative embodiments, 1F4 or an antigen-binding fragment thereof for use in the methods provided herein comprises a heavy chain variable region comprising the amino acid sequence of SEQ ID NO: 1045; and/or a light chain variable region comprising the amino acid sequence of SEQ ID NO: 1046.

In an embodiment, the targeting moiety comprises the anti-PD-L1 antibody 2G11, or fragments thereof, as disclosed in US 2014/0044738, the entire disclosures of which are hereby incorporated by reference. In illustrative embodiments, 2G11 or an antigen-binding fragment thereof for use in the methods provided herein comprises a heavy chain variable region comprising the amino acid sequence of SEQ ID NO: 1047; and/or a light chain variable region comprising the amino acid sequence of SEQ ID NO: 1048.

In an embodiment, the targeting moiety comprises the anti-PD-L1 antibody 3B6, or fragments thereof, as disclosed in US 2014/0044738, the entire disclosures of which are hereby incorporated by reference. In illustrative embodiments, 3B6 or an antigen-binding fragment thereof for use in the methods provided herein comprises a heavy chain variable region comprising the amino acid sequence of SEQ ID NO: 1049; and/or a light chain variable region comprising the amino acid sequence of SEQ ID NO: 1050.

In an embodiment, the targeting moiety comprises the anti-PD-L1 antibody 3D10, or fragments thereof, as disclosed in US 2014/0044738 and WO2012/145493, the entire disclosures of which are hereby incorporated by reference. In illustrative embodiments, 3D10 or an antigen-binding fragment thereof for use in the methods provided herein comprises a heavy chain variable region comprising the amino acid sequence of SEQ ID NO: 1051; and/or a light chain variable region comprising the amino acid sequence of SEQ ID NO: 1052.

In an embodiment, the targeting moiety comprises any one of the anti-PD-L1 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 34-38 of US2011/0271358: SEQ ID No: 34 of US2011/0271358 (SEQ ID NO: 1053); SEQ ID No: 35 of US2011/0271358 (SEQ ID NO: 1054); SEQ ID No: 36 of US2011/0271358 (SEQ ID NO: 1055); SEQ ID No: 37 of US2011/0271358 (SEQ ID NO: 1056); SEQ ID No: 38 of US2011/0271358 (SEQ ID NO: 1057); and/or a light chain comprising an amino acid sequence selected from SEQ ID Nos: 39-42 of US2011/0271358: SEQ ID No: 39 of US2011/

0271358 (SEQ ID NO: 1058); SEQ ID No: 40 of US2011/0271358 (SEQ ID NO: 1059); SEQ ID No: 41 of US2011/0271358 (SEQ ID NO: 1060); or SEQ ID No: 42 of US2011/0271358 (SEQ ID NO: 1061).

In an embodiment, the targeting moiety comprises the anti-PD-L1 antibody 2.7A4, or fragments thereof, as disclosed in WO 2011/066389, U.S. Pat. No. 8,779,108, and US2014/0356353, the entire disclosures of which are hereby incorporated by reference. In illustrative embodiments, 2.7A4 or an antigen-binding fragment thereof for use in the methods provided herein comprises a heavy chain variable region comprising the amino acid sequence of: SEQ ID No: 2 of WO 2011/066389 (SEQ ID NO: 1062); and/or a light chain variable region comprising the amino acid sequence of SEQ ID NO: 1063.

In an embodiment, the targeting moiety comprises the anti-PD-L1 antibody 2.9D10, or fragments thereof, as disclosed in WO 2011/066389, U.S. Pat. No. 8,779,108, and US2014/0356353, the entire disclosures of which are hereby incorporated by reference. In illustrative embodiments, 2.9D10 or an antigen-binding fragment thereof for use in the methods provided herein comprises a heavy chain variable region comprising the amino acid sequence of: SEQ ID No: 12 of WO 2011/066389 (SEQ ID NO: 1064); and/or a light chain variable region comprising the amino acid sequence of SEQ ID NO: 1065.

In an embodiment, the targeting moiety comprises the anti-PD-L1 antibody 2.14H9, or fragments thereof, as disclosed in WO 2011/066389, U.S. Pat. No. 8,779,108, and US2014/0356353, the entire disclosures of which are hereby incorporated by reference. In illustrative embodiments, 2.14H9 or an antigen-binding fragment thereof for use in the methods provided herein comprises a heavy chain variable region comprising the amino acid sequence of: SEQ ID No: 22 of WO 2011/066389 (SEQ ID NO: 1066); and/or a light chain variable region comprising the amino acid sequence of SEQ ID No: 27 of WO 2011/066389 (SEQ ID NO: 1067).

In an embodiment, the targeting moiety comprises the anti-PD-L1 antibody 2.20A8, or fragments thereof, as disclosed in WO 2011/066389, U.S. Pat. No. 8,779,108, and US2014/0356353, the entire disclosures of which are hereby incorporated by reference. In illustrative embodiments, 2.20A8 or an antigen-binding fragment thereof for use in the methods provided herein comprises a heavy chain variable region comprising the amino acid sequence of: SEQ ID No: 32 of WO 2011/066389 (SEQ ID NO: 1068); and/or a light chain variable region comprising the amino acid sequence of SEQ ID No: 37 of WO 2011/066389 (SEQ ID NO: 1069).

In an embodiment, the targeting moiety comprises the anti-PD-L1 antibody 3.15G8, or fragments thereof, as disclosed in WO 2011/066389, U.S. Pat. No. 8,779,108, and US2014/0356353, the entire disclosures of which are hereby incorporated by reference. In illustrative embodiments, 3.15G8 or an antigen-binding fragment thereof for use in the methods provided herein comprises a heavy chain variable region comprising the amino acid sequence of: SEQ ID No: 42 of WO 2011/066389 (SEQ ID NO: 1070); and/or a light chain variable region comprising the amino acid sequence of SEQ ID No: 47 of WO 2011/066389 (SEQ ID NO: 1071).

In an embodiment, the targeting moiety comprises the anti-PD-L1 antibody 3.18G1, or fragments thereof, as disclosed in WO 2011/066389, U.S. Pat. No. 8,779,108, and US2014/0356353, the entire disclosures of which are hereby incorporated by reference. In illustrative embodiments, 3.18G1 or an antigen-binding fragment thereof for use in the methods provided herein comprises a heavy chain variable region comprising the amino acid sequence of SEQ ID No: 52 of WO 2011/066389 (SEQ ID NO: 1072); and/or a light chain variable region comprising the amino acid sequence of SEQ ID No: 57 of WO 2011/066389 (SEQ ID NO: 1073).

In an embodiment, the targeting moiety comprises the anti-PD-L1 antibody 2.7A4OPT, or fragments thereof, as disclosed in WO 2011/066389, U.S. Pat. No. 8,779,108, and US2014/0356353, and US2014/0356353, the entire disclosures of which are hereby incorporated by reference. In illustrative embodiments, 2.7A4OPT or an antigen-binding fragment thereof for use in the methods provided herein comprises a heavy chain variable region comprising the amino acid sequence of SEQ ID No: 62 of WO 2011/066389 (SEQ ID NO: 1074); and/or a light chain variable region comprising the amino acid sequence of SEQ ID No: 67 of WO 2011/066389 (SEQ ID NO: 1075).

In an embodiment, the targeting moiety comprises the anti-PD-L1 antibody 2.14H9OPT, or fragments thereof, as disclosed in WO 2011/066389, U.S. Pat. No. 8,779,108, and US2014/0356353, the entire disclosures of which are hereby incorporated by reference. In illustrative embodiments, 2.14H9OPT or an antigen-binding fragment thereof for use in the methods provided herein comprises a heavy chain variable region comprising the amino acid sequence of: SEQ ID No: 72 of WO 2011/066389 (SEQ ID NO: 1076); and/or a light chain variable region comprising the amino acid sequence of SEQ ID No: 77 of WO 2011/066389 (SEQ ID NO: 1077).

In an embodiment, the targeting moiety comprises any one of the anti-PD-L1 antibodies disclosed in WO2016/061142, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 18, 30, 38, 46, 50, 54, 62, 70, and 78 of WO2016/061142: SEQ ID No: 18 of WO2016/061142 (SEQ ID NO: 1078); SEQ ID No: 30 of WO2016/061142 (SEQ ID NO: 1079); SEQ ID No: 38 of WO2016/061142 (SEQ ID NO: 1080); SEQ ID No: 46 of WO2016/061142 (SEQ ID NO: 1081); SEQ ID No: 50 of WO2016/061142 (SEQ ID NO: 1082); SEQ ID No: 54 of WO2016/061142 (SEQ ID NO: 1083); SEQ ID No: 62 of WO2016/061142 (SEQ ID NO: 1084); SEQ ID No: 70 of WO2016/061142 (SEQ ID NO: 1085); SEQ ID No: 78 of WO2016/061142 (SEQ ID NO: 1086); and/or a light chain comprising an amino acid sequence selected from SEQ ID Nos: 22, 26, 34, 42, 58, 66, 74, 82, and 86 of WO2016/061142: SEQ ID No: 22 of WO2016/061142 (SEQ ID NO: 1087); SEQ ID No: 26 of WO2016/061142 (SEQ ID NO: 1088); SEQ ID No: 34 of WO2016/061142 (SEQ ID NO: 1089); SEQ ID No: 42 of WO2016/061142 (SEQ ID NO: 1090); SEQ ID No: 58 of WO2016/061142 (SEQ ID NO: 1091); SEQ ID No: 66 of WO2016/061142 (SEQ ID NO: 1092); SEQ ID No: 74 of WO2016/061142 (SEQ ID NO: 1093); SEQ ID No: 82 of WO2016/061142 (SEQ ID NO: 1094); or SEQ ID No: 86 of WO2016/061142 (SEQ ID NO: 1095).

In an embodiment, the targeting moiety comprises any one of the anti-PD-L1 antibodies disclosed in WO2016/022630, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 2, 6, 10, 14, 18, 22, 26, 30, 34, 38, 42, and 46 of WO2016/022630: SEQ ID No: 2 of WO2016/022630 (SEQ ID NO: 1096); SEQ ID No: 6 of WO2016/022630 (SEQ ID NO: 1097); SEQ ID No: 10 of WO2016/022630 (SEQ ID NO: 1098);

SEQ ID No: 14 of WO2016/022630 (SEQ ID NO: 1099); SEQ ID No: 18 of WO2016/022630 (SEQ ID NO: 1100); SEQ ID No: 22 of WO2016/022630 (SEQ ID NO: 1101); SEQ ID No: 26 of WO2016/022630 (SEQ ID NO: 1102); SEQ ID No: 30 of WO2016/022630 (SEQ ID NO: 1103); SEQ ID No: 34 of WO2016/022630 (SEQ ID NO: 1104); SEQ ID No: 38 of WO2016/022630 (SEQ ID NO: 1105); SEQ ID No: 42 of WO2016/022630 (SEQ ID NO: 1106); SEQ ID No: 46 of WO2016/022630 (SEQ ID NO: 1107); and/or a light chain comprising an amino acid sequence selected from SEQ ID Nos: 4, 8, 12, 16, 20, 24, 28, 32, 36, 40, 44, and 48 of WO2016/022630: SEQ ID No: 4 of WO2016/022630 (SEQ ID NO: 1108); SEQ ID No: 8 of WO2016/022630 (SEQ ID NO: 1109); SEQ ID No: 12 of WO2016/022630 (SEQ ID NO: 1110); SEQ ID No: 16 of WO2016/022630 (SEQ ID NO: 1111); SEQ ID No: 20 of WO2016/022630 (SEQ ID NO: 1112); SEQ ID No: 24 of WO2016/022630 (SEQ ID NO: 1113); SEQ ID No: 28 of WO2016/022630 (SEQ ID NO: 1114); SEQ ID No: 32 of WO2016/022630 (SEQ ID NO: 1115); SEQ ID No: 36 of WO2016/022630 (SEQ ID NO: 1116); SEQ ID No: 40 of WO2016/022630 (SEQ ID NO: 1117); SEQ ID No: 44 of WO2016/022630 (SEQ ID NO: 1118); or SEQ ID No: 48 of WO2016/022630 (SEQ ID NO: 1119).

In an embodiment, the targeting moiety comprises any one of the anti-PD-L1 antibodies disclosed in WO2015/112900, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 38, 50, 82, and 86 of WO 2015/112900: SEQ ID No: 38 of WO2015/112900 (SEQ ID NO: 1120); SEQ ID No: 50 of WO 2015/112900 (SEQ ID NO: 1121); SEQ ID No: 82 of WO 2015/112900 (SEQ ID NO: 1122); SEQ ID No: 86 of WO 2015/112900 (SEQ ID NO: 1123); and/or a light chain comprising an amino acid sequence selected from SEQ ID Nos: 42, 46, 54, 58, 62, 66, 70, 74, and 78 of WO 2015/112900: SEQ ID No: 42 of WO2015/112900 (SEQ ID NO: 1124); SEQ ID No: 46 of WO 2015/112900 (SEQ ID NO: 1125); SEQ ID No: 54 of WO 2015/112900 (SEQ ID NO: 1126); SEQ ID No: 58 of WO 2015/112900 (SEQ ID NO: 1127); SEQ ID No: 62 of WO 2015/112900 (SEQ ID NO: 1128); SEQ ID No: 66 of WO 2015/112900 (SEQ ID NO: 1129); SEQ ID No: 70 of WO 2015/112900 (SEQ ID NO: 1130); SEQ ID No: 74 of WO 2015/112900 (SEQ ID NO: 1131); or SEQ ID No: 78 of WO 2015/112900 (SEQ ID NO: 1132).

In an embodiment, the targeting moiety comprises any one of the anti-PD-L1 antibodies disclosed in WO 2010/077634 and U.S. Pat. No. 8,217,149, the entire disclosures of which are hereby incorporated by reference. In illustrative embodiments, the anti-PD-L1 antibody or an antigen-binding fragment thereof for use in the methods provided herein comprises a heavy chain region comprising the amino acid sequence of: SEQ ID No: 20 of WO 2010/077634 (SEQ ID NO: 1133); and/or a light chain variable region comprising the amino acid sequence of SEQ ID No: 21 of WO 2010/077634 (SEQ ID NO: 1134).

In an embodiment, the targeting moiety comprises any one of the anti-PD-L1 antibodies obtainable from the hybridoma accessible under CNCM deposit numbers CNCM I-4122, CNCM I-4080 and CNCM I-4081 as disclosed in US 20120039906, the entire disclosures of which are hereby incorporated by reference.

In an embodiment, the targeting moiety comprises a VHH directed against PD-L1 as disclosed, for example, in U.S. Pat. No. 8,907,065 and WO 2008/071447, the entire disclosures of which are hereby incorporated by reference. In illustrative embodiments, the VHHs against PD-L1 comprise SEQ ID NOS: 394-399 of U.S. Pat. No. 8,907,065: SEQ ID No: 394 of U.S. Pat. No. 8,907,065 (SEQ ID NO: 1135); SEQ ID No: 395 of U.S. Pat. No. 8,907,065 (SEQ ID NO: 1136); SEQ ID No: 396 of U.S. Pat. No. 8,907,065 (SEQ ID NO: 1137); SEQ ID No: 397 of U.S. Pat. No. 8,907,065 (SEQ ID NO: 1138); SEQ ID No: 398 of U.S. Pat. No. 8,907,065 (SEQ ID NO: 1139); or SEQ ID No: 399 of U.S. Pat. No. 8,907,065 (SEQ ID NO: 1140).

In some embodiments, the PD-L1 targeting moiety comprising an amino acid sequence selected from SEQ ID NOs: 1135-1140 having one or more substitutions at positions 11, 37, 44, 45, 47, 83, 84, 103, 104, and 108 (according to Kabat numbering). In some embodiments, the amino acid at position 11 is L, M, S, V, or W. In some embodiments, the amino acid at position 37 is F, Y, H, I, L, or V. In some embodiments, the amino acid at position 44 is G, E, A, D, Q, R, S, or L. In some embodiments, the amino acid at position 45 is L, R, C, I, L, P, Q, or V. In some embodiments, the amino acid at position 47 is W, L, F, A, G, I, M, R, S, V or Y. In some embodiments, the amino acid at position 83 is R, K, N, E, G, I, M, Q or T. In some embodiments, the amino acid at position 84 is P, A, L, R, S, T, D, or V. In some embodiments, the amino acid at position 103 is W, P, R, or S; 104-G or D. In some embodiments, the amino acid at position 108 is Q, L, or R.

In various embodiments, the present multi-specific PD-1 or PD-L1 binding agent has one or more targeting moieties directed against PD-L2. In some embodiments, the PD-1 or PD-L1 binding agent has one or more targeting moieties which selectively bind a PD-L2 polypeptide. In some embodiments, the PD-1 or PD-L1 binding agent comprises one or more antibodies, antibody derivatives or formats, peptides or polypeptides, or fusion proteins that selectively bind a PD-L2 polypeptide.

In an embodiment, the targeting moiety comprises a VHH directed against PD-L2 as disclosed, for example, in U.S. Pat. No. 8,907,065 and WO 2008/071447, the entire disclosures of which are hereby incorporated by reference. In illustrative embodiments, the VHHs against PD-1 comprise SEQ ID Nos: 449-455 of U.S. Pat. No. 8,907,065: SEQ ID No: 449 of U.S. Pat. No. 8,907,065 (SEQ ID NO: 1141); SEQ ID No: 450 of U.S. Pat. No. 8,907,065 (SEQ ID NO: 1142); SEQ ID No: 451 of U.S. Pat. No. 8,907,065 (SEQ ID NO: 1143); SEQ ID No: 452 of U.S. Pat. No. 8,907,065 (SEQ ID NO: 1144); SEQ ID No: 453 of U.S. Pat. No. 8,907,065 (SEQ ID NO: 1145); SEQ ID No: 454 of U.S. Pat. No. 8,907,065 (SEQ ID NO: 1146); or SEQ ID No: 455 of U.S. Pat. No. 8,907,065 (SEQ ID NO: 1147).

In some embodiments, the PD-L2 targeting moiety comprising an amino acid sequence selected from SEQ ID NOs: 1141-1147 having one or more substitutions at positions 11, 37, 44, 45, 47, 83, 84, 103, 104, and 108 (according to Kabat numbering). In some embodiments, the amino acid at position 11 is L, M, S, V, or W. In some embodiments, the amino acid at position 37 is F, Y, H, I, L, or V. In some embodiments, the amino acid at position 44 is G, E, A, D, Q, R, S, or L. In some embodiments, the amino acid at position 45 is L, R, C, I, L, P, Q, or V. In some embodiments, the amino acid at position 47 is W, L, F, A, G, I, M, R, S, V or Y. In some embodiments, the amino acid at position 83 is R, K, N, E, G, I, M, Q or T. In some embodiments, the amino acid at position 84 is P, A, L, R, S, T, D, or V. In some embodiments, the amino acid at position 103 is W, P, R, or S; 104-G or D. In some embodiments, the amino acid at position 108 is Q, L, or R.

In various embodiments, the PD-L2 targeting moiety comprises a VHH having a variable domain comprising at least one CDR1, CDR2, and/or CDR3 sequences. In various embodiments, the PD-L2 binding agent comprises a VHH having a variable region comprising at least one FR1, FR2, FR3, and FR4 sequences.

In some embodiments, the PD-L2 CDR1 sequence is selected from SEQ ID NO: 1148 to SEQ ID NO: 1154.

In some embodiments, the PD-L2 CDR2 sequence is selected from SEQ ID NO: 1155 to SEQ ID NO: 1161.

In some embodiments, the PD-L2 CDR3 sequence is selected from SEQ ID NO: 1162 to SEQ ID NO: 1168.

In an embodiment, the targeting moiety comprises any one of the anti-PD-L2 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 43-47 of US2011/0271358: SEQ ID No: 43 of US2011/0271358 (SEQ ID NO: 1169); SEQ ID No: 44 of US2011/0271358 (SEQ ID NO: 1170); SEQ ID No: 45 of US2011/0271358 (SEQ ID NO: 1171); SEQ ID No: 46 of US2011/0271358 (SEQ ID NO: 1172); SEQ ID No: 47 of US2011/0271358 (SEQ ID NO: 1173); and/or a light chain comprising an amino acid sequence selected from SEQ ID Nos: 48-51 of US2011/0271358: SEQ ID No: 48 of US2011/0271358 (SEQ ID NO: 1174); SEQ ID No: 49 of US2011/0271358 (SEQ ID NO: 1175); SEQ ID No: 50 of US2011/0271358 (SEQ ID NO: 1176); or SEQ ID No: 51 of US2011/0271358 (SEQ ID NO: 1177).

In various embodiments, the targeting moieties of the invention may comprise a sequence that targets PD-1, PD-L1, and/or PD-L2 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target PD-1, PD-L1, and/or PD-L2 as disclosed herein.

Additional antibodies, antibody derivatives or formats, peptides or polypeptides, or fusion proteins that selectively bind or target PD-1, PD-L1 and/or PD-L2 are disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

In various embodiments, the multispecific PD-1 or PD-L1 binding agent of the present technology comprises a targeting moiety against signal regulatory protein α-1 (SIRP1α). SIRP1α (also known as SIRPα) belongs to a family of cell immune receptors encompassing inhibitory (SIRPα), activating (SIRPβ), nonsignaling (SIRPγ) and soluble (SIRPδ) members. SIRP1α is expressed primarily on myeloid cells, including macrophages, granulocytes, myeloid dendritic cells (DCs), mast cells, and their precursors, including hematopoietic stem cells. SIRP1α acts as an inhibitory receptor that interacts with a broadly expressed transmembrane glycoprotein CD47 to regulate phagocytosis. In particular, the binding of SIRP1α on macrophages by CD47 expressed on target cells, generates an inhibitory signal that negatively regulates phagocytosis of the target cell.

In various embodiments, the SIRP1α targeting moiety is a targeting moiety that specifically recognizes and binds SIRP1α on macrophages.

In various embodiments, the SIRP1α targeting moiety is a targeting moiety that specifically recognizes and binds SIRP1α on monocytes.

In various embodiments, the SIRP1α targeting moiety is a targeting moiety that specifically recognizes and binds SIRP1α on TAMs (Tumor Associated Macrophages).

In various embodiments, the SIRP1α targeting moiety is a targeting moiety that specifically recognizes and binds SIRP1α on dendritic cells, including without limitation cDC2 and pDC.

In various embodiments, the SIRP1α targeting moiety comprises a targeting moiety having a recognition domain that recognizes SIRP1α. In an embodiment, the recognition domain recognizes one or more linear epitopes present on SIRP1α. As used herein, a linear epitope refers to any continuous sequence of amino acids present on SIRP1α. In another embodiment, the recognition domain recognizes one or more conformational epitopes present on SIRP1α. As used herein, a conformation epitope refers to one or more sections of amino acids (which may be discontinuous) which form a three-dimensional surface with features and/or shapes and/or tertiary structures capable of being recognized by an antigen recognition domain.

In some embodiments, the SIRP1α targeting moiety may bind to the full-length and/or mature forms and/or isoforms and/or splice variants and/or fragments and/or any other naturally occurring or synthetic analogs, variants, or mutants of SIRP1α. In an embodiment, the SIRP1α is human SIRP1α. In various embodiments, the SIRP1α targeting moiety may bind to any forms of the human SIRP1α, including monomeric, dimeric, heterodimeric, multimeric and associated forms. In an embodiment, the SIRP1α targeting moiety binds to the monomeric form of SIRP1α. In another embodiment, the SIRP1α targeting moiety binds to a dimeric form of SIRP1α.

In an embodiment, the SIRP1α targeting moiety comprises a recognition domain that recognizes one or more epitopes present on human SIRP1α. In an embodiment, the SIRP1α targeting moiety comprises a recognition domain that recognizes human SIRP1α with a signal peptide sequence. An exemplary human SIRP1α polypeptide with a signal peptide sequence is SEQ ID NO: 1178.

In an embodiment, the SIRP1α targeting moiety comprises a recognition domain that recognizes human SIRP1α without a signal peptide sequence. An exemplary human SIRP1α polypeptide without a signal peptide sequence is SEQ ID NO: 1179.

In an embodiment, the SIRP1α targeting moiety comprises a recognition domain that recognizes a polypeptide encoding human SIRP1α isoform 2 is SEQ ID NO: 1180.

In an embodiment, the SIRP1α targeting moiety comprises a recognition domain that recognizes a polypeptide encoding human SIRP1α isoform 4 is SEQ ID NO: 1181.

In various embodiments, the SIRP1α targeting moieties may be any protein-based agent capable of specific binding, such as an antibody or derivatives thereof. In an embodiment, the SIRP1α targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the SIRP1α targeting moiety comprises antibody derivatives or formats. In some embodiments, the SIRP1α targeting moiety is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibodies; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')$_2$, a peptide mimetic molecule, or a synthetic molecule, as described in US patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In one embodiment, the SIRP1α targeting comprises a single-domain antibody, such as VHH from, for example, an organism that produces VHH antibody such as a camelid, a shark, or a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3).

In an embodiment, the SIRP1α targeting moiety comprises a VHH. In some embodiments, the VHH is a humanized VHH or camelized VHH.

In some embodiments, the VHH comprises a fully human $V_H$ domain, e.g. a HUMABODY (Crescendo Biologics, Cambridge, UK). In some embodiments, fully human $V_H$ domain, e.g. a HUMABODY is monovalent, bivalent, or trivalent. In some embodiments, the fully human $V_H$ domain, e.g. a HUMABODY is mono- or multi-specific such as monospecific, bispecific, or trispecific. Illustrative fully human $V_H$ domains, e.g. a HUMABODIES are described in, for example, WO 2016/113555 and WO2016/113557, the entire disclosure of which is incorporated by reference.

For example, in some embodiments, the SIRP1α targeting moiety comprises one or more antibodies, antibody derivatives or formats, peptides or polypeptides, VHHs, or fusion proteins that selectively bind SIRP1α. In some embodiments, the SIRP1α targeting moiety comprises an antibody or derivative thereof that specifically binds to SIRP1α. In some embodiments, the SIRP1α targeting moiety is a camelid heavy chain antibody (VHH) that specifically binds to SIRP1α.

In various embodiments, the SIRP1α targeting moieties may comprise any combination of heavy chain, light chain, heavy chain variable region, light chain variable region, complementarity determining region (CDR), and framework region sequences that is known to recognize and bind to SIRP1α.

In various embodiments, the present technology contemplates the use of any natural or synthetic analogs, mutants, variants, alleles, homologs and orthologs (herein collectively referred to as "analogs") of the SIRP1α targeting moiety described herein. In various embodiments, the amino acid sequence of the SIRP1α targeting moiety further includes an amino acid analog, an amino acid derivative, or other non-classical amino acids.

In various embodiments, the SIRP1α targeting moieties comprise an amino acid sequence having one or more amino acid mutations with respect to any targeting moiety sequence that is known to recognize and bind to SIRP1α. In various embodiments, the SIRP1α targeting moiety comprises an amino acid sequence having one, or two, or three, or four, or five, or six, or seen, or eight, or nine, or ten, or fifteen, twenty, thirty, forty, or fifty amino acid mutations with respect to any targeting moiety sequence, which is known to recognize and bind to SIRP1α. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3)

acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids. Exemplary non-classical amino acids include, but are not limited to, selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, 3-alanine, fluoro-amino acids, designer amino acids such as β methyl amino acids, C α-methyl amino acids, N α-methyl amino acids, and amino acid analogs in general.

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the SIRP1α targeting moiety's capability to specifically recognize and bind to SIRP1α. In various embodiments, the mutations do not substantially reduce the SIRP1α targeting moiety's capability to specifically bind to SIRP1α and without functionally modulating (e.g., partially or fully neutralizing) SIRP1α.

In various embodiments, the SIRP1α targeting moiety binds but does not functionally modulate the antigen of interest, i.e., SIRP1α. For instance, in various embodiments, the SIRP1α targeting moiety simply targets the antigen but does not substantially functionally modulate (e.g. substantially inhibit, reduce or neutralize) a biological effect that the antigen has. In various embodiments, the SIRP1α targeting moiety binds an epitope that is physically separate from an antigen site that is important for its biological activity (e.g. an antigen's active site).

In other embodiments, the SIRP1α targeting moiety binds and functionally modulates the antigen of interest, i.e., SIRP1α. For instance, in various embodiments, the SIRP1α targeting moiety targets the antigen, i.e., SIRP1α, and functionally modulates (e.g. inhibit, reduce or neutralize) a biological effect that the antigen has. Such binding along with functional modulation may find use in various embodiments of the present invention including methods in which the present chimeric protein is used to directly or indirectly recruit active immune cells to a site of need via an effector antigen.

In various embodiments, the multi-specific PD-1 or PD-L1 binding agent of the invention comprises a targeting moiety having an antigen recognition domain that specifically binds to XCR1, e.g. on DCs. In various embodiments, the multi-specific PD-1 or PD-L1 binding agent of the invention comprises a targeting moiety having an antigen recognition domain that comprise all of or part of XCL1.

In various embodiments, the multi-specific PD-1 or PD-L1 binding agents have targeting moieties having recognition domains which specifically bind to a target (e.g. antigen, receptor) which is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic tumor cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In various embodiments, the target (e.g. antigen, receptor) of interest is part of the non-cellular component of the stroma such as the extracellular matrix and extracellular molecules. As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In various embodiments, the chimeric protein of the invention comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes a target (e.g. antigen, receptor) on ECM proteoglycans. Proteoglycans are glycosylated proteins. The basic proteoglycan unit includes a core protein with one or more covalently attached glycosaminoglycan (GAG) chains. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Illustrative proteoglycans that may be targeted by the chimeric proteins of the invention include, but are not limited to, heparan sulfate, chondroitin sulfate, and keratan sulfate. In an embodiment, the targeting moiety recognizes a target (e.g. antigen, receptor) on non-proteoglycan polysaccharides such as hyaluronic acid.

In some embodiments, the targeting moiety recognizes a target (e.g. antigen, receptor) on ECM fibers. ECM fibers include collagen fibers and elastin fibers. In some embodiments, the targeting moiety recognizes one or more epitopes on collagens or collagen fibers. Collagens are the most abundant proteins in the ECM. Collagens are present in the ECM as fibrillar proteins and provide structural support to resident cells. In one or more embodiments, the targeting moiety recognizes and binds to various types of collagens present within the ECM including, without limitation, fibrillar collagens (types I, II, III, V, XI), facit collagens (types IX, XII, XIV), short chain collagens (types VIII, X), basement membrane collagens (type IV), and/or collagen types VI, VII, or XIII. Elastin fibers provide elasticity to tissues, allowing them to stretch when needed and then return to their original state. In some embodiments, the target moiety recognizes one or more epitopes on elastins or elastin fibers.

In some embodiments, the targeting moiety recognizes one or more ECM proteins including, but not limited to, a tenascin, a fibronectin, a fibrin, a laminin, or a nidogen/entactin.

In an embodiment, the targeting moiety recognizes and binds to tenascin. The tenascin (TN) family of glycoproteins includes at least four members, tenascin-C, tenascin-R, tenascin-X, and tenascin W. The primary structures of tenascin proteins include several common motifs ordered in the same consecutive sequence: amino-terminal heptad repeats, epidermal growth factor (EGF)-like repeats, fibronectin type III domain repeats, and a carboxyl-terminal fibrinogen-like globular domain. Each protein member is associated with typical variations in the number and nature of EGF-like and fibronectin type III repeats. Isoform variants also exist particularly with respect to tenascin-C. Over 27 splice variants and/or isoforms of tenascin-C are known. In a particular embodiment, the targeting moiety recognizes and binds to tenascin-CA1. Similarly, tenascin-R also has various splice variants and isoforms. Tenascin-R usually exists as dimers or trimers. Tenascin-X is the largest member of the tenascin family and is known to exist as trimers. Tenascin-W exists as trimers. In some embodiments, the targeting moiety recognizes one or more epitopes on a tenascin protein. In some embodiments, the targeting moiety recognizes the monomeric and/or the dimeric and/or the trimeric and/or the hexameric forms of a tenascin protein.

In an embodiment, the targeting moieties recognize and bind to fibronectin. Fibronectins are glycoproteins that connect cells with collagen fibers in the ECM, allowing cells to move through the ECM. Upon binding to integrins, fibronectins unfolds to form functional dimers. In some embodiments, the targeting moiety recognizes the monomeric and/or the dimeric forms of fibronectin. In some embodiments, the targeting moiety recognizes one or more epitopes on fibronectin. In illustrative embodiments, the targeting moiety recognizes fibronectin extracellular domain A (EDA) or fibronectin extracellular domain B (EDB). Elevated levels of EDA are associated with various diseases and disorders including psoriasis, rheumatoid arthritis, diabetes, and cancer. In some embodiments, the targeting moiety recognizes fibronectin that contains the EDA isoform and may be utilized to target the chimeric protein to diseased cells including cancer cells. In some embodiments, the targeting moiety recognizes fibronectin that contains the EDB isoform. In various embodiments, such targeting moieties may be utilized to target the chimeric protein to tumor cells including the tumor neovasculature.

In an embodiment, the targeting moiety recognizes and binds to fibrin. Fibrin is another protein substance often found in the matrix network of the ECM. Fibrin is formed by the action of the protease thrombin on fibrinogen which causes the fibrin to polymerize. In some embodiments, the targeting moiety recognizes one or more epitopes on fibrin. In some embodiments, the targeting moiety recognizes the monomeric as well as the polymerized forms of fibrin.

In an embodiment, the targeting moiety recognizes and binds to laminin. Laminin is a major component of the basal lamina, which is a protein network foundation for cells and organs. Laminins are heterotrimeric proteins that contain an α-chain, a β-chain, and a γ-chain. In some embodiments, the targeting moiety recognizes one or more epitopes on laminin. In some embodiments, the targeting moiety recognizes the monomeric, the dimeric as well as the trimeric forms of laminin.

In an embodiment, the targeting moiety recognizes and binds to a nidogen or entactin. Nidogens/entactins are a family of highly conserved, sulfated glycoproteins. They make up the major structural component of the basement membranes and function to link laminin and collagen IV networks in basement membranes. Members of this family include nidogen-1 and nidogen-2. In various embodiments, the targeting moiety recognizes an epitope on nidogen-1 and/or nidogen-2.

In various embodiments, the targeting moiety comprises an antigen recognition domain that recognizes an epitope present on any of the targets (e.g., ECM proteins) described herein. In an embodiment, the antigen-recognition domain recognizes one or more linear epitopes present on the protein. As used herein, a linear epitope refers to any continuous sequence of amino acids present on the protein. In another embodiment, the antigen-recognition domain recognizes one or more conformational epitopes present on the protein. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the targeting moiety may bind to the full-length and/or mature forms and/or isoforms and/or splice variants and/or fragments and/or any other naturally occurring or synthetic analogs, variants, or mutants of any of the targets (e.g., ECM proteins) described herein. In various embodiments, the targeting moiety may bind to any forms of the proteins described herein, including monomeric, dimeric, trimeric, tetrameric, heterodimeric, multimeric and associated forms. In various embodiments, the targeting moiety may bind to any post-translationally modified forms of the proteins described herein, such as glycosylated and/or phosphorylated forms.

In various embodiments, the targeting moiety comprises an antigen recognition domain that recognizes extracellular molecules such as DNA. In some embodiments, the targeting moiety comprises an antigen recognition domain that recognizes DNA. In an embodiment, the DNA is shed into the extracellular space from necrotic or apoptotic tumor cells or other diseased cells.

In various embodiments, the targeting moiety comprises an antigen recognition domain that recognizes one or more non-cellular structures associated with atherosclerotic plaques. Two types of atherosclerotic plaques are known. The fibro-lipid (fibro-fatty) plaque is characterized by an accumulation of lipid-laden cells underneath the intima of the arteries. Beneath the endothelium there is a fibrous cap covering the atheromatous core of the plaque. The core includes lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger foamy cells and capillaries. A fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and lipid-laden cells. In some embodiments, the targeting moiety recognizes and binds to one or more of the non-cellular components of these plaques such as the fibrin, proteoglycans, collagen, elastin, cellular debris, and calcium or other mineral deposits or precipitates. In some embodiments, the cellular debris is a nucleic acid, e.g. DNA or RNA, released from dead cells.

In various embodiments, the targeting moiety comprises an antigen recognition domain that recognizes one or more non-cellular structures found in the brain plaques associated with neurodegenerative diseases. In some embodiments, the targeting moiety recognizes and binds to one or more non-cellular structures located in the amyloid plaques found in the brains of patients with Alzheimer's disease. For example, the targeting moiety may recognize and bind to the peptide amyloid beta, which is a major component of the amyloid plaques. In some embodiments, the targeting moiety recognizes and binds to one or more non-cellular structures located in the brains plaques found in patients with Huntington's disease. In various embodiments, the targeting moiety recognizes and binds to one or more non-cellular structures found in plaques associated with other neurodegenerative or musculoskeletal diseases such as Lewy body dementia and inclusion body myositis. Linkers and Functional Groups In various embodiments, the PD-1 or PD-L1 binding agent may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the PD-1 or PD-L1 binding agent of the invention. Examples of such functional groups and of techniques for introducing them into the PD-1 or PD-L1 binding agent are known in the art, for example, see Remington's Pharmaceutical Sciences, 16th ed., Mack Publishing Co., Easton, Pa. (1980).

In various embodiments, the PD-1 or PD-L1 binding agent may by conjugated and/or fused with another agent to extend half-life or otherwise improve pharmacodynamic and pharmacokinetic properties. In some embodiments, the PD-1 or PD-L1 binding agent may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the PD-1 or PD-L1 binding agent may be fused or conjugated with an antibody or an antibody fragment such as an Fc fragment. For example, the chimeric protein may be fused to either the N-terminus or the C-terminus of the Fc domain of human immunoglobulin (Ig) G. In various embodiments, each of the individual chimeric proteins is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenecity of the PD-1 or PD-L1 binding protein. Generally, any suitable form of pegylation can be used, such as the pegylation used in the art for antibodies and antibody fragments (including but not limited to single domain antibodies such as VHHs); see, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). For example, for this purpose, PEG may be attached to a cysteine residue that naturally occurs in the PD-1 or PD-L1 binding agent of the invention. In some embodiments, the PD-1 or PD-L1 binding agent of the invention is modified so as to suitably introduce one or more cysteine residues for attachment of PEG, or an amino acid sequence comprising one or more cysteine residues for attachment of PEG may be fused to the amino- and/or carboxy-terminus of the PD-1 or PD-L1 binding agent, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the PD-1 or PD-L1 binding agent. In some embodiments, the PD-1 or PD-L1 binding agent may include a single tag or multiple tags. The tag for example is a peptide, sugar, or DNA molecule that does not inhibit or prevent binding of the PD-1 or PD-L1 binding agent to PD-1 or PD-L1 or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the PD-1 or PD-L1 binding agent comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the PD-1 or PD-L1 binding agent of the invention to another protein, polypeptide or chemical compound that is bound to the other half of the binding pair, i.e., through formation of the binding pair. For example, a PD-1 or PD-L1 binding agent of the invention may be conjugated to biotin, and linked to another protein, polypeptide, compound or carrier conjugated to avidin or streptavidin. For example, such a conjugated PD-1 or PD-L1 binding agent may be used as a reporter, for example, in a diagnostic system where a detectable signal-producing agent is conjugated to avidin or streptavidin. Such binding pairs may, for example, also be used to bind the PD-1 or PD-L1 binding agent to a carrier, including carriers suitable for pharmaceutical purposes. One non-limiting example are the liposomal formulations described by Cao and Suresh, *Journal of Drug Targeting*, 8, 4, 257 (2000). Such binding pairs may also be used to link a therapeutically active agent to the PD-1 or PD-L1 binding agent of the invention.

In some embodiments, the present PD-1 or PD-L1 binding agent optionally comprises one or more linkers. In some embodiments, the PD-1 or PD-L1 binding agent includes a linker that connects each binding region and/or targeting moieties. In some embodiments, the PD-1 or PD-L1 binding agent includes a linker that connects each signaling agent and targeting moiety (or, if more than one targeting moiety, a signaling agent to one of the targeting moieties). In some embodiments, the linker may be utilized to link various functional groups, residues, or moieties as described herein to the PD-1 or PD-L1 binding agent. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments, the present PD-1 or PD-L1 binding agent comprises a linker connecting the targeting moiety and the signaling agent. In some embodiments, the present chimeric protein comprises a linker within the signaling agent (e.g. in the case of single chain TNF, which can comprise two linkers to yield a trimer).

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present PD-1 or PD-L1 binding agent.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments, the linker length allows for efficient binding of a targeting moiety and the signaling agent to their receptors. For instance, in some embodiments, the linker length allows for efficient binding of one of the targeting moieties and the signaling agent to receptors on the same cell as well as the efficient binding of the other targeting moiety to another cell. Illustrative pairs of cells are provided elsewhere herein.

In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

In some embodiments, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is (Gly4Ser)$_n$, where n is from about 1 to about 8, e.g. 1, 2, 3, 4, 5, 6, 7, or 8 (SEQ ID NOs: 1182-1189). In an embodiment, the linker sequence is GGSGGSGGGGSGGGS (SEQ ID NO: 1190). Additional illustrative linkers include, but are not limited to, linkers having the sequence LE, GGGGS (SEQ ID NO: 1182), (GGGGS)$_n$ (n=1-4) (SEQ ID NOs: 1182-1185), (Gly)$_8$ (SEQ ID NO: 1191), (Gly)$_6$ (SEQ ID NO: 1192), (EAAAK)$_n$ (n=1-3) (SEQ ID NOs: 1193-1195), A(EAAAK)$_n$A (n=2-5) (SEQ ID NOs: 1196-1199), AEAAAKEAAAKA (SEQ ID NO: 1196), A(EAAAK)$_4$ALEA(EAAAK)$_4$A (SEQ ID NO: 1200), PAPAP (SEQ ID NO: 1201), KESGSVSSE-QLAQFRSLD (SEQ ID NO: 1202), EGKSSGSGSESKST (SEQ ID NO: 1203), GSAGSAAGSGEF (SEQ ID NO: 1204), and (XP)$_n$, with X designating any amino acid, e.g., Ala, Lys, or Glu. In various embodiments, the linker is (GGS)n (n=1-20) (SEQ ID NO: 1205-SEQ ID NO: 1224). In some embodiments, the linker is G. In some embodiments, the linker is MA. In some embodiments, the linker is (GGGGS)n (n=9-20) (SEQ ID NOs: 1225-1236).

In some embodiments, the linker is one or more of GGGSE (SEQ ID NO: 1237), GSESG (SEQ ID NO: 1238), GSEGS (SEQ ID NO: 1239), GEGGSGEGSSGEGSSSEGGGSEGGGSEGGGSEGGS (SEQ ID NO: 1240), and a linker of randomly placed G, S, and E every 4 amino acid intervals.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence SEQ ID NO: 1241, which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites. In various embodiments, the linker is a hinge-CH2-CH3 domain of a human IgG4 antibody.

If desired, the present PD-1 or PD-L1 binding agent can be linked to an antibody Fc region, comprising one or both of $C_H2$ and $C_H3$ domains, and optionally a hinge region. For example, vectors encoding the present PD-1 or PD-L1 binding agents linked as a single nucleotide sequence to an Fc region can be used to prepare such polypeptides.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present PD-1 or PD-L1 binding agent. In another example, the linker may function to target the PD-1 or PD-L1 binding agent to a particular cell type or location.

Modifications and Production of PD-1 or PD-L1 Binding Agents

In various embodiments, the PD-1 or PD-L1 binding agent comprises a targeting moiety that is a VHH. In various embodiments, the VHH is not limited to a specific biological source or to a specific method of preparation. For example, the VHH can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the PD-1 or PD-L1 binding agent comprises a VHH that corresponds to the VHH domains of naturally occurring heavy chain antibodies directed against human PD-1 or PD-L1. In some embodiments, such VHH sequences can generally be generated or obtained by suitably immunizing a species of Camelid with a PD-1 or PD-L1 molecule, (i.e., so as to raise an immune response and/or heavy chain antibodies directed against PD-1 or PD-L1), by obtaining a suitable biological sample from the Camelid (such as a blood sample, or any sample of B-cells), and by generating VHH sequences directed against PD-1 or PD-L1, starting from the sample, using any suitable known techniques. In some embodiments, naturally occurring VHH domains against PD-1 or PD-L1 can be obtained from naive libraries of Camelid VHH sequences, for example, by screening such a library using PD-1 or PD-L1 or at least one part, fragment, antigenic determinant or epitope thereof using one or more screening techniques known in the art. Such libraries and techniques are, for example, described in WO9937681, WO0190190, WO03025020 and WO03035694, the entire contents of which are hereby incorporated by reference. In some embodiments, improved synthetic or semi-synthetic libraries derived from naive $V_HH$ libraries may be used, such as VHH libraries obtained from naive $V_HH$ libraries by techniques such as random mutagenesis and/or CDR shuffling, as for example, described in WO0043507, the entire contents of which are hereby incorporated by reference. In some embodiments, another technique for obtaining VHH sequences directed against a PD-1 or PD-L1 involves suitably immunizing a transgenic mammal that is capable of expressing heavy chain antibodies (i.e., so as to raise an immune response and/or heavy chain antibodies directed against PD-1 or PD-L1), obtaining a suitable biological sample from the transgenic mammal (such as a blood sample, or any sample of B-cells), and then generating VHH sequences directed against PD-1 or PD-L1 starting from the sample, using any suitable known techniques. For example, for this purpose, the heavy chain antibody-expressing mice and the further methods and techniques described in WO02085945 and in WO04049794 (the entire contents of which are hereby incorporated by reference) can be used.

In an embodiment, the PD-1 or PD-L1 binding agent comprises a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring VHH domains. In various embodiments, the humanized VHHs of the invention can be obtained in any suitable manner known in the art and thus are not strictly limited to polypeptides that have been obtained using a polypeptide that comprises a naturally occurring VHH domain as a starting material.

In an embodiment, the PD-1 or PD-L1 binding agent comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_HH$ domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_HH$ domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_HH$ domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_HH$ sequences, are known in the art, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Methods for producing the PD-1 or PD-L1 binding agents of the invention are described herein. For example, DNA sequences encoding the PD-1 or PD-L1 binding agents of the invention can be chemically synthesized using methods known in the art. Synthetic DNA sequences can be ligated to other appropriate nucleotide sequences, including, e.g., expression control sequences, to produce gene expression constructs encoding the desired PD-1 or PD-L1 binding agents. Accordingly, in various embodiments, the present invention provides for isolated nucleic acids comprising a nucleotide sequence encoding the PD-1 or PD-L1 binding agent of the invention.

Nucleic acids encoding the PD-1 or PD-L1 binding agent of the invention can be incorporated (ligated) into expression vectors, which can be introduced into host cells through transfection, transformation, or transduction techniques. For example, nucleic acids encoding the PD-1 or PD-L1 binding agent of the invention can be introduced into host cells by retroviral transduction. Illustrative host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the PD-1 or PD-L1 binding agent of the invention. Accordingly, in various embodiments, the present invention provides expression vectors comprising nucleic acids that encode the PD-1 or PD-L1 binding agent of the invention. In various embodiments, the present invention additional provides host cells comprising such expression vectors.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The PD-1 or PD-L1 binding agent of the invention can be produced by growing a host cell transfected with an expression vector encoding the PD-1 or PD-L1 binding agent under conditions that permit expression of the protein. Following expression, the protein can be harvested and purified using techniques well known in the art, e.g., affinity tags such as glutathione-S-transferase (GST) and histidine (His) tags or by chromatography. In an embodiment, the PD-1 or PD-L1 binding agent comprises a His tag. In an embodiment, the PD-1 or PD-L1 binding agent comprises a His tag and a proteolytic site to allow cleavage of the His tag.

Accordingly, in various embodiments, the present invention provides for a nucleic acid encoding a PD-1 or PD-L1 binding agent of the present invention. In various embodiments, the present invention provides for a host cell comprising a nucleic acid encoding a PD-1 or PD-L1 binding agent of the present invention.

In various embodiments, the present PD-1 or PD-L1 binding agent or chimeric protein comprising the same may be expressed in vivo, for instance, in a patient. For example, in various embodiments, the present PD-1 or PD-L1 binding agent or chimeric protein comprising the same may administered in the form of nucleic acid which encodes the present PD-1 or PD-L1 binding agents or chimeric proteins comprising the same. In various embodiments, the nucleic acid is DNA or RNA. In some embodiments, present PD-1 or PD-L1 binding agent or chimeric protein comprising the same is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, LP, and 2'-O-methyl-U. In some embodiments, the present invention relates to administering a modified mRNA encoding one or more of the present chimeric proteins. In some embodiments, the present invention relates to gene therapy vectors comprising the same. In some embodiments, the present invention relates to gene therapy methods comprising the same. In various embodiments, the nucleic acid is in the form of an oncolytic virus, e.g. an adenovirus, reovirus, measles, herpes simplex, Newcastle disease virus or vaccinia.

Pharmaceutically Acceptable Salts and Excipients

The PD-1 or PD-L1 binding agents (and/or any other therapeutic agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use.* P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-0H-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the PD-1 or PD-L1 binding agents (and/or any other therapeutic agents) described herein and a pharmaceutically acceptable carrier or excipient. In some embodiments, the present invention pertains to pharmaceutical compositions comprising the present PD-1 or PD-L1 binding agents. In another embodiment, the present invention pertains to pharmaceutical compositions comprising any other therapeutic agents described herein. In a further embodiment, the present invention pertains to pharmaceutical compositions comprising a combination of the present PD-1 or PD-L1 binding agents and any other therapeutic agents described herein. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the PD-1 or PD-L1 binding agent described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any PD-1 or PD-L1 binding agents described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the PD-1 or PD-L1 binding agent and/or any therapeutic agents described herein to be administered according to the present invention will vary according to the particular dosage form, and the mode of administration. Many factors that may modify the action of the PD-1 or PD-L1 binding agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the PD-1 or PD-L1 binding agent and/or any therapeutic agents described herein is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

Individual doses of the PD-1 or PD-L1 binding agent and/or any therapeutic agents described herein can be administered in unit dosage forms containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the PD-1 or PD-L1 binding agent and/or any therapeutic agents described herein are administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the PD-1 or PD-L1 binding agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the invention, the pharmaceutical composition comprising the PD-1 or PD-L1 binding agent and/or any therapeutic agents described herein may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the PD-1 or PD-L1 binding agent of the present invention are administered to a subject simultaneously. The term "simultaneously" as used herein, means that the additional therapeutic agent and the PD-1 or PD-L1 binding agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the PD-1 or PD-L1 binding agent can be by simultaneous administration of a single formulation (e.g., a formulation comprising the additional therapeutic agent and the PD-1 or PD-L1 binding agent) or of separate formulations (e.g., a first formulation including the additional therapeutic agent and a second formulation including the PD-1 or PD-L1 binding agent).

Co-administration does not require the therapeutic agents to be administered simultaneously, if the timing of their administration is such that the pharmacological activities of the additional therapeutic agent and the PD-1 or PD-L1 binding agent overlap in time, thereby exerting a combined therapeutic effect. For example, the additional therapeutic agent and the PD-1 or PD-L1 binding agent can be administered sequentially. The term "sequentially" as used herein means that the additional therapeutic agent and the PD-1 or PD-L1 binding agent are administered with a time separation of more than about 60 minutes. For example, the time between the sequential administration of the additional therapeutic agent and the PD-1 or PD-L1 binding agent can be more than about 60 minutes, more than about 2 hours, more than about 5 hours, more than about 10 hours, more than about 1 day, more than about 2 days, more than about 3 days, more than about 1 week, or more than about 2 weeks, or more than about one month apart. The optimal administration times will depend on the rates of metabolism, excretion, and/or the pharmacodynamic activity of the additional therapeutic agent and the PD-1 or PD-L1 binding agent being administered. Either the additional therapeutic agent or the PD-1 or PD-L1 binding agent cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the PD-1 or PD-L1 binding agent described herein acts synergistically when co-administered with another therapeutic agent. In such embodiments, the PD-1 or PD-L1 binding agent and the additional therapeutic agent may be administered at doses that are lower than the doses employed when the agents are used in the context of monotherapy.

In some embodiments, the present invention pertains to chemotherapeutic agents as additional therapeutic agents. For example, without limitation, such combination of the present PD-1 or PD-L1 binding agents and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Accordingly, in some embodiments, the present invention relates to combination therapies using the PD-1 or PD-L1 binding agent and a chemotherapeutic agent. In some embodiments, the present invention relates to administration of the PD-1 or PD-L1 binding agent to a patient undergoing treatment with a chemotherapeutic agent. In some embodiments, the chemotherapeutic agent is a DNA-intercalating agent such as, without limitation, doxorubicin, cisplatin, daunorubicin, and epirubicin. In an embodiment, the DNA-intercalating agent is doxorubicin.

In illustrative embodiments, the PD-1 or PD-L1 binding agent acts synergistically when co-administered with doxorubicin. In an illustrative embodiment, the PD-1 or PD-L1 binding agent acts synergistically when co-administered with doxorubicin for use in treating tumor or cancer. For example, co-administration of the PD-1 or PD-L1 binding agent and doxorubicin may act synergistically to reduce or eliminate the tumor or cancer, or slow the growth and/or progression and/or metastasis of the tumor or cancer. In illustrative embodiments, the combination of the PD-1 or PD-L1 binding agent and doxorubicin may exhibit improved safety profiles when compared to the agents used alone in the context of monotherapy. In illustrative embodiments, the PD-1 or PD-L1 binding agent and doxorubicin may be administered at doses that are lower than the doses employed when the agents are used in the context of monotherapy. In some embodiments, the PD-1 or PD-L1 binding agent comprises a mutated interferon such as a mutated IFNα. In illustrative embodiments, the mutated IFNα comprises one or more mutations at positions 148, 149, and 153 with reference to SEQ ID NO: 317 or SEQ ID NO: 318, such as the substitutions M148A, R149A, and L153A.

In some embodiments, the present invention relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric protein is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric protein is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present invention relates to combination therapy using the PD-1 or PD-L1 binding agent and a checkpoint inhibitor. In some embodiments, the present invention relates to administration of the PD-1 or PD-L1 binding agent to a patient undergoing treatment with a checkpoint inhibitor. In some embodiments, the checkpoint inhibitor is an agent that targets one or more of PD-1, PD-L1, PD-L2, and CTLA-4 (including any of the anti-PD-1, anti-PD-L1, anti-PD-L2, and anti-CTLA-4 agents described herein). In some embodiment, the checkpoint inhibitor is one or more of nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE), ipilimumab (MDX-010, MDX-101, Yervoy, BMS) and tremelimumab (Pfizer). In an embodiment, the checkpoint inhibitor is an antibody against PD-L1.

In illustrative embodiments, the PD-1 or PD-L1 binding agent acts synergistically when co-administered with the anti-PD-L1 antibody. In an illustrative embodiment, the PD-1 or PD-L1 binding agent acts synergistically when co-administered with the anti-PD-L1 antibody for use in treating tumor or cancer. For example, co-administration of the PD-1 or PD-L1 binding agent and the anti-PD-L1 antibody may act synergistically to reduce or eliminate the tumor or cancer, or slow the growth and/or progression and/or metastasis of the tumor or cancer. In some embodiments, the combination of the PD-1 or PD-L1 binding agent and the anti-PD-L1 antibody may exhibit improved safety profiles when compared to the agents used alone in the context of monotherapy. In some embodiments, the PD-1 or PD-L1 binding agent and the anti-PD-L1 antibody may be administered at doses that are lower than the doses employed when the agents are used in the context of monotherapy. In some embodiments, the PD-1 or PD-L1 binding agent comprises a mutated interferon such as a mutated IFNα. In illustrative embodiments, the mutated IFNα comprises one or more mutations at positions 148, 149, and 153 with reference to SEQ ID NO: 317 or SEQ ID NO: 318, such as the substitutions M148A, R149A, and L153A.

In some embodiments, the present invention relates to combination therapies using the PD-1 or PD-L1 binding agent and an immunosuppressive agent. In some embodiments, the present invention relates to administration of the PD-1 or PD-L1 binding agent to a patient undergoing treatment with an immunosuppressive agent. In an embodiment, the immunosuppressive agent is TNF.

In illustrative embodiments, the PD-1 or PD-L1 binding agent acts synergistically when co-administered with TNF. In an illustrative embodiment, the PD-1 or PD-L1 binding agent acts synergistically when co-administered with TNF for use in treating tumor or cancer. For example, co-administration of the PD-1 or PD-L1 binding agent and TNF may act synergistically to reduce or eliminate the tumor or cancer, or slow the growth and/or progression and/or metastasis of the tumor or cancer. In some embodiments, the combination of the PD-1 or PD-L1 binding agent and TNF may exhibit improved safety profiles when compared to the agents used alone in the context of monotherapy. In some embodiments, the PD-1 or PD-L1 binding agent and TNF may be administered at doses that are lower than the doses employed when the agents are used in the context of monotherapy. In some embodiments, the PD-1 or PD-L1 binding agent comprises a mutated interferon such as a mutated IFNα. In illustrative embodiments, the mutated IFNα comprises one or more mutations at positions 148, 149, and 153 with reference to SEQ ID NO: 317 or SEQ ID NO: 318, such as the substitutions M148A, R149A, and L153A.

In some embodiments, the PD-1 or PD-L1 binding agent acts synergistically when used in combination with Chimeric Antigen Receptor (CAR) T-cell therapy. In an illustrative embodiment, the PD-1 or PD-L1 binding agent acts synergistically when used in combination with CAR T-cell therapy in treating tumor or cancer. In an embodiment, the PD-1 or PD-L1 binding agent acts synergistically when used in combination with CAR T-cell therapy in treating blood-based tumors. In an embodiment, the PD-1 or PD-L1 binding agent acts synergistically when used in combination with CAR T-cell therapy in treating solid tumors. For example, use of the PD-1 or PD-L1 binding agent and CAR T-cells may act synergistically to reduce or eliminate the tumor or cancer, or slow the growth and/or progression and/or metastasis of the tumor or cancer. In various embodiments, the PD-1 or PD-L1 binding agent of the invention induces CAR T-cell division. In various embodiments, the PD-1 or PD-L1 binding agent of the invention induces CAR T-cell proliferation. In various embodiments, the PD-1 or PD-L1 binding agent of the invention prevents anergy of the CAR T cells.

In various embodiments, the CAR T-cell therapy comprises CAR T cells that target antigens (e.g., tumor antigens) such as, but not limited to, carbonic anhydrase IX (CAIX), 5T4, CD19, CD20, CD22, CD30, CD33, CD38, CD47, CS1, CD138, Lewis-Y, L1-CAM, MUC16, ROR-1, IL13Rα2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-α), GD2, human epidermal growth factor receptor 2 (HER2), mesothelin, EGFRvIII, fibroblast activation protein (FAP), carcinoembryonic antigen (CEA), and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

Exemplary CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford BioMedica, MB-101 (Mustang Bio) and CAR T-cells developed by Innovative Cellular Therapeutics.

In some embodiments, the PD-1 or PD-L1 binding agent is used in a method of treating multiple sclerosis (MS) in combination with one or more MS therapeutics including, but not limited to, 3-interferons, glatiramer acetate, T-interferon, IFN-β-2 (U.S. Patent Publication No. 2002/0025304), spirogermaniums (e.g., N-(3-dimethylaminopropyl)-2-aza-8,8-dimethyl-8-germanspiro [4:5] decane, N-(3-dimethylaminopropyl)-2-aza-8,8-diethyl-8-germaspiro[4:5] decane, N-(3-dimethylaminopropyl)-2-aza-8,8-dipropyl-8-germaspiro[4:5] decane, and N-(3-dimethylaminopropyl)-2-aza-8,8-dibutyl-8-germaspiro[4:5] decane), vitamin D analogs (e.g., 1,25 (OH) 2D3, (see, e.g., U.S. Pat. No. 5,716, 946)), prostaglandins (e.g., latanoprost, brimonidine, PGE1, PGE2 and PGE3, see, e.g., U.S. Patent Publication No. 2002/0004525), tetracycline and derivatives (e.g., minocycline and doxycycline, see, e.g., U.S. Patent Publication No. 20020022608), a VLA-4 binding antibody (see, e.g., U.S. Patent Publication No. 2009/0202527), adrenocorticotrophic hormone, corticosteroid, prednisone, methylprednisone, 2-chlorodeoxyadenosine, mitoxantrone, sulphasalazine, methotrexate, azathioprine, cyclophosphamide, cyclosporin, fumarate, anti-CD20 antibody (e.g., rituximab), and tizanidine hydrochloride.

In some embodiments, the PD-1 or PD-L1 binding agent is used in combination with one or more therapeutic agents that treat one or more symptoms or side effects of MS. Such agents include, but are not limited to, amantadine, baclofen, papaverine, meclizine, hydroxyzine, sulfamethoxazole, ciprofloxacin, docusate, pemoline, dantrolene, desmopressin, dexamethasone, tolterodine, phenyloin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline.

In some embodiments, the PD-1 or PD-L1 binding agent is used in a method of treating multiple sclerosis in combination with one or more of the disease modifying therapies (DMTs) described herein (e.g. the agents of Table A). In some embodiments, the present invention provides an improved therapeutic effect as compared to use of one or more of the DMTs described herein (e.g. the agents listed in the Table below) without the one or more disclosed binding agent. In an embodiment, the combination of the PD-1 or PD-L1 binding agent and the one or more DMTs produces synergistic therapeutic effects.

In some embodiments, the PD-1 or PD-L1 binding agent is used in a method of treating multiple sclerosis in combination with one or more of the disease modifying therapies (DMTs) described herein (e.g. the agents of Table A). In some embodiments, the present invention provides an improved therapeutic effect as compared to use of one or more of the DMTs described herein (e.g. the agents listed in the Table below) without the one or more disclosed binding agent. In an embodiment, the combination of the PD-1 or PD-L1 binding agent and the one or more DMTs produces synergistic therapeutic effects.

| Illustrative Disease Modifying Therapies | | |
|---|---|---|
| Generic Name | Branded Name/Company | Frequency/Route of Delivery/Usual Dose |
| teriflunomide | AUBAGIO (GENZYME) | Every day; pill taken orally; 7 mg or 14 mg. |
| interferon beta-1a | AVONEX (BIOGEN IDEC) | Once a week; intramuscular (into the muscle) injection; 30 mcg |
| interferon beta-1b | BETASERON (BAYER HEALTHCARE PHARMACEUTICALS, INC.) | Every other day; subcutaneous (under the skin) injection; 250 mcg. |
| glatiramer acetate | COPAXONE (TEVA NEUROSCIENCE) | Every day; subcutaneous (under the skin) injection; 20 mg (20,000 mcg) OR Three times a week; subcutaneous (under the skin) injection; 40 mg (40,000 mcg) |

-continued

Illustrative Disease Modifying Therapies

| Generic Name | Branded Name/Company | Frequency/Route of Delivery/Usual Dose |
| --- | --- | --- |
| interferon beta-1b | EXTAVIA (NOVARTIS PHARMACEUTICALS CORP.) | Every other day; subcutaneous (under the skin) injection; 250 mcg. |
| fingolimod | GILENYA (NOVARTIS PHARMACEUTICALS CORP.) | Every day; capsule taken orally; 0.5 mg. |
| Alemtuzumab (anti-CD52 monoclonal antibody) | LEMTRADA (GENZYME) | Intravenous infusion on five consecutive days, followed by intravenous infusion on three consecutive days one year later (12 mg) |
| mitoxantrone | NOVANTRONE (EMD SERONO) | Four times a year by IV infusion in a medical facility. Lifetime cumulative dose limit of approximately 8-12 doses over 2-3 years (140 mg/m2). |
| pegylated interferon beta-1a | PLEGRIDY (BIOGEN IDEC) | Every 14 days; subcutaneous (under the skin) injection; 125 mcg |
| interferon beta-1a | REBIF (EMD SERONO, INC.) | Three times a week; subcutaneous (under the skin) injection; 44 mcg |
| dimethyl fumarate (BG-12) | TECFIDERA (BIOGEN IDEC) | Twice a day; capsule taken orally; 120 mg for one week and 240 mg therafter |
| Natalizumab (humanized monoclonal antibody VLA-4 antagonist) | TYSABRI (BIOGEN IDEC) | Every four weeks by IV infusion in a registered infusion facility; 300 mg |
| DMTs in Development | | |
| Amiloride (targets Acid-sensing ion channel-1 Epithelial sodium channel Na+/H+ exchanger) | PAR PHARMACEUTICAL, PERRIGO COMPANY, SIGMAPHARM LABORATORIES | Oral |
| ATX-MS-1467 (targets Major histocompatibility complex class II T cell responses to myelin basic protein) | APITOPE/MERCK SERONO | Intradermal Subcutaneous |
| BAF312 (targets Sphingosine 1-phosphate (S1P) receptor subtypes S1P1 and S1P5 B cell distrubution T cell distribution) | NOVARTIS PHARMA | Oral |
| BGC20-0134 (targets Proinflammatory and anti-inflammatory cytokines) | BTG PLC | Oral |
| BIIB033 (targets LINGO-1 ("leucine-rich repeat and immunoglobulin-like domain-containing, Nogo receptor-interacting protein")) | BIOGEN | Intravenous infusion used in Phase I and Phase II trials Subcutaneous injection used in Phase I trial |
| Cladribine (targets CD4+ T cells DNA synthesis and repair E-selectin Intracellular adhesion molecule-1 Pro-inflammatory cytokines interleukin 2 and interleukin 2R Pro-inflammatory cytokines interleukin 8 and RANTES Cytokine secretion Monocyte and lymphocyte migration) | MERCK SERONO | Oral |
| Cyclophosphamide (targets T cells, particularly CD4+ helper T cells B cells) | BAXTER HEALTHCARE CORPORATION | Oral, monthly intravenous pulses |
| Daclizumab (humanized monoclonal antibody targeting CD25 Immune modulator of T cells) | BIOGEN IDEC/ABBVIE BIOTHERAPEUTICS | Projected to be IM injection once monthly |
| Dalfampridine (targets Voltage-gated potassium channels Degenerin/epithelial sodium channels L-type calcium channels that contain subunit Cavbeta3 | ACORDA THERAPEUTICS/ BIOGEN IDEC | One tablet every 12 hours (extended release), 10 mg twice a day |
| Dronabinol (targets Cannabinoid receptor CB1 Cannabinoid receptor CB2) | ABBVIE INC. | Oral |
| Firategrast (targets Alpha4beta1 integrin) | GLAXOSMITHKLINE | Oral |

Illustrative Disease Modifying Therapies

| Generic Name | Branded Name/Company | Frequency/Route of Delivery/Usual Dose |
|---|---|---|
| GNbAC1MSRV-Env (targets envelope protein of the MS-associated retrovirus) | GENEURO SA/SERVIER | Intravenous infusion |
| Idebenone (targets Reactive oxygen species) | SANTHERA PHARMACEUTICALS | Oral Dose in clinical trial for PPMS is 2250 mg per day (750 mg dose, 3 times per day) |
| Imilecleucel-T (targets Myelin-specific, autoreactive T cells) | OPEXA THERAPEUTICS/ MERCK SERONO | Subcutaneous Given 5 times per year, according to information from the manufacturer |
| Laquinimod | TEVA | Projected to be 0.6 mg or 1.2 mg oral tablet taken daily |
| Masitinib (targets KIT (a stem cell factor, also called c-KIT) receptor as well as select other tyrosine kinases Mast cells) | AB SCIENCE | Oral |
| MEDI-551 (targets CD19, a B cell-specific antigen that is part of the B cell receptor complex and that functions in determining the threshold for B cell activation B cells Plasmablasts, B cells that express CD19 (but not CD20) and that secrete large quantities of antibodies; depletion of plasmablasts may be useful in autoimmune diseases involving pathogenic autoantibodies | MEDIMMUNE | Intravenous Subcutaneous |
| Minocycline (targets T cells Microglia Leukocyte migration Matrix metalloproteinases) | VARIOUS | Oral Available as pellet-filled capsules and an oral suspension |
| MIS416 (targets Innate immune system Pathogen-associated molecular pattern recognition receptors of the innate immune system Myeloid cells of the innate immune system, which might be able to remodel the deregulated immune system activity that occurs in SPMS) | INNATE IMMUNOTHERAPEUTICS | Intravenous |
| Mycophenolate mofetil (targets Purine synthesis) | MANUFACTURED BY GENENTECH | Oral |
| Naltrexone (targets Opioid receptors Toll-like receptor 4) | VARIOUS | Given at low doses (3 to 4.5 mg per day) in oral form as "Low-dose naltrexone" (or "LDN") |
| Ocrelizumab and Ofatumumab (humanized monoclonal antibodies targeting CD20 B cell suppression | ROCHE/GSK | Projected to be IV infusion |
| ONO-4641 (targets Sphingosine 1-phosphate receptor) | ONO PHARMACEUTICAL CO. | Oral |
| Phenytoin (targets Sodium channels) | PFIZER | Intravenous Intramuscular (less favored option) Oral |
| Ponesimod | ACTELION | To be determined |
| Raltegravir (targets Retroviral integrase Herpesvirus DNA packaging terminase) | MERCK | Oral 400 mg tablet twice daily, according to information from the manufacturer |
| RHB-104 | REDHILL BIOPHARMA LIMITED | 95 mg clarithromycin, 45 mg rifabutin, and 10 mg clofazimine |
| Riluzole (targets Glutamatergic neurotransmission Glutamate uptake and release Voltage-gated sodium channels Protein kinase C) | COVIS PHARMA/SANOFI | Oral |

MS disease progression may be most intensive, and most damaging, at the earliest stages of disease progression. Accordingly, counter to many reimbursement policies and physician practice in light of, for example, costs and side effect mitigation, it may be most beneficial for a patient's long term disease status to begin treatment with the most intensive DMTs, for instance so-called second-line therapies. In some embodiments, a patient is treated with a regimen of the PD-1 or PD-L1 binding agent in combination with a second-line therapy. Such a combination is used to reduce the side effect profile of one or more second-line therapies. In some embodiments, the combination is used to reduce dose of frequency of administration of one or more second-line therapies. For example, the doses of agents listed in the Table provided above may be reduced by about 50%, or about 40%, or about 30%, or about 25% in the context of the combination and the/or the frequency of dosing may be decreased to be half as often, or a third as often or may be reduced from, for example, daily to every other day or weekly, every other day to weekly or bi-weekly, weekly to bi-weekly or monthly, etc. Accordingly, in some embodiments, the PD-1 or PD-L1 binding agent increase patient adherence by allowing for more convenient treatment regimens. Further, some DMTs have a suggested lifetime dose limitation e.g. for mitoxantrone, the lifetime cumulative dose should be strictly limited to 140 mg/m2, or 2 to 3 years of therapy. In some embodiments, supplementation with the PD-1 or PD-L1 binding agent preserves patient's access to mitoxantrone by allowing for lower or less frequent dosing with this DMT.

In some embodiments, the patient is a naive patient, who has not received treatment with one or more DMTs, and the PD-1 or PD-L1 binding agent is used to buffer the side effects of a second-line therapy. Accordingly, the naive patient is able to benefit from the long-term benefits of a second-line therapy at disease outset. In some embodiments, the PD-1 or PD-L1 binding agent is used as an entry therapy that precedes the use of a second-line therapy. For example, the PD-1 or PD-L1 binding agent may be administered for an initial treatment period of about 3 months to stabilize disease and then the patient may be transitioned to a maintenance therapy of a second line agent.

It is generally believed that naive patients are more likely to respond to therapy as compared to patients that have received, and perhaps failed one or more DMT. In some embodiments, the PD-1 or PD-L1 binding agent finds use in patients that have received, and perhaps failed one or more DMT. For example, in some embodiments, the PD-1 or PD-L1 binding agent increases the therapeutic effect in patients that have received, and perhaps failed one or more DMT and may allow these patients to respond like naive patients.

In some embodiments, the patient has received or is receiving treatment with one or more DMTs and is not responding well. For example, the patient may be refractory or poorly responsive to one or more DMTs. In some embodiments, the patient is refractory, or poorly responsive to one or more of teriflunomide (AUBAGIO (GENZYME)); interferon beta-1a (AVONEX (BIOGEN IDEC); interferon beta-1b (BETASERON (BAYER HEALTHCARE PHARMACEUTICALS, INC.); glatiramer acetate (COPAXONE (TEVA NEUROSCIENCE); interferon beta-1b (EXTAVIA (NOVARTIS PHARMACEUTICALS CORP.); fingolimod (GILENYA (NOVARTIS PHARMACEUTICALS CORP.); alemtuzumab (LEMTRADA (GENZYME); mitoxantrone (NOVANTRONE (EMD SERONO); pegylated interferon beta-1a (PLEGRIDY (BIOGEN IDEC); interferon beta-1a (REBIF (EMD SERONO, INC.); dimethyl fumarate (BG-12) (TECFIDERA (BIOGEN IDEC); and natalizumab (TYSABRI (BIOGEN IDEC). In some embodiments, the one or more disclosed binding agent results in a therapeutic benefit of one or more DMTs in the patient and therefore reduces or eliminates the non-responsiveness to the DMT. For instance, this may spare the patient therapy with one or more DMTs at a higher dosing or frequency.

In patients with more aggressive disease, one approach is an induction treatment model, where a therapy with strong efficacy but strong safety concerns would be given first, followed by a maintenance therapy. An example of such a model might include initial treatment with alemtuzumab, followed by IFN-β, GA, or BG-12. In some embodiments, the one or more disclosed binding agent is used to prevent the need to switch therapies for maintenance. In some embodiments, the one or more disclosed binding agent is used to as maintenance therapy to one or more DMTs, including second line therapies. In some embodiments, the one or more disclosed binding agent is used to as first therapy in an induction, followed by another DMT as a maintenance therapy—such as, for example, a first line therapy.

In some embodiments, the one or more disclosed binding agent may be administered for an initial treatment period of about 3 months to stabilize disease and then the patient may be transitioned to a maintenance therapy of a first line agent.

In various embodiments, the one or more disclosed binding agent is used to reduce one or more side effects of a DMT, including without limitation any agent disclosed herein. For example, the one or more disclosed binding agent may be used in a regimen that allows dose sparing for one or more DMTs and therefore results in fewer side effects. For example, in some embodiments, the one or more disclosed binding agent may reduce one or more side effects of AUBAGIO or related agents, which may include hair thinning, diarrhea, flu, nausea, abnormal liver tests and unusual numbness or tingling in the hands or feet (paresthesias), levels of white blood cells, which can increase the risk of infections; increase in blood pressure; and severe liver damage. In some embodiments, the one or more disclosed binding agent may reduce one or more side effects of AVONEX or related agents which include flu-like symptoms following injection, depression, mild anemia, liver abnormalities, allergic reactions, and heart problems. In some embodiments, the one or more disclosed binding agent may reduce one or more side effects of BETASERON or related agents which include flu-like symptoms following injection, injection site reactions, allergic reactions, depression, liver abnormalities, and low white blood cell counts. In some embodiments, the one or more disclosed binding agent may reduce one or more side effects of COPAXONE or related agents which include injection site reactions, vasodilation (dilation of blood vessels); chest pain; a reaction immediately after injection, which includes anxiety, chest pain, palpitations, shortness of breath, and flushing. In some embodiments, the one or more disclosed binding agent may reduce one or more side effects of EXTAVIA or related agents which include flu-like symptoms following injection, injection site reactions, allergic reactions, depression, liver abnormalities, and low white blood cell counts. In some embodiments, the one or more disclosed binding agent may reduce one or more side effects of GILENYA or related agents which include headache, flu, diarrhea, back pain, liver enzyme elevations, cough, slowed heart rate following first dose, infections, and swelling in the eye. In some embodiments, the one or more disclosed binding agent may reduce one or more side effects of LEMTRADA or related agents which include rash, headache, fever, nasal congestion, nausea, urinary tract infection, fatigue, insomnia, upper respiratory tract infection, hives, itching, thyroid gland disorders, fungal Infection, pain in joints, extremities and back, diarrhea, vomiting, flushing, and infusion reactions (including nausea, hives, itching, insomnia, chills, flushing, fatigue, shortness of breath, changes in the sense of taste, indigestion, dizziness, pain). In some embodiments, the one or more disclosed binding agent may reduce one or more side effects of NOVANTRONE or related agents which include blue-green urine 24 hours after administration; infections, bone marrow suppression (fatigue, bruising, low blood cell counts), nausea, hair thinning, bladder infections, mouth sores, and serious liver and heart damage. In some embodiments, the one or more disclosed binding agent may reduce one or more side effects of PLEGRIDY or related agents which include flu-like symptoms following injection, injection site reactions, depression, mild anemia, liver abnormalities, allergic reactions, and heart problems. In some embodiments, the one or more disclosed binding agent may reduce one or more side effects of REBIF or related agents which include flu-like symptoms following injection, injection site reactions, liver abnormalities, depression, allergic reactions, and low red or white blood cell counts. In some embodiments, one or more disclosed binding agent may reduce one or more side effects of TECFIDERA or related agents which include flushing (sensation of heat or itching and a blush on the skin), gastrointestinal issues (nausea, diarrhea, abdominal pain), rash, protein in the urine, elevated liver enzymes; and reduction in blood lymphocyte (white blood cell) counts. In some embodiments, the one or more disclosed binding agent may reduce one or more side effects of TYSABRI or related agents which include headache, fatigue, urinary tract infections, depression, respiratory tract infections, joint pain, upset stomach, abdominal discomfort, diarrhea, vaginitis, pain in the arms or legs, rash, allergic or hypersensitivity reactions within two hours of infusion (dizziness, fever, rash, itching, nausea, flushing, low blood pressure, difficulty breathing, chest pain).

In some embodiments, the present invention relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the PD-1 or PD-L1 binding agent described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the PD-1 or PD-L1 binding agent described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The PD-1 or PD-L1 binding agent described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *Vinca* alkaloids, vincristine and vinblastine. Other cytotoxic agents include paclitaxel (taxol), ricin, *Pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the PD-1 or PD-L1 binding agent, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, and inflammatory diseases or conditions.

Further, any of the present agents may be for use in the treating, or the manufacture of a medicament for treating, various diseases and disorders, including, but not limited to cancer, infections, immune disorders, inflammatory diseases or conditions, and autoimmune diseases.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); acute myeloid leukemia (AML); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In various embodiments, the present invention provides PD-1 or PD-L1 binding agents which are part of a chimera that further comprises modified signaling agents for the treatment of cancer. In some embodiments, the PD-1 or PD-L1 binding agents of the invention significantly reduce and/or eliminate tumors. In some embodiments, the present PD-1 or PD-L1 binding agents significant reduce and/or eliminate tumors when administered to a subject in combination with other anti-cancer agents such as chemotherapeutic agents, checkpoint inhibitors, and immunosuppressive agents. In various embodiments, the combination of PD-1 or PD-L1 binding agents and other anti-cancer agents synergistically reduced tumor size and/or eliminated tumor cells.

In various embodiments, the present invention relates to cancer combination therapies with a PD-1 or PD-L1 binding agent that is part of a chimera comprising one or more targeting moieties and one or more modified signaling agents. Accordingly, the present invention provides for chimeric or fusion proteins that include, for example, a targeting moiety against PD-1 or PD-L1 and one or more signaling agents and uses thereof in combination with anti-cancer agents.

For instance, in various embodiments, the present invention pertains to combination therapies for cancer involving chimeras of a PD-1 or PD-L1 binding agent described herein and a modified signaling agent, including, without limitation a mutated human interferon, such as IFN alpha, including human interferon alpha 2.

In some embodiments, the present invention relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present compositions are used to treat or prevent one or more autoimmune and/or neurodegenerative diseases or conditions, such as MS, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, myasthenia gravis, Reiter's syndrome, Grave's disease, and other autoimmune diseases.

In various embodiments, the present invention is used to treat or prevent various autoimmune and/or neurodegenerative diseases. In some embodiments, the autoimmune and/or neurodegenerative diseases selected from MS (including without limitation the subtypes described herein), Alzheimer's disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

Kits

The present invention also provides kits for the administration of any PD-1 or PD-L1 binding agent described herein (e.g. with or without additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired therapeutic outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the 1050 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

The term "AcTaferon (AFN)" is occasionally used herein to reference an interferon-based chimera.

In the following examples, unless noted, mutations to IFN are relative to human IFN-α2.

Example 1. Efficiency of Human PD-1 or PD-L1 Targeting of Mono-Specific Human Chimeras Efficiency of targeting by human AcTaferon alpha comprising PD-1 or PD-L1 antibodies was examined by FACS-based quantification of STAT1 phosphorylation. Specifically, targeting was analyzed in primary peripheral blood mononuclear cells (PBMCs), transfected Hek293T cells (for PD-1 targeting), or the human breast-cancer cell-line MDA-MB-321 (for PD-L1 targeting). The following antibodies were used:

Anti-PD-1 Antibodies:
 Pem: Pembrolizumab/Keytruda (Merck)
 Niv: Nivolumab/Opdivo (BMS)
Anti-PD-L1 Antibodies:
 Ate: Atezolizumab/Tecentriq/MPDL3280 (Roche/Genetech)
 Dur: Durvalumab/MED14736 (Celgene/AstraZeneca)
 Ave: Avelumab/MSB0010718C (Merck/Pfizer)
 Bms: BMS-936559/MDX-1105 (BMS)

The sequences of these antibodies are described elsewhere herein. With respect to the anti-PD-L1 BMS-936559/MDX-1105 antibody particularly, the variable domains of this antibody was grafted on an univesal human IgG. Accordingly, BMS-936559 or an antigen-binding fragment thereof for use in the methods provided herein comprises a heavy chain variable region comprising the amino acid sequence of SEQ ID NO: 1242; and/or a light chain variable region comprising the amino acid sequence of SEQ ID NO: 1243.

Following enfragment of the variable domains onto human IgG, the following heavy and light chain sequences are obtained:

Heavy: SEQ ID NO: 1244
Light: SEQ ID NO: 1245

The various antibody heavy chains were genetically fused to hIFNa2_R149 sequence (e.g., human IFN-α2 having a R149A mutation) via a flexible 20*GGS linker in the pMTW expression-vector (resulting vector: pMTW-SIgK-heavy chain-(GGS)$_{20}$-hIFNa2_R149A-GGS-(His)$_9$. The light chains were cloned in the same vector (resulting vector: pMTW-SIgK-light chain). A schematic of the cloning strategy is provided in FIG. 1. PD-L1 AFN's were produced by transient transfection of both plasmids in FreeStyle 293-F cells (ThermoFisher) with 25K PEI (polyethylenimine) according to standard protocols. Medium was harvested, cells removed by centrifugation and filter-sterilised. Recombinant proteins were purified using Ni Excel resin (GE Healthcare) according to the manufacturers instructions and imidazole removed from the samples with PD-10 columns (GE Healthcare).

Binding of PD-L1 Ab-AFN's to Transfected Hek293T Cells

Hek293T cells were transfected with the membrane-bound PD-1 or PD-L1 using calcium phosphate. Two days after transfection, cells were resuspended and incubated with PD-L1 Ab-AFN's (1 g/ml in FACS buffer: PBS supplemented with 2% FBS; 0.5 mM EDTA) for two hours at 4° C. After two washes, cells were incubated with FITC-coupled THE HIS antibody (GenScript; 1 hr at 4° C.). Binding was measured with a FACSCalibur instrument (BD Biosciences), with the CellQuest Pro Version 4.0.2 software (BD Biosciences). Data in FIG. 2 clearly illustrate that PD-L1 AFN's selectively bound to PD-L1 transfected cells, while PD-1 AFN's only bound to PD-1 expressing cells.

PD-1-Targeting: pSTAT1 in Peripheral Blood Mononuclear Cells (PBMC's)

Figure 3:
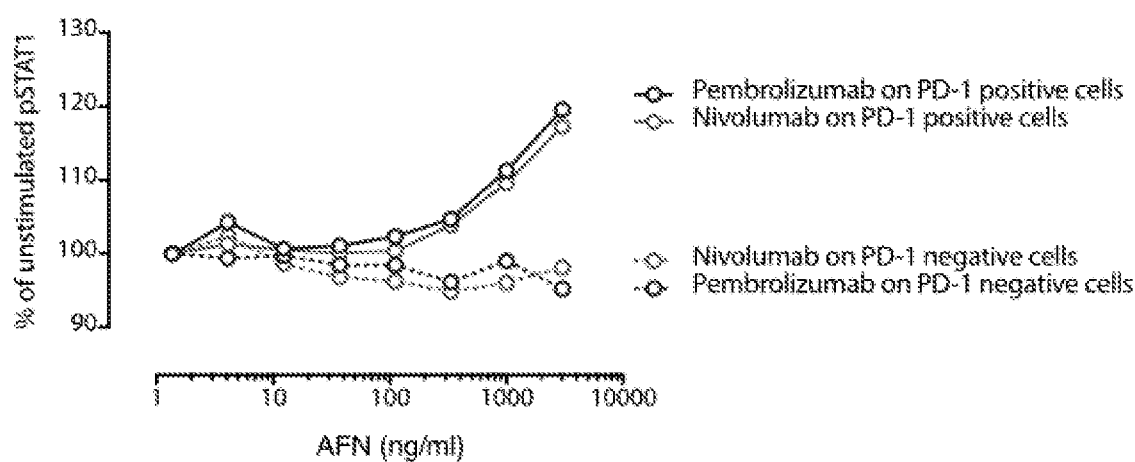
FIG. 3 shows PD-1-targeting as assessed by pSTAT1 status in peripheral blood mononuclear cells (PBMC's). Data are plotted as percentage of unstimulated pSTAT1 mean fluorescence intensity (MFI)

PBMCs from buffy coats of healthy donors were isolated using density gradient centrifugation with Lymphoprep (StemCell Technologies). Cells were washed twice with FACS buffer (2% FBS, 0.5 mM EDTA in PBS) and stained with FITC coupled anti-human PD-1 (clone PD-1.3.1.3; Miltenyi Biotec) for 20 minutes at 4° C. After two washes, cells were stimulated with a serial dilution PD-1 Ab-AFN's for 15 minutes at 37° C. After fixation (10 minutes, 37° C., Fix Buffer 1; BD Biosciences) and permeabilisation (30 minutes, on ice, Perm III Buffer I; BD Biosciences) and washing, cells were stained with anti-STAT1 pY701 Ab (BD Biosciences). Samples were acquired with a FACSCalibur (BD Biosciences), with the CellQuest Pro Version 4.0.2 software (BD Biosciences). Data in FIG. 3 show that Pembrolizumab and Nivolumab coupled AcTaferon's were able to phosphorylate STAT1 in PD-1 positive, but not PD-1 negative PBMC's.

PD-1-Targeting: pSTAT1 in Transfected Hek293T Cells

Figure 4:
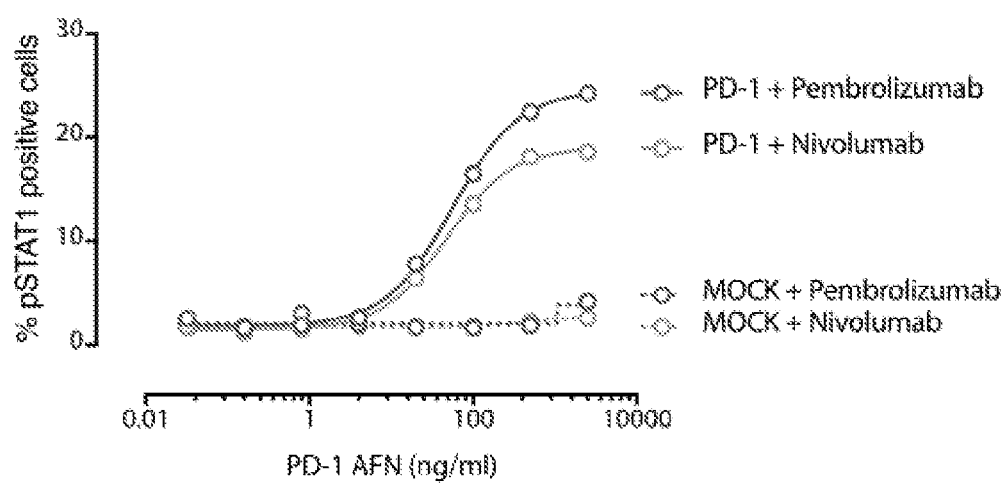
FIG. 4 shows PD-1-targeting as assessed by pSTAT1 status in transfected Hek293T cells. Percentage of pSTAT1 cells is plotted.

Hek293T cells were transfected with human PD-1 or an empty vector using calcium phosphate. After two days, cells were resuspended and stimulated with a serial dilution PD-1 AFN's (15 min; 37° C.). pSTAT1 was quantified as described above. Data in FIG. 4 illustrate that PD-1 Ab AFN's efficiently induce STAT1 phosphorylation in PD-1 expressing Hek293T cells, but not in MOCK transfected cells.

PD-L1-Targeting: pSTAT1 in MDA-MB-231 Cells

Figure 5:
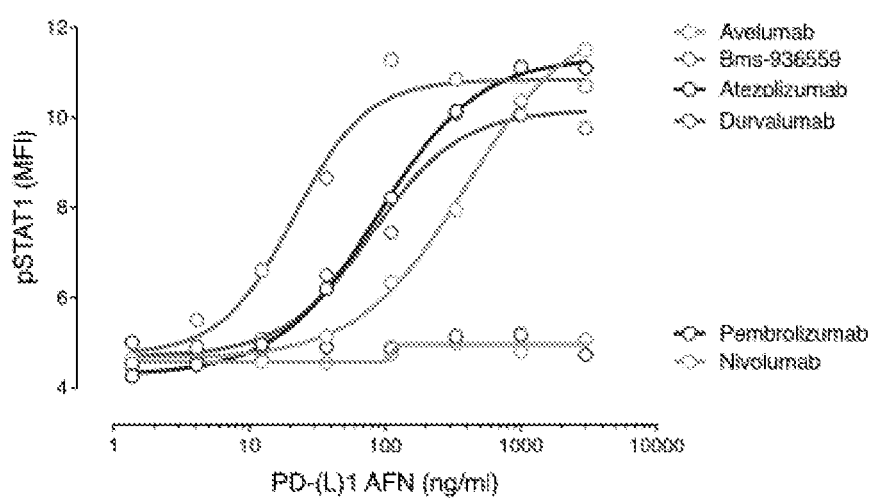
FIG. 5 shows PD-L1-targeting as assessed by pSTAT1 status in MDA-MB-231 cells. Data are plotted mean fluorescence intensities (MFI's).

MDA-MB-321 cells were stimulated with PD-(L) 1 AFN's for 15 minutes at 37° C. in DMEM medium supplemented with 10% FBS. After stimulation, pSTAT1 was quantified as described previously. PD-L1, but not PD-1, coupled AFN's were able to efficiently phosphorylate STAT1, thereby illustrating the PD-L1 targeting effect (FIG. 5).

Example 2. Construction and Evaluation of VHHs Specific for Human PD-1 or PD-L1

ELISA assays were performed to evaluate the binding affinity of the various PD-1 VHHs as described elsewhere herein for the PD-1 antigen. The affinities of the PD-1 VHHs are presented in Table 1 below (see column A/control):

TABLE 1

| Clone | Collection nr. | Family | ELISA A | ELISA control | A/control |
|---|---|---|---|---|---|
| 2PD23 | 6418 | 1 | 0.9399 | 0.2061 | 4.56041 |
| 2PD26 | 6419 | 1 | 0.7177 | 0.1708 | 4.20199 |
| 2PD90 | 6423 | 1 | 1.3425 | 0.2566 | 5.23188 |
| 2PD106 | 6424 | 1 | 1.462 | 0.2118 | 6.90274 |
| 2PD16 | 6417 | 2 | 1.8255 | 0.475 | 3.84316 |
| 2PD71 | 6421 | 2 | 2.5085 | 0.6984 | 3.59178 |
| 2PD152 | 6425 | 2 | 2.3148 | 0.3628 | 6.38037 |
| 2PD12 | 6416 | 3 | 3.8075 | 0.1775 | 21.4507 |
| 3PD55 | 6427 | 3 | 3.578 | 0.0886 | 40.3837 |
| 3PD82 | 6428 | 3 | 4 | 0.0886 | 45.1467 |
| 2PD8 | 6415 | 4 | 0.7629 | 0.2521 | 3.02618 |
| 2PD27 | 6420 | 4 | 1.1358 | 0.329 | 3.45228 |
| 2PD82 | 6422 | 5 | 2.9666 | 0.6775 | 4.37875 |
| 3PD36 | 6426 | 6 | 3.9512 | 0.0957 | 41.2874 |

The binding affinities of the various PD-L1 VHHs as described herein for the PD-L1 antigen were also assessed by ELISA. The affinities of the PD-1 VHHs are presented in Table 2 below (see column A/control):

TABLE 2

| Clone | Collection nr. | Family | ELISA | ELISA control | A/control |
|---|---|---|---|---|---|
| 2LIG2 | 6283 | 5 | 0.5099 | 0.1322 | 3.85703 |
| 2LIG3 | 6284 | 1 | 1.4632 | 0.15 | 9.75467 |
| 2LIG16 | 6285 | 3 | 3.0203 | 0.1144 | 26.4012 |
| 2LIG22 | 6286 | 6 | 0.4687 | 0.1031 | 4.54607 |
| 2LIG27 | 6287 | 1 | 0.4289 | 0.1134 | 3.78219 |
| 2LIG29 | 6288 | 2 | 3.772 | 0.109 | 34.6055 |
| 2LIG30 | 6289 | 7 | 1.1105 | 0.1158 | 9.58981 |
| 2LIG34 | 6290 | 1 | 0.5681 | 0.1581 | 3.5933 |
| 2LIG35 | 6291 | 2 | 0.8438 | 0.1031 | 8.18429 |
| 2LIG48 | 6292 | 3 | 4 | 0.1204 | 33.2226 |
| 2LIG65 | 6293 | 4 | 2.108 | 0.0892 | 23.6323 |
| 2LIG85 | 6294 | 10 | 2.6661 | 0.1182 | 22.558 |
| 2LIG86 | 6295 | 9 | 3.803 | 0.1133 | 33.5658 |
| 2LIG89 | 6296 | 4 | 2.8804 | 0.106 | 27.1736 |
| 2LIG97 | 6297 | 1 | 1.0302 | 0.201 | 5.12537 |
| 2LIG99 | 6298 | 1 | 2.1105 | 0.2304 | 9.16016 |
| 2LIG109 | 6299 | 2 | 3.5455 | 0.1088 | 32.5873 |
| 2LIG127 | 6300 | 1 | 3.7303 | 0.1079 | 34.5718 |
| 2LIG139 | 6301 | 4 | 4 | 0.1202 | 33.2779 |
| 2LIG176 | 6302 | 11 | 0.4153 | 0.0983 | 4.22482 |
| 2LIG189 | 6303 | 7 | 2.2343 | 0.1726 | 12.945 |
| 3LIG3 | 6304 | 5 | 0.5797 | 0.081 | 7.15679 |

TABLE 2-continued

| Clone | Collection nr. | Family | ELISA | ELISA control | A/ control |
|---|---|---|---|---|---|
| 3LIG7 | 6305 | 2 | 3.6414 | 0.0968 | 37.6178 |
| 3LIG8 | 6306 | 1 | 0.4292 | 0.0978 | 4.38855 |
| 3LIG9 | 6307 | 2 | 3.6634 | 0.0972 | 37.6893 |
| 3LIG18 | 6308 | 4 | 3.505 | 0.0877 | 39.9658 |
| 3LIG20 | 6309 | 8 | 0.5131 | 0.1179 | 4.35199 |
| 3LIG28 | 6310 | 6 | 3.0276 | 0.0913 | 33.161 |
| 3LIG29 | 6311 | 2 | 3.9596 | 0.0967 | 40.9473 |
| 3LIG30 | 6312 | 3 | 4 | 0.0845 | 47.3373 |
| 3LIG33 | 6313 | 5 | 1.7581 | 0.0921 | 19.089 |

Figure 6:
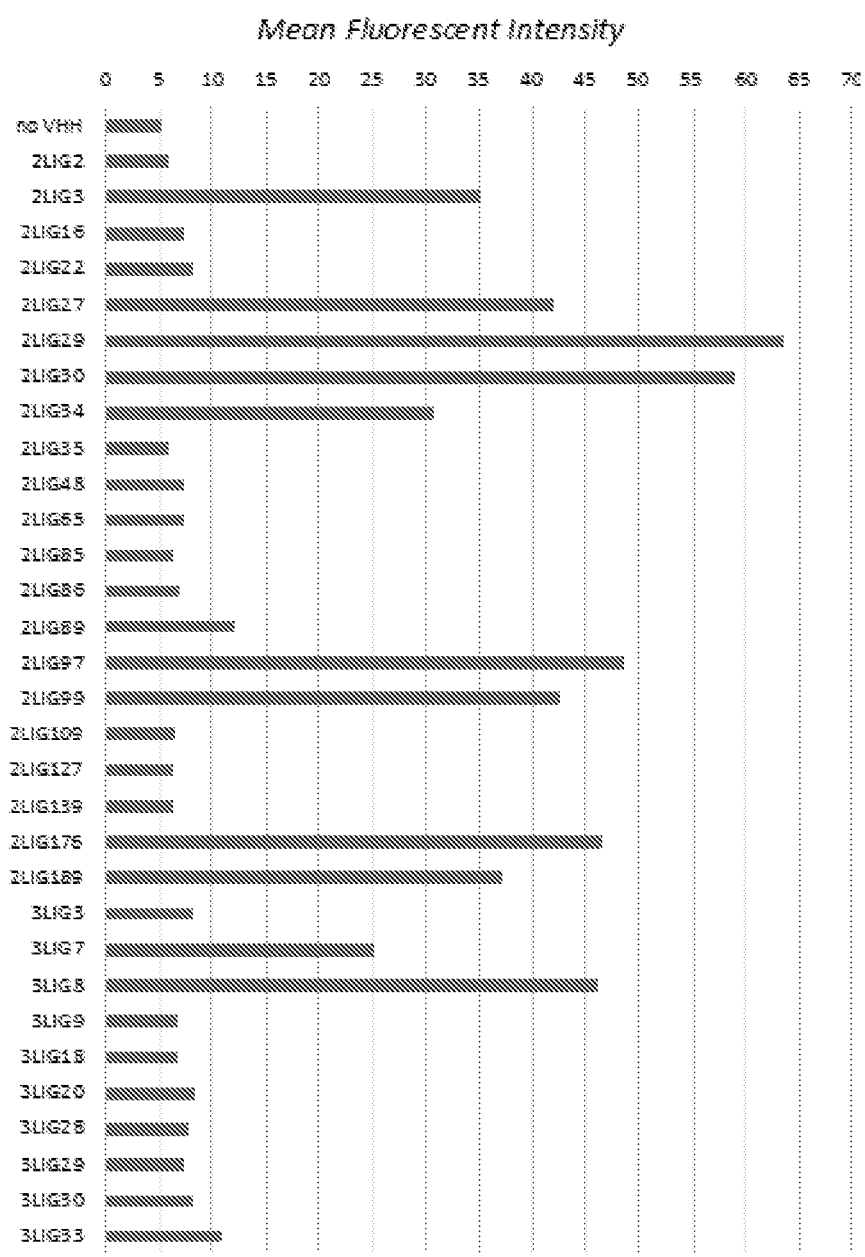
FIG. 6 shows binding of PD-L1 VHHs to transfected Hek293T cells. Data are plotted mean fluorescence intensities (MFI's).
Figure 7B:
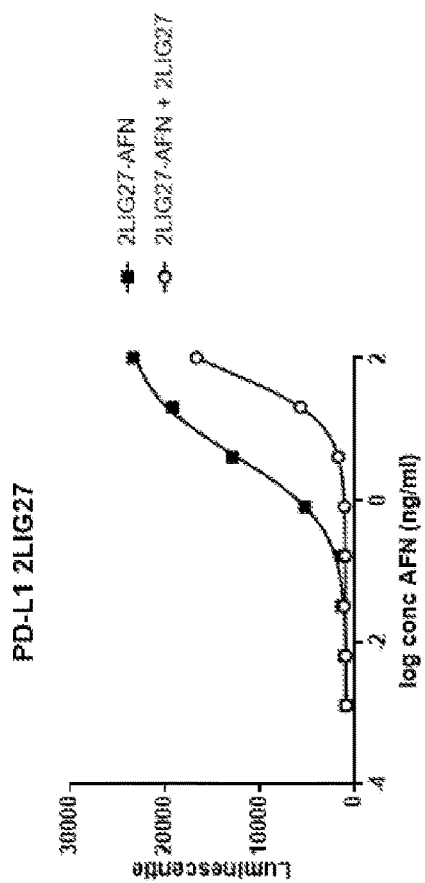
FIGS. 7A-G are graphs showing the biological activity of PD-L1 VHH Actaferons (AFNs). Biological activity was measured on parental HL116 cells (an IFN responsive cell-line stably transfected with a p6-16 luciferase reporter). Luciferase activity was induced by serial dilutions of PD-L1 VHH AFNs in the presence or absence of an excess (20 µg/ml) of the corresponding PD-L1 VHH. The PD-L1 VHHS tested were 2LIG3 (FIG. 7A), 2LIG27 (FIG. 7B), 2LIG97 (FIG. 7C), 2LIG99 (FIG. 7D), 2LIG176 (FIG. 7E), 2LIG189 (FIG. 7F), and 3LIG8 (FIG. 7G).
Figure 7A:
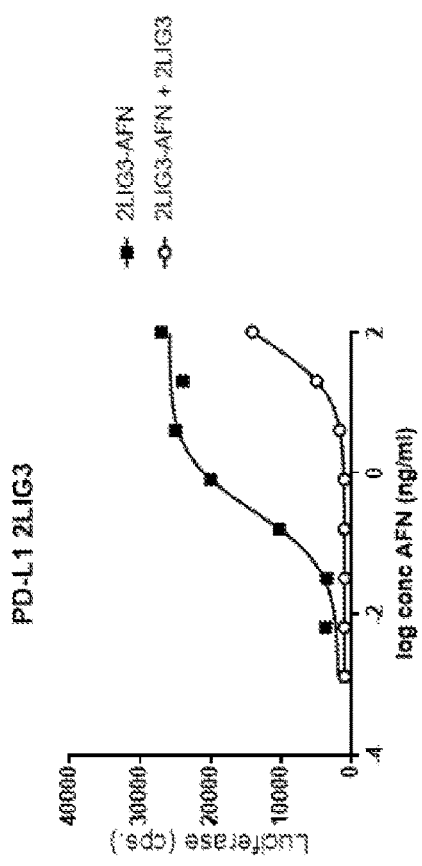
Figure 7C:
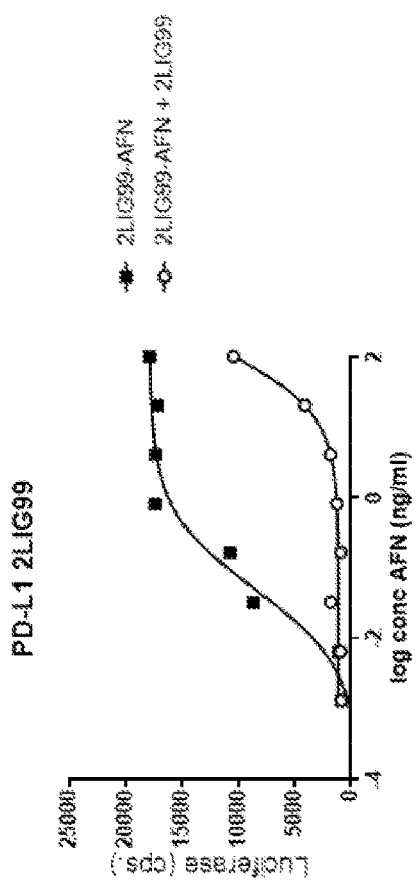
Figure 7D:
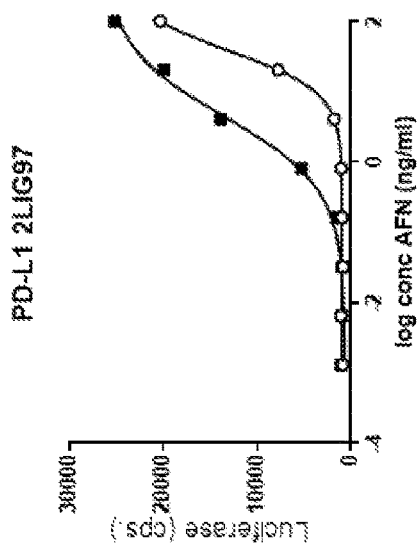
Figure 7E:
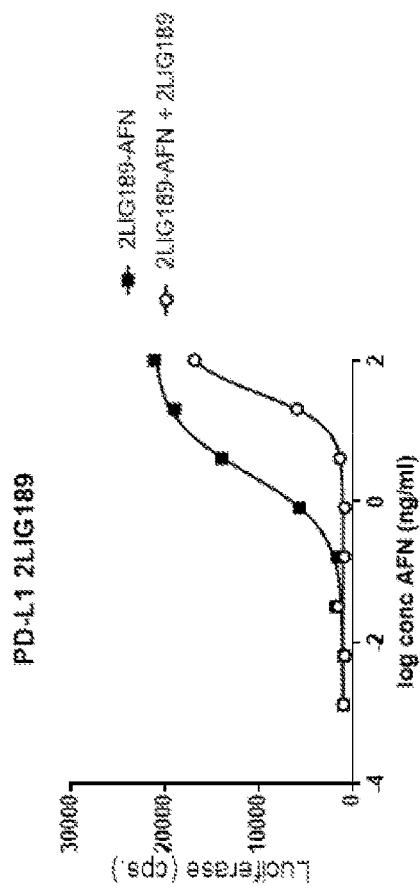
Figure 7F:
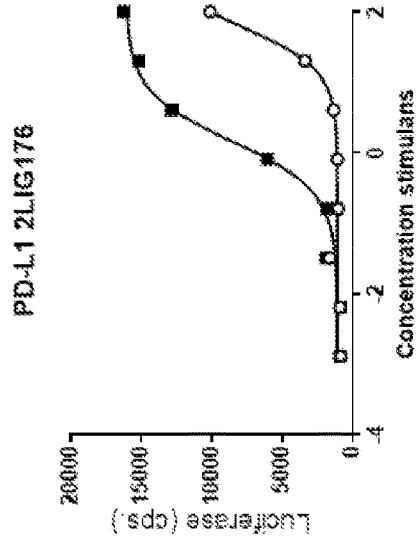
Figure 7G:
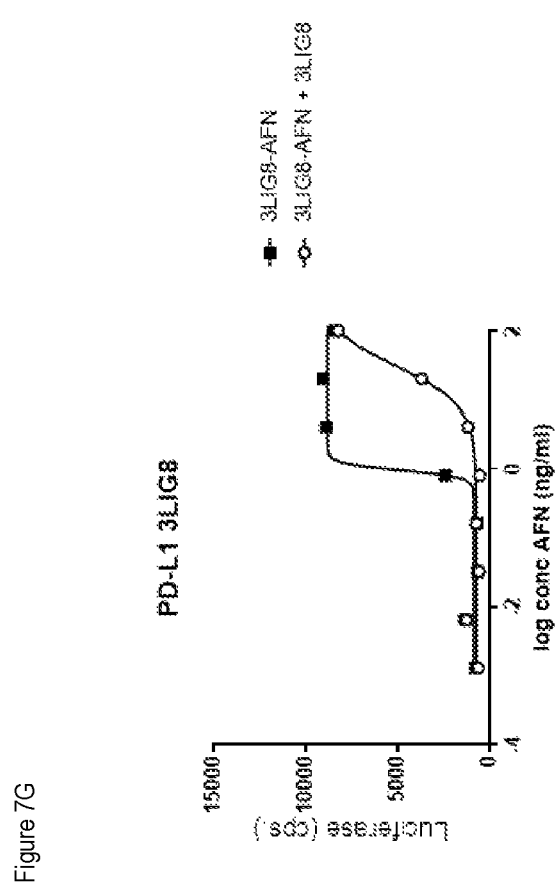

The binding of the PD-L1 VHHs to transfected Hek293T cells was also examined. Specifically, human PD-L1 transfected Hek293T cells were stained with PD-L1 VHH's (2 μg/ml; 2 hours at 4° C.) and a FITC-coupled anti-His antibody (GenScript; 1 hour at 4° C.). Binding was measured with a FACSCalibur instrument (BD Biosciences), with the CellQuest Pro Version 4.0.2 software (BD Biosciences). Results of the binding assays are shown in FIG. 6.

Example 3. Characterization of Human PD-L1 VHH AcTaferons

After an initial screen of anti-human PD-L1 VHHs for their capacity to inhibit the interaction with PD-1, the following PD-L1 VHHs were selected for further characterization: 2LIG3 (SEQ ID NO: 287), 2LIG27 (SEQ ID NO: 290), 2LIG 97 (SEQ ID NO: 300), 2LIG99 (SEQ ID NO: 301), 3LIG8 (SEQ ID NO: 309), 2LIG189 (SEQ ID NO: 306), and 2LIG176 (SEQ ID NO: 305).

PD-L1 VHHs 2LIG3, 2LIG27, 2LIG97, 2LIG99, 3LIG8, 2LIG189, and 2LIG176 were cloned in the pHEN6C expression vector as follows: pHEN6C-PelB-PD-L1 VHH-(His) 6. Proteins were produced overnight in E. coli upon IPTG stimulation and purified from periplasmic extracts using the TALON metal affinity resin (Clontech) according to the manufacturer's instructions.

The effect of the PD-L1 VHH's on the interaction between PD-1 and PD-L1 was tested in a plate binding assay. The recombinant extracellular domains of PD-L1 were immobilized overnight on MaxiSorp plates (Nunc) using its C-terminal FLAG-tag and the M2 anti-FLAG Ab (Sigma). Plates were block (PBS+0.1% Casein) and incubated with hPD-1-hFc fusion-protein (SinoBiologicals) in the presence or absence of a serial dilution VHH's. After washing, bound PD-1 was measured using a HRP (horseradish peroxidase) coupled anti-human Ab (Jackson ImmunoReasearch) and the TMB peroxidase substrate (KPL).

Affinities of the PD-L1 VHH's for human and cynomolgus PD-L1 were measured using bio-layer interferometry an Octet RED96 system (FortéBio): VHH's were immobilized on Penta-HIS (HIS1K) biosensors (FortéBio) and dipped in a serial dilution human PD-L1-Fc or cynomolgus PD-L1-Fc proteins (both from SinoBiological). Affinities were calculated with the Octet software (FortéBio).

Table 3 shows that all PD-L1 VHHs tested were able to potently inhibit the PD-L1/PD-1 interaction. In addition, all PD-L1 VHHs showed a similar binding affinity for human and cynomolgus PD-L1.

TABLE 3

| Clone | $IC_{50}$ neutralisation PD1-PDL2 (ng/ml) | Human PD-L1 affinity | | | Cyno PD-L1 affinity | | | EC50 luciferase in HL116 cells (ng/ml) |
|---|---|---|---|---|---|---|---|---|
| | | KD (M) | kon (1/Ms) | kdis (1/s) | KD (M) | kon (1/M) | kdis (1/s) | |
| 2LIG3 | 18.87 | 1.19E−09 | 3.73E+05 | 4.48E−04 | 8.90E−10 | 3.58E+05 | 3.18E−04 | 0.0220 |
| 2LIG27 | 9.57 | 7.51E−09 | 4.72E+05 | 3.50E−03 | 8.74E−09 | 3.21E+05 | 2.80E−03 | 1.0380 |
| 2LIG97 | 4.81 | 4.35E−09 | 4.23E+05 | 1.98E−03 | 9.16E−09 | 3.19E+05 | 2.93E−03 | 1.1100 |
| 2LIG99 | 6.21 | 8.75E−10 | 7.29E+05 | 6.34E−04 | 1.01E−09 | 5.84E+05 | 5.85E−04 | 0.0062 |
| 3LIG8 | 12.79 | 8.77E−09 | 4.84E+05 | 4.19E−03 | 5.98E−09 | 5.12E+05 | 3.05E−03 | 0.2400 |
| 2LIG189 | 8.81 | 3.03E−09 | 1.74E+05 | 5.24E−04 | 3.80E−09 | 1.44E+05 | 4.37E−04 | 0.4900 |
| 2LIG176 | 5.68 | 6.87E−09 | 1.18E+06 | 8.05E−03 | 1.13E−08 | 5.08E+05 | 5.73E−03 | 0.2300 |

The PD-L1 VHH's (i.e., 2LIG3, 2LIG27, 2LIG97, 2LIG99, 3LIG8, 2LIG189, and 2LIG176) were then cloned into an Actaferon (AFN) format in the pHEN6C expression vector (i.e., pHEN6C-PelB-PD-L1_VHH-(GGS) 20-hIFNa2_R149A-GGS-(His) 6, wherein the PD-L1_VHH is selected from 2LIG3, 2LIG27, 2LIG97, 2LIG99, 3LIG8, 2LIG189, and 2LIG176). Proteins were produced overnight in E. coli upon IPTG stimulation and purified from periplasmic extracts using the TALON metal affinity resin (Clontech) according to the manufacturer's instructions.

Biological activity was measured on parental HL116 cells (an IFN responsive cell-line stably transfected with a p6-16 luciferase reporter). Cells were seeded overnight and stimulated for 6 hours with a serial dilution PD-L1 AFN's in the presence or absence of an excess (20 μg/ml) of the corresponding VHH (this latter to mimic the untargeted situation). Luciferase activity was measured on an EnSight Multimode Plate Reader (Perkin Elmer).

As shown in FIGS. 7A-G, all the PD-L1 VHHs formatted as an AcTaferon were able to induce the IFN luciferase reporter in HL116 cells. The specificity of the AcTaferon activity was assessed by comparing the luciferase reporter activity in the presence of an excess of each respective PD-L1 VHH not linked to an IFN moiety (see FIGS. 7A-G).

Example 4. In Vitro Efficacy of Human PD-L1 Antibody AcTaferons

The monoclonal antibody atezolizumab (Ate), a PD-L1 targeted monoclonal antibody, was selected as an example to evaluate the specificity of the interferon activity to targeted cells.

Atezolizumab was obtained from InVivogen. Atezolizumab_hIFNa2 (R149A) (Ate-IFNa2mut) was generated as follows: the Ab heavy chain was genetically fused to hIFNa2_R149 sequence via a flexible 20*GGS linker in the pMTW expression-vector (resulting vector: pMTW-SlgK-heavy chain-(GGS)$_{20}$-hIFNa2_R149A-GGS-(His)$_9$. The light chains were cloned in the same vector (resulting vector: pMTW-SlgK-light chain). Both plasmids were co-transfected in ExpiCHO cells (ThermoFisher) according to the manufacturers guidelines. The resulting Ate-IFNa2mut was purified from the medium using the Ni Sepharose excel resin (GE Healthcare). The effect of the Ate-IFNa2mut was demonstrated in vitro using the same assay as described in previous Example 3 using an excess of atezolizumab (Ate) (50 µg/ml) to demonstrate specificity (see FIG. 8).

Figure 8:
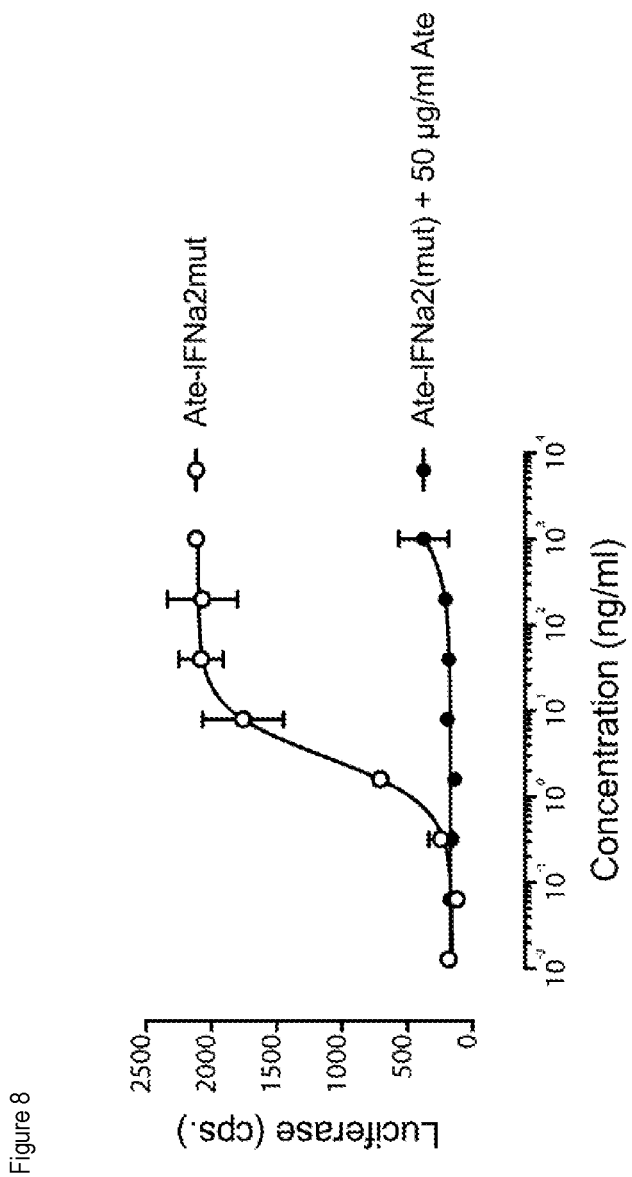
FIG. 8 is a graph showing the biological activity of an atezolizumab-Actaferon (ate-AFN; i.e., Ate-IFNa2mut) on parental HL116 cells (an IFN responsive cell-line stably transfected with a p6-16 luciferase reporter). Biological activity was measure by luciferase activity induced by a serial dilution of ate-AFN in the presence or absence of an excess (50 µg/ml) of atezolizumab (ate).

FIG. 8 shows that the Ate-IFNa2mut was able to induce the IFN luciferase reporter in HL116 cells. The specificity of the Ate-IFNa2mut activity was assessed by comparing the luciferase reporter activity in the presence of an excess of atezolizumab (Ate) not linked to an IFN moiety.

Example 5. In Vivo Efficacy of Human PD-L1 Antibody AcTaferons

The PD-L1 VHH 2LIG99 was selected to evaluate the antitumor efficacy of human PD-L1 VHH targeted AcTaferon (AFN) in vivo.

Human RL follicular lymphoma cell line (RL) tumor model in mice with humanized immune system: Mice with a humanized immune system were generated according to the following protocol. Mononuclear cells were collected following density gradient centrifugation using Lymphoprep from HLA-A2+ human cord blood samples. Human CD34+ hematopoietic stem cells (HSC) were subsequently isolated by MACS technology and examined for CD34+ purity and CD3+ contamination using FACS. HSC's with a CD34 purity of >80% were then intrahepatically injected in 2-3 day old NSG mice that underwent myeloablative irradiation treatment at 100 cGy. At 8-12 weeks post HSC injection, human cell engraftment was analyzed with panleukocyte human and mouse CD45 markers using FACS and mice with >5% human CD45 cells, of total viable blood lymphocytes, were selected for tumor implantation. Twelve weeks post HSC injection, mice were subcutaneously injected with 2×10$^6$ RL tumor cells. Five days later, mice were treated with Flt3L injected peritoneally on a daily basis until day 18. Treatment with PBS (control) or 2LIG99-based AFN (i.e., AFN comprising 2LIG99 linked to hIFNa2_R149A) was initiated by perilesional administration as of day 9 (when tumors had reached sizes of about 10 mm$^2$) post tumor injection.

Figure 9:
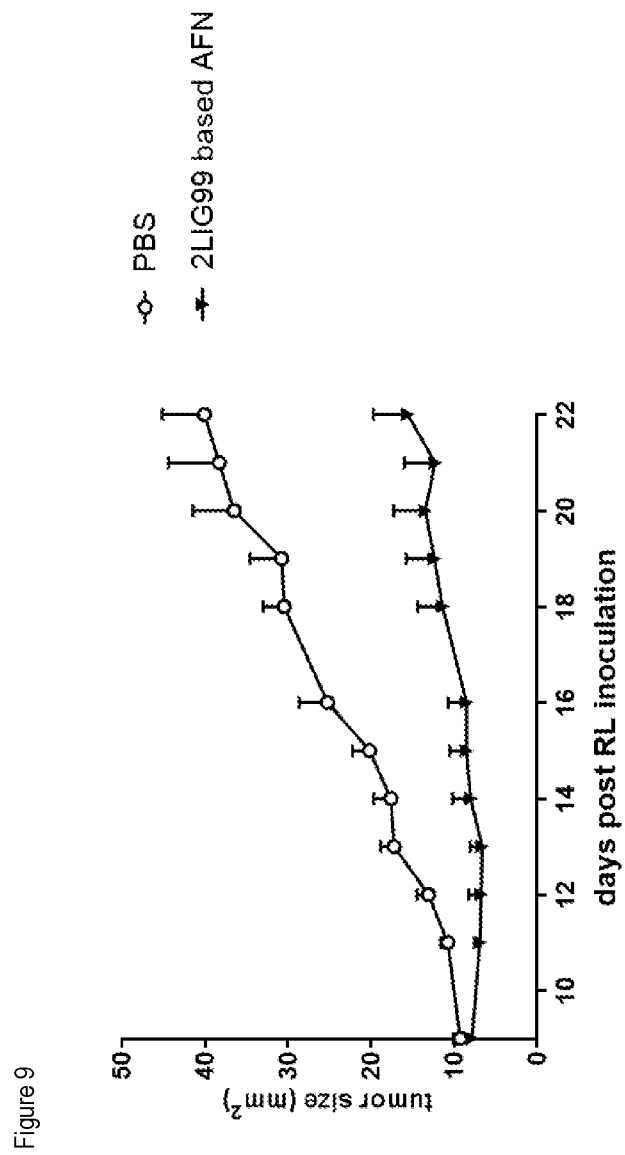
FIG. 9 is a graph showing the in vivo anti-tumoral activity of 2LIG99 based-AFN in a RL tumor model in mice with a humanized immune system.

As shown in FIG. 9, the 2LIG99-based AFN had antitumoral effects in vivo.

Example 6. In Vitro Efficacy of Human PD-1 AcTaferons

The efficiency of human PD-1 (programmed death-1) targeting of AcTaferons (AFN) was examined by quantification of STAT1 phosphorylation in PD-1 or empty vector transfected Hek293T cells in FACS.

Two different PD-1 VHH's were selected for analysis:

102C3:
(SEQ ID NO: 1246)
QVQLQESGGGLVQAGKSLRLSCAASGSIFSIHAMGWFRQAPGKEREFV

AAITWSGGITYYEDSVKGRFTISRDNAKNTVYLQMNSLKPEDTAIYYC

AADRAESSWYDYWGQGTQVTVSS;

and

102C12:
(SEQ ID NO: 1247)
QVQLQESGGGLVQAGKSLRLSCAASGSIASIHAMGWFRQAPGKEREFV

AVITWSGGITYYADSVKGRFTISRDNAKNTVYLQMNSLKPEDTAIYYC

AGDKHQSSWYDYWGQGTQVTVSS.

These PD-1 VHH's were cloned into an AcTaferon (AFN): AFN's were cloned in the pHEN6C expression vector as follows: pHEN6C-PelB-PD-1_VHH-(GGS)$_{20}$-hIFNa2_R149A-GGS-(His)$_6$ (wherein PD-1_VHH is 102C3 or 102C12; i.e., 102C3 AFN and 102C12 AFN). Proteins were produced overnight in E. coli upon IPTG stimulation and purified from periplasmic extracts using the TALON metal affinity resin (Clontech) according to the manufacturer's instructions.

Hek293T cells were transfected with an empty vector or a human PD-1 expression plasmid using the standard calcium phosphate technique. Two days after transfection, cells were re-suspended, washed twice with FACS buffer (2% FBS, 1 mM EDTA in PBS) and stimulated with a serial dilution of 102C3 AFN or 102C12 AFN or wild type IFNa2 (positive control) for 15 minutes at 37° C. After fixation (10 minutes, 37° C., Fix Buffer I; BD Biosciences) and permeabilization (30 minutes, on ice, Perm III Buffer; BD Biosciences) and washing, cells were stained with anti-STAT1 pY701 Ab (BD Biosciences). Samples were acquired on a FACSCalibur (BD Biosciences), with the CellQuest Pro Version 4.0.2 software (BD Biosciences) and analyzed using the FlowJo software (FlowJo).

Figure 10A:
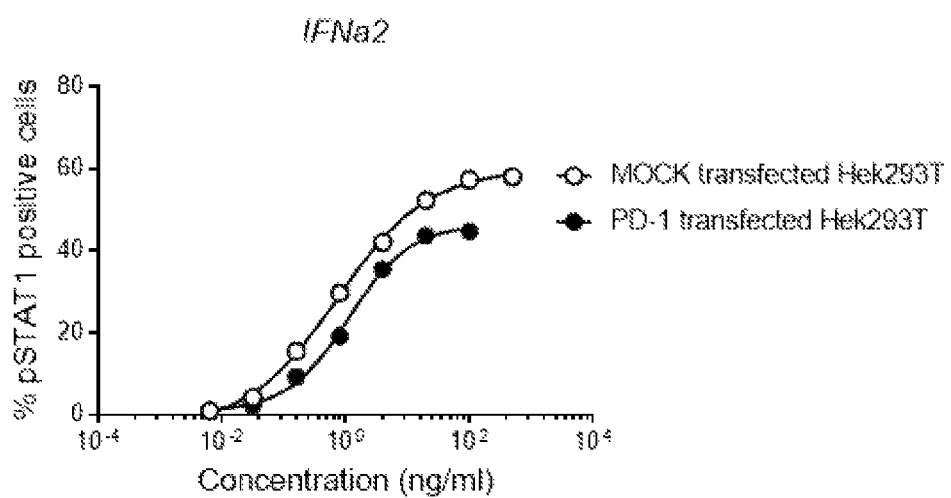
FIGS. 10A-C are graphs showing pSTAT1 in Hek293T cells transfected with human PD-1 or an empty vector that were stimulated with serial dilutions of 102C3 AFN (FIG. 10A), 102C12 AFN (FIG. 10B), or wild type IFNa2 (FIG. 10C). Percentage of pSTAT1 positive cells are plotted in the graphs.
Figure 10B:
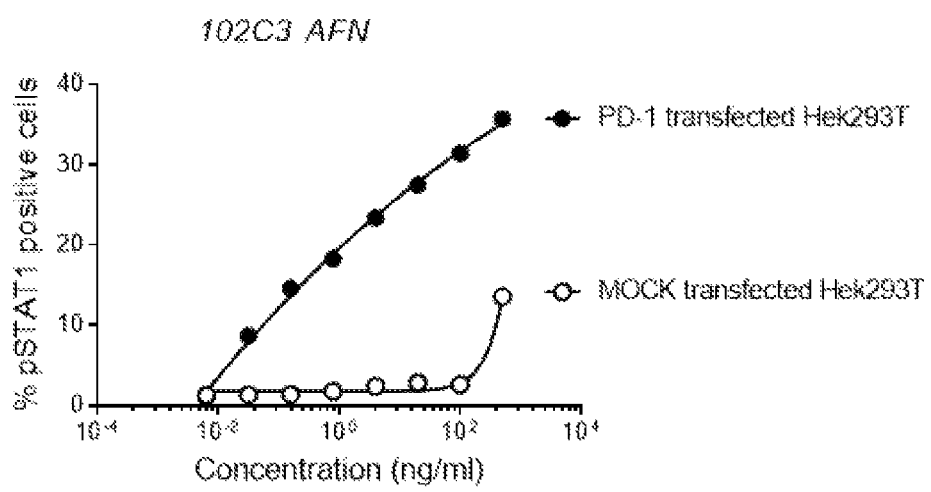
Figure 10C:
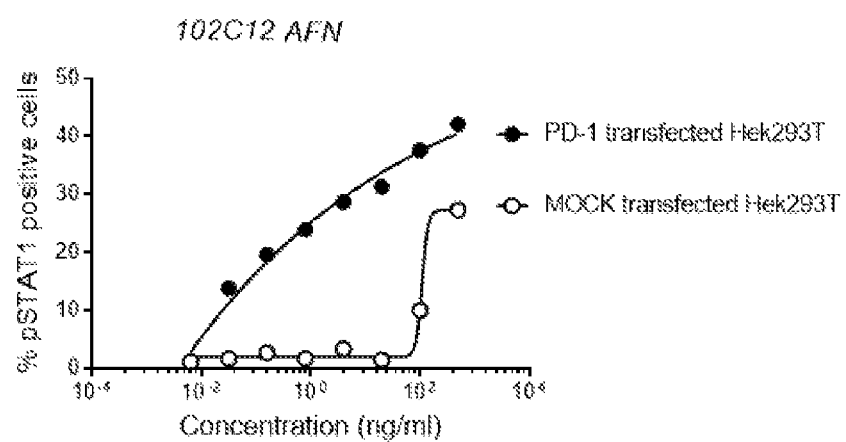

The percentages of pSTAT1 positive cells were quantified in FACS and plotted in function of the concentration. FIGS. 10A-C show that 102C3 AFN and 102C12 AFN efficiently induce STAT1 phosphorylation in PD-1 expressing Hek293T cells, but to a much lesser extent in MOCK transfected cells. This in contrast to wild type IFNa2, which is equally active on PD-1 and MOCK transfected HEK293T cells.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A PD-1 binding agent comprising at least one targeting moiety comprising three complementarity determining regions (CDR1, CDR2, and CDR3), wherein:
(a) CDR1 comprises the amino acid sequence of SEQ ID NO: 2, (b) CDR2 comprises the amino acid sequence of SEQ ID NO: 24; and (c) CDR3 comprises the amino acid sequence of SEQ ID NO: 55;
(a) CDR1 comprises the amino acid sequence of SEQ ID NO: 3, (b) CDR2 comprises the amino acid sequence of SEQ ID NO: 24; and (c) CDR3 comprises the amino acid sequence of SEQ ID NO: 56;
(a) CDR1 comprises the amino acid sequence of SEQ ID NO: 4, (b) CDR2 comprises the amino acid sequence of SEQ ID NO: 25; and (c) CDR3 comprises the amino acid sequence of SEQ ID NO: 57;
(a) CDR1 comprises the amino acid sequence of SEQ ID NO: 5, (b) CDR2 comprises the amino acid sequence of SEQ ID NO: 26; and (c) CDR3 comprises the amino acid sequence of SEQ ID NO: 58;
(a) CDR1 comprises the amino acid sequence of SEQ ID NO: 6, (b) CDR2 comprises the amino acid sequence of SEQ ID NO: 27; and (c) CDR3 comprises the amino acid sequence of SEQ ID NO: 59;
(a) CDR1 comprises the amino acid sequence of SEQ ID NO: 7, (b) CDR2 comprises the amino acid sequence of SEQ ID NO: 27; and (c) CDR3 comprises the amino acid sequence of SEQ ID NO: 59;
(a) CDR1 comprises the amino acid sequence of SEQ ID NO: 8, (b) CDR2 comprises the amino acid sequence of SEQ ID NO: 28; and (c) CDR3 comprises the amino acid sequence of SEQ ID NO: 60;
(a) CDR1 comprises the amino acid sequence of SEQ ID NO: 9, (b) CDR2 comprises the amino acid sequence of SEQ ID NO: 29; and (c) CDR3 comprises the amino acid sequence of SEQ ID NO: 61; or
(a) CDR1 comprises the amino acid sequence of SEQ ID NO: 10, (b) CDR2 comprises the amino acid sequence of SEQ ID NO: 30; and (c) CDR3 comprises the amino acid sequence of SEQ ID NO: 62.

2. The PD-1 binding agent of claim 1, wherein
(a) CDR1 comprises the amino acid sequence of SEQ ID NO: 2, (b) CDR2 comprises the amino acid sequence of SEQ ID NO: 24; and (c) CDR3 comprises the amino acid sequence of SEQ ID NO: 55.

3. The PD-1 binding agent of claim 1, wherein the targeting moiety is a single-domain antibody.

4. The PD-1 binding agent of claim 3, wherein the targeting moiety comprises a VHH or a humanized VHH.

5. The PD-1 binding agent of claim 1, wherein the targeting moiety comprises an amino acid sequence having at least 90% identity with one of SEQ ID NOs: 70-83 without the AAA linker, HA tag, and terminal histidine tag sequence.

6. The PD-1 binding agent of claim 1, wherein the targeting moiety comprises one or more additional targeting moieties.

7. A recombinant nucleic acid composition encoding the PD-1 binding agent of claim 1.

8. A host cell comprising the nucleic acid of claim 7.

9. The PD-1 binding agent of claim 1, wherein (a) CDR1 comprises the amino acid sequence of SEQ ID NO: 3, (b) CDR2 comprises the amino acid sequence of SEQ ID NO: 24; and (c) CDR3 comprises the amino acid sequence of SEQ ID NO: 56.

10. The PD-1 binding agent of claim 1, wherein (a) CDR1 comprises the amino acid sequence of SEQ ID NO: 4, (b) CDR2 comprises the amino acid sequence of SEQ ID NO: 25; and (c) CDR3 comprises the amino acid sequence of SEQ ID NO: 57.

11. The PD-1 binding agent of claim 1, wherein (a) CDR1 comprises the amino acid sequence of SEQ ID NO: 5, (b) CDR2 comprises the amino acid sequence of SEQ ID NO: 26; and (c) CDR3 comprises the amino acid sequence of SEQ ID NO: 58.

12. The PD-1 binding agent of claim 1, wherein (a) CDR1 comprises the amino acid sequence of SEQ ID NO: 6, (b) CDR2 comprises the amino acid sequence of SEQ ID NO: 27; and (c) CDR3 comprises the amino acid sequence of SEQ ID NO: 59.

13. The PD-1 binding agent of claim 1, wherein (a) CDR1 comprises the amino acid sequence of SEQ ID NO: 7, (b)

CDR2 comprises the amino acid sequence of SEQ ID NO: 27; and (c) CDR3 comprises the amino acid sequence of SEQ ID NO: 59.

14. The PD-1 binding agent of claim 1, wherein (a) CDR1 comprises the amino acid sequence of SEQ ID NO: 8, (b) CDR2 comprises the amino acid sequence of SEQ ID NO: 28; and (c) CDR3 comprises the amino acid sequence of SEQ ID NO: 60.

15. The PD-1 binding agent of claim 1, wherein (a) CDR1 comprises the amino acid sequence of SEQ ID NO: 9, (b) CDR2 comprises the amino acid sequence of SEQ ID NO: 29; and (c) CDR3 comprises the amino acid sequence of SEQ ID NO: 61.

16. The PD-1 binding agent of claim 1, wherein (a) CDR1 comprises the amino acid sequence of SEQ ID NO: 10, (b) CDR2 comprises the amino acid sequence of SEQ ID NO: 30; and (c) CDR3 comprises the amino acid sequence of SEQ ID NO: 62.

* * * * *

SEQUENCE LISTING

```
Sequence total quantity: 1247
SEQ ID NO: 1            moltype = AA  length = 288
FEATURE                 Location/Qualifiers
REGION                  1..288
                        note = Synthetic polymer
source                  1..288
                        mol_type = protein
                        organism = synthetic construct
SEQUENCE: 1
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL                288

SEQ ID NO: 2            moltype = AA  length = 10
FEATURE                 Location/Qualifiers
REGION                  1..10
                        note = Synthetic polymer
source                  1..10
                        mol_type = protein
                        organism = synthetic construct
SEQUENCE: 2
GFSMDYYAIA                                                           10

SEQ ID NO: 3            moltype = AA  length = 10
FEATURE                 Location/Qualifiers
REGION                  1..10
                        note = Synthetic polymer
source                  1..10
                        mol_type = protein
                        organism = synthetic construct
SEQUENCE: 3
GFSVDYYAIA                                                           10

SEQ ID NO: 4            moltype = AA  length = 10
FEATURE                 Location/Qualifiers
REGION                  1..10
                        note = Synthetic polymer
source                  1..10
                        mol_type = protein
                        organism = synthetic construct
SEQUENCE: 4
GGFNRVSYMG                                                           10

SEQ ID NO: 5            moltype = AA  length = 10
FEATURE                 Location/Qualifiers
REGION                  1..10
                        note = Synthetic polymer
source                  1..10
                        mol_type = protein
                        organism = synthetic construct
SEQUENCE: 5
GIIKSINFMG                                                           10

SEQ ID NO: 6            moltype = AA  length = 10
FEATURE                 Location/Qualifiers
REGION                  1..10
                        note = Synthetic polymer
source                  1..10
                        mol_type = protein
                        organism = synthetic construct
SEQUENCE: 6
GFILDYYGIG                                                           10

SEQ ID NO: 7            moltype = AA  length = 10
FEATURE                 Location/Qualifiers
REGION                  1..10
                        note = Synthetic polymer
source                  1..10
```

```
                        mol_type = protein
                        organism = synthetic construct
SEQUENCE: 7
GLSLDYDGVG                                                              10

SEQ ID NO: 8            moltype = AA   length = 10
FEATURE                 Location/Qualifiers
REGION                  1..10
                        note = Synthetic polymer
source                  1..10
                        mol_type = protein
                        organism = synthetic construct
SEQUENCE: 8
GRTFSSLGMG                                                              10

SEQ ID NO: 9            moltype = AA   length = 10
FEATURE                 Location/Qualifiers
REGION                  1..10
                        note = Synthetic polymer
source                  1..10
                        mol_type = protein
                        organism = synthetic construct
SEQUENCE: 9
GFAFGSYDMG                                                              10

SEQ ID NO: 10           moltype = AA   length = 10
FEATURE                 Location/Qualifiers
REGION                  1..10
                        note = Synthetic polymer
source                  1..10
                        mol_type = protein
                        organism = synthetic construct
SEQUENCE: 10
GFSFGNNDMS                                                              10

SEQ ID NO: 11           moltype = AA   length = 5
FEATURE                 Location/Qualifiers
REGION                  1..5
                        note = Synthetic polymer
source                  1..5
                        mol_type = protein
                        organism = synthetic construct
SEQUENCE: 11
IHAMG                                                                   5

SEQ ID NO: 12           moltype = AA   length = 5
FEATURE                 Location/Qualifiers
REGION                  1..5
                        note = Synthetic polymer
source                  1..5
                        mol_type = protein
                        organism = synthetic construct
SEQUENCE: 12
INAMA                                                                   5

SEQ ID NO: 13           moltype = AA   length = 5
FEATURE                 Location/Qualifiers
REGION                  1..5
                        note = Synthetic polymer
source                  1..5
                        mol_type = protein
                        organism = synthetic construct
SEQUENCE: 13
SGTMG                                                                   5

SEQ ID NO: 14           moltype = AA   length = 9
FEATURE                 Location/Qualifiers
REGION                  1..9
                        note = Synthetic polymer
source                  1..9
                        mol_type = protein
                        organism = synthetic construct
SEQUENCE: 14
GSIASIHAM                                                               9

SEQ ID NO: 15           moltype = AA   length = 10
FEATURE                 Location/Qualifiers
REGION                  1..10
                        note = Synthetic polymer
```

```
source                  1..10
                        mol_type = protein
                        organism = synthetic construct
SEQUENCE: 15
GSIASIHAMG                                                                10

SEQ ID NO: 16           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 16
FYGMG                                                                     5

SEQ ID NO: 17           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 17
GGTFSFYGMG                                                                10

SEQ ID NO: 18           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 18
YYAIA                                                                     5

SEQ ID NO: 19           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 19
VSYMG                                                                     5

SEQ ID NO: 20           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 20
INFMG                                                                     5

SEQ ID NO: 21           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 21
SLGMG                                                                     5

SEQ ID NO: 22           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 22
SYDMG                                                                     5

SEQ ID NO: 23           moltype = AA  length = 5
FEATURE                 Location/Qualifiers
REGION                  1..5
```

```
                              note = Synthetic polymer
source                        1..5
                              mol_type = protein
                              organism = synthetic construct
SEQUENCE: 23
NNDMS                                                                      5

SEQ ID NO: 24                 moltype = AA  length = 11
FEATURE                       Location/Qualifiers
REGION                        1..11
                              note = Synthetic polymer
source                        1..11
                              mol_type = protein
                              organism = synthetic construct
SEQUENCE: 24
CITGSDFMVD T                                                              11

SEQ ID NO: 25                 moltype = AA  length = 8
FEATURE                       Location/Qualifiers
REGION                        1..8
                              note = Synthetic polymer
source                        1..8
                              mol_type = protein
                              organism = synthetic construct
SEQUENCE: 25
SVTSGGEI                                                                   8

SEQ ID NO: 26                 moltype = AA  length = 8
FEATURE                       Location/Qualifiers
REGION                        1..8
                              note = Synthetic polymer
source                        1..8
                              mol_type = protein
                              organism = synthetic construct
SEQUENCE: 26
STTSDGRT                                                                   8

SEQ ID NO: 27                 moltype = AA  length = 9
FEATURE                       Location/Qualifiers
REGION                        1..9
                              note = Synthetic polymer
source                        1..9
                              mol_type = protein
                              organism = synthetic construct
SEQUENCE: 27
CISSSDGST                                                                  9

SEQ ID NO: 28                 moltype = AA  length = 9
FEATURE                       Location/Qualifiers
REGION                        1..9
                              note = Synthetic polymer
source                        1..9
                              mol_type = protein
                              organism = synthetic construct
SEQUENCE: 28
AIAWNGAST                                                                  9

SEQ ID NO: 29                 moltype = AA  length = 9
FEATURE                       Location/Qualifiers
REGION                        1..9
                              note = Synthetic polymer
source                        1..9
                              mol_type = protein
                              organism = synthetic construct
SEQUENCE: 29
GINSGGRIT                                                                  9

SEQ ID NO: 30                 moltype = AA  length = 9
FEATURE                       Location/Qualifiers
REGION                        1..9
                              note = Synthetic polymer
source                        1..9
                              mol_type = protein
                              organism = synthetic construct
SEQUENCE: 30
AINSGGGST                                                                  9

SEQ ID NO: 31                 moltype = AA  length = 17
FEATURE                       Location/Qualifiers
```

```
REGION                      1..17
                            note = Synthetic polymer
source                      1..17
                            mol_type = protein
                            organism = synthetic construct
SEQUENCE: 31
AITWSGGITY YEDSVKG                                                          17

SEQ ID NO: 32               moltype = AA  length = 17
FEATURE                     Location/Qualifiers
REGION                      1..17
                            note = Synthetic polymer
source                      1..17
                            mol_type = protein
                            organism = synthetic construct
SEQUENCE: 32
VITWSGGITY YADSVKG                                                          17

SEQ ID NO: 33               moltype = AA  length = 17
FEATURE                     Location/Qualifiers
REGION                      1..17
                            note = Synthetic polymer
source                      1..17
                            mol_type = protein
                            organism = synthetic construct
SEQUENCE: 33
VITVSGGITY YADSVKG                                                          17

SEQ ID NO: 34               moltype = AA  length = 17
FEATURE                     Location/Qualifiers
REGION                      1..17
                            note = Synthetic polymer
source                      1..17
                            mol_type = protein
                            organism = synthetic construct
SEQUENCE: 34
AITWSGGITY YADSLKG                                                          17

SEQ ID NO: 35               moltype = AA  length = 17
FEATURE                     Location/Qualifiers
REGION                      1..17
                            note = Synthetic polymer
source                      1..17
                            mol_type = protein
                            organism = synthetic construct
SEQUENCE: 35
LISWSGGSTY YEDSVKG                                                          17

SEQ ID NO: 36               moltype = AA  length = 17
FEATURE                     Location/Qualifiers
REGION                      1..17
                            note = Synthetic polymer
source                      1..17
                            mol_type = protein
                            organism = synthetic construct
SEQUENCE: 36
SIPWSGGRIY YADSVKG                                                          17

SEQ ID NO: 37               moltype = AA  length = 10
FEATURE                     Location/Qualifiers
REGION                      1..10
                            note = Synthetic polymer
source                      1..10
                            mol_type = protein
                            organism = synthetic construct
SEQUENCE: 37
VITWSGGITY                                                                  10

SEQ ID NO: 38               moltype = AA  length = 10
FEATURE                     Location/Qualifiers
REGION                      1..10
                            note = Synthetic polymer
source                      1..10
                            mol_type = protein
                            organism = synthetic construct
SEQUENCE: 38
VITVSGGITY                                                                  10

SEQ ID NO: 39               moltype = AA  length = 17
```

```
FEATURE              Location/Qualifiers
REGION               1..17
                     note = Synthetic polymer
source               1..17
                     mol_type = protein
                     organism = synthetic construct
SEQUENCE: 39
DIRTSAGRTY YADSVKG                                                      17

SEQ ID NO: 40        moltype = AA  length = 10
FEATURE              Location/Qualifiers
REGION               1..10
                     note = Synthetic polymer
source               1..10
                     mol_type = protein
                     organism = synthetic construct
SEQUENCE: 40
DIRTSAGRTY                                                              10

SEQ ID NO: 41        moltype = AA  length = 12
FEATURE              Location/Qualifiers
REGION               1..12
                     note = Synthetic polymer
source               1..12
                     mol_type = protein
                     organism = synthetic construct
SEQUENCE: 41
CITGSDFMVD TY                                                           12

SEQ ID NO: 42        moltype = AA  length = 19
FEATURE              Location/Qualifiers
REGION               1..19
                     note = Synthetic polymer
source               1..19
                     mol_type = protein
                     organism = synthetic construct
SEQUENCE: 42
CITGSDFMVD TYYVASVKG                                                    19

SEQ ID NO: 43        moltype = AA  length = 9
FEATURE              Location/Qualifiers
REGION               1..9
                     note = Synthetic polymer
source               1..9
                     mol_type = protein
                     organism = synthetic construct
SEQUENCE: 43
SVTSGGEIT                                                                9

SEQ ID NO: 44        moltype = AA  length = 16
FEATURE              Location/Qualifiers
REGION               1..16
                     note = Synthetic polymer
source               1..16
                     mol_type = protein
                     organism = synthetic construct
SEQUENCE: 44
SVTSGGEITI ADSVKG                                                       16

SEQ ID NO: 45        moltype = AA  length = 16
FEATURE              Location/Qualifiers
REGION               1..16
                     note = Synthetic polymer
source               1..16
                     mol_type = protein
                     organism = synthetic construct
SEQUENCE: 45
SVTSGGEITV ADSVKG                                                       16

SEQ ID NO: 46        moltype = AA  length = 9
FEATURE              Location/Qualifiers
REGION               1..9
                     note = Synthetic polymer
source               1..9
                     mol_type = protein
                     organism = synthetic construct
SEQUENCE: 46
STTSDGRTT                                                                9
```

```
SEQ ID NO: 47           moltype = AA  length = 16
FEATURE                 Location/Qualifiers
REGION                  1..16
                        note = Synthetic polymer
source                  1..16
                        mol_type = protein
                        organism = synthetic construct
SEQUENCE: 47
STTSDGRTTV ADSVKG                                                           16

SEQ ID NO: 48           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 48
CISSSDGSTY                                                                  10

SEQ ID NO: 49           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 49
AIAWNGASTY                                                                  10

SEQ ID NO: 50           moltype = AA  length = 17
FEATURE                 Location/Qualifiers
REGION                  1..17
                        note = Synthetic polymer
source                  1..17
                        mol_type = protein
                        organism = synthetic construct
SEQUENCE: 50
AIAWNGASTY YTESVKG                                                          17

SEQ ID NO: 51           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 51
GINSGGRITD                                                                  10

SEQ ID NO: 52           moltype = AA  length = 17
FEATURE                 Location/Qualifiers
REGION                  1..17
                        note = Synthetic polymer
source                  1..17
                        mol_type = protein
                        organism = synthetic construct
SEQUENCE: 52
GINSGGRITD YADSVTG                                                          17

SEQ ID NO: 53           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 53
AINSGGGSTY                                                                  10

SEQ ID NO: 54           moltype = AA  length = 17
FEATURE                 Location/Qualifiers
REGION                  1..17
                        note = Synthetic polymer
source                  1..17
                        mol_type = protein
                        organism = synthetic construct
SEQUENCE: 54
AINSGGGSTY YADSVKG                                                          17
```

```
SEQ ID NO: 55              moltype = AA   length = 19
FEATURE                    Location/Qualifiers
REGION                     1..19
                           note = Synthetic polymer
source                     1..19
                           mol_type = protein
                           organism = synthetic construct
SEQUENCE: 55
AVRSTANTLC PSHYSVMDY                                                    19

SEQ ID NO: 56              moltype = AA   length = 19
FEATURE                    Location/Qualifiers
REGION                     1..19
                           note = Synthetic polymer
source                     1..19
                           mol_type = protein
                           organism = synthetic construct
SEQUENCE: 56
AVRSTANTLC PSHYSIMDY                                                    19

SEQ ID NO: 57              moltype = AA   length = 14
FEATURE                    Location/Qualifiers
REGION                     1..14
                           note = Synthetic polymer
source                     1..14
                           mol_type = protein
                           organism = synthetic construct
SEQUENCE: 57
NADIWVSDAR MYNY                                                         14

SEQ ID NO: 58              moltype = AA   length = 14
FEATURE                    Location/Qualifiers
REGION                     1..14
                           note = Synthetic polymer
source                     1..14
                           mol_type = protein
                           organism = synthetic construct
SEQUENCE: 58
NADIWLPSDR MYNY                                                         14

SEQ ID NO: 59              moltype = AA   length = 13
FEATURE                    Location/Qualifiers
REGION                     1..13
                           note = Synthetic polymer
source                     1..13
                           mol_type = protein
                           organism = synthetic construct
SEQUENCE: 59
ATATLCDGGI WGY                                                          13

SEQ ID NO: 60              moltype = AA   length = 17
FEATURE                    Location/Qualifiers
REGION                     1..17
                           note = Synthetic polymer
source                     1..17
                           mol_type = protein
                           organism = synthetic construct
SEQUENCE: 60
AASGLGSVVV TANEYDY                                                      17

SEQ ID NO: 61              moltype = AA   length = 15
FEATURE                    Location/Qualifiers
REGION                     1..15
                           note = Synthetic polymer
source                     1..15
                           mol_type = protein
                           organism = synthetic construct
SEQUENCE: 61
AQGDRSSWHY YGMDY                                                        15

SEQ ID NO: 62              moltype = AA   length = 13
FEATURE                    Location/Qualifiers
REGION                     1..13
                           note = Synthetic polymer
source                     1..13
                           mol_type = protein
                           organism = synthetic construct
SEQUENCE: 62
```

```
ATKSDPMTNE YDL                                                               13

SEQ ID NO: 63           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 63
DRAESSWYDY                                                                   10

SEQ ID NO: 64           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 64
DKHQSSWYDY                                                                   10

SEQ ID NO: 65           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 65
DKHQSSFYDY                                                                   10

SEQ ID NO: 66           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 66
DRAQSSWYDY                                                                   10

SEQ ID NO: 67           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 67
DRVDSNWYDY                                                                   10

SEQ ID NO: 68           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 68
KERSTGWDFA S                                                                 11

SEQ ID NO: 69           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 69
EMSGISGWDY                                                                   10

SEQ ID NO: 70           moltype = AA  length = 147
FEATURE                 Location/Qualifiers
REGION                  1..147
                        note = Synthetic polymer
source                  1..147
                        mol_type = protein
                        organism = synthetic construct
```

```
SEQUENCE: 70
QVQLQESGGG LVQPGGSLRL SCAASGFSMD YYAIAWFRQA PGKEREEISC ITGSDFMVDT    60
YYVASVKGRF TISRDNAENT AYLQMNNLKP EDTGVYFCAV RSTANTLCPS HYSVMDYWGK   120
GTQVTVSSAA AYPYDVPDYG SHHHHHH                                      147

SEQ ID NO: 71           moltype = AA   length = 147
FEATURE                 Location/Qualifiers
REGION                  1..147
                        note = Synthetic polymer
source                  1..147
                        mol_type = protein
                        organism = synthetic construct
SEQUENCE: 71
QVQLQESGGG LVQAGGSLRL SCAASGFSMD YYAIAWFRQA PGKEREEISC ITGSDFMVDT    60
YYVASVKGRF TISRDNAENT AYLQMNNLKP EDTGVYFCAV RSTANTLCPS HYSVMDYWGK   120
GTQVTVSSAA AYPYDVPDYG SHHHHHH                                      147

SEQ ID NO: 72           moltype = AA   length = 147
FEATURE                 Location/Qualifiers
REGION                  1..147
                        note = Synthetic polymer
source                  1..147
                        mol_type = protein
                        organism = synthetic construct
SEQUENCE: 72
QVQLQESGGG LVQPGGSLRL SCSASGFSVD YYAIAWFRQA PGKEREEISC ITGSDFMVDT    60
YYVASVKGRF TISRDNAKNT AYLQMNSLKP EDTGVYFCAV RSTANTLCPS HYSIMDYWGK   120
GTQVTVSSAA AYPYDVPDYG SHHHHHH                                      147

SEQ ID NO: 73           moltype = AA   length = 147
FEATURE                 Location/Qualifiers
REGION                  1..147
                        note = Synthetic polymer
source                  1..147
                        mol_type = protein
                        organism = synthetic construct
SEQUENCE: 73
QVQLQESGGG LVQPGGSLRL SCSASGFSMD YYAIAWFRQA PGKEREEISC ITGSDFMVDT    60
YYVASVKGRF TISRDNAKNT AHLQMNSLKP EDTGVYFCAV RSTANTLCPS HYSVMDYWGK   120
GTQVTVSSAA AYPYDVPDYG SHHHHHH                                      147

SEQ ID NO: 74           moltype = AA   length = 139
FEATURE                 Location/Qualifiers
REGION                  1..139
                        note = Synthetic polymer
source                  1..139
                        mol_type = protein
                        organism = synthetic construct
SEQUENCE: 74
QVQLQESGGG LVQAGGSLRL SCAASGGFNR VSYMGWYRQA PGTKRELVAS VTSGGEITIA    60
DSVKGRFTVS RDNSKNTLYL QMNGLKPEDG ATYWCNADIW VSDARMYNYW GQGTQVTVSS   120
AAAYPYDVPD YGSHHHHHH                                               139

SEQ ID NO: 75           moltype = AA   length = 139
FEATURE                 Location/Qualifiers
REGION                  1..139
                        note = Synthetic polymer
source                  1..139
                        mol_type = protein
                        organism = synthetic construct
SEQUENCE: 75
QVQLQESGGG LVQTGESLRL SCAASGGFNR VSYMGWYRQA PGSKRELVAS VTSGGEITVA    60
DSVKGRFTVS RDNNKNTLYL QMNGLKPEDG ATYWCNADIW VSDARMYNYW GQGTQVTVSS   120
AAAYPYDVPD YGSHHHHHH                                               139

SEQ ID NO: 76           moltype = AA   length = 139
FEATURE                 Location/Qualifiers
REGION                  1..139
                        note = Synthetic polymer
source                  1..139
                        mol_type = protein
                        organism = synthetic construct
SEQUENCE: 76
QVQLQESGGG LVQTGESLRL SCAASGIIKS INFMGWYRQP PGTKRELVAS TTSDGRTTVA    60
DSVKGRFTIS RDNAKNTIYL EMSSLKPEDT ATYWCNADIW LPSDRMYNYW GQGTQVTVSS   120
AAAYPYDVPD YGSHHHHHH                                               139

SEQ ID NO: 77           moltype = AA   length = 139
FEATURE                 Location/Qualifiers
```

```
REGION                    1..139
                          note = Synthetic polymer
source                    1..139
                          mol_type = protein
                          organism = synthetic construct
SEQUENCE: 77
QVQLQESGGG LVQAGGSLRL SCAVSGFILD YYGIGWFRQA PGKEREAVSC ISSSDGSTYY     60
ADSVKGRFTI SRDNALNTLY LQMNSLKPED TAVYHCATAT LCDGGIWGYW GQGTQVTVSS    120
AAAYPYDVPD YGSHHHHHH                                                 139

SEQ ID NO: 78             moltype = AA  length = 139
FEATURE                   Location/Qualifiers
REGION                    1..139
                          note = Synthetic polymer
source                    1..139
                          mol_type = protein
                          organism = synthetic construct
SEQUENCE: 78
QVQLQESGGG LAQAGGSLRL SCEGSGLSLD YDGVGWFRQA PGKEREAVSC ISSSDGSTYY     60
ADSVKGRFTI SRGNALNTLY LQMNSLKPED TAVYYCATAT LCDGGIWGYW GQGTQVTVSS    120
AAAYPYDVPD YGSHHHHHH                                                 139

SEQ ID NO: 79             moltype = AA  length = 139
FEATURE                   Location/Qualifiers
REGION                    1..139
                          note = Synthetic polymer
source                    1..139
                          mol_type = protein
                          organism = synthetic construct
SEQUENCE: 79
QVQLQESGGG SVQPGGSLRL SCAVSGFILD YYGIGWFRQA PGKEREAVSC ISSSDGSTYY     60
ADSVKGRFTI SRDNALNTLY LQMNSLKPED TAVYYCATAT LCDGGIWGYW GQGTQVTVSS    120
AAAYPYDVPD YGSHHHHHH                                                 139

SEQ ID NO: 80             moltype = AA  length = 143
FEATURE                   Location/Qualifiers
REGION                    1..143
                          note = Synthetic polymer
source                    1..143
                          mol_type = protein
                          organism = synthetic construct
SEQUENCE: 80
QVQLQESGGG SVQAGDSLRL SCTASGRTFS SLGMGWFRQA PGKEREFVSA IAWNGASTYY     60
TESVKGRFTI SRDDAKNTVY LQMNSLKPTD TAVYFCAASG LGSVVVTANE YDYWGQGTQV    120
TVSSAAAYPY DVPDYGSHHH HHH                                            143

SEQ ID NO: 81             moltype = AA  length = 143
FEATURE                   Location/Qualifiers
REGION                    1..143
                          note = Synthetic polymer
source                    1..143
                          mol_type = protein
                          organism = synthetic construct
SEQUENCE: 81
QVQLQESGGG SVQPGKSLRL SCAASGRTFS SLGMGWFRQA PGKEREFVSA IAWNGASTYY     60
TESVKGRFTI SRDDAKNTVY LQMNSLKPTD TAVYFCAASG LGSVVVTANE YDYWGQGTQV    120
TVSSAAAYPY DVPDYGSHHH HHH                                            143

SEQ ID NO: 82             moltype = AA  length = 141
FEATURE                   Location/Qualifiers
REGION                    1..141
                          note = Synthetic polymer
source                    1..141
                          mol_type = protein
                          organism = synthetic construct
SEQUENCE: 82
QVQLQESGGG LVQPGGSLRL SCTTSGFAFG SYDMGWVRQA PGKGPEWVSG INSGGRITDY     60
ADSVTGRFTI SRDNAKNTLY LQMNSLKPED TAVYYCAQGD RSSWHYYGMD YWGKGTQVTV    120
SSAAAYPYDV PDYGSHHHHH H                                              141

SEQ ID NO: 83             moltype = AA  length = 139
FEATURE                   Location/Qualifiers
REGION                    1..139
                          note = Synthetic polymer
SITE                      112
                          note = misc_feature - Xaa can be any naturally occurring
                             amino acid
source                    1..139
                          mol_type = protein
```

```
                        organism = synthetic construct
SEQUENCE: 83
QVQLQESGGG LVQPGGSLRL SCAASGFSFG NNDMSWVRQA PGKGPEWVSA INSGGGSTYY    60
ADSVKGRFTI SRDNAKNTLY LQMNSLKPED TAVYYCATKS DPMTNEYDLW GXGTQVTVSS   120
AAAYPYDVPD YGSHHHHHH                                                139

SEQ ID NO: 84           moltype = AA  length = 6
FEATURE                 Location/Qualifiers
REGION                  1..6
                        note = Synthetic polymer
source                  1..6
                        mol_type = protein
                        organism = synthetic construct
SEQUENCE: 84
HHHHHH                                                                6

SEQ ID NO: 85           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 85
YPYDVPDYGS                                                           10

SEQ ID NO: 86           moltype = AA  length = 19
FEATURE                 Location/Qualifiers
REGION                  1..19
                        note = Synthetic polymer
source                  1..19
                        mol_type = protein
                        organism = synthetic construct
SEQUENCE: 86
AAAYPYDVPD YGSHHHHHH                                                 19

SEQ ID NO: 87           moltype = AA  length = 119
FEATURE                 Location/Qualifiers
REGION                  1..119
                        note = Synthetic polymer
source                  1..119
                        mol_type = protein
                        organism = synthetic construct
SEQUENCE: 87
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTLVTVSS    119

SEQ ID NO: 88           moltype = AA  length = 119
FEATURE                 Location/Qualifiers
REGION                  1..119
                        note = Synthetic polymer
source                  1..119
                        mol_type = protein
                        organism = synthetic construct
SEQUENCE: 88
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TATYYCAGDK HQSSWYDYWG QGTLVTVSS    119

SEQ ID NO: 89           moltype = AA  length = 119
FEATURE                 Location/Qualifiers
REGION                  1..119
                        note = Synthetic polymer
source                  1..119
                        mol_type = protein
                        organism = synthetic construct
SEQUENCE: 89
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TATYYCAGDK HQSSWYDYWG QGTLVKVSS    119

SEQ ID NO: 90           moltype = AA  length = 119
FEATURE                 Location/Qualifiers
REGION                  1..119
                        note = Synthetic polymer
source                  1..119
                        mol_type = protein
                        organism = synthetic construct
SEQUENCE: 90
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TAVYYCAAEM SGISGWDYWG QGTQVQVSS    119
```

```
SEQ ID NO: 91            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 91
EVQLVESGGG VVQAGGSLRL SCAASGGTFS FYGMGWFRQA PGKEQEFVAD IRTSAGRTYY   60
ADSVKGRFTI SRDNAKNTVY LQMNSLKPED TAVYYCAAEM SGISGWDYWG QGTLVTVKS   119

SEQ ID NO: 92            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 92
EVQLVESGGG VVQAGGSLRL SCAASGGTFS FYGMGWFRQA PGKEQEFVAD IRTSAGRTYY   60
ADSVKGRFTI SRDNAKNTVY LQMNSLKPED TAVYYCAAEM SGISGWDYWG QGTLVTVQS   119

SEQ ID NO: 93            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 93
EVQLVESGGG LVQAGGSLRL SCAASGSIAS IHAMGWFRQA PGKEQEFVAD IRTSAGRTYY   60
ADSVKGRFTI SRDNAKNTVY LQMNSLKPED TALYYCAAEM SGISGWDYWG QGTLVKVSS   119

SEQ ID NO: 94            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 94
EVQLVESGGG LVQAGGSLRL SCAASGGTFS FYGMGWFRQA PGKEQEFVAD IRTSAGRTYY   60
ADSVKGRFTI SRDNAKNTVY LQMNSLKPED TALYYCAAEM SGISGWDYWG QGTLVQVSS   119

SEQ ID NO: 95            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 95
EVQLVESGGG LVQAGGSLRL SCAASGGTFS FYGMGWFRQA PGKEQEFVAD IRTSAGRTYY   60
ADSVKGRFTI SRDNAKNTVY LQMNSLKPED TALYYCAAEM SGISGWDYWG QGTLVTVKS   119

SEQ ID NO: 96            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 96
EVQLVESGGG VVQAGGSLRL SCAASGGTFS FYGMGWFRQA PGKEQEFVAD IRTSAGRTYY   60
ADSVKGRFTI SRDNAKNTVY LQMNSLKPED TALYYCAAEM SGISGWDYWG QGTLVTVQS   119

SEQ ID NO: 97            moltype = AA   length = 119
FEATURE                  Location/Qualifiers
REGION                   1..119
                         note = Synthetic polymer
source                   1..119
                         mol_type = protein
                         organism = synthetic construct
SEQUENCE: 97
EVQLVESGGG VVQAGGSLRL SCAASGGTFS FYGMGWFRQA PGKEQEFVAD IRTSAGRTYY   60
ADSVKGRFTI SRDNAKNTVY LQMNSLKPED TALYYCAAEM SGISGWDYWG QGTLVTVSS   119

SEQ ID NO: 98            moltype = AA   length = 119
```

```
FEATURE                 Location/Qualifiers
REGION                  1..119
                        note = Synthetic polymer
source                  1..119
                        mol_type = protein
                        organism = synthetic construct
SEQUENCE: 98
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVKVSS    119

SEQ ID NO: 99           moltype = AA   length = 119
FEATURE                 Location/Qualifiers
REGION                  1..119
                        note = Synthetic polymer
source                  1..119
                        mol_type = protein
                        organism = synthetic construct
SEQUENCE: 99
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVQVSS    119

SEQ ID NO: 100          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 100
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVKS    119

SEQ ID NO: 101          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 101
EVQLVESGGG VVQPGGSLRL SCAASGGTFS FYGMGWFRQA PGKEQEFVAD IRTSAGRTYY    60
ADSVKGRFTI SRDNSKNTVY LQMNSLRPED TALYYCAAEM SGISGWDYWG QGTLVTVQS    119

SEQ ID NO: 102          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 102
EVQLVESGGG VVQPGGSLRL SCAASGGTFS FYGMGWFRQA PGKEREFVAD IRTSAGRTYY    60
ADSVKGRFTI SRDNSKNTVY LQMNSLRPED TALYYCAAEM SGISGWDYWG QGTLVTVSS    119

SEQ ID NO: 103          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 103
DVQLVESGGG VVQPGGSLRL SCAASGGTFS FYGMGWFRQA PGKEQEFVAD IRTSAGRTYY    60
ADSVKGRFTI SRDNSKNTVY LQMNSLRPED TALYYCAAEM SGISGWDYWG QGTLVTVSS    119

SEQ ID NO: 104          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 104
DVQLVESGGG VVQPGGSLRL SCAASGGTFS FYGMGWFRQA PGKEREFVAD IRTSAGRTYY    60
ADSVKGRFTI SRDNSKNTVY LQMNSLRPED TALYYCAAEM SGISGWDYWG QGTLVTSSA    119

SEQ ID NO: 105          moltype = AA   length = 120
FEATURE                 Location/Qualifiers
REGION                  1..120
```

```
                        note = Synthetic polymer
source                  1..120
                        mol_type = protein
                        organism = synthetic construct
SEQUENCE: 105
EVQLVESGGG LVQAGGSLRL SCAASGGTFS FYGMGWFRQA PGKEQEFVAD IRTSAGRTYY     60
ADSVKGRFTI SRDNAKNTVY LQMNSLKPED TATYYCAAEM SGISGWDYWG QGTLVKVSSA    120

SEQ ID NO: 106          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 106
EVQLVESGGG VVQAGGSLRL SCAASGGTFS FYGMGWFRQA PGKEQEFVAD IRTSAGRTYY     60
ADSVKGRFTI SRDNAKNTVY LQMNSLKPED TAVYYCAAEM SGISGWDYWG QGTLVQVSSA    120

SEQ ID NO: 107          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 107
EVQLVESGGG VVQAGGSLRL SCAASGGTFS FYGMGWFRQA PGKEQEFVAD IRTSAGRTYY     60
ADSVKGRFTI SRDNAKNTVY LQMNSLKPED TAVYYCAAEM SGISGWDYWG QGTLVTVKSA    120

SEQ ID NO: 108          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 108
EVQLVESGGG VVQAGGSLRL SCAASGGTFS FYGMGWFRQA PGKEQEFVAD IRTSAGRTYY     60
ADSVKGRFTI SRDNAKNTVY LQMNSLKPED TAVYYCAAEM SGISGWDYWG QGTLVTVQSA    120

SEQ ID NO: 109          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 109
EVQLVESGGG VVQAGGSLRL SCAASGGTFS FYGMGWFRQA PGKEQEFVAD IRTSAGRTYY     60
ADSVKGRFTI SRDNAKNTVY LQMNSLKPED TAVYYCAAEM SGISGWDYWG QGTLVKVSSA    120

SEQ ID NO: 110          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 110
EVQLVESGGG LVQAGGSLRL SCAASGGTFS FYGMGWFRQA PGKEQEFVAD IRTSAGRTYY     60
ADSVKGRFTI SRDNAKNTVY LQMNSLKPED TALYYCAAEM SGISGWDYWG QGTLVQVSSA    120

SEQ ID NO: 111          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 111
EVQLVESGGG LVQAGGSLRL SCAASGGTFS FYGMGWFRQA PGKEQEFVAD IRTSAGRTYY     60
ADSVKGRFTI SRDNAKNTVY LQMNSLKPED TALYYCAAEM SGISGWDYWG QGTLVTVKSA    120

SEQ ID NO: 112          moltype = AA   length = 120
FEATURE                 Location/Qualifiers
REGION                  1..120
                        note = Synthetic polymer
source                  1..120
```

```
                         mol_type = protein
                         organism = synthetic construct
SEQUENCE: 112
EVQLVESGGG LVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVQSA   120

SEQ ID NO: 113           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 113
EVQLVESGGG LVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVSSA   120

SEQ ID NO: 114           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 114
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVKVSSA   120

SEQ ID NO: 115           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 115
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVQVSSA   120

SEQ ID NO: 116           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 116
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVKSA   120

SEQ ID NO: 117           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 117
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVQSA   120

SEQ ID NO: 118           moltype = AA   length = 120
FEATURE                  Location/Qualifiers
REGION                   1..120
                         note = Synthetic polymer
source                   1..120
                         mol_type = protein
                         organism = synthetic construct
SEQUENCE: 118
EVQLVESGGG VVQAGGSLRL SCAASGGTFS FYGMGWFRQA PGKEQEFVAD IRTSAGRTYY    60
ADSVKGRFTI SRDNAKNTVY LQMNSLKPED TALYYCAAEM SGISGWDYWG QGTLVTVSSA   120

SEQ ID NO: 119           moltype = AA   length = 120
FEATURE                  Location/Qualifiers
REGION                   1..120
                         note = Synthetic polymer
source                   1..120
                         mol_type = protein
                         organism = synthetic construct
```

```
SEQUENCE: 119
EVQLVESGGG VVQPGGSLRL SCAASGGTFS FYGMGWFRQA PGKEQEFVAD IRTSAGRTYY    60
ADSVKGRFTI SRDNSKNTVY LQMNSLRPED TALYYCAAEM SGISGWDYWG QGTLVTVSSA   120

SEQ ID NO: 120          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 120
DVQLVESGGG VVQPGGSLRL SCAASGSIAS IHAMGWFRQA PGKEREFVAV ITWSGGITYY    60
ADSVKGRFTI SRDNSKNTVY LQMNSLRPED TALYYCAGDK HQSSWYDYWG QGTLVTVSS    119

SEQ ID NO: 121          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 121
EVQLVESGGG LVQPGGSLRL SCAASGSIAS IHAMGWERQA PGKEREEVAV ITWSGGITYY    60
ADSVKGRFTI SRDNSKNTVY LQMNSLRPED TAIYYCAGDK HQSSWYDYWG QGTLVTVSS    119

SEQ ID NO: 122          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 122
EVQLVESGGG VVQPGGSLRL SCAASGSIAS IHAMGWERQA PGKEREEVAV ITWSGGITYY    60
ADSVKGRFTI SRDNSKNTVY LQMNSLRPED TALYYCAGDK HQSSWYDYWG QGTLVTVSS    119

SEQ ID NO: 123          moltype = AA   length = 270
FEATURE                 Location/Qualifiers
REGION                  1..270
                        note = Synthetic polymer
source                  1..270
                        mol_type = protein
                        organism = synthetic construct
SEQUENCE: 123
DVQLVESGGG VVQPGGSLRL SCAASGSIAS IHAMGWERQA PGKEREEVAV ITWSGGITYY    60
ADSVKGRFTI SRDNSKNTVY LQMNSLRPED TALYYCAGDK HQSSWYDYWG QGTLVTVSSG   120
GGGSGGGGSG GGGSGGGGSG GGGSGGGGSG GGGSEVQLVE SGGGVVQPGN SLRLSCAASG   180
FTFSSFGMSW VRQAPGKGLE WVSSISGSGS DTLYADSVKG RFTISRDNAK TTLYLQMNSL   240
RPEDTALYYC TIGGSLSRSS QGTLVTVSSA                                   270

SEQ ID NO: 124          moltype = AA   length = 424
FEATURE                 Location/Qualifiers
REGION                  1..424
                        note = Synthetic polymer
source                  1..424
                        mol_type = protein
                        organism = synthetic construct
SEQUENCE: 124
DVQLVESGGG VVQPGGSLRL SCAASGSIAS IHAMGWERQA PGKEREEVAV ITWSGGITYY    60
ADSVKGRFTI SRDNSKNTVY LQMNSLRPED TALYYCAGDK HQSSWYDYWG QGTLVTVSSG   120
GGGSGGGGSG GGGSGGGGSG GGGSGGGGSG GGGSEVQLVE SGGGVVQPGG SLRLSCAASG   180
SIASIHAMGW FRQAPGKERE FVAVITWSGG ITYYADSVKG RFTISRDNSK NTVYLQMNSL   240
RPEDTALYYC AGDKHQSSWY DYWGQGTLVT VSSGGGGSGG GGSGGGGSGG GGSGGGGSGG   300
GGSGGGGSEV QLVESGGGVV QPGNSLRLSC AASGFTFSSF GMSWVRQAPG KGLEWVSSIS   360
GSGSDTLYAD SVKGRFTISR DNAKTTLYLQ MNSLRPEDTA LYYCTIGGSL SRSSQGTLVT   420
VSSA                                                               424

SEQ ID NO: 125          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 125
DVQLVESGGG VVQPGGSLRL SCAASGSIAS IHAMGWERQA PGKEREEVAV ITVSGGITYY    60
ADSVKGRFTI SRDNSKNTVY LQMNSLRPED TALYYCAGDK HQSSFYDYWG QGTLVTVSS    119
```

```
SEQ ID NO: 126            moltype = AA  length = 119
FEATURE                   Location/Qualifiers
REGION                    1..119
                          note = Synthetic polymer
source                    1..119
                          mol_type = protein
                          organism = synthetic construct
SEQUENCE: 126
DVQLVESGGG VVQPGGSLRL SCAASGSIAS IHAMGWFRQA PGKEREFVAV ITVSGGITYY   60
ADSVKGRFTI SRDQSKNTVY LQMNSLRPED TALYYCAGDK HQSSFYDYWG QGTLVTVSS   119

SEQ ID NO: 127            moltype = AA  length = 119
FEATURE                   Location/Qualifiers
REGION                    1..119
                          note = Synthetic polymer
source                    1..119
                          mol_type = protein
                          organism = synthetic construct
SEQUENCE: 127
DVQLVESGGG VVQPGGSLRL SCAASGSIAS IHAMGWFRQA PGKEREFVAV ITVSGGITYY   60
ADSVKGRFTI SRDPSKNTVY LQMNSLRPED TALYYCAGDK HQSSFYDYWG QGTLVTVSS   119

SEQ ID NO: 128            moltype = AA  length = 119
FEATURE                   Location/Qualifiers
REGION                    1..119
                          note = Synthetic polymer
source                    1..119
                          mol_type = protein
                          organism = synthetic construct
SEQUENCE: 128
DVQLVESGGG VVQPGGSLRL SCAASGSIAS IHAMGWFRQA PGKEREFVAV ITVSGGITYY   60
ADSVKGRFTI SRDPSKNTVY LQMNSLRPED TALYYCAGDK HQSSFYDYWG QGTLVTVSS   119

SEQ ID NO: 129            moltype = AA  length = 119
FEATURE                   Location/Qualifiers
REGION                    1..119
                          note = Synthetic polymer
source                    1..119
                          mol_type = protein
                          organism = synthetic construct
SEQUENCE: 129
DVQLVESGGG VVQPGGSLRL SCAASGSIAS IHAMGWFRQA PGKEREFVAV ITVSGGITYY   60
ADSVKGRFTI SRDQSKNTVY LQMNSLRPED TALYYCAGDK HQSSFYDYWG QGTLVTVSS   119

SEQ ID NO: 130            moltype = AA  length = 119
FEATURE                   Location/Qualifiers
REGION                    1..119
                          note = Synthetic polymer
source                    1..119
                          mol_type = protein
                          organism = synthetic construct
SEQUENCE: 130
DVQLVESGGG VVQPGGSLRL SCAASGSIAS IHAMGWFRQA PGKEREFVAV ITVSGGITYY   60
ADSVKGRFTI SRDSSKNTVY LQMNSLRPED TALYYCAGDK HQSSFYDYWG QGTLVTVSS   119

SEQ ID NO: 131            moltype = AA  length = 423
FEATURE                   Location/Qualifiers
REGION                    1..423
                          note = Synthetic polymer
source                    1..423
                          mol_type = protein
                          organism = synthetic construct
SEQUENCE: 131
EVQLVESGGG LVQPGGSLRL SCAASGSIAS IHAMGWERQA PGKEREVAV ITWSGGITYY    60
ADSVKGRFTI SRDNSKNTVY LQMNSLRPED TAIYYCAGDK HQSSWYDYWG QGTLVTVSSG  120
GGGSGGGGSG GGGSGGGGSG GGGSGGGGSG GGGSEVQLVE SGGGLVQPGG SLRLSCAASG  180
SIASIHAMGW ERQAPGKERE EVAVITWSGG ITTYADSVKG RFTISRDNSK NTVYLQMNSL  240
RPEDTAIYYC AGDKHQSSWY DYWGQGTLVT VSSGGGGSGG GGSGGGGSGG GGSGGGGSGG  300
GGSGGGGSEV QLVESGGGLV QPGNSLRLSC AASGFTFSSF GMSWVRQAPG KGLEWVSSIS  360
GSGSDTLYAD SVKGRFTISR DNAKTTLYLQ MNSLRPEDTA VYYCTIGGSL SRSSQGTLVT  420
VSS                                                                423

SEQ ID NO: 132            moltype = AA  length = 287
FEATURE                   Location/Qualifiers
REGION                    1..287
                          note = Synthetic polymer
source                    1..287
                          mol_type = protein
                          organism = synthetic construct
```

```
SEQUENCE: 132
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFV DYGELDFQWR EKTPEPPVPC   240
VPEQTEYATI VFPSGMGTSS PARRGSADGP RSAQPLRPED GHCSWPL                287

SEQ ID NO: 133          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 133
EVQLVESGGG LVQAGGSLRL SCAASGGTFS FYGMGWFRQA PGKEQEFVAD IRTSAGRTYY    60
ADSVKGRFTI SRDNAKNTVY LQMNSLKPED TAVYYCAAEM SGISGWDYWG QGTQVTVSS    119

SEQ ID NO: 134          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 134
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TATYYCAGDK HQSSWYDYWG QGTLVTVSS    119

SEQ ID NO: 135          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 135
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTLVKVSS    119

SEQ ID NO: 136          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 136
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTLVQVSS    119

SEQ ID NO: 137          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 137
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTLVTVKS    119

SEQ ID NO: 138          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 138
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTLVTVQS    119

SEQ ID NO: 139          moltype = AA  length = 119
FEATURE                 Location/Qualifiers
REGION                  1..119
                        note = Synthetic polymer
source                  1..119
                        mol_type = protein
```

-continued

```
                           organism = synthetic construct
SEQUENCE: 139
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVKVSS    119

SEQ ID NO: 140          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 140
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVQVSS    119

SEQ ID NO: 141          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 141
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVKS    119

SEQ ID NO: 142          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 142
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVQS    119

SEQ ID NO: 143          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 143
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVSS    119

SEQ ID NO: 144          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 144
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVKVSS    119

SEQ ID NO: 145          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 145
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVQVSS    119

SEQ ID NO: 146          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 146
```

```
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TALYYCAGDK HQSSWYDYWG QGTLVTVKS   119

SEQ ID NO: 147            moltype = AA   length = 119
FEATURE                   Location/Qualifiers
REGION                    1..119
                          note = Synthetic polymer
source                    1..119
                          mol_type = protein
                          organism = synthetic construct
SEQUENCE: 147
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TALYYCAGDK HQSSWYDYWG QGTLVTVQS   119

SEQ ID NO: 148            moltype = AA   length = 119
FEATURE                   Location/Qualifiers
REGION                    1..119
                          note = Synthetic polymer
source                    1..119
                          mol_type = protein
                          organism = synthetic construct
SEQUENCE: 148
EVQLVESGGG VVQPGGSLRL SCAASGSIAS IHAMGWFRQA PGKEREFVAV ITWSGGITYY   60
ADSVKGRFTI SRDNSKNTVY LQMNSLRPED TALYYCAGDK HQSSWYDYWG QGTLVTVSS   119

SEQ ID NO: 149            moltype = AA   length = 119
FEATURE                   Location/Qualifiers
REGION                    1..119
                          note = Synthetic polymer
source                    1..119
                          mol_type = protein
                          organism = synthetic construct
SEQUENCE: 149
DVQLVESGGG VVQPGGSLRL SCAASGSIAS IHAMGWFRQA PGKEREFVAV ITWSGGITYY   60
ADSVKGRFTI SRDNSKNTVY LQMNSLRPED TALYYCAGDK HQSSWYDYWG QGTLVTVSS   119

SEQ ID NO: 150            moltype = AA   length = 120
FEATURE                   Location/Qualifiers
REGION                    1..120
                          note = Synthetic polymer
source                    1..120
                          mol_type = protein
                          organism = synthetic construct
SEQUENCE: 150
EVQLVESGGG LVQAGGSLRL SCAASGSIAS IHAMGWFRQA PGKEREFVAV ITWSGGITYY   60
ADSVKGRFTI SRDNAKNTVY LQMNSLKPED TATYYCAGDK HQSSWYDYWG QGTLVTVSSA  120

SEQ ID NO: 151            moltype = AA   length = 120
FEATURE                   Location/Qualifiers
REGION                    1..120
                          note = Synthetic polymer
source                    1..120
                          mol_type = protein
                          organism = synthetic construct
SEQUENCE: 151
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TAIYYCAGDK HQSSWYDYWG QGTLVKVSSA  120

SEQ ID NO: 152            moltype = AA   length = 120
FEATURE                   Location/Qualifiers
REGION                    1..120
                          note = Synthetic polymer
source                    1..120
                          mol_type = protein
                          organism = synthetic construct
SEQUENCE: 152
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TAIYYCAGDK HQSSWYDYWG QGTLVQVSSA  120

SEQ ID NO: 153            moltype = AA   length = 120
FEATURE                   Location/Qualifiers
REGION                    1..120
                          note = Synthetic polymer
source                    1..120
                          mol_type = protein
                          organism = synthetic construct
SEQUENCE: 153
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TAIYYCAGDK HQSSWYDYWG QGTLVTVKSA  120
```

```
SEQ ID NO: 154          moltype = AA  length = 121
FEATURE                 Location/Qualifiers
REGION                  1..121
                        note = Synthetic polymer
source                  1..121
                        mol_type = protein
                        organism = synthetic construct
SEQUENCE: 154
EVQLVESGGG VVQAGGSLRL SCAASGSIAS IHATVCWFRQ APGKEREFVA VITWSGGITY    60
YADSVKGRFT ISRDNAKNTV YLQMNSLKPE DTAIYYCAGD KHQSSWYDYW GQGTLVTVQS   120
A                                                                  121

SEQ ID NO: 155          moltype = AA  length = 121
FEATURE                 Location/Qualifiers
REGION                  1..121
                        note = Synthetic polymer
source                  1..121
                        mol_type = protein
                        organism = synthetic construct
SEQUENCE: 155
EVQLVESGGG LVQAGGSLRL SCAASGSIAS IHATVCWFRQ APGKEREFVA VITWSGGITY    60
YADSVKGRFT ISRDNAKNTV YLQMNSLKPE DTALYYCAGD KHQSSWYDYW GQGTLVKVSS   120
A                                                                  121

SEQ ID NO: 156          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 156
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVQVSSA   120

SEQ ID NO: 157          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 157
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVKSA   120

SEQ ID NO: 158          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 158
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVQSA   120

SEQ ID NO: 159          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 159
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVTVSSA   120

SEQ ID NO: 160          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 160
EVQLVESGGG VVQAGGSLRL SCAASGSIAS IHAMGWFRQA PGKEREFVAV ITWSGGITYY    60
ADSVKGRFTI SRDNAKNTVY LQMNSLKPED TALYYCAGDK HQSSWYDYWG QGTLVKVSSA   120
```

```
SEQ ID NO: 161          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 161
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TALYYCAGDK HQSSWYDYWG QGTLVQVSSA  120

SEQ ID NO: 162          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 162
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TALYYCAGDK HQSSWYDYWG QGTLVTVKSA  120

SEQ ID NO: 163          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 163
EVQLVESGGG VVQAGGSLRL SCAASGSIAS IHAMGWFRQA PGKEREFVAV ITWSGGITYY   60
ADSVKGRFTI SRDNAKNTVY LQMNSLKPED TALYYCAGDK HQSSWYDYWG QGTLVTVQSA  120

SEQ ID NO: 164          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 164
EVQLVESGGG VVQPGGSLRL SCAASGSIAS IHAMGWFRQA PGKEREFVAV ITWSGGITYY   60
ADSVKGRFTI SRDNSKNTVY LQMNSLRPED TALYYCAGDK HQSSWYDYWG QGTLVTVSSA  120

SEQ ID NO: 165          moltype = AA   length = 120
FEATURE                 Location/Qualifiers
REGION                  1..120
                        note = Synthetic polymer
source                  1..120
                        mol_type = protein
                        organism = synthetic construct
SEQUENCE: 165
DVQLVESGGG VVQPGGSLRL SCAASGSIAS IHAMGWFRQA PGKEREFVAV ITWSGGITYY   60
ADSVKGRFTI SRDNSKNTVY LQMNSLRPED TALYYCAGDK HQSSWYDYWG QGTLVTVSSA  120

SEQ ID NO: 166          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 166
DVQLVESGGG VVQPGGSLRL SCAASGSIAS IHAMGWFRQA PGKEREFVAI ITWSGGITYY   60
ADSVKGRFTI SRDNSKNTVY LQMNSLRPED TALYYCAGDK HQSSWYDYWG QGTLVTVSS   119

SEQ ID NO: 167          moltype = AA   length = 119
FEATURE                 Location/Qualifiers
REGION                  1..119
                        note = Synthetic polymer
source                  1..119
                        mol_type = protein
                        organism = synthetic construct
SEQUENCE: 167
EVQLVESGGG LVQPGGSLRL SCAASGSIAS IHAMGWFRQA PGKEREFVAV ITWSGGITYY   60
ADSVKGRFTI SRDNSKNTVY LQMNSLRPED TAIYYCAGDK HQSSWYDYWG QGTLVTVSS   119

SEQ ID NO: 168          moltype = AA   length = 119
```

```
FEATURE                 Location/Qualifiers
REGION                  1..119
                        note = Synthetic polymer
source                  1..119
                        mol_type = protein
                        organism = synthetic construct
SEQUENCE: 168
EVQLVESGGG VVQPGGSLRL SCAASGSIAS IHAMGWFRQA PGKEREFVAV ITWSGGITYY  60
ADSVKGRFTI SRDNSKNTVY LQMNSLRPED TALYYCAGDK HQSSWYDYWG QGTLVTVSS  119

SEQ ID NO: 169          moltype = AA  length = 270
FEATURE                 Location/Qualifiers
REGION                  1..270
                        note = Synthetic polymer
source                  1..270
                        mol_type = protein
                        organism = synthetic construct
SEQUENCE: 169
DVQLVESGGG VVQPGGSLRL SCAASGSIAS IHAMGWFRQA PGKEREFVAV ITWSGGITYY  60
ADSVKGRFTI SRDNSKNTVY LQMNSLRPED TALYYCAGDK HQSSWYDYWG QGTLVTVSSG 120
GGGSGGGGSG GGGSGGGGSG GGGSGGGGSG GGGSEVQLVE SGGGVVQPGN SLRLSCAASG 180
FTFSSFGMSW VRQAPGKGLE WVSSISGSGS DTLYADSVKG RFTISRDNAK TTLYLQMNSL 240
RPEDTALYYC TIGGSLSRSS QGTLVTVSSA                                 270

SEQ ID NO: 170          moltype = AA  length = 424
FEATURE                 Location/Qualifiers
REGION                  1..424
                        note = Synthetic polymer
source                  1..424
                        mol_type = protein
                        organism = synthetic construct
SEQUENCE: 170
DVQLVESGGG VVQPGGSLRL SCAASGSIAS IHAMGWFRQA PGKEREFVAV ITWSGGITYY  60
ADSVKGRFTI SRDNSKNTVY LQMNSLRPED TALYYCAGDK HQSSWYDYWG QGTLVTVSSG 120
GGGSGGGGSG GGGSGGGGSG GGGSGGGGSG GGGSEVQLVE SGGGVVQPGG SLRLSCAASG 180
SIASIHAMGW FRQAPGKERE FVAVITWSGG ITYYADSVKG RFTISRDNSK NTVYLQMNSL 240
RPEDTALYYC AGDKHQSSWY DYWGQGTLVT VSSGGGGSGG GGSGGGGSGG GGSGGGGSGG 300
GGSGGGGSEV QLVESGGGVV QPGNSLRLSC AASGFTFSSF GMSWVRQAPG KGLEWVSSIS 360
GSGSDTLYAD SVKGRFTISR DNAKTTLYLQ MNSLRPEDTA LYYCTIGGSL SRSSQGTLVT 420
VSSA                                                             424

SEQ ID NO: 171          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 171
DVQLVESGGG VVQPGGSLRL SCAASGSIAS IHAMGWFRQA PGKEREFVAV ITVSGGITYY  60
ADSVKGRFTI SRDNSKNTVY LQMNSLRPED TALYYCAGDK HQSSFYDYWG QGTLVTVSS  119

SEQ ID NO: 172          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 172
DVQLVESGGG VVQPGGSLRL SCAASGSIAS IHAMGWFRQA PGKEREFVAV ITVSGGITYY  60
ADSVKGRFTI SRDQSKNTVY LQMNSLRPED TALYYCAGDK HQSSFYDYWG QGTLVTVSS  119

SEQ ID NO: 173          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 173
DVQLVESGGG VVQPGGSLRL SCAASGSIAS IHAMGWFRQA PGKEREFVAV ITVSGGITYY  60
ADSVKGRFTI SRDPSKNTVY LQMNSLRPED TALYYCAGDK HQSSFYDYWG QGTLVTVSS  119

SEQ ID NO: 174          moltype = AA  length = 290
FEATURE                 Location/Qualifiers
REGION                  1..290
                        note = Synthetic polymer
source                  1..290
```

```
                        mol_type = protein
                        organism = synthetic construct
SEQUENCE: 174
MRIFAVFIFM  TYWHLLNAFT  VTVPKDLYVV  EYGSNMTIEC  KFPVEKQLDL  AALIVYWEME   60
DKNIIQFVHG  EEDLKVQHSS  YRQRARLLKD  QLSLGNAALQ  ITDVKLQDAG  VYRCMISYGG  120
ADYKRITVKV  NAPYNKINQR  ILVVDPVTSE  HELTCQAEGY  PKAEVIWTSS  DHQVLSGKTT  180
TTNSKREEKL  FNVTSTLRIN  TTTNEIFYCT  FRRLDPEENH  TAELVIPELP  LAHPPNERTH  240
LVILGAILLC  LGVALTFIFR  LRKGRMMDVK  KCGIQDTNSK  KQSDTHLEET              290

SEQ ID NO: 175          moltype = AA   length = 176
FEATURE                 Location/Qualifiers
REGION                  1..176
                        note = Synthetic polymer
source                  1..176
                        mol_type = protein
                        organism = synthetic construct
SEQUENCE: 175
MRIFAVFIFM  TYWHLLNAPY  NKINQRILVV  DPVTSEHELT  CQAEGYPKAE  VIWTSSDHQV   60
LSGKTTTTNS  KREEKLFNVT  STLRINTTTN  EIFYCTFRRL  DPEENHTAEL  VIPELPLAHP  120
PNERTHLVIL  GAILLCLGVA  LTFIFRLRKG  RMMDVKKCGI  QDTNSKKQSD  THLEET      176

SEQ ID NO: 176          moltype = AA   length = 178
FEATURE                 Location/Qualifiers
REGION                  1..178
                        note = Synthetic polymer
source                  1..178
                        mol_type = protein
                        organism = synthetic construct
SEQUENCE: 176
MRIFAVFIFM  TYWHLLNAFT  VTVPKDLYVV  EYGSNMTIEC  KFPVEKQLDL  AALIVYWEME   60
DKNIIQFVHG  EEDLKVQHSS  YRQRARLLKD  QLSLGNAALQ  ITDVKLQDAG  VYRCMISYGG  120
ADYKRITVKV  NAPYNKINQR  ILVVDPVTSE  HELTCQAEGY  PKAEVIWTSS  DHQVLSGD    178

SEQ ID NO: 177          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 177
GFTLDYYAIG                                                               10

SEQ ID NO: 178          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 178
GTIFSINHMD                                                               10

SEQ ID NO: 179          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 179
GFTFDDYGMS                                                               10

SEQ ID NO: 180          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 180
GFTLDYYAIN                                                               10

SEQ ID NO: 181          moltype = AA   length = 10
FEATURE                 Location/Qualifiers
REGION                  1..10
                        note = Synthetic polymer
source                  1..10
                        mol_type = protein
```

```
                           organism = synthetic construct
SEQUENCE: 181
GTIFSINRMD                                                                      10

SEQ ID NO: 182             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 182
GFTFSSYGMS                                                                      10

SEQ ID NO: 183             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 183
GKIFSGNDMG                                                                      10

SEQ ID NO: 184             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 184
GFTFNDYAMS                                                                      10

SEQ ID NO: 185             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 185
GFNLDPYAIA                                                                      10

SEQ ID NO: 186             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 186
GFTFTAYAMS                                                                      10

SEQ ID NO: 187             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 187
GFTFDYYAIG                                                                      10

SEQ ID NO: 188             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 188
GFNLDPYAIG                                                                      10

SEQ ID NO: 189             moltype = AA  length = 10
FEATURE                    Location/Qualifiers
REGION                     1..10
                           note = Synthetic polymer
source                     1..10
```

```
                              mol_type = protein
                              organism = synthetic construct
SEQUENCE: 189
ESIFSIEAMG                                                                  10

SEQ ID NO: 190               moltype = AA   length = 10
FEATURE                      Location/Qualifiers
REGION                       1..10
                             note = Synthetic polymer
source                       1..10
                             mol_type = protein
                             organism = synthetic construct
SEQUENCE: 190
GRTFSISAMG                                                                  10

SEQ ID NO: 191               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 191
YYAIG                                                                        5

SEQ ID NO: 192               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 192
YYAKC                                                                        5

SEQ ID NO: 193               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 193
QYDVG                                                                        5

SEQ ID NO: 194               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 194
NSAMG                                                                        5

SEQ ID NO: 195               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 195
DSIVS                                                                        5

SEQ ID NO: 196               moltype = AA   length = 5
FEATURE                      Location/Qualifiers
REGION                       1..5
                             note = Synthetic polymer
source                       1..5
                             mol_type = protein
                             organism = synthetic construct
SEQUENCE: 196
INHMD                                                                        5

SEQ ID NO: 197               moltype = AA   length = 5
FEATURE                      Location/Qualifiers
REGION                       1..5
                             note = Synthetic polymer
```

```
source                          1..5
                                mol_type = protein
                                organism = synthetic construct
SEQUENCE: 197
DYGMS                                                                    5

SEQ ID NO: 198                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 198
YYAIN                                                                    5

SEQ ID NO: 199                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 199
INRMD                                                                    5

SEQ ID NO: 200                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 200
SYGMS                                                                    5

SEQ ID NO: 201                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 201
GNDMG                                                                    5

SEQ ID NO: 202                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 202
DYAMS                                                                    5

SEQ ID NO: 203                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 203
PYAIA                                                                    5

SEQ ID NO: 204                  moltype = AA  length = 5
FEATURE                         Location/Qualifiers
REGION                          1..5
                                note = Synthetic polymer
source                          1..5
                                mol_type = protein
                                organism = synthetic construct
SEQUENCE: 204
AYAMS                                                                    5

SEQ ID NO: 205                  moltype = AA  length = 5
FEATURE                         Location/Qualifiers
REGION                          1..5
```

| | | |
|---|---|---|
| | note = Synthetic polymer | |
| source | 1..5 | |
| | mol_type = protein | |
| | organism = synthetic construct | |
| SEQUENCE: 205 | | |
| PYAIG | | 5 |
| | | |
| SEQ ID NO: 206 | moltype = AA length = 5 | |
| FEATURE | Location/Qualifiers | |
| REGION | 1..5 | |
| | note = Synthetic polymer | |
| source | 1..5 | |
| | mol_type = protein | |
| | organism = synthetic construct | |
| SEQUENCE: 206 | | |
| IEAMG | | 5 |
| | | |
| SEQ ID NO: 207 | moltype = AA length = 5 | |
| FEATURE | Location/Qualifiers | |
| REGION | 1..5 | |
| | note = Synthetic polymer | |
| source | 1..5 | |
| | mol_type = protein | |
| | organism = synthetic construct | |
| SEQUENCE: 207 | | |
| ISAMG | | 5 |
| | | |
| SEQ ID NO: 208 | moltype = AA length = 9 | |
| FEATURE | Location/Qualifiers | |
| REGION | 1..9 | |
| | note = Synthetic polymer | |
| source | 1..9 | |
| | mol_type = protein | |
| | organism = synthetic construct | |
| SEQUENCE: 208 | | |
| ISSSDGSTY | | 9 |
| | | |
| SEQ ID NO: 209 | moltype = AA length = 8 | |
| FEATURE | Location/Qualifiers | |
| REGION | 1..8 | |
| | note = Synthetic polymer | |
| source | 1..8 | |
| | mol_type = protein | |
| | organism = synthetic construct | |
| SEQUENCE: 209 | | |
| ITSDGFPT | | 8 |
| | | |
| SEQ ID NO: 210 | moltype = AA length = 9 | |
| FEATURE | Location/Qualifiers | |
| REGION | 1..9 | |
| | note = Synthetic polymer | |
| source | 1..9 | |
| | mol_type = protein | |
| | organism = synthetic construct | |
| SEQUENCE: 210 | | |
| IRWNGGSTN | | 9 |
| | | |
| SEQ ID NO: 211 | moltype = AA length = 8 | |
| FEATURE | Location/Qualifiers | |
| REGION | 1..8 | |
| | note = Synthetic polymer | |
| source | 1..8 | |
| | mol_type = protein | |
| | organism = synthetic construct | |
| SEQUENCE: 211 | | |
| ITSDGTPT | | 8 |
| | | |
| SEQ ID NO: 212 | moltype = AA length = 9 | |
| FEATURE | Location/Qualifiers | |
| REGION | 1..9 | |
| | note = Synthetic polymer | |
| source | 1..9 | |
| | mol_type = protein | |
| | organism = synthetic construct | |
| SEQUENCE: 212 | | |
| IDSGGGSTS | | 9 |
| | | |
| SEQ ID NO: 213 | moltype = AA length = 8 | |
| FEATURE | Location/Qualifiers | |

```
                          -continued

REGION                    1..8
                          note = Synthetic polymer
source                    1..8
                          mol_type = protein
                          organism = synthetic construct
SEQUENCE: 213
ITSGGITD                                                                 8

SEQ ID NO: 214            moltype = AA  length = 8
FEATURE                   Location/Qualifiers
REGION                    1..8
                          note = Synthetic polymer
source                    1..8
                          mol_type = protein
                          organism = synthetic construct
SEQUENCE: 214
ITSDGTPT                                                                 8

SEQ ID NO: 215            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 215
IDSGGGSTS                                                                9

SEQ ID NO: 216            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 216
IRSNGGYTN                                                                9

SEQ ID NO: 217            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 217
ISSSDVGTY                                                                9

SEQ ID NO: 218            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 218
INSSDGSTY                                                                9

SEQ ID NO: 219            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 219
ISGSDSSTY                                                                9

SEQ ID NO: 220            moltype = AA  length = 9
FEATURE                   Location/Qualifiers
REGION                    1..9
                          note = Synthetic polymer
source                    1..9
                          mol_type = protein
                          organism = synthetic construct
SEQUENCE: 220
ISSSDVGTY                                                                9

SEQ ID NO: 221            moltype = AA  length = 8
```

```
                              -continued

FEATURE               Location/Qualifiers
REGION                1..8
                      note = Synthetic polymer
source                1..8
                      mol_type = protein
                      organism = synthetic construct
SEQUENCE: 221
ITSDGTPT                                                                    8

SEQ ID NO: 222        moltype = AA  length = 8
FEATURE               Location/Qualifiers
REGION                1..8
                      note = Synthetic polymer
source                1..8
                      mol_type = protein
                      organism = synthetic construct
SEQUENCE: 222
ITSDGTPA                                                                    8

SEQ ID NO: 223        moltype = AA  length = 9
FEATURE               Location/Qualifiers
REGION                1..9
                      note = Synthetic polymer
source                1..9
                      mol_type = protein
                      organism = synthetic construct
SEQUENCE: 223
IDSGGGSTS                                                                   9

SEQ ID NO: 224        moltype = AA  length = 9
FEATURE               Location/Qualifiers
REGION                1..9
                      note = Synthetic polymer
source                1..9
                      mol_type = protein
                      organism = synthetic construct
SEQUENCE: 224
ISSGDGSKY                                                                   9

SEQ ID NO: 225        moltype = AA  length = 9
FEATURE               Location/Qualifiers
REGION                1..9
                      note = Synthetic polymer
source                1..9
                      mol_type = protein
                      organism = synthetic construct
SEQUENCE: 225
ISSSDVGTY                                                                   9

SEQ ID NO: 226        moltype = AA  length = 8
FEATURE               Location/Qualifiers
REGION                1..8
                      note = Synthetic polymer
source                1..8
                      mol_type = protein
                      organism = synthetic construct
SEQUENCE: 226
IFGGGFTN                                                                    8

SEQ ID NO: 227        moltype = AA  length = 8
FEATURE               Location/Qualifiers
REGION                1..8
                      note = Synthetic polymer
source                1..8
                      mol_type = protein
                      organism = synthetic construct
SEQUENCE: 227
ITSGGITD                                                                    8

SEQ ID NO: 228        moltype = AA  length = 9
FEATURE               Location/Qualifiers
REGION                1..9
                      note = Synthetic polymer
source                1..9
                      mol_type = protein
                      organism = synthetic construct
SEQUENCE: 228
IDSGGGSTS                                                                   9
```

```
SEQ ID NO: 229         moltype = AA   length = 8
FEATURE                Location/Qualifiers
REGION                 1..8
                       note = Synthetic polymer
source                 1..8
                       mol_type = protein
                       organism = synthetic construct
SEQUENCE: 229
ITSDGTPT                                                                  8

SEQ ID NO: 230         moltype = AA   length = 9
FEATURE                Location/Qualifiers
REGION                 1..9
                       note = Synthetic polymer
source                 1..9
                       mol_type = protein
                       organism = synthetic construct
SEQUENCE: 230
IDSGGGSTS                                                                 9

SEQ ID NO: 231         moltype = AA   length = 9
FEATURE                Location/Qualifiers
REGION                 1..9
                       note = Synthetic polymer
source                 1..9
                       mol_type = protein
                       organism = synthetic construct
SEQUENCE: 231
ISSSDVGTY                                                                 9

SEQ ID NO: 232         moltype = AA   length = 9
FEATURE                Location/Qualifiers
REGION                 1..9
                       note = Synthetic polymer
source                 1..9
                       mol_type = protein
                       organism = synthetic construct
SEQUENCE: 232
ITWSGGSTS                                                                 9

SEQ ID NO: 233         moltype = AA   length = 9
FEATURE                Location/Qualifiers
REGION                 1..9
                       note = Synthetic polymer
source                 1..9
                       mol_type = protein
                       organism = synthetic construct
SEQUENCE: 233
IDSGGGSTS                                                                 9

SEQ ID NO: 234         moltype = AA   length = 9
FEATURE                Location/Qualifiers
REGION                 1..9
                       note = Synthetic polymer
source                 1..9
                       mol_type = protein
                       organism = synthetic construct
SEQUENCE: 234
IRSNGGYTN                                                                 9

SEQ ID NO: 235         moltype = AA   length = 17
FEATURE                Location/Qualifiers
REGION                 1..17
                       note = Synthetic polymer
source                 1..17
                       mol_type = protein
                       organism = synthetic construct
SEQUENCE: 235
SISSSDGSTY YADSVKG                                                       17

SEQ ID NO: 236         moltype = AA   length = 17
FEATURE                Location/Qualifiers
REGION                 1..17
                       note = Synthetic polymer
source                 1..17
                       mol_type = protein
                       organism = synthetic construct
SEQUENCE: 236
CISSSDGSTY YADSVKG                                                       17
```

| | | |
|---|---|---|
| SEQ ID NO: 237 | moltype = AA  length = 17 | |
| FEATURE | Location/Qualifiers | |
| REGION | 1..17 | |
| | note = Synthetic polymer | |
| source | 1..17 | |
| | mol_type = protein | |
| | organism = synthetic construct | |
| SEQUENCE: 237 | | |
| CISGGDNSTY YADSVKG | | 17 |
| | | |
| SEQ ID NO: 238 | moltype = AA  length = 16 | |
| FEATURE | Location/Qualifiers | |
| REGION | 1..16 | |
| | note = Synthetic polymer | |
| source | 1..16 | |
| | mol_type = protein | |
| | organism = synthetic construct | |
| SEQUENCE: 238 | | |
| FSSSGGRTIY PDSVKG | | 16 |
| | | |
| SEQ ID NO: 239 | moltype = AA  length = 16 | |
| FEATURE | Location/Qualifiers | |
| REGION | 1..16 | |
| | note = Synthetic polymer | |
| source | 1..16 | |
| | mol_type = protein | |
| | organism = synthetic construct | |
| SEQUENCE: 239 | | |
| RITGGGLIAY TDSVKG | | 16 |
| | | |
| SEQ ID NO: 240 | moltype = AA  length = 16 | |
| FEATURE | Location/Qualifiers | |
| REGION | 1..16 | |
| | note = Synthetic polymer | |
| source | 1..16 | |
| | mol_type = protein | |
| | organism = synthetic construct | |
| SEQUENCE: 240 | | |
| GISNGGTIKY AESVLG | | 16 |
| | | |
| SEQ ID NO: 241 | moltype = AA  length = 9 | |
| FEATURE | Location/Qualifiers | |
| REGION | 1..9 | |
| | note = Synthetic polymer | |
| source | 1..9 | |
| | mol_type = protein | |
| | organism = synthetic construct | |
| SEQUENCE: 241 | | |
| LITSDGFPT | | 9 |
| | | |
| SEQ ID NO: 242 | moltype = AA  length = 16 | |
| FEATURE | Location/Qualifiers | |
| REGION | 1..16 | |
| | note = Synthetic polymer | |
| source | 1..16 | |
| | mol_type = protein | |
| | organism = synthetic construct | |
| SEQUENCE: 242 | | |
| LITSDGFPTY ADSAKG | | 16 |
| | | |
| SEQ ID NO: 243 | moltype = AA  length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 243 | | |
| AIRWNGGSTN | | 10 |
| | | |
| SEQ ID NO: 244 | moltype = AA  length = 17 | |
| FEATURE | Location/Qualifiers | |
| REGION | 1..17 | |
| | note = Synthetic polymer | |
| source | 1..17 | |
| | mol_type = protein | |
| | organism = synthetic construct | |
| SEQUENCE: 244 | | |

AIRWNGGSTN YADSVKG                                                      17

SEQ ID NO: 245          moltype = AA   length = 9
FEATURE                 Location/Qualifiers
REGION                  1..9
                        note = Synthetic polymer
source                  1..9
                        mol_type = protein
                        organism = synthetic construct
SEQUENCE: 245
LITSDGTPT                                                               9

SEQ ID NO: 246          moltype = AA   length = 16
FEATURE                 Location/Qualifiers
REGION                  1..16
                        note = Synthetic polymer
source                  1..16
                        mol_type = protein
                        organism = synthetic construct
SEQUENCE: 246
LITSDGTPTY ADSAKG                                                       16

SEQ ID NO: 247          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 247
AIDSGGGSTS                                                              10

SEQ ID NO: 248          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 248
AIDSGGGSTS YADSVKG                                                      17

SEQ ID NO: 249          moltype = AA   length = 9
FEATURE                 Location/Qualifiers
REGION                  1..9
                        note = Synthetic polymer
source                  1..9
                        mol_type = protein
                        organism = synthetic construct
SEQUENCE: 249
IITSGGITD                                                               9

SEQ ID NO: 250          moltype = AA   length = 16
FEATURE                 Location/Qualifiers
REGION                  1..16
                        note = Synthetic polymer
source                  1..16
                        mol_type = protein
                        organism = synthetic construct
SEQUENCE: 250
IITSGGITDY ADAVKG                                                       16

SEQ ID NO: 251          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 251
GIRSNGGYTN                                                              10

SEQ ID NO: 252          moltype = AA   length = 17
FEATURE                 Location/Qualifiers
REGION                  1..17
                        note = Synthetic polymer
source                  1..17
                        mol_type = protein
                        organism = synthetic construct

```
SEQUENCE: 252
GIRSNGGYTN YADSVKG                                                          17

SEQ ID NO: 253          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 253
CISSSDVGTY                                                                  10

SEQ ID NO: 254          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 254
CISSSDVGTY YADSVKG                                                          17

SEQ ID NO: 255          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 255
CINSSDGSTY                                                                  10

SEQ ID NO: 256          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 256
CINSSDGSTY YADSVKG                                                          17

SEQ ID NO: 257          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 257
CISGSDSSTY                                                                  10

SEQ ID NO: 258          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 258
CISGSDSSTY YADSVKG                                                          17

SEQ ID NO: 259          moltype = AA   length = 9
FEATURE                 Location/Qualifiers
REGION                  1..9
                        note = Synthetic polymer
source                  1..9
                        mol_type = protein
                        organism = synthetic construct
SEQUENCE: 259
LITSDGTPA                                                                   9

SEQ ID NO: 260          moltype = AA   length = 16
FEATURE                 Location/Qualifiers
REGION                  1..16
                        note = Synthetic polymer
source                  1..16
                        mol_type = protein
```

```
                                      -continued
                           organism = synthetic construct
SEQUENCE: 260
LITSDGTPAY ADSAKG                                                          16

SEQ ID NO: 261             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 261
CISSGDGSKY                                                                 10

SEQ ID NO: 262             moltype = AA  length = 17
FEATURE                    Location/Qualifiers
REGION                     1..17
                           note = Synthetic polymer
source                     1..17
                           mol_type = protein
                           organism = synthetic construct
SEQUENCE: 262
CISSGDGSKY YADSVKG                                                         17

SEQ ID NO: 263             moltype = AA  length = 9
FEATURE                    Location/Qualifiers
REGION                     1..9
                           note = Synthetic polymer
source                     1..9
                           mol_type = protein
                           organism = synthetic construct
SEQUENCE: 263
AIFGGGFTN                                                                   9

SEQ ID NO: 264             moltype = AA  length = 16
FEATURE                    Location/Qualifiers
REGION                     1..16
                           note = Synthetic polymer
source                     1..16
                           mol_type = protein
                           organism = synthetic construct
SEQUENCE: 264
AIFGGGFTNY ADSVKG                                                          16

SEQ ID NO: 265             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 265
AITWSGGSTS                                                                 10

SEQ ID NO: 266             moltype = AA  length = 17
FEATURE                    Location/Qualifiers
REGION                     1..17
                           note = Synthetic polymer
source                     1..17
                           mol_type = protein
                           organism = synthetic construct
SEQUENCE: 266
AITWSGGSTS YTDSVKG                                                         17

SEQ ID NO: 267             moltype = AA  length = 16
FEATURE                    Location/Qualifiers
REGION                     1..16
                           note = Synthetic polymer
source                     1..16
                           mol_type = protein
                           organism = synthetic construct
SEQUENCE: 267
DGWSSCRHGI NEYLYW                                                          16

SEQ ID NO: 268             moltype = AA  length = 8
FEATURE                    Location/Qualifiers
REGION                     1..8
                           note = Synthetic polymer
source                     1..8
```

```
                        mol_type = protein
                        organism = synthetic construct
SEQUENCE: 268
SSGVYNYW                                                                        8

SEQ ID NO: 269          moltype = AA   length = 12
FEATURE                 Location/Qualifiers
REGION                  1..12
                        note = Synthetic polymer
source                  1..12
                        mol_type = protein
                        organism = synthetic construct
SEQUENCE: 269
QGYYCSGYGC PR                                                                  12

SEQ ID NO: 270          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 270
SGWRLCRPTD EYDYSYW                                                             17

SEQ ID NO: 271          moltype = AA   length = 14
FEATURE                 Location/Qualifiers
REGION                  1..14
                        note = Synthetic polymer
source                  1..14
                        mol_type = protein
                        organism = synthetic construct
SEQUENCE: 271
QGYYCSGYGC SDYW                                                                14

SEQ ID NO: 272          moltype = AA   length = 7
FEATURE                 Location/Qualifiers
REGION                  1..7
                        note = Synthetic polymer
source                  1..7
                        mol_type = protein
                        organism = synthetic construct
SEQUENCE: 272
RDRTIWW                                                                         7

SEQ ID NO: 273          moltype = AA   length = 12
FEATURE                 Location/Qualifiers
REGION                  1..12
                        note = Synthetic polymer
source                  1..12
                        mol_type = protein
                        organism = synthetic construct
SEQUENCE: 273
QGYYCSGYGC YP                                                                  12

SEQ ID NO: 274          moltype = AA   length = 15
FEATURE                 Location/Qualifiers
REGION                  1..15
                        note = Synthetic polymer
source                  1..15
                        mol_type = protein
                        organism = synthetic construct
SEQUENCE: 274
DGYYYCSDYP HPLYW                                                               15

SEQ ID NO: 275          moltype = AA   length = 15
FEATURE                 Location/Qualifiers
REGION                  1..15
                        note = Synthetic polymer
source                  1..15
                        mol_type = protein
                        organism = synthetic construct
SEQUENCE: 275
DGWRDCTWSN EYAYW                                                               15

SEQ ID NO: 276          moltype = AA   length = 15
FEATURE                 Location/Qualifiers
REGION                  1..15
                        note = Synthetic polymer
```

```
source                      1..15
                            mol_type = protein
                            organism = synthetic construct
SEQUENCE: 276
TGWRTCRGLN EYDYW                                                          15

SEQ ID NO: 277              moltype = AA  length = 13
FEATURE                     Location/Qualifiers
REGION                      1..13
                            note = Synthetic polymer
source                      1..13
                            mol_type = protein
                            organism = synthetic construct
SEQUENCE: 277
DLVSGSSRLY DYW                                                            13

SEQ ID NO: 278              moltype = AA  length = 18
FEATURE                     Location/Qualifiers
REGION                      1..18
                            note = Synthetic polymer
source                      1..18
                            mol_type = protein
                            organism = synthetic construct
SEQUENCE: 278
MGRTNYGVIY DPNMYNYW                                                       18

SEQ ID NO: 279              moltype = AA  length = 17
FEATURE                     Location/Qualifiers
REGION                      1..17
                            note = Synthetic polymer
source                      1..17
                            mol_type = protein
                            organism = synthetic construct
SEQUENCE: 279
SGWRLCRPTD EYDYLYW                                                        17

SEQ ID NO: 280              moltype = AA  length = 17
FEATURE                     Location/Qualifiers
REGION                      1..17
                            note = Synthetic polymer
source                      1..17
                            mol_type = protein
                            organism = synthetic construct
SEQUENCE: 280
SQAPITIATM MKPFYDY                                                        17

SEQ ID NO: 281              moltype = AA  length = 14
FEATURE                     Location/Qualifiers
REGION                      1..14
                            note = Synthetic polymer
source                      1..14
                            mol_type = protein
                            organism = synthetic construct
SEQUENCE: 281
RHGGPLTVEY FFDY                                                           14

SEQ ID NO: 282              moltype = AA  length = 15
FEATURE                     Location/Qualifiers
REGION                      1..15
                            note = Synthetic polymer
source                      1..15
                            mol_type = protein
                            organism = synthetic construct
SEQUENCE: 282
GGWKYCSGYD PEYIY                                                          15

SEQ ID NO: 283              moltype = AA  length = 7
FEATURE                     Location/Qualifiers
REGION                      1..7
                            note = Synthetic polymer
source                      1..7
                            mol_type = protein
                            organism = synthetic construct
SEQUENCE: 283
DWYLNSY                                                                   7

SEQ ID NO: 284              moltype = AA  length = 6
FEATURE                     Location/Qualifiers
REGION                      1..6
```

```
                              note = Synthetic polymer
source                        1..6
                              mol_type = protein
                              organism = synthetic construct
SEQUENCE: 284
INSRDG                                                                       6

SEQ ID NO: 285           moltype =    length =
SEQUENCE: 285
000

SEQ ID NO: 286           moltype = AA   length = 143
FEATURE                  Location/Qualifiers
REGION                   1..143
                         note = Synthetic polymer
source                   1..143
                         mol_type = protein
                         organism = synthetic construct
SEQUENCE: 286
QVQLQESGGG LVQAGGSLRL SCAASGFTLD YYAIGWFRQA PGKEREEVSC ISSSDGSTYY            60
ADSVKGRFTI SRDNAKNTVN LQMNSLKPED TAVYYCATDG WSSCRHGINE YLYWGQGTQV           120
TVSSAAAYPY DVPDYGSHHH HHH                                                  143

SEQ ID NO: 287           moltype = AA   length = 134
FEATURE                  Location/Qualifiers
REGION                   1..134
                         note = Synthetic polymer
source                   1..134
                         mol_type = protein
                         organism = synthetic construct
SEQUENCE: 287
QVQLQESGGG LVQAGGSLRL SCTASGTIFS INHMDWFRQA PGKQRELVAL ITSDGFPTYA            60
DSAKGRFTIS RDNTKKTVSL QMNSLKPEDT AVYYCHVSSG VYNYWGQGTQ VTVSSAAAYP           120
YDVPDYGSHH HHHH                                                            134

SEQ ID NO: 288           moltype = AA   length = 138
FEATURE                  Location/Qualifiers
REGION                   1..138
                         note = Synthetic polymer
source                   1..138
                         mol_type = protein
                         organism = synthetic construct
SEQUENCE: 288
QVQLQESGGG LVQPGGSLRL SCAASGFTFD DYGMSWVRQA PGKGLEWVSA IRWNGGSTNY            60
ADSVKGRFTI SRDNAKNTLY LQMNSLKSED TAVYYCAQGY YCSGYGCPRG QGTQVTVSSA           120
AAYPYDVPDY GSHHHHHH                                                        138

SEQ ID NO: 289           moltype = AA   length = 144
FEATURE                  Location/Qualifiers
REGION                   1..144
                         note = Synthetic polymer
source                   1..144
                         mol_type = protein
                         organism = synthetic construct
SEQUENCE: 289
QVQLQESGGG LVQPGGSLRL SCAASGFTLD YYAINWFRQA PGKEREEVSC ISSSDGSTYY            60
ADSVKGRFTI SRDNAKNTVY LQMNSLKPED TAVYYCATSG WRLCRPTDEY DYSYWGQGTQ           120
VTVSSAAAYP YDVPDYGSHH HHHH                                                  144

SEQ ID NO: 290           moltype = AA   length = 134
FEATURE                  Location/Qualifiers
REGION                   1..134
                         note = Synthetic polymer
source                   1..134
                         mol_type = protein
                         organism = synthetic construct
SEQUENCE: 290
QVQLQESGGG VVQAGGSLRL SCTASGTIFS INRMDWFRQA PGKQRELVAL ITSDGTPTYA            60
DSAKGRFTIS RDNTKKTVSL QMNSLKPEDT AVYYCHVSSG VYNYWGQGTQ VTVSSAAAYP           120
YDVPDYGSHH HHHH                                                            134

SEQ ID NO: 291           moltype = AA   length = 140
FEATURE                  Location/Qualifiers
REGION                   1..140
                         note = Synthetic polymer
source                   1..140
                         mol_type = protein
                         organism = synthetic construct
SEQUENCE: 291
```

```
QVQLQESGGG LVQTGGSLRL SCAASGFTFS SYGMSWVRQT PGKGPEWVSA IDSGGGSTSY   60
ADSVKGRFTI SRDNAKNTLY LQMNSLKPED TAVYYCAQGY YCSGYGCSDY WGQGTQVTVS  120
SAAAYPYDVP DYGSHHHHHH                                             140

SEQ ID NO: 292           moltype = AA  length = 133
FEATURE                  Location/Qualifiers
REGION                   1..133
                         note = Synthetic polymer
source                   1..133
                         mol_type = protein
                         organism = synthetic construct
SEQUENCE: 292
QVQLQESGGG LVQPGGSLRL SCAASGKIFS GNDMGWYRQA PGKQRELVGI ITSGGITDYA   60
DAVKGRFTIS RDNAKNMMYL QMNSLKPEDT AVYYCNMRDR TIWWGQGTQV TVSSAAAYPY  120
DVPDYGSHHH HHH                                                    133

SEQ ID NO: 293           moltype = AA  length = 134
FEATURE                  Location/Qualifiers
REGION                   1..134
                         note = Synthetic polymer
source                   1..134
                         mol_type = protein
                         organism = synthetic construct
SEQUENCE: 293
QVQLQESGGG SVQAGGSLRL SCTASGTIFS INRMDWFRQA PGKQRELVAL ITSDGTPTYA   60
DSAKGRFTIS RDNTKKTVSL QMNSLKPEDT AVYYCHVSSG VYNYWGQGTQ VTVSSAAAYP  120
YDVPDYGSHH HHHH                                                   134

SEQ ID NO: 294           moltype = AA  length = 97
FEATURE                  Location/Qualifiers
REGION                   1..97
                         note = Synthetic polymer
source                   1..97
                         mol_type = protein
                         organism = synthetic construct
SEQUENCE: 294
QVQLQESGGG LVQPGGSLRL SCAASGFTFS SYGMSWVRQT PGKGPEWVSA IDSGGGSTSY   60
ADSVKGRFTT SRDNAKNTLY LQMNSLKPED TAVYYCA                            97

SEQ ID NO: 295           moltype = AA  length = 138
FEATURE                  Location/Qualifiers
REGION                   1..138
                         note = Synthetic polymer
source                   1..138
                         mol_type = protein
                         organism = synthetic construct
SEQUENCE: 295
QVQLQESGGG LVQPGGSLRL SCAASGFTFN DYAMSWVRQA PGKGLEWVSG IRSNGGYTNY   60
ADSVKGRFTI SRDNAKNTLY LQMNSLKSED TAVYYCAQGY YCSGYGCYPG QGTQVTVSSA  120
AAYPYDVPDY GSHHHHHH                                               138

SEQ ID NO: 296           moltype = AA  length = 142
FEATURE                  Location/Qualifiers
REGION                   1..142
                         note = Synthetic polymer
source                   1..142
                         mol_type = protein
                         organism = synthetic construct
SEQUENCE: 296
QVQLQESGGG LVQAGGSLRL SCAASGFNLD PYAIAWFRQA PGKEREEVSC ISSSDVGTYY   60
ADSVKGRFTI SRDNAKKTVY LQMNSLKPED TAVYYCATDG YYYCSDYPHP LYWGQGTQVT  120
VSSAAAYPYD VPDYGSHHHH HH                                          142

SEQ ID NO: 297           moltype = AA  length = 142
FEATURE                  Location/Qualifiers
REGION                   1..142
                         note = Synthetic polymer
source                   1..142
                         mol_type = protein
                         organism = synthetic construct
SEQUENCE: 297
QVQLQESGGG LVQPGGSLRL SCAASGFTFT AYAMSWFRQA PGKEREEVSC INSSDGSTYY   60
ADSVKGRFTI SRDNAKNTVY LQMNSLKPED TAVYHCATDG WRDCTWSNEY AYWGQGTQVT  120
VSSAAAYPYD VPDYGSHHHH HH                                          142

SEQ ID NO: 298           moltype = AA  length = 142
FEATURE                  Location/Qualifiers
REGION                   1..142
                         note = Synthetic polymer
```

```
source                         1..142
                               mol_type = protein
                               organism = synthetic construct
SEQUENCE: 298
QVQLQESGGG LVQPGGSLRL SCAASGFTFD YYAIGWFRQA PGKEREEVSC ISGSDSSTYY    60
ADSVKGRFTI VRDNAQNTVY LQMNSLKPED TAIYYCAVTG WRTCRGLNEY DYWGQGTQVT   120
VSSAAAYPYD VPDYGSHHHH HH                                            142

SEQ ID NO: 299                 moltype = AA  length = 142
FEATURE                        Location/Qualifiers
REGION                         1..142
                               note = Synthetic polymer
source                         1..142
                               mol_type = protein
                               organism = synthetic construct
SEQUENCE: 299
QVQLQESGGG LVQPGGSLRL SCAASGFNLD PYAIAWFRQA PGKEREEVSC ISSSDVGTYY    60
ADSVKGRFTI SRDNTKKTVY LQMNSLKPED TAVYYCATDG YYYCSDYPHP LYWGQGTQVT   120
VSSAAAYPYD VPDYGSHHHH HH                                            142

SEQ ID NO: 300                 moltype = AA  length = 134
FEATURE                        Location/Qualifiers
REGION                         1..134
                               note = Synthetic polymer
source                         1..134
                               mol_type = protein
                               organism = synthetic construct
SEQUENCE: 300
QVQLQESGGG LVQAGESLRL SCTASGTIFS INRMDWFRQA PGKQRELVAL ITSDGTPTYA    60
DSAKGRFTIS RDNTKKTVSL QMNSLKPEDT AVYYCHVSSG VYNYWGQGTQ VTVSSAAAYP   120
YDVPDYGSHH HHHH                                                     134

SEQ ID NO: 301                 moltype = AA  length = 134
FEATURE                        Location/Qualifiers
REGION                         1..134
                               note = Synthetic polymer
source                         1..134
                               mol_type = protein
                               organism = synthetic construct
SEQUENCE: 301
QVQLQESGGG LVQAGGSLRL SCTASGTIFS INRMDWFRQA PGKQRELVAL ITSDGTPAYA    60
DSAKGRFTIS RDNTKKTVSL QMNSLKPEDT AVYYCHVSSG VYNYWGQGTQ VTVSSAAAYP   120
YDVPDYGSHH HHHH                                                     134

SEQ ID NO: 302                 moltype = AA  length = 140
FEATURE                        Location/Qualifiers
REGION                         1..140
                               note = Synthetic polymer
source                         1..140
                               mol_type = protein
                               organism = synthetic construct
SEQUENCE: 302
QVQLQESGGG LVQSGGSLRL SCKTSGFTFS SYGMSWVRQT PGKGPEWVSA IDSGGGSTSY    60
ADSVKGRFTI SRDNAKNTLY LQMNSLKPED TAVYYCAQGY YCSGYGCSDY WGQGTQVTVS   120
SAAAYPYDVP DYGSHHHHHH                                               140

SEQ ID NO: 303                 moltype = AA  length = 142
FEATURE                        Location/Qualifiers
REGION                         1..142
                               note = Synthetic polymer
source                         1..142
                               mol_type = protein
                               organism = synthetic construct
SEQUENCE: 303
QVQLQESGGG LVQPGGSLRL SCAASGFNLD PYAIGWFRQA PGKEREEVSC ISSGDGSKYY    60
ADSVKGRFTM SRDNAKKTVY LQMNSLKPED TAVYYCATDG YYYCSDYPHP LYWGQGTQVT   120
VSSAAAYPYD VPDYGSHHHH HH                                            142

SEQ ID NO: 304                 moltype = AA  length = 142
FEATURE                        Location/Qualifiers
REGION                         1..142
                               note = Synthetic polymer
source                         1..142
                               mol_type = protein
                               organism = synthetic construct
SEQUENCE: 304
QVQLQESGGG LVQPGGSLRL SCAVSGFNLD PYAIAWFRQA PGKEREEVSC ISSSDVGTYY    60
ADSVKGRFTI SRDNAKKTVY LQMNSLKPED TAVYYCATDG YYYCSDYPHP LYWGQGTQVT   120
VSSAAAYPYD VPDYGSHHHH HH                                            142
```

```
SEQ ID NO: 305           moltype = AA  length = 139
FEATURE                  Location/Qualifiers
REGION                   1..139
                         note = Synthetic polymer
source                   1..139
                         mol_type = protein
                         organism = synthetic construct
SEQUENCE: 305
QVQLQESGGG LVQAGGSLRL SCAASESIFS IEAMGWYRQA PGKQRELVAA IFGGGFTNYA    60
DSVKGRFTIS RDNANRTVYL QMNSLKPEDT AVYYCNADLV SGSSRLYDYW GQGTQVTVSS   120
AAAYPYDVPD YGSHHHHHH                                                139

SEQ ID NO: 306           moltype = AA  length = 133
FEATURE                  Location/Qualifiers
REGION                   1..133
                         note = Synthetic polymer
source                   1..133
                         mol_type = protein
                         organism = synthetic construct
SEQUENCE: 306
QVQLQESGGG LVQAGGSLRL SCAASGKIFS GNDMGWYRQA PGKQRELVGI ITSGGITDYA    60
DAVKGRFTIS RDNAKNMMYL QMNSLKPEDT AVYYCNMRDR TIWWGQGTQV TVSSAAAYPY   120
DVPDYGSHHH HHH                                                      133

SEQ ID NO: 307           moltype = AA  length = 143
FEATURE                  Location/Qualifiers
REGION                   1..143
                         note = Synthetic polymer
source                   1..143
                         mol_type = protein
                         organism = synthetic construct
SEQUENCE: 307
QVQLQESGGG LVQPGGSLRL SCAASGFTLD YYAIGWFRQA PGKEREEVSC ISSSDGSTYY    60
ADSVKGRFTI SRDNAKNTVN LQMNSLKPED TAVYYCATDG WSSCRHGINE YLYWGQGTQV   120
TVSSAAAYPY DVPDYGSHHH HHH                                           143

SEQ ID NO: 308           moltype = AA  length = 140
FEATURE                  Location/Qualifiers
REGION                   1..140
                         note = Synthetic polymer
source                   1..140
                         mol_type = protein
                         organism = synthetic construct
SEQUENCE: 308
QVQLQESGGG LVQAGGSLRL SCAASGFTFS SYGMSWVRQT PGKGPEWVSA IDSGGGSTSY    60
ADSVKGRFTI SRDNAKNTLY LQMNSLKPED TAVYYCAQGY YCSGYGCSDY WGQGTQVTVS   120
SAAAYPYDVP DYGSHHHHHH                                               140

SEQ ID NO: 309           moltype = AA  length = 134
FEATURE                  Location/Qualifiers
REGION                   1..134
                         note = Synthetic polymer
source                   1..134
                         mol_type = protein
                         organism = synthetic construct
SEQUENCE: 309
QVQLQESGGG LVQPGGSLRL SCTASGTIFS INRMDWFRQA PGKQRELVAL ITSDGTPTYA    60
DSAKGRFTIS RDNTKKTVSL QMNSLKPEDT AVYYCHVSSG VYNYWGQGTQ VTVSSAAAYP   120
YDVPDYGSHH HHHH                                                     134

SEQ ID NO: 310           moltype = AA  length = 140
FEATURE                  Location/Qualifiers
REGION                   1..140
                         note = Synthetic polymer
source                   1..140
                         mol_type = protein
                         organism = synthetic construct
SEQUENCE: 310
QVQLQESGGG LVQPGGSLRL SCAASGFTFS SYGMSWVRQT PGKGPEWVSA IDSGGGSTSY    60
ADSVKGRFTI SRDNAKNTLY LQMNSLKPED TAVYYCAQGY YCSGYGCSDY WGQGTQVTVS   120
SAAAYPYDVP DYGSHHHHHH                                               140

SEQ ID NO: 311           moltype = AA  length = 142
FEATURE                  Location/Qualifiers
REGION                   1..142
                         note = Synthetic polymer
source                   1..142
                         mol_type = protein
```

```
                        organism = synthetic construct
SEQUENCE: 311
QVQLQESGGG LVQPGGSLRL SCAASGFNLD PYAIAWFRQA PGKEREEVSC ISSSDVGTYY    60
ADSVKGRFTI SRDNAKKTVY LQMNSLKPED TAVYYCATDG YYYCSDYPHP LYWGQGTQVT   120
VSSAAAYPYD VPDYGSHHHH HH                                           142

SEQ ID NO: 312          moltype = AA  length = 145
FEATURE                 Location/Qualifiers
REGION                  1..145
                        note = Synthetic polymer
SITE                    13
                        note = misc_feature - Xaa can be any naturally occurring
                         amino acid
source                  1..145
                        mol_type = protein
                        organism = synthetic construct
SEQUENCE: 312
QVQLQESGGG LVXAGGSLRL SCAASGRTFS ISAMGWFRQA PGKEREFVAA ITWSGGSTSY    60
TDSVKGRFTI SRDNAKNTLY LQMNSLKPED TAIYYCAAMG RTNYGVIYDP NMYNYWGQGT   120
QVTVSSAAAY PYDVPDYGSH HHHHH                                        145

SEQ ID NO: 313          moltype = AA  length = 144
FEATURE                 Location/Qualifiers
REGION                  1..144
                        note = Synthetic polymer
source                  1..144
                        mol_type = protein
                        organism = synthetic construct
SEQUENCE: 313
QVQLQESGGG LVQPGGSLRL SCAASGFTLD YYAINWFRQA PGKEREEVSC ISSSDGSTYY    60
ADSVKGRFTI SRDNAKNTVY LQMNSLKPED TAVYYCATSG WRLCRPTDEY DYLYWGQGTQ   120
VTVSSAAAYP YDVPDYGSHH HHHH                                         144

SEQ ID NO: 314          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 314
QVQLQESGGG LVQAGGSMRL SCAASGFTFS SYGMSWVRQT PGKGPEWVSA IDSGGGSTSY    60
ADSVKGRFTI SRDNAKNTLY LQMNSLKPED TAVYYCAQGY YCSGYGCSDY WGQGTQVTVS   120
SAAAYPYDVP DYGSHHHHHH                                              140

SEQ ID NO: 315          moltype = AA  length = 138
FEATURE                 Location/Qualifiers
REGION                  1..138
                        note = Synthetic polymer
source                  1..138
                        mol_type = protein
                        organism = synthetic construct
SEQUENCE: 315
QVQLQESGGG TVQAGGSLRL SCAASGFTFN DYAMSWVRQA PGKGLEWVSG IRSNGGYTNY    60
ADSVKGRFTI SRDNAKNTLY LQMNSLKSED TAVYYCAQGY YCSGYGCYPG QGTQVTVSSA   120
AAYPYDVPDY GSHHHHHH                                                138

SEQ ID NO: 316          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 316
QVQLQESGGG LVQPGTSLRL SCAASGFTLD YYAIGWFRQA PGKEREEVSC ISSSDGSTYY    60
ADSVKGRFTI SRDNAKNTVN LQMNSLKPED TAVYYCATDG WSSCRHGINE YLYWGQGTQV   120
TVSSAAAYPY DVPDYGSHHH HHH                                          143

SEQ ID NO: 317          moltype = AA  length = 165
FEATURE                 Location/Qualifiers
REGION                  1..165
                        note = Synthetic polymer
source                  1..165
                        mol_type = protein
                        organism = synthetic construct
SEQUENCE: 317
CDLPQTHSLG SRRTLMLLAQ MRKISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
```

```
KYFQRITLYL KEKKYSPCAW EVVRAEIMRS FSLSTNLQES LRSKE              165

SEQ ID NO: 318          moltype = AA   length = 165
FEATURE                 Location/Qualifiers
REGION                  1..165
                        note = Synthetic polymer
source                  1..165
                        mol_type = protein
                        organism = synthetic construct
SEQUENCE: 318
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR 120
KYFQRITLYL KEKKYSPCAW EVVRAEIMRS FSLSTNLQES LRSKE               165

SEQ ID NO: 319          moltype = AA   length = 166
FEATURE                 Location/Qualifiers
REGION                  1..166
                        note = Synthetic polymer
source                  1..166
                        mol_type = protein
                        organism = synthetic construct
SEQUENCE: 319
MSYNLLGFLQ RSSNFQCQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL 120
HLKRYYGRIL HYLKAKEYSH CAWTIVRVEI LRNFYFINRL TGYLRN              166

SEQ ID NO: 320          moltype = AA   length = 166
FEATURE                 Location/Qualifiers
REGION                  1..166
                        note = Synthetic polymer
source                  1..166
                        mol_type = protein
                        organism = synthetic construct
SEQUENCE: 320
MKYTSYILAF QLCIVLGSLG CYCQDPYVKE AENLKKYFNA GHSDVADNGT LFLGILKNWK  60
EESDRKIMQS QIVSFYFKLF KNFKDDQSIQ KSVETIKEDM NVKFFNSNKK KRDDFEKLTN 120
YSVTDLNVQR KAIHELIQVM AELSPAAKTG KRKRSQMLFR GRRASQ              166

SEQ ID NO: 321          moltype = AA   length = 143
FEATURE                 Location/Qualifiers
REGION                  1..143
                        note = Synthetic polymer
source                  1..143
                        mol_type = protein
                        organism = synthetic construct
SEQUENCE: 321
QDPYVKEAEN LKKYFNAGHS DVADNGTLFL GILKNWKEES DRKIMQSQIV SFYFKLFKNF  60
KDDQSIQKSV ETIKEDMNVK FFNSNKKKRD DFEKLTNYSV TDLNVQRKAI HELIQVMAEL 120
SPAAKTGKRK RSQMLFRGRR ASQ                                       143

SEQ ID NO: 322          moltype = AA   length = 167
FEATURE                 Location/Qualifiers
REGION                  1..167
                        note = Synthetic polymer
source                  1..167
                        mol_type = protein
                        organism = synthetic construct
SEQUENCE: 322
MCDLPQTHSL GNRRALILLA QMRRISPFSC LKDRHDFGFP QEEFDGNQFQ KAQAISVLHE  60
MIQQTFNLFS TKDSSAAWDE SLLEKFYTEL YQQLNDLEAC VIQEVGVEET PLMNVDSILA 120
VKKYFQRITL YLTEKKYSPC AWEVVRAEIM RSFSLSTNLQ ERLRRKE             167

SEQ ID NO: 323          moltype = AA   length = 166
FEATURE                 Location/Qualifiers
REGION                  1..166
                        note = Synthetic polymer
source                  1..166
                        mol_type = protein
                        organism = synthetic construct
SEQUENCE: 323
CDLPQTHSLG NRRALILLAQ MRRISPFSCL KDRHDFGFPQ EEFDGNQFQK AQAISVLHEM  60
IQQTFNLFST KDSSAAWDES LLEKFYTELY QQLNDLEACV IQEVGVEETP LMNVDSILAV 120
KKYFQRITLY LTEKKYSPCA WEVVRAEIMR SFSLSTNLQE RLRRKE              166

SEQ ID NO: 324          moltype = AA   length = 166
FEATURE                 Location/Qualifiers
REGION                  1..166
                        note = Synthetic polymer
source                  1..166
```

```
                         mol_type = protein
                         organism = synthetic construct
SEQUENCE: 324
CDLPQTHSLG NRRTLMLLAQ MRRISPFSCL KDRHDFGFPQ EEFDGNQFQK AQAISVLHEM    60
IQQTFNLFST KDSSAAWDES LLEKFYTELY QQLNDLEACV IQEVGVEETP LMNVDSILAV   120
KKYFQRITLY LTEKKYSPCA WEVVRAEIMR SFSLSTNLQE RLRRKE                  166

SEQ ID NO: 325           moltype = AA   length = 166
FEATURE                  Location/Qualifiers
REGION                   1..166
                         note = Synthetic polymer
source                   1..166
                         mol_type = protein
                         organism = synthetic construct
SEQUENCE: 325
CDLPQTHSLG NRRALILLAQ MRRISPFSCL KDRHDFGFPQ EEFDGNQFQK AQAISVLHEM    60
IQQTFNLFST KDSSAAWDES LLEKFYTELY QQLNDLEACV IQEVGVEETP LMNEDSILAV   120
RKYFQRITLY LTEKKYSPCA WEVVRAEIMR SFSLSTNLQE RLRRKE                  166

SEQ ID NO: 326           moltype = AA   length = 167
FEATURE                  Location/Qualifiers
REGION                   1..167
                         note = Synthetic polymer
source                   1..167
                         mol_type = protein
                         organism = synthetic construct
SEQUENCE: 326
MCDLPQTHSL GNRRALILLA QMRRISPFSC LKDRHDFGFP QEEFDGNQFQ KAQAISVLHE    60
MIQQTFNLFS TKDSSAAWDE SLLEKFYTEL YQQLNDLEAC VIQEVGVEET PLMNEDSILA   120
VRKYFQRITL YLTEKKYSPC AWEVVRAEIM RSFSLSTNLQ ERLRRKE                 167

SEQ ID NO: 327           moltype = AA   length = 167
FEATURE                  Location/Qualifiers
REGION                   1..167
                         note = Synthetic polymer
source                   1..167
                         mol_type = protein
                         organism = synthetic construct
SEQUENCE: 327
MCDLPQTHSL GNRRALILLA QMRRISPFSC LKDRHDFGFP QEEFDGNQFQ KAQAISVLHE    60
MIQQTFNLFS TKDSSAAWDE SLLEKFYTEL YQQLNDLEAC VIQEVGVEET PLMNEDSILA   120
VRKYFQRITL YLTEKKYSPC AWEVVRAEIM RSFSLCTNLQ ERLRRKE                 167

SEQ ID NO: 328           moltype = AA   length = 6
FEATURE                  Location/Qualifiers
REGION                   1..6
                         note = Synthetic polymer
source                   1..6
                         mol_type = protein
                         organism = synthetic construct
SEQUENCE: 328
EEFGNQ                                                                6

SEQ ID NO: 329           moltype = AA   length = 7
FEATURE                  Location/Qualifiers
REGION                   1..7
                         note = Synthetic polymer
source                   1..7
                         mol_type = protein
                         organism = synthetic construct
SEQUENCE: 329
EEFDGNQ                                                               7

SEQ ID NO: 330           moltype = AA   length = 165
FEATURE                  Location/Qualifiers
REGION                   1..165
                         note = Synthetic polymer
source                   1..165
                         mol_type = protein
                         organism = synthetic construct
SEQUENCE: 330
APMAEGGGQN HHEVVKFMDV YQRSYCHPIE TLVDIFQEYP DEIEYIFKPS CVPLMRCGGC    60
CNDEGLECVP TEESNITMQI MRIKPHQGQH IGEMSFLQHN KCECRPKKDR ARQENPCGPC   120
SERRKHLFVQ DPQTCKCSCK NTDSRCKARQ LELNERTCRC DKPRR                   165

SEQ ID NO: 331           moltype = AA   length = 165
FEATURE                  Location/Qualifiers
REGION                   1..165
                         note = Synthetic polymer
```

```
source                        1..165
                              mol_type = protein
                              organism = synthetic construct
SEQUENCE: 331
APMAEGGGQN HHEVVKFMDV YQRSYCHPIE TLVDIFQEYP DEIEYIFKPS CVPLMRCGGC   60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRS LTRKD                 165

SEQ ID NO: 332                moltype = AA   length = 157
FEATURE                       Location/Qualifiers
REGION                        1..157
                              note = Synthetic polymer
source                        1..157
                              mol_type = protein
                              organism = synthetic construct
SEQUENCE: 332
VRSSSRTPSD KPVAHVVANP QAEGQLQWLN RRANALLANG VELRDNQLVV PSEGLYLIYS   60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                          157

SEQ ID NO: 333                moltype = AA   length = 171
FEATURE                       Location/Qualifiers
REGION                        1..171
                              note = Synthetic polymer
source                        1..171
                              mol_type = protein
                              organism = synthetic construct
SEQUENCE: 333
LPGVGLTPSA AQTARQHPKM HLAHSNLKPA AHLIGDPSKQ NSLLWRANTD RAFLQDGFSL   60
SNNSLLVPTS GIYFVYSQVV FSGKAYSPKA TSSPLYLAHE VQLFSSQYPF HVPLLSSQKM  120
VYPGLQEPWL HSMYHGAAFQ LTQGDQLSTH TDGIPHLVLS PSTVFFGAFA L          171

SEQ ID NO: 334                moltype = AA   length = 281
FEATURE                       Location/Qualifiers
REGION                        1..281
                              note = Synthetic polymer
source                        1..281
                              mol_type = protein
                              organism = synthetic construct
SEQUENCE: 334
MAMMEVQGGP SLGQTCVLIV IFTVLLQSLC VAVTVYFTN ELKQMQDKYS KSGIACFLKE    60
DDSYWDPNDE ESMNSPCWQV KWQLRQLVRK MILRTSEETI STVQEKQQNI SPLVRERGPQ  120
RVAAHITGTR GRSNTLSSPN SKNEKALGRK INSWESSRSG HSFLSNLHLR NGELVIHEKG  180
FYYIYSQTYF RFQEEIKENT KNDKQMVQYI YKYTSYPDPI LLMKSARNSC WSKDAEYGLY  240
SIYQGGIFEL KENDRIFVSV TNEHLIDMDH EASFFGAFLV G                     281

SEQ ID NO: 335                moltype = AA   length = 153
FEATURE                       Location/Qualifiers
REGION                        1..153
                              note = Synthetic polymer
source                        1..153
                              mol_type = protein
                              organism = synthetic construct
SEQUENCE: 335
APVRSLNCTL RDSQQKSLVM SGPYELKALH LQGQDMEQQV VFSMSFVQGE ESNDKIPVAL   60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                              153

SEQ ID NO: 336                moltype = AA   length = 133
FEATURE                       Location/Qualifiers
REGION                        1..133
                              note = Synthetic polymer
source                        1..133
                              mol_type = protein
                              organism = synthetic construct
SEQUENCE: 336
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFPMCEYAD E TATIVEFLNR  120
WITFCQSIIS TLT                                                    133

SEQ ID NO: 337                moltype = AA   length = 129
FEATURE                       Location/Qualifiers
REGION                        1..129
                              note = Synthetic polymer
source                        1..129
                              mol_type = protein
                              organism = synthetic construct
SEQUENCE: 337
HKCDITLQEI IKTLNSLTEQ KTLCTELTVT DIFAASKNTT EKETFCRAAT VLRQFYSHHE   60
```

```
KDTRCLGATA QQFHRHKQLI RFLKRLDRNL WGLAGLNSCP VKEANQSTLE NFLERLKTIM    120
REKYSKCSS                                                            129

SEQ ID NO: 338          moltype = AA   length = 185
FEATURE                 Location/Qualifiers
REGION                  1..185
                        note = Synthetic polymer
source                  1..185
                        mol_type = protein
                        organism = synthetic construct
SEQUENCE: 338
APVPPGEDSK DVAAPHRQPL TSSERIDKQI RYILDGISAL RKETCNKSNM CESSKEALAE    60
NNLNLPKMAE KDGCFQSGFN EETCLVKIIT GLLEFEVYLE YLQNRFESSE EQARAVQMST    120
KVLIQFLQKK AKNLDAITTP DPTTNASLTT KLQAQNQWLQ DMTTHLILRS FKEFLQSSLR    180
ALRQM                                                                185

SEQ ID NO: 339          moltype = AA   length = 114
FEATURE                 Location/Qualifiers
REGION                  1..114
                        note = Synthetic polymer
source                  1..114
                        mol_type = protein
                        organism = synthetic construct
SEQUENCE: 339
SPGPVPPSTA LRELIEELVN ITQNQKAPLC NGSMVWSINL TAGMYCAALE SLINVSGCSA    60
IEKTQRMLSG FCPHKVSAGQ FSSLHVRDTK IEVAQFVKDL LLHLKKLFRE GRFN          114

SEQ ID NO: 340          moltype = AA   length = 194
FEATURE                 Location/Qualifiers
REGION                  1..194
                        note = Synthetic polymer
source                  1..194
                        mol_type = protein
                        organism = synthetic construct
SEQUENCE: 340
MAAEPVEDNC INFVAMKFID NTLYFIAEDD ENLESDYFGK LESKLSVIRN LNDQVLFIDQ    60
GNRPLFEDMT DSDCRDNAPR TIFIISMYKD SQPRGMAVTI SVKCEKISTL SCENKIISFK    120
EMNPPDNIKD TKSDIIFFQR SVPGHDNKMQ FESSSYEGYF LACEKERDLF KLILKKEDEL    180
GDRSIMFTVQ NEDL                                                      194

SEQ ID NO: 341          moltype = AA   length = 270
FEATURE                 Location/Qualifiers
REGION                  1..270
                        note = Synthetic polymer
source                  1..270
                        mol_type = protein
                        organism = synthetic construct
SEQUENCE: 341
MKPKMKYSTN KISTAKWKNT ASKALCFKLG KSQQKAKEVC PMYFMKLRSG LMIKKEACYF    60
RRETTKRPSL KTGRKHKRHL VLAACQQQST VECFAFGISG VQKYTRALHD SSITGISPIT    120
EYLASLSTYN DQSITFALED ESYEIYVEDL KKDEKKDKVL LSYYESQHPS NESGDGVDGK    180
MLMVTLSPTK DFWLHANNKE HSVELHKCEK PLPDQAFFVL HNMHSNCVSF ECKTDPGVFI    240
GVKDNHLALI KVDSSENLCT ENILFKLSET                                     270

SEQ ID NO: 342          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 342
GFTFDDYAMS                                                           10

SEQ ID NO: 343          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 343
GFTFDDYAIG                                                           10

SEQ ID NO: 344          moltype = AA   length = 17
FEATURE                 Location/Qualifiers
REGION                  1..17
                        note = Synthetic polymer
source                  1..17
```

```
                        mol_type = protein
                        organism = synthetic construct
SEQUENCE: 344
TINWNGGSAE YAEPVKG                                                      17

SEQ ID NO: 345          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 345
CIRVSDGSTY YADPVKG                                                      17

SEQ ID NO: 346          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 346
KDADLVWYNL S                                                            11

SEQ ID NO: 347          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 347
KDADLVWYNL R                                                            11

SEQ ID NO: 348          moltype = AA  length = 24
FEATURE                 Location/Qualifiers
REGION                  1..24
                        note = Synthetic polymer
source                  1..24
                        mol_type = protein
                        organism = synthetic construct
SEQUENCE: 348
AGSLYTCVQS IVVVPARPYY DMDY                                              24

SEQ ID NO: 349          moltype = AA  length = 132
FEATURE                 Location/Qualifiers
REGION                  1..132
                        note = Synthetic polymer
source                  1..132
                        mol_type = protein
                        organism = synthetic construct
SEQUENCE: 349
QVQLQESGGG SVQPGGSLRL SCAASGFTFD DYAMSWVRQV PGKGLEWVST INWNGGSAEY        60
AEPVKGRFTI SRDNAKNTVY LQMNSLKLED TAVYYCAKDA DLVWYNLSTG QGTQVTVSSA       120
AAYPYDVPDY GS                                                          132

SEQ ID NO: 350          moltype = AA  length = 132
FEATURE                 Location/Qualifiers
REGION                  1..132
                        note = Synthetic polymer
source                  1..132
                        mol_type = protein
                        organism = synthetic construct
SEQUENCE: 350
QVQLQESGGG LVQPGGSLRL SCAASGFTFD DYAMSWVRQV PGKGLEWVST INWNGGSAEY        60
AEPVKGRFTI SRDNAKNTVY LQMNSLKLED TAVYYCAKDA DLVWYNLRTG QGTQVTVSSA       120
AAYPYDVPDY GS                                                          132

SEQ ID NO: 351          moltype = AA  length = 145
FEATURE                 Location/Qualifiers
REGION                  1..145
                        note = Synthetic polymer
source                  1..145
                        mol_type = protein
                        organism = synthetic construct
SEQUENCE: 351
QVQLQESGGG LVQAGGSLRL SCAASGFTFD DYAIGWFRQA PGKEREGVSC IRVSDGSTYY        60
ADPVKGRFTI SSDNAKNTVY LQMNSLKPED AAVYYCAAGS LYTCVQSIVV VPARPYYDMD       120
```

```
YWGKGTQVTV SSAAAYPYDV PDYGS                                              145

SEQ ID NO: 352          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 352
GRSFSSYTLA                                                                10

SEQ ID NO: 353          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 353
GRTFSSYTMG                                                                10

SEQ ID NO: 354          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 354
GRTFSSYIMG                                                                10

SEQ ID NO: 355          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 355
GRTFSSYTMG                                                                10

SEQ ID NO: 356          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 356
GRTSGRTFSS YTMG                                                           14

SEQ ID NO: 357          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 357
GRTFSSYAMG                                                                10

SEQ ID NO: 358          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 358
GLTFSNYIMG                                                                10

SEQ ID NO: 359          moltype = AA  length = 10
FEATURE                 Location/Qualifiers
REGION                  1..10
                        note = Synthetic polymer
source                  1..10
                        mol_type = protein
                        organism = synthetic construct
```

```
SEQUENCE: 359
GRTFSSYTMG                                                                      10

SEQ ID NO: 360          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 360
GRTFSSDTMG                                                                      10

SEQ ID NO: 361          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 361
GLTFSNYIMG                                                                      10

SEQ ID NO: 362          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 362
GFTLDYYGIG                                                                      10

SEQ ID NO: 363          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 363
GHTFSSYTMG                                                                      10

SEQ ID NO: 364          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 364
GRTFSSYVIG                                                                      10

SEQ ID NO: 365          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 365
GFAFDGYAIG                                                                      10

SEQ ID NO: 366          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 366
GFAFGFFDMT                                                                      10

SEQ ID NO: 367          moltype = AA  length = 10
FEATURE                 Location/Qualifiers
REGION                  1..10
                        note = Synthetic polymer
source                  1..10
                        mol_type = protein
```

```
                        organism = synthetic construct
SEQUENCE: 367
GRTFSNYVIG                                                                          10

SEQ ID NO: 368          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 368
GSIFSINVMG                                                                          10

SEQ ID NO: 369          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 369
GRTFSNYNVG                                                                          10

SEQ ID NO: 370          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 370
GHTFSSYTMG                                                                          10

SEQ ID NO: 371          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 371
GRTFSTYPVG                                                                          10

SEQ ID NO: 372          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 372
GRTFSNYAMG                                                                          10

SEQ ID NO: 373          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 373
GRTFSDYRMG                                                                          10

SEQ ID NO: 374          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 374
GLTFSNYIMA                                                                          10

SEQ ID NO: 375          moltype = AA   length = 10
FEATURE                 Location/Qualifiers
REGION                  1..10
                        note = Synthetic polymer
source                  1..10
```

```
                        mol_type = protein
                        organism = synthetic construct
SEQUENCE: 375
GRTFSNSVMG                                                              10

SEQ ID NO: 376          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 376
GRTFSSYIIG                                                              10

SEQ ID NO: 377          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 377
GRTFSSYVMG                                                              10

SEQ ID NO: 378          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 378
GGTFSNYVMG                                                              10

SEQ ID NO: 379          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 379
GRTFSNYGIG                                                              10

SEQ ID NO: 380          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 380
GFTFDDYAIA                                                              10

SEQ ID NO: 381          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 381
GRTFSSYTVA                                                              10

SEQ ID NO: 382          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 382
GFPFDDYAIA                                                              10

SEQ ID NO: 383          moltype = AA  length = 10
FEATURE                 Location/Qualifiers
REGION                  1..10
                        note = Synthetic polymer
```

-continued

```
source                  1..10
                        mol_type = protein
                        organism = synthetic construct
SEQUENCE: 383
GRTFSSYVMG                                                                    10

SEQ ID NO: 384          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 384
GRTLSSNPMA                                                                    10

SEQ ID NO: 385          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 385
GFTFDNYAIG                                                                    10

SEQ ID NO: 386          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 386
GRAFSSYFMG                                                                    10

SEQ ID NO: 387          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 387
TPTFSSYNMG                                                                    10

SEQ ID NO: 388          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 388
GFTFDDYAIA                                                                    10

SEQ ID NO: 389          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 389
GGTFSGYIMG                                                                    10

SEQ ID NO: 390          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 390
GRSFSSYTIA                                                                    10

SEQ ID NO: 391          moltype = AA  length = 10
FEATURE                 Location/Qualifiers
REGION                  1..10
```

```
                    note = Synthetic polymer
source              1..10
                    mol_type = protein
                    organism = synthetic construct
SEQUENCE: 391
GFSSDDYTIG                                                          10

SEQ ID NO: 392      moltype = AA  length = 10
FEATURE             Location/Qualifiers
REGION              1..10
                    note = Synthetic polymer
source              1..10
                    mol_type = protein
                    organism = synthetic construct
SEQUENCE: 392
GFTFDDYTIG                                                          10

SEQ ID NO: 393      moltype = AA  length = 10
FEATURE             Location/Qualifiers
REGION              1..10
                    note = Synthetic polymer
source              1..10
                    mol_type = protein
                    organism = synthetic construct
SEQUENCE: 393
GFSSDDYTIG                                                          10

SEQ ID NO: 394      moltype = AA  length = 10
FEATURE             Location/Qualifiers
REGION              1..10
                    note = Synthetic polymer
source              1..10
                    mol_type = protein
                    organism = synthetic construct
SEQUENCE: 394
GFTFDQYTIA                                                          10

SEQ ID NO: 395      moltype = AA  length = 10
FEATURE             Location/Qualifiers
REGION              1..10
                    note = Synthetic polymer
source              1..10
                    mol_type = protein
                    organism = synthetic construct
SEQUENCE: 395
GRTFSSYAMA                                                          10

SEQ ID NO: 396      moltype = AA  length = 10
FEATURE             Location/Qualifiers
REGION              1..10
                    note = Synthetic polymer
source              1..10
                    mol_type = protein
                    organism = synthetic construct
SEQUENCE: 396
GFAFDGYAIG                                                          10

SEQ ID NO: 397      moltype = AA  length = 10
FEATURE             Location/Qualifiers
REGION              1..10
                    note = Synthetic polymer
source              1..10
                    mol_type = protein
                    organism = synthetic construct
SEQUENCE: 397
GFSSDDYTIA                                                          10

SEQ ID NO: 398      moltype = AA  length = 10
FEATURE             Location/Qualifiers
REGION              1..10
                    note = Synthetic polymer
source              1..10
                    mol_type = protein
                    organism = synthetic construct
SEQUENCE: 398
GFSSDDYTIG                                                          10

SEQ ID NO: 399      moltype = AA  length = 10
FEATURE             Location/Qualifiers
```

```
REGION                     1..10
                           note = Synthetic polymer
source                     1..10
                           mol_type = protein
                           organism = synthetic construct
SEQUENCE: 399
GFTFDDYTIG                                                                   10

SEQ ID NO: 400             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 400
GFSSDDYTIG                                                                   10

SEQ ID NO: 401             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 401
GFSSDDYTIG                                                                   10

SEQ ID NO: 402             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 402
GFSFDDYAIA                                                                   10

SEQ ID NO: 403             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 403
GFSSDDYTIG                                                                   10

SEQ ID NO: 404             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 404
GFTGNDLAIG                                                                   10

SEQ ID NO: 405             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 405
GFSSDDYTIA                                                                   10

SEQ ID NO: 406             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 406
EGTLSSYGIG                                                                   10

SEQ ID NO: 407             moltype = AA  length = 10
```

```
FEATURE            Location/Qualifiers
REGION             1..10
                   note = Synthetic polymer
source             1..10
                   mol_type = protein
                   organism = synthetic construct
SEQUENCE: 407
GFSSDDYTIA                                                                     10

SEQ ID NO: 408     moltype = AA  length = 10
FEATURE            Location/Qualifiers
REGION             1..10
                   note = Synthetic polymer
source             1..10
                   mol_type = protein
                   organism = synthetic construct
SEQUENCE: 408
GFTFDDYAIA                                                                     10

SEQ ID NO: 409     moltype = AA  length = 10
FEATURE            Location/Qualifiers
REGION             1..10
                   note = Synthetic polymer
source             1..10
                   mol_type = protein
                   organism = synthetic construct
SEQUENCE: 409
GLSSDDYTIG                                                                     10

SEQ ID NO: 410     moltype = AA  length = 10
FEATURE            Location/Qualifiers
REGION             1..10
                   note = Synthetic polymer
source             1..10
                   mol_type = protein
                   organism = synthetic construct
SEQUENCE: 410
GLSSDDYTIG                                                                     10

SEQ ID NO: 411     moltype = AA  length = 10
FEATURE            Location/Qualifiers
REGION             1..10
                   note = Synthetic polymer
source             1..10
                   mol_type = protein
                   organism = synthetic construct
SEQUENCE: 411
GFSSDDYTIG                                                                     10

SEQ ID NO: 412     moltype = AA  length = 10
FEATURE            Location/Qualifiers
REGION             1..10
                   note = Synthetic polymer
source             1..10
                   mol_type = protein
                   organism = synthetic construct
SEQUENCE: 412
GFSFDDYTIG                                                                     10

SEQ ID NO: 413     moltype = AA  length = 10
FEATURE            Location/Qualifiers
REGION             1..10
                   note = Synthetic polymer
source             1..10
                   mol_type = protein
                   organism = synthetic construct
SEQUENCE: 413
GFTFDDYAIA                                                                     10

SEQ ID NO: 414     moltype = AA  length = 10
FEATURE            Location/Qualifiers
REGION             1..10
                   note = Synthetic polymer
source             1..10
                   mol_type = protein
                   organism = synthetic construct
SEQUENCE: 414
GFTFDDYAIG                                                                     10
```

```
SEQ ID NO: 415          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 415
GFTFGDYTIG                                                              10

SEQ ID NO: 416          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 416
EGTFSSYGIG                                                              10

SEQ ID NO: 417          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 417
GFSSDDYTIG                                                              10

SEQ ID NO: 418          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 418
GVSIGDYNIG                                                              10

SEQ ID NO: 419          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 419
GFTFDDYTIA                                                              10

SEQ ID NO: 420          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 420
GFTFDDYTIA                                                              10

SEQ ID NO: 421          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 421
ASITWGGGNT Y                                                            11

SEQ ID NO: 422          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 422
AATVWTGAGT V                                                            11
```

```
SEQ ID NO: 423           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 423
AAIGWSADIT V                                                              11

SEQ ID NO: 424           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 424
AFIDWSGGGT Y                                                              11

SEQ ID NO: 425           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 425
ATITWGGGST Y                                                              11

SEQ ID NO: 426           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 426
AAISWSGGPT V                                                              11

SEQ ID NO: 427           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 427
AAITWGGGST V                                                              11

SEQ ID NO: 428           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 428
AAITWSGVST V                                                              11

SEQ ID NO: 429           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 429
GAIMWSGAFT H                                                              11

SEQ ID NO: 430           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 430
```

```
AAITWGGGST V                                                                     11

SEQ ID NO: 431        moltype = AA   length = 11
FEATURE               Location/Qualifiers
REGION                1..11
                      note = Synthetic polymer
source                1..11
                      mol_type = protein
                      organism = synthetic construct
SEQUENCE: 431
SCISSSDRNT Y                                                                     11

SEQ ID NO: 432        moltype = AA   length = 11
FEATURE               Location/Qualifiers
REGION                1..11
                      note = Synthetic polymer
source                1..11
                      mol_type = protein
                      organism = synthetic construct
SEQUENCE: 432
AFIDWSGGGT Y                                                                     11

SEQ ID NO: 433        moltype = AA   length = 11
FEATURE               Location/Qualifiers
REGION                1..11
                      note = Synthetic polymer
source                1..11
                      mol_type = protein
                      organism = synthetic construct
SEQUENCE: 433
AVITWSGDST Y                                                                     11

SEQ ID NO: 434        moltype = AA   length = 11
FEATURE               Location/Qualifiers
REGION                1..11
                      note = Synthetic polymer
source                1..11
                      mol_type = protein
                      organism = synthetic construct
SEQUENCE: 434
ACISSKDGST Y                                                                     11

SEQ ID NO: 435        moltype = AA   length = 11
FEATURE               Location/Qualifiers
REGION                1..11
                      note = Synthetic polymer
source                1..11
                      mol_type = protein
                      organism = synthetic construct
SEQUENCE: 435
SGINSIGGST T                                                                     11

SEQ ID NO: 436        moltype = AA   length = 11
FEATURE               Location/Qualifiers
REGION                1..11
                      note = Synthetic polymer
source                1..11
                      mol_type = protein
                      organism = synthetic construct
SEQUENCE: 436
AVVTWSGDST Y                                                                     11

SEQ ID NO: 437        moltype = AA   length = 10
FEATURE               Location/Qualifiers
REGION                1..10
                      note = Synthetic polymer
source                1..10
                      mol_type = protein
                      organism = synthetic construct
SEQUENCE: 437
AKITNFGITS                                                                       10

SEQ ID NO: 438        moltype = AA   length = 11
FEATURE               Location/Qualifiers
REGION                1..11
                      note = Synthetic polymer
source                1..11
                      mol_type = protein
                      organism = synthetic construct
```

```
SEQUENCE: 438
SFISWISDIT Y                                                                  11

SEQ ID NO: 439          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 439
AFIDWSGGGT Y                                                                  11

SEQ ID NO: 440          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 440
AVILWSGVST Y                                                                  11

SEQ ID NO: 441          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 441
AAIVWSGGST Y                                                                  11

SEQ ID NO: 442          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 442
AAISSSGYHT Y                                                                  11

SEQ ID NO: 443          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 443
SCISSPDGST Y                                                                  11

SEQ ID NO: 444          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 444
AAVLWSGVST A                                                                  11

SEQ ID NO: 445          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 445
VAITWDGSAT T                                                                  11

SEQ ID NO: 446          moltype = AA  length = 11
FEATURE                 Location/Qualifiers
REGION                  1..11
                        note = Synthetic polymer
source                  1..11
                        mol_type = protein
```

```
                          -continued organism = synthetic construct
SEQUENCE: 446
AAIGWNGGIT Y                                                              11

SEQ ID NO: 447            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 447
GFITWSGAST Y                                                              11

SEQ ID NO: 448            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 448
AGINWSGESA D                                                              11

SEQ ID NO: 449            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 449
SCIERSDGST Y                                                              11

SEQ ID NO: 450            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 450
SCISNTDSST Y                                                              11

SEQ ID NO: 451            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 451
SCISNTDSST Y                                                              11

SEQ ID NO: 452            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 452
AQISWSAGSI Y                                                              11

SEQ ID NO: 453            moltype = AA  length = 11
FEATURE                   Location/Qualifiers
REGION                    1..11
                          note = Synthetic polymer
source                    1..11
                          mol_type = protein
                          organism = synthetic construct
SEQUENCE: 453
AGMSWNPGPA V                                                              11

SEQ ID NO: 454            moltype = AA  length = 11
FEATURE                   Location/Qualifiers
REGION                    1..11
                          note = Synthetic polymer
source                    1..11
```

```
                              mol_type = protein
                              organism = synthetic construct
SEQUENCE: 454
SCISRSDGST Y                                                              11

SEQ ID NO: 455                moltype = AA   length = 11
FEATURE                       Location/Qualifiers
REGION                        1..11
                              note = Synthetic polymer
source                        1..11
                              mol_type = protein
                              organism = synthetic construct
SEQUENCE: 455
ANIGWTGDMT Y                                                              11

SEQ ID NO: 456                moltype = AA   length = 11
FEATURE                       Location/Qualifiers
REGION                        1..11
                              note = Synthetic polymer
source                        1..11
                              mol_type = protein
                              organism = synthetic construct
SEQUENCE: 456
AAIIWSGSMT Y                                                              11

SEQ ID NO: 457                moltype = AA   length = 11
FEATURE                       Location/Qualifiers
REGION                        1..11
                              note = Synthetic polymer
source                        1..11
                              mol_type = protein
                              organism = synthetic construct
SEQUENCE: 457
SCISNTDSST Y                                                              11

SEQ ID NO: 458                moltype = AA   length = 11
FEATURE                       Location/Qualifiers
REGION                        1..11
                              note = Synthetic polymer
source                        1..11
                              mol_type = protein
                              organism = synthetic construct
SEQUENCE: 458
AANTWSGGPT Y                                                              11

SEQ ID NO: 459                moltype = AA   length = 10
FEATURE                       Location/Qualifiers
REGION                        1..10
                              note = Synthetic polymer
source                        1..10
                              mol_type = protein
                              organism = synthetic construct
SEQUENCE: 459
SCISSDGSTG                                                                10

SEQ ID NO: 460                moltype = AA   length = 11
FEATURE                       Location/Qualifiers
REGION                        1..11
                              note = Synthetic polymer
source                        1..11
                              mol_type = protein
                              organism = synthetic construct
SEQUENCE: 460
SCYSSSDGST G                                                              11

SEQ ID NO: 461                moltype = AA   length = 10
FEATURE                       Location/Qualifiers
REGION                        1..10
                              note = Synthetic polymer
source                        1..10
                              mol_type = protein
                              organism = synthetic construct
SEQUENCE: 461
SCISSDGSTG                                                                10

SEQ ID NO: 462                moltype = AA   length = 11
FEATURE                       Location/Qualifiers
REGION                        1..11
                              note = Synthetic polymer
```

```
                                          -continued source                     1..11
                           mol_type = protein
                           organism = synthetic construct
SEQUENCE: 462
GCIKSSDGTT G                                                         11

SEQ ID NO: 463             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 463
SCISNTDSST Y                                                         11

SEQ ID NO: 464             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 464
AAIAWSAGST Y                                                         11

SEQ ID NO: 465             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 465
SCISSKEGST Y                                                         11

SEQ ID NO: 466             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 466
SCISSSDGST G                                                         11

SEQ ID NO: 467             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 467
SCYSSRDGTT G                                                         11

SEQ ID NO: 468             moltype = AA   length = 10
FEATURE                    Location/Qualifiers
REGION                     1..10
                           note = Synthetic polymer
source                     1..10
                           mol_type = protein
                           organism = synthetic construct
SEQUENCE: 468
SCISSDGSTG                                                           10

SEQ ID NO: 469             moltype = AA   length = 11
FEATURE                    Location/Qualifiers
REGION                     1..11
                           note = Synthetic polymer
source                     1..11
                           mol_type = protein
                           organism = synthetic construct
SEQUENCE: 469
SCYSSSDGST G                                                         11

SEQ ID NO: 470             moltype = AA   length = 11
FEATURE                    Location/Qualifiers
REGION                     1..11
```

```
                            note = Synthetic polymer
source                      1..11
                            mol_type = protein
                            organism = synthetic construct
SEQUENCE: 470
SCFSSSDGST G                                                                    11

SEQ ID NO: 471              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 471
SCISNTDSST F                                                                    11

SEQ ID NO: 472              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 472
SCYSSSDGST G                                                                    11

SEQ ID NO: 473              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 473
SCISNTDSST Y                                                                    11

SEQ ID NO: 474              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 474
SCISSSDGST G                                                                    11

SEQ ID NO: 475              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 475
GGINWSGDST D                                                                    11

SEQ ID NO: 476              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 476
SCFSSSDGSA G                                                                    11

SEQ ID NO: 477              moltype = AA   length = 11
FEATURE                     Location/Qualifiers
REGION                      1..11
                            note = Synthetic polymer
source                      1..11
                            mol_type = protein
                            organism = synthetic construct
SEQUENCE: 477
SCISNTDSST Y                                                                    11

SEQ ID NO: 478              moltype = AA   length = 11
FEATURE                     Location/Qualifiers
```

```
REGION                     1..11
                           note = Synthetic polymer
source                     1..11
                           mol_type = protein
                           organism = synthetic construct
SEQUENCE: 478
SCFSTRDGNA G                                                              11

SEQ ID NO: 479             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 479
SCFSSRDGST G                                                              11

SEQ ID NO: 480             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 480
SCFSSRDGST G                                                              11

SEQ ID NO: 481             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 481
SCISSDGSTG                                                                10

SEQ ID NO: 482             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 482
SCISNTDSST Y                                                              11

SEQ ID NO: 483             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 483
SCISSPDGST Y                                                              11

SEQ ID NO: 484             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 484
SCYSSSDGNT G                                                              11

SEQ ID NO: 485             moltype = AA  length = 11
FEATURE                    Location/Qualifiers
REGION                     1..11
                           note = Synthetic polymer
source                     1..11
                           mol_type = protein
                           organism = synthetic construct
SEQUENCE: 485
GGINWSGDST D                                                              11

SEQ ID NO: 486             moltype = AA  length = 11
```

```
FEATURE                 Location/Qualifiers
REGION                  1..11
                        note = Synthetic polymer
source                  1..11
                        mol_type = protein
                        organism = synthetic construct
SEQUENCE: 486
SCFSSSDGST G                                                          11

SEQ ID NO: 487          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 487
SCISSGDGTT Y                                                          11

SEQ ID NO: 488          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 488
SCISSDGSTG                                                            10

SEQ ID NO: 489          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 489
SCISSDGSTG                                                            10

SEQ ID NO: 490          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 490
AKGLRNSDWD LRRGYEYDY                                                  19

SEQ ID NO: 491          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 491
ADQASVPPPY GSERYDIASP SEYDY                                           25

SEQ ID NO: 492          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 492
ANSRAYYSSS YDLGRLASYD Y                                               21

SEQ ID NO: 493          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 493
AAQRLGSVTD YTKYDY                                                     16
```

```
SEQ ID NO: 494          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 494
ASVKVVAGSG IDISGSRNYD Y                                                   21

SEQ ID NO: 495          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 495
AKRLDYSATD KGVDLSDEYD Y                                                   21

SEQ ID NO: 496          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 496
AAGGSGRLRD LKVGQNYDY                                                      19

SEQ ID NO: 497          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 497
ADSPPRTYSS GSVNLEDGSE YDY                                                 23

SEQ ID NO: 498          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 498
VIPGRGSALP IDVGKSDEYE Y                                                   21

SEQ ID NO: 499          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 499
AAGASGRLRD LKVGQNYDY                                                      19

SEQ ID NO: 500          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 500
ADGNVWSPPI CGSAGPPPGG MDY                                                 23

SEQ ID NO: 501          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 501
AAQRLGSVTD YTKYDY                                                         16
```

```
SEQ ID NO: 502          moltype = AA   length = 22
FEATURE                 Location/Qualifiers
REGION                  1..22
                        note = Synthetic polymer
source                  1..22
                        mol_type = protein
                        organism = synthetic construct
SEQUENCE: 502
AIPPRAYSGG SYSLKDQSKY EY                                              22

SEQ ID NO: 503          moltype = AA   length = 23
FEATURE                 Location/Qualifiers
REGION                  1..23
                        note = Synthetic polymer
source                  1..23
                        mol_type = protein
                        organism = synthetic construct
SEQUENCE: 503
ADGNVWSPPI CSSAGPPPGG MDY                                             23

SEQ ID NO: 504          moltype = AA   length = 9
FEATURE                 Location/Qualifiers
REGION                  1..9
                        note = Synthetic polymer
source                  1..9
                        mol_type = protein
                        organism = synthetic construct
SEQUENCE: 504
KSRSSYSNN                                                              9

SEQ ID NO: 505          moltype = AA   length = 22
FEATURE                 Location/Qualifiers
REGION                  1..22
                        note = Synthetic polymer
source                  1..22
                        mol_type = protein
                        organism = synthetic construct
SEQUENCE: 505
AMPPRAYTGR SVSLKDQSKY EY                                              22

SEQ ID NO: 506          moltype = AA   length = 13
FEATURE                 Location/Qualifiers
REGION                  1..13
                        note = Synthetic polymer
source                  1..13
                        mol_type = protein
                        organism = synthetic construct
SEQUENCE: 506
LDTTGWGPPP YQY                                                        13

SEQ ID NO: 507          moltype = AA   length = 22
FEATURE                 Location/Qualifiers
REGION                  1..22
                        note = Synthetic polymer
source                  1..22
                        mol_type = protein
                        organism = synthetic construct
SEQUENCE: 507
AHPPDPSRGG EWRLQTPSEY DY                                              22

SEQ ID NO: 508          moltype = AA   length = 16
FEATURE                 Location/Qualifiers
REGION                  1..16
                        note = Synthetic polymer
source                  1..16
                        mol_type = protein
                        organism = synthetic construct
SEQUENCE: 508
AAQRLGSVTD YTKYDY                                                     16

SEQ ID NO: 509          moltype = AA   length = 24
FEATURE                 Location/Qualifiers
REGION                  1..24
                        note = Synthetic polymer
source                  1..24
                        mol_type = protein
                        organism = synthetic construct
SEQUENCE: 509
```

```
VPRSHFTTAQ DMGQDMGAPS WYEY                                            24

SEQ ID NO: 510        moltype = AA  length = 22
FEATURE               Location/Qualifiers
REGION                1..22
                      note = Synthetic polymer
source                1..22
                      mol_type = protein
                      organism = synthetic construct
SEQUENCE: 510
AVLIRYYSGG YQGLSDANEY DY                                              22

SEQ ID NO: 511        moltype = AA  length = 17
FEATURE               Location/Qualifiers
REGION                1..17
                      note = Synthetic polymer
source                1..17
                      mol_type = protein
                      organism = synthetic construct
SEQUENCE: 511
VVKYLSGSYS YAGQYNF                                                    17

SEQ ID NO: 512        moltype = AA  length = 23
FEATURE               Location/Qualifiers
REGION                1..23
                      note = Synthetic polymer
source                1..23
                      mol_type = protein
                      organism = synthetic construct
SEQUENCE: 512
ADFNVWSPPI CGSVGPPPGG MDY                                             23

SEQ ID NO: 513        moltype = AA  length = 21
FEATURE               Location/Qualifiers
REGION                1..21
                      note = Synthetic polymer
source                1..21
                      mol_type = protein
                      organism = synthetic construct
SEQUENCE: 513
AHESTYYSGT YYLTDPRRYV Y                                               21

SEQ ID NO: 514        moltype = AA  length = 19
FEATURE               Location/Qualifiers
REGION                1..19
                      note = Synthetic polymer
source                1..19
                      mol_type = protein
                      organism = synthetic construct
SEQUENCE: 514
AVPARGLTMD LENSDIYDH                                                  19

SEQ ID NO: 515        moltype = AA  length = 22
FEATURE               Location/Qualifiers
REGION                1..22
                      note = Synthetic polymer
source                1..22
                      mol_type = protein
                      organism = synthetic construct
SEQUENCE: 515
AATLQVTGSY YLDLSTVDIY DN                                              22

SEQ ID NO: 516        moltype = AA  length = 20
FEATURE               Location/Qualifiers
REGION                1..20
                      note = Synthetic polymer
source                1..20
                      mol_type = protein
                      organism = synthetic construct
SEQUENCE: 516
ATLFRSNGPK DLSSGYEYDY                                                 20

SEQ ID NO: 517        moltype = AA  length = 13
FEATURE               Location/Qualifiers
REGION                1..13
                      note = Synthetic polymer
source                1..13
                      mol_type = protein
                      organism = synthetic construct
```

```
SEQUENCE: 517
AGESGVWVGG LDY                                                             13

SEQ ID NO: 518         moltype = AA  length = 22
FEATURE                Location/Qualifiers
REGION                 1..22
                       note = Synthetic polymer
source                 1..22
                       mol_type = protein
                       organism = synthetic construct
SEQUENCE: 518
VGSANSGEFR FGWVLKPDLY NY                                                   22

SEQ ID NO: 519         moltype = AA  length = 23
FEATURE                Location/Qualifiers
REGION                 1..23
                       note = Synthetic polymer
source                 1..23
                       mol_type = protein
                       organism = synthetic construct
SEQUENCE: 519
ADGNVWSPPI CGSAGPPPGG MDY                                                  23

SEQ ID NO: 520         moltype = AA  length = 23
FEATURE                Location/Qualifiers
REGION                 1..23
                       note = Synthetic polymer
source                 1..23
                       mol_type = protein
                       organism = synthetic construct
SEQUENCE: 520
ADGNVWSPPI CGSAGPPPGG MDY                                                  23

SEQ ID NO: 521         moltype = AA  length = 20
FEATURE                Location/Qualifiers
REGION                 1..20
                       note = Synthetic polymer
source                 1..20
                       mol_type = protein
                       organism = synthetic construct
SEQUENCE: 521
ERGYAYCSDD GCQRTQDYDY                                                      20

SEQ ID NO: 522         moltype = AA  length = 21
FEATURE                Location/Qualifiers
REGION                 1..21
                       note = Synthetic polymer
source                 1..21
                       mol_type = protein
                       organism = synthetic construct
SEQUENCE: 522
GAARAWWSGS YDYTRMNNYD Y                                                    21

SEQ ID NO: 523         moltype = AA  length = 23
FEATURE                Location/Qualifiers
REGION                 1..23
                       note = Synthetic polymer
source                 1..23
                       mol_type = protein
                       organism = synthetic construct
SEQUENCE: 523
AETSADSGEF RFGWVLKPSL YDY                                                  23

SEQ ID NO: 524         moltype = AA  length = 21
FEATURE                Location/Qualifiers
REGION                 1..21
                       note = Synthetic polymer
source                 1..21
                       mol_type = protein
                       organism = synthetic construct
SEQUENCE: 524
AAGSAYSGSY WNITMAANYD Y                                                    21

SEQ ID NO: 525         moltype = AA  length = 18
FEATURE                Location/Qualifiers
REGION                 1..18
                       note = Synthetic polymer
source                 1..18
                       mol_type = protein
```

```
                          -continued organism = synthetic construct
SEQUENCE: 525
AQRIFGAQPM DLSGDYEY                                                 18

SEQ ID NO: 526          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 526
ADGNVWSPPI CGSAGPPPGG MDY                                           23

SEQ ID NO: 527          moltype = AA  length = 18
FEATURE                 Location/Qualifiers
REGION                  1..18
                        note = Synthetic polymer
source                  1..18
                        mol_type = protein
                        organism = synthetic construct
SEQUENCE: 527
ARDYRGIKDL DLKGDYDY                                                 18

SEQ ID NO: 528          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 528
ADFNVWSPPI CGSIWYGPPP RGMDY                                         25

SEQ ID NO: 529          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 529
ADSNVWSPPI CGSRWYGPPP GGMAY                                         25

SEQ ID NO: 530          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 530
ADFNVWSPPI CGSNWYGPPP GGMDY                                         25

SEQ ID NO: 531          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 531
ADFNVWSPPI CGSIWYGPPP GGMDY                                         25

SEQ ID NO: 532          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 532
ADGNVWSPPI CGSAGPPPGG MDY                                           23

SEQ ID NO: 533          moltype = AA  length = 17
FEATURE                 Location/Qualifiers
REGION                  1..17
                        note = Synthetic polymer
source                  1..17
```

```
                              mol_type = protein
                              organism = synthetic construct
SEQUENCE: 533
ARIITVATMR LDSDYDY                                                         17

SEQ ID NO: 534          moltype = AA   length = 23
FEATURE                 Location/Qualifiers
REGION                  1..23
                        note = Synthetic polymer
source                  1..23
                        mol_type = protein
                        organism = synthetic construct
SEQUENCE: 534
ADGNVWSPPI CGSAGPPPGG MDY                                                  23

SEQ ID NO: 535          moltype = AA   length = 25
FEATURE                 Location/Qualifiers
REGION                  1..25
                        note = Synthetic polymer
source                  1..25
                        mol_type = protein
                        organism = synthetic construct
SEQUENCE: 535
ADSNVWSPPI CGRTWYGPPP GGMDY                                                25

SEQ ID NO: 536          moltype = AA   length = 25
FEATURE                 Location/Qualifiers
REGION                  1..25
                        note = Synthetic polymer
source                  1..25
                        mol_type = protein
                        organism = synthetic construct
SEQUENCE: 536
ADFNVWSPPI CGSIWYGPPP GGMAY                                                25

SEQ ID NO: 537          moltype = AA   length = 25
FEATURE                 Location/Qualifiers
REGION                  1..25
                        note = Synthetic polymer
source                  1..25
                        mol_type = protein
                        organism = synthetic construct
SEQUENCE: 537
ADFNVWSPPI CGSNWYGPPP GGMDY                                                25

SEQ ID NO: 538          moltype = AA   length = 25
FEATURE                 Location/Qualifiers
REGION                  1..25
                        note = Synthetic polymer
source                  1..25
                        mol_type = protein
                        organism = synthetic construct
SEQUENCE: 538
ADFNVWSPPI CGSSWYGPPP GGMDY                                                25

SEQ ID NO: 539          moltype = AA   length = 25
FEATURE                 Location/Qualifiers
REGION                  1..25
                        note = Synthetic polymer
source                  1..25
                        mol_type = protein
                        organism = synthetic construct
SEQUENCE: 539
ADFNVWSPPI CGSRWYGPPP GGMEY                                                25

SEQ ID NO: 540          moltype = AA   length = 23
FEATURE                 Location/Qualifiers
REGION                  1..23
                        note = Synthetic polymer
source                  1..23
                        mol_type = protein
                        organism = synthetic construct
SEQUENCE: 540
ADGNVWSPPI CGSAGPPPGG MDY                                                  23

SEQ ID NO: 541          moltype = AA   length = 25
FEATURE                 Location/Qualifiers
REGION                  1..25
                        note = Synthetic polymer
```

```
source                 1..25
                       mol_type = protein
                       organism = synthetic construct
SEQUENCE: 541
ADFNWSPPI CGSRWYGPPP GGMAY                                               25

SEQ ID NO: 542         moltype = AA  length = 23
FEATURE                Location/Qualifiers
REGION                 1..23
                       note = Synthetic polymer
source                 1..23
                       mol_type = protein
                       organism = synthetic construct
SEQUENCE: 542
ADGNWSPPI CGSAGPPPGG MDY                                                 23

SEQ ID NO: 543         moltype = AA  length = 25
FEATURE                Location/Qualifiers
REGION                 1..25
                       note = Synthetic polymer
source                 1..25
                       mol_type = protein
                       organism = synthetic construct
SEQUENCE: 543
ADSNWSPPI CGKTWYGPPP GGMDY                                               25

SEQ ID NO: 544         moltype = AA  length = 13
FEATURE                Location/Qualifiers
REGION                 1..13
                       note = Synthetic polymer
source                 1..13
                       mol_type = protein
                       organism = synthetic construct
SEQUENCE: 544
AGESGVWVGG LDY                                                           13

SEQ ID NO: 545         moltype = AA  length = 25
FEATURE                Location/Qualifiers
REGION                 1..25
                       note = Synthetic polymer
source                 1..25
                       mol_type = protein
                       organism = synthetic construct
SEQUENCE: 545
ADSNWSPPI CGSTWYGPPP GGMAY                                               25

SEQ ID NO: 546         moltype = AA  length = 23
FEATURE                Location/Qualifiers
REGION                 1..23
                       note = Synthetic polymer
source                 1..23
                       mol_type = protein
                       organism = synthetic construct
SEQUENCE: 546
ADGNWSPPI CGSAGPPPGG MDY                                                 23

SEQ ID NO: 547         moltype = AA  length = 25
FEATURE                Location/Qualifiers
REGION                 1..25
                       note = Synthetic polymer
source                 1..25
                       mol_type = protein
                       organism = synthetic construct
SEQUENCE: 547
ADFNWSPPI CGSRWYGPPP GGMDY                                               25

SEQ ID NO: 548         moltype = AA  length = 25
FEATURE                Location/Qualifiers
REGION                 1..25
                       note = Synthetic polymer
source                 1..25
                       mol_type = protein
                       organism = synthetic construct
SEQUENCE: 548
ADFNWSPPI CGSRWYGPPP GGMDY                                               25

SEQ ID NO: 549         moltype = AA  length = 25
FEATURE                Location/Qualifiers
REGION                 1..25
```

```
                        note = Synthetic polymer
source                  1..25
                        mol_type = protein
                        organism = synthetic construct
SEQUENCE: 549
ADFNVWSPPI CGSRWYGPPP GGMDY                                        25

SEQ ID NO: 550          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 550
ADFNVWSPPI CGSIWYGPPP GGMDY                                        25

SEQ ID NO: 551          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 551
ADGNVWSPPI CGSAGPPPGG MDY                                          23

SEQ ID NO: 552          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 552
ADFNVWSPPI CGSVGPPPGG MDY                                          23

SEQ ID NO: 553          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 553
ADFNVWSPPI CGSSWYGPPP GGMAY                                        25

SEQ ID NO: 554          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 554
AGESGVWVGG LDY                                                     13

SEQ ID NO: 555          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 555
ADFNVWSPPI CGSSWYGPPP GGMEY                                        25

SEQ ID NO: 556          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 556
ADGNVWSPPI CGSAGPPPGG MDY                                          23

SEQ ID NO: 557          moltype = AA  length = 25
FEATURE                 Location/Qualifiers
```

-continued

```
REGION                    1..25
                          note = Synthetic polymer
source                    1..25
                          mol_type = protein
                          organism = synthetic construct
SEQUENCE: 557
ADFNWSPPI CSSNWYGPPP RGMDY                                              25

SEQ ID NO: 558            moltype = AA  length = 25
FEATURE                   Location/Qualifiers
REGION                    1..25
                          note = Synthetic polymer
source                    1..25
                          mol_type = protein
                          organism = synthetic construct
SEQUENCE: 558
ADFNWSPPI CGSIWYGPPP RGMDY                                              25

SEQ ID NO: 559            moltype = AA  length = 146
FEATURE                   Location/Qualifiers
REGION                    1..146
                          note = Synthetic polymer
source                    1..146
                          mol_type = protein
                          organism = synthetic construct
SEQUENCE: 559
QVQLQESGGG LVQAGGSLRL SCAASGRSFS SYTLAWFRQA PGKEREFVAS ITWGGGNTYY        60
PDSVKGRFTI SRDDAKNTVY LQMNSLKPED TAVYYCAAKG LRNSDWDLRR GYEYDYWGQG       120
TQVTVSSAAA YPYDVPDYGS HHHHHH                                           146

SEQ ID NO: 560            moltype = AA  length = 152
FEATURE                   Location/Qualifiers
REGION                    1..152
                          note = Synthetic polymer
source                    1..152
                          mol_type = protein
                          organism = synthetic construct
SEQUENCE: 560
QVQLQESGGG LVQDGGSLRL SCAFSGRTFS SYTMGWFRQG PGKEREFVAA TVWTGAGTVY        60
ADSVKGRFTI SRDNAKNTVY LQMNSLRPED TAVYYCAADQ ASVPPPYGSE RYDIASPSEY       120
DYWGQGTQVT VSSAAAYPYD VPDYGSHHHH HH                                    152

SEQ ID NO: 561            moltype = AA  length = 148
FEATURE                   Location/Qualifiers
REGION                    1..148
                          note = Synthetic polymer
source                    1..148
                          mol_type = protein
                          organism = synthetic construct
SEQUENCE: 561
QVQLQESGGG LVQAGASLRL SCAASGRTFS SYIMGWFRQA PGKEREFVAA IGWSADITVY        60
ADSVKGRFTI SRDNAENMVY LQMNSLNPED TAVYYCAANS RAYYSSSYDL GRLASYDYWG       120
QGTQVTVSSA AAYPYDVPDY GSHHHHHH                                         148

SEQ ID NO: 562            moltype = AA  length = 143
FEATURE                   Location/Qualifiers
REGION                    1..143
                          note = Synthetic polymer
source                    1..143
                          mol_type = protein
                          organism = synthetic construct
SEQUENCE: 562
QVQLQESGGG LVQAGGSLRL SCAASGRTFS SYTMGWFRQA PGKEREFVAF IDWSGGGTYY        60
DDSVKGRFTI SRDNAENTVY LQMNNLEPED TAVYYCAAAQ RLGSVTDYTK YDYWGQGTQV       120
TVSSAAAYPY DVPDYGSHHH HHH                                              143

SEQ ID NO: 563            moltype = AA  length = 152
FEATURE                   Location/Qualifiers
REGION                    1..152
                          note = Synthetic polymer
source                    1..152
                          mol_type = protein
                          organism = synthetic construct
SEQUENCE: 563
QVQLQESGGG LVQAGGSLRL SCAASGRTSG RTFSSYTMGW FRQAPGKERE FVATITWGGG        60
STYYADSVKG RFTISRDNAN NTVYLQMNSL KPEDTAVYYC AASVKVVAGS GIDISGSRNY       120
DYWGQGTQVT VSSAAAYPYD VPDYGSHHHH HH                                    152

SEQ ID NO: 564            moltype = AA  length = 148
```

```
FEATURE                 Location/Qualifiers
REGION                  1..148
                        note = Synthetic polymer
source                  1..148
                        mol_type = protein
                        organism = synthetic construct
SEQUENCE: 564
QVQLQESGGG LVQPGGSLRL SCLASGRTFS SYAMGWFRQA PGKEREFVAA ISWSGGPTVY    60
ADHVKGRFTI SRDNAKNTVY LQVNSLKPED TADYYCAAKR LDYSATDKGV DLSDEYDYWG   120
QGTQVTVSSA AAYPYDVPDY GSHHHHHH                                     148

SEQ ID NO: 565          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 565
QVQLQESGGG LVQAGDSLRL SCAASGLTFS NYIMGWFRQA PGKEREFVAA ITWGGGSTVY    60
ADSVEGRFTI SRDGTKNTVS LQMNSLLPED TAVYYCAAAG GSGRLRDLKV GQNYDYWGQG   120
TQVTVSSAAA YPYDVPDYGS HHHHHH                                       146

SEQ ID NO: 566          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 566
QVQLQESGGG LVQAGGSLRL SCAASGRTFS SYTMGWFRQA PGREREFVAA ITWSGVSTVY    60
TDSVKGRFTV SRDNAKNTVY LQMNSLKPED TAVYYCAADS PPRTYSSGSV NLEDGSEYDY   120
WGQGTQVTVS SAAAYPYDVP DYGSHHHHHH                                   150

SEQ ID NO: 567          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 567
QVQLQESGGG LVQAGGSLRL SCAASGRTFS SDTMGWFRQA PGKEREFVGA IMWSGAFTHY    60
ADSVKGRFTI SRDNAKNTVY LQMNALKPED TAVYYCAVIP GRGSALPIDV GKSDEYEYWG   120
QGTQVTVSSA AAYPYDVPDY GSHHHHHH                                     148

SEQ ID NO: 568          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 568
QVQLQESGGG LVQAGDSLRL SCAASGLTFS NYIMGWFRQA PGKEREFVAA ITWGGGSTVY    60
ADSVEGRFTI SRDGTKNTVS LQMNSLQPED TAVYYCAAAG ASGRLRDLKV GQNYDYWGQG   120
TQVTVSSAAA YPYDVPDYGS HHHHHH                                       146

SEQ ID NO: 569          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 569
QVQLQESGGG LVQAGGSLRL SCAGSGFTLD YYGIGWFRQA PGKEREGVSC ISSSDRNTYY    60
ADSVKGRFTI SGDNAKNTVY LQMNNLKPED TAVYYCAADG NVWSPPICGS AGPPPGGMDY   120
WGKGTQVTVS SAAAYPYDVP DYGSHHHHHH                                   150

SEQ ID NO: 570          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 570
```

```
QVQLQESGGG LVQAGGSLRL SCVASGHTFS SYTMGWFRQA PGKEREFVAF IDWSGGGTYY    60
ANSVKGRFTI SRDNAENTVY LQMNNLKPED TAVYYCAAAQ RLGSVTDYTK YDYWGQGTQV   120
TVSSAAYPY DVPDYGSHHH HHH                                           143

SEQ ID NO: 571          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 571
QVQLQESGGG LVQAGGSLRL SCAASGRTFS SYVIGWFRQA PGKEREFVAV ITWSGDSTYS    60
SDSLKGRFTI SRDNAKNTVY LQMNALNPED TAVYYCAAIP PRAYSGGSYS LKDQSKYEYW   120
GQGTQVTVSS AAAYPYDVPD YGSHHHHHH                                    149

SEQ ID NO: 572          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 572
QVQLQESGGG LVQAEGSLKL SCISGFAFDG YAIGWFRQAP GKEREGVACI SSKDGSTYYA    60
DSVKGRFTMS VDKTKNTVYL QMSSLKPEDT AVYYCAADGN VWSPPICSSA GPPPGGMDYW   120
GKGTQVTVSS AAAYPYDVPD YGSHHHHHH                                    149

SEQ ID NO: 573          moltype = AA   length = 139
FEATURE                 Location/Qualifiers
REGION                  1..139
                        note = Synthetic polymer
source                  1..139
                        mol_type = protein
                        organism = synthetic construct
SEQUENCE: 573
QVQLQESGGG LVQPGGSLTL SCAASGFAFG FFDMTWVRQA PGKGLEWVSG INSIGGSTTY    60
ADSVKGRFTI SRDNAKNELY LQMNSLKPDD TAVYYCAKSR SSYSNNWRPP GQGTQVTVSS   120
AAAYPYDVPD YGSHHHHHH                                                139

SEQ ID NO: 574          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 574
QVQLQESGGG LVQARGSLTL SCAASGRTFS NYVIGWFRQA PGEEREFVAV VTWSGDSTYS    60
SDSLKGRFTI SRDNAKNTVY LQMNNLNPED TAVYYCAAMP PRAYTGRSVS LKDQSKYEYW   120
GQGTQVTVSS AAAYPYDVPD YGSHHHHHH                                    149

SEQ ID NO: 575          moltype = AA   length = 139
FEATURE                 Location/Qualifiers
REGION                  1..139
                        note = Synthetic polymer
source                  1..139
                        mol_type = protein
                        organism = synthetic construct
SEQUENCE: 575
QVQLQESGGG LVQPGGSLRL SCAASGSIFS INVMGWYRQT PGKERELVAK ITNFGITSYA    60
DSAQGRFTIS RGNAKNTVYL QMNSLKPEDT AVYYCNLDTT GWGPPPYQYW GQGTQVTVSS   120
AAAYPYDVPD YGSHHHHHH                                                139

SEQ ID NO: 576          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 576
QVQLQESGGG LVQAGASLRL SCAASGRTFS NYNVGWFRQA PGKEREFVSF ISWISDITYY    60
SDSVKGRFII SRDNAKNMVY LQMNSLKPED TAVYYCAAHP PDPSRGGEWR LQTPSEYDYW   120
GQGTQVTVSS AAAYPYDVPD YGSHHHHHH                                    149

SEQ ID NO: 577          moltype = AA   length = 143
FEATURE                 Location/Qualifiers
REGION                  1..143
```

```
                        note = Synthetic polymer
source                  1..143
                        mol_type = protein
                        organism = synthetic construct
SEQUENCE: 577
QVQLQESGGG LVQAGGSLRL SCAASGHTFS SYTMGWFRQA PGKEREFVAF IDWSGGGTYY     60
ADSVKGRFTI SRDNAENTVY LQMNNLKPED TAVYYCAAAQ RLGSVTDYTK YDYWGQGTQV    120
TVSSAAAYPY DVPDYGSHHH HHH                                            143

SEQ ID NO: 578          moltype = AA   length = 151
FEATURE                 Location/Qualifiers
REGION                  1..151
                        note = Synthetic polymer
source                  1..151
                        mol_type = protein
                        organism = synthetic construct
SEQUENCE: 578
QVQLQESGGG LVQAGGSLRL SCAASGRTFS TYPVGWFRQA PGKEREFVAV ILWSGVSTYY     60
ADSVKGRFTI SRDNAQNTVY LQMDSLKPED TAVYYCAVPR SHFTTAQDMG QDMGAPSWYE    120
YWGQGTQVTV SSAAAYPYDV PDYGSHHHHH H                                   151

SEQ ID NO: 579          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 579
QVQLQESGGG LVQAGGSLRL SCAASGRTFS NYAMGWFRQA PGKEREFVAA IVWSGGSTYY     60
ADSVKGRFTI SRDNAKNTVY LQMNSLKPED TAVYYCAAVL IRYYSGGYQG LSDANEYDYW    120
GQGTQVTVSS AAAYPYDVPD YGSHHHHHH                                      149

SEQ ID NO: 580          moltype = AA   length = 144
FEATURE                 Location/Qualifiers
REGION                  1..144
                        note = Synthetic polymer
source                  1..144
                        mol_type = protein
                        organism = synthetic construct
SEQUENCE: 580
QVQLQESGGG LVQAGASLRL SCSASGRTFS DYRMGWFRQA PGKEREWVAA ISSSGYHTYY     60
ADSVKGRFTI SRDNAKNTGY LQMSSLKPED TAVYYCAVVK YLSGSYSYAG QYNFWGQGTQ    120
VTVSSAAAYP YDVPDYGSHH HHHH                                           144

SEQ ID NO: 581          moltype = AA   length = 150
FEATURE                 Location/Qualifiers
REGION                  1..150
                        note = Synthetic polymer
source                  1..150
                        mol_type = protein
                        organism = synthetic construct
SEQUENCE: 581
QVQLQESGGG LVQAGDSLKL SCAASGLTFS NYIMAWFRQA PGKEREGVSC ISSPDGSTYY     60
ADSVKGRFTI SSDNAKNTVY LQMNSLKPED TAVYYCAADF NVWSPPICGS VGPPPGGMDY    120
WGKGTQVTVS SAAAYPYDVP DYGSHHHHHH                                     150

SEQ ID NO: 582          moltype = AA   length = 148
FEATURE                 Location/Qualifiers
REGION                  1..148
                        note = Synthetic polymer
source                  1..148
                        mol_type = protein
                        organism = synthetic construct
SEQUENCE: 582
QVQLQESGGG LVQAGGSLRL SCAASGRTFS NSVMGWFRQP PGKEREFVAA VLWSGVSTAY     60
ADSVKGRFTI SRDNAKNTVY LQMNNLKPDD TAVYYCAAHE STYYSGTYYL TDPRRYVYWG    120
QGTQVTVSSA AAYPYDVPDY GSHHHHHH                                       148

SEQ ID NO: 583          moltype = AA   length = 146
FEATURE                 Location/Qualifiers
REGION                  1..146
                        note = Synthetic polymer
source                  1..146
                        mol_type = protein
                        organism = synthetic construct
SEQUENCE: 583
QVQLQESGGG LVQAGGSLRL SCVGDGRTFS SYIIGWFRQA PGNEREFVVA ITWDGSATTY     60
ADSVKGRFTV SRDSAKNTAY LQMNSLKPED TAVYYCAAVP ARGLTMDLEN SDIYDHWGRG    120
```

```
TQVTVSSAAA YPYDVPDYGS HHHHHH                                             146

SEQ ID NO: 584          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 584
QVQLQESGGG LVQAGGSLRL SCAASGRTFS SYVMGWFRQA LGKEREFVAA IGWNGGITYY    60
ADSVKGRFAI SRDNAKNTVY LQMNSLKPED TAVYYCAAAT LQVTGSYYLD LSTVDIYDNW   120
GQGTQVTVSS AAAYPYDVPD YGSHHHHHH                                      149

SEQ ID NO: 585          moltype = AA   length = 147
FEATURE                 Location/Qualifiers
REGION                  1..147
                        note = Synthetic polymer
source                  1..147
                        mol_type = protein
                        organism = synthetic construct
SEQUENCE: 585
QVQLQESGGG LVQAGGSLRL SCAASGGTFS NYVMGWFRQA PGKEREFVGF ITWSGASTYY    60
ADSVKGRFTI SRDNAENTVY LQMNSLKPED TAVYYCAATL FRSNGPKDLS SGYEYDYWGQ   120
GTQVTVSSAA AYPYDVPDYG SHHHHHH                                        147

SEQ ID NO: 586          moltype = AA   length = 140
FEATURE                 Location/Qualifiers
REGION                  1..140
                        note = Synthetic polymer
SITE                    112
                        note = misc_feature - Xaa can be any naturally occurring
                         amino acid
source                  1..140
                        mol_type = protein
                        organism = synthetic construct
SEQUENCE: 586
QVQLQESGGG LVQAGDSLRL TCTASGRTFS NYGIGWFRQA PGKEREFVAG INWSGESADY    60
ADSVKGRFTI SRDNAKNTVY LQMNSLKPED TAVYYCAAGE SGVWVGGLDY WXQGTQVTVS   120
SAAAYPYDVP DYGSHHHHHH                                                140

SEQ ID NO: 587          moltype = AA   length = 149
FEATURE                 Location/Qualifiers
REGION                  1..149
                        note = Synthetic polymer
source                  1..149
                        mol_type = protein
                        organism = synthetic construct
SEQUENCE: 587
QVQLQESGGG LVQAGGSLRL SCAASGFTFD DYAIAWFRQA PGKEREGVSC IERSDGSTYY    60
ADSVKGRFTI SSDNAKNTVY LQMNSLKPED TAVYYCAVGS ANSGEFRFGW VLKPDLYNYW   120
GQGTQVTVSS AAAYPYDVPD YGSHHHHHH                                      149

SEQ ID NO: 588          moltype = AA   length = 150
FEATURE                 Location/Qualifiers
REGION                  1..150
                        note = Synthetic polymer
source                  1..150
                        mol_type = protein
                        organism = synthetic construct
SEQUENCE: 588
QVQLQESGGG LVQAGGSLRL SCTASGRTFS SYTVAWFRQS PGKEREGISC ISNTDSSTYY    60
ADSVKGRFTI SSDNAKSTVH LQMSSLKPED TAVYYCAADG NVWSPPICGS AGPPPGGMDY   120
WGKGTQVTVS SAAAYPYDVP DYGSHHHHHH                                     150

SEQ ID NO: 589          moltype = AA   length = 150
FEATURE                 Location/Qualifiers
REGION                  1..150
                        note = Synthetic polymer
source                  1..150
                        mol_type = protein
                        organism = synthetic construct
SEQUENCE: 589
QVQLQESGGG LVQPGGSLRL SCATFGFPFD DYAIAWFRQA PGKEREGVSC ISNTDSSTYY    60
ADSVKGRFTI SSDNAKNTVH LQMSSLKPED TAVYYCAADG NVWSPPICGS AGPPPGGMDY   120
WGKGTQVTVS SAAAYPYDVP DYGSHHHHHH                                     150

SEQ ID NO: 590          moltype = AA   length = 147
FEATURE                 Location/Qualifiers
```

```
REGION                      1..147
                            note = Synthetic polymer
source                      1..147
                            mol_type = protein
                            organism = synthetic construct
SEQUENCE: 590
QVQLQESGGG LVQAGGSLRL SCAASGRTFS SYVMGWFRQA PGKEREFVAQ ISWSAGSIYY     60
ADSVKGRFTI SNDNAKRTVY LQMNSLKPED TAVYYCAERG YAYCSDDGCQ RTQDYDYWGQ    120
GTQVTVSSAA AYPYDVPDYG SHHHHHH                                        147

SEQ ID NO: 591              moltype = AA  length = 148
FEATURE                     Location/Qualifiers
REGION                      1..148
                            note = Synthetic polymer
source                      1..148
                            mol_type = protein
                            organism = synthetic construct
SEQUENCE: 591
QVQLQESGGG LVQAGGSLRL SCAASGRTLS SNPMAWFRQA AGKEREFVAG MSWNPGPAVY     60
ADSVKGRFTI SRDSAENTVY LQMNSLKPED TAVYYCAGAA RAWWSGSYDY TRMNNYDYWG    120
PGTQVTVSSA AAYPYDVPDY GSHHHHHH                                       148

SEQ ID NO: 592              moltype = AA  length = 150
FEATURE                     Location/Qualifiers
REGION                      1..150
                            note = Synthetic polymer
source                      1..150
                            mol_type = protein
                            organism = synthetic construct
SEQUENCE: 592
QVQLQESGGG LVQAGGSLRL SCAVSGFTFD NYAIGWFRQA PGKEREGVSC ISRSDGSTYY     60
ADSVRGRFTI SSDNAKNTVY LQMNSLKPED TAVYYCAAET SADSGEFRFG WVLKPSLYDY    120
WGQGTQVTVS SAAAYPYDVP DYGSHHHHHH                                     150

SEQ ID NO: 593              moltype = AA  length = 148
FEATURE                     Location/Qualifiers
REGION                      1..148
                            note = Synthetic polymer
source                      1..148
                            mol_type = protein
                            organism = synthetic construct
SEQUENCE: 593
QVQLQESGGG LVQAGGSLRL SCAASGRAFS SYFMGWFRQT PGKEREFVAN IGWTGDMTYY     60
ADSVKGRFTI SRDNAKNTVY LQMNSLKPED TAVYYCAAAG SAYSGSYWNI TMAANYDYWG    120
QGTQVTVSSA AAYPYDVPDY GSHHHHHH                                       148

SEQ ID NO: 594              moltype = AA  length = 145
FEATURE                     Location/Qualifiers
REGION                      1..145
                            note = Synthetic polymer
source                      1..145
                            mol_type = protein
                            organism = synthetic construct
SEQUENCE: 594
QVQLQESGGG LVQAGGSLRL SCAASTPTFS SYNMGWFRQA PGKEREFVAA IIWSGSMTYY     60
ADSMKGRFTV SIDNAKNTVY LQMNSLKPED TAVYYCAAQR IFGAQPMDLS GDYEYWGQGT    120
QVTVSSAAAY PYDVPDYGSH HHHHH                                          145

SEQ ID NO: 595              moltype = AA  length = 150
FEATURE                     Location/Qualifiers
REGION                      1..150
                            note = Synthetic polymer
source                      1..150
                            mol_type = protein
                            organism = synthetic construct
SEQUENCE: 595
QVQLQESGGG LVQAGGSLRL SCATFGFTFD DYAIAWFRQA PGKEREGISC ISNTDSSTYY     60
ADSVKGRFTI SSDSAKNTVH LQMSSLKPED TAVYYCAADG NVWSPPICGS AGPPPGGMDY    120
WGKGTQVTVS SAAAYPYDVP DYGSHHHHHH                                     150

SEQ ID NO: 596              moltype = AA  length = 145
FEATURE                     Location/Qualifiers
REGION                      1..145
                            note = Synthetic polymer
source                      1..145
                            mol_type = protein
                            organism = synthetic construct
SEQUENCE: 596
QVQLQESGGG LVQAGGSLRL SCKASGGTFS GYIMGWFRQA PGKEREFVAA NTWSGGPTYY     60
```

```
-continued

SDSVKGRFTI SRDNAKNTVY LQMNTLKPED TAVYQCAARD YRGIKDLDLK GDYDYWGQGT    120
QVTVSSAAAY PYDVPDYGSH HHHHH                                         145

SEQ ID NO: 597          moltype = AA  length = 151
FEATURE                 Location/Qualifiers
REGION                  1..151
                        note = Synthetic polymer
source                  1..151
                        mol_type = protein
                        organism = synthetic construct
SEQUENCE: 597
QVQLQESGGG LVQAGDSLKL SCATSGRSFS SYTIAWFRQA PGKEREGISC ISSDGSTGYA    60
DSVRGRFTIS SDNAKNTVYL QMNSLKPEDT AVYYCAADFN VWSPPICGSI WYGPPPRGMD    120
YWGKGTQVTV SSAAAYPYDV PDYGSHHHHH H                                   151

SEQ ID NO: 598          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 598
QVQLQESGGG LVQAGGYLRL SCAASGFSSD DYTIGWFRQA PGKEREGISC YSSSDGSTGF    60
ADSVKGRFTI SSDNAKNTVY LQMNNLRPED TAVYYCAADS NVWSPPICGS RWYGPPPGGM    120
AYWGKGTQVT VSSAAAYPYD VPDYGSHHHH HH                                  152

SEQ ID NO: 599          moltype = AA  length = 151
FEATURE                 Location/Qualifiers
REGION                  1..151
                        note = Synthetic polymer
source                  1..151
                        mol_type = protein
                        organism = synthetic construct
SEQUENCE: 599
QVQLQESGGG LAQVGGSLRL SCTASGFTFD DYTIGWFRQA PGKEREGISC ISSDGSTGYA    60
DSVKGRFTIS SDNAKNTVYL QMNSLKPEDT AVYYCAADFN VWSPPICGSN WYGPPPGGMD    120
YWGKGTQVTV SSAAAYPYDV PDYGSHHHHH H                                   151

SEQ ID NO: 600          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 600
QVQLQESGGG LVQAGGSLRL SCAASGFSSD DYTIGWFRQA PGKEREGIGC IKSSDGTTGY    60
ADSVKGRFTI SSDNAKNTVY LQMNSLKPED TAVYYCAADF NVWSPPICGS IWYGPPPGGM    120
DYWGKGTQVT VSSAAAYPYD VPDYGSHHHH HH                                  152

SEQ ID NO: 601          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 601
QVQLQESGGG LAQAGGSLRL SCAASGFTFD QYTIAWFRQA PGKEREGVSC ISNTDSSTYY    60
ADSVKGRFTI SSDNAKNTVY LQMSSLKPED TAVYYCAADG NVWSPPICGS AGPPPGGMDY    120
WGKGTQVTVS SAAAYPYDVP DYGSHHHHHH                                     150

SEQ ID NO: 602          moltype = AA  length = 144
FEATURE                 Location/Qualifiers
REGION                  1..144
                        note = Synthetic polymer
source                  1..144
                        mol_type = protein
                        organism = synthetic construct
SEQUENCE: 602
QVQLQESGGG LVQAGGSLRL SCAASGRTFS SYAMAWFRQA PGKEREFVAA IAWSAGSTYY    60
ADSVKGRFAI SRDNAENTVY LQMNSLKPED TAVYYCAARI ITVATMRLDS DYDYWGQGTQ    120
VTVSSAAAYP YDVPDYGSHH HHHH                                           144

SEQ ID NO: 603          moltype = AA  length = 150
FEATURE                 Location/Qualifiers
REGION                  1..150
                        note = Synthetic polymer
```

```
source                          1..150
                                mol_type = protein
                                organism = synthetic construct
SEQUENCE: 603
QVQLQESGGG LVQAGGSLRL SCAASGFAFD GYAIGWFRQA PGKEREGVSC ISSKEGSTYY     60
ADSVKGRFTI SSDNAKNTVY LQMSSLKPED TAVYYCAADG NVWSPPICGS AGPPPGGMDY    120
WGKGTQVTVS SAAAYPYDVP DYGSHHHHHH                                    150

SEQ ID NO: 604                  moltype = AA   length = 152
FEATURE                         Location/Qualifiers
REGION                          1..152
                                note = Synthetic polymer
source                          1..152
                                mol_type = protein
                                organism = synthetic construct
SEQUENCE: 604
QVQLQESGGG LVQAGGSLRL SCAASGFSSD DYTIAWFRRA PGKEREGISC ISSSDGSTGY     60
ADSVKGRFTI TSDSAKNTVY LQMNSLKPED TAVYYCAADS NVWSPPICGR TWYGPPPGGM    120
DYWGKGTQVT VSSAAAYPYD VPDYGSHHHH HH                                 152

SEQ ID NO: 605                  moltype = AA   length = 152
FEATURE                         Location/Qualifiers
REGION                          1..152
                                note = Synthetic polymer
source                          1..152
                                mol_type = protein
                                organism = synthetic construct
SEQUENCE: 605
QVQLQESGGG LVQPGGSLRL SCAASGFSSD DYTIGWFRQA PGKEREGISC YSSRDGTTGY     60
ADSVKGRFTI SSDNAKNTVY LQMNSLKPED TAVYYCAADF NVWSPPICGS IWYGPPPGGM    120
AYWGQGTQVT VSSAAAYPYD VPDYGSHHHH HH                                 152

SEQ ID NO: 606                  moltype = AA   length = 151
FEATURE                         Location/Qualifiers
REGION                          1..151
                                note = Synthetic polymer
source                          1..151
                                mol_type = protein
                                organism = synthetic construct
SEQUENCE: 606
QVQLQESGGG LVQAGGSLRL SCAASGFTFD DYTIGWFRQA PGKEREGISC ISSDGSTGYA     60
DSVKGRFTIS SDNAKNTVYL QMNSLKPEDT AVYYCAADFN VWSPPICGSN WYGPPPGGMD    120
YWGKGTQVTV SSAAAYPYDV PDYGSHHHHH H                                  151

SEQ ID NO: 607                  moltype = AA   length = 152
FEATURE                         Location/Qualifiers
REGION                          1..152
                                note = Synthetic polymer
source                          1..152
                                mol_type = protein
                                organism = synthetic construct
SEQUENCE: 607
QVQLQESGGG LVQAGGSLRL SCAASGFSSD DYTIGWFRQA PGKEREGISC YSSSDGSTGY     60
ADSVKGRFTI SSDNAKNTVY LQMNSLKPED TAVYYCAADF NVWSPPICGS SWYGPPPGGM    120
DYWGKGTQVT VSSAAAYPYD VPDYGSHHHH HH                                 152

SEQ ID NO: 608                  moltype = AA   length = 152
FEATURE                         Location/Qualifiers
REGION                          1..152
                                note = Synthetic polymer
source                          1..152
                                mol_type = protein
                                organism = synthetic construct
SEQUENCE: 608
QVQLQESGGG LVQAGGSLRL SCAASGFSSD DYTIGWFRQA PGKEREGISC FSSSDGSTGF     60
ADSVKGRFTI SSDNATNTVY LEMNSLKPED TAVYYCAADF NVWSPPICGS RWYGPPPGGM    120
EYWGKGTQVT VSSAAAYPYD VPDYGSHHHH HH                                 152

SEQ ID NO: 609                  moltype = AA   length = 150
FEATURE                         Location/Qualifiers
REGION                          1..150
                                note = Synthetic polymer
source                          1..150
                                mol_type = protein
                                organism = synthetic construct
SEQUENCE: 609
QVQLQESGGG LVQAGGSLRL SCATFGFSFD DYAIAWFRQA PGKEREGISC ISNTDSSTFY     60
ADSVKGRFTI SSDNAKNTVH LQMSSLKPED TAVYYCAADG NVWSPPICGS AGPPPGGMDY    120
WGKGTQVTVS SAAAYPYDVP DYGSHHHHHH                                    150
```

```
SEQ ID NO: 610          moltype = AA   length = 152
FEATURE                 Location/Qualifiers
REGION                  1..152
                        note = Synthetic polymer
source                  1..152
                        mol_type = protein
                        organism = synthetic construct
SEQUENCE: 610
QVQLQESGGG LVQAGGSLRL SCAASGFSSD DYTIGWFRQA PGKEREGISC YSSSDGSTGF    60
ADSVKGRFTI SSDNAKNTVY LQMNSLRPED TAVYYCAADF NVWSPPICGS RWYGPPPGGM   120
AYWGKGTQVT VSSAAAYPYD VPDYGSHHHH HH                                 152

SEQ ID NO: 611          moltype = AA   length = 151
FEATURE                 Location/Qualifiers
REGION                  1..151
                        note = Synthetic polymer
source                  1..151
                        mol_type = protein
                        organism = synthetic construct
SEQUENCE: 611
QVQLQESGGG LVQVGGSLRL SCTISGFTGN DLAIGWFRQA PGKDQREGIS CISNTDSSTY    60
YADSVKGRFT ISSDNAKNTV HLQMSSLKPE DTAVYYCAAD GNVWSPPICG SAGPPPGGMD   120
YWGKGTQVTV SSAAAYPYDV PDYGSHHHHH H                                  151

SEQ ID NO: 612          moltype = AA   length = 152
FEATURE                 Location/Qualifiers
REGION                  1..152
                        note = Synthetic polymer
source                  1..152
                        mol_type = protein
                        organism = synthetic construct
SEQUENCE: 612
QVQLQESGGG LVQAGGSLRL SCAASGFSSD DYTIAWFRRA PGKEREGISC ISSSDGSTGY    60
ADSVKGRFTI SSDNAKNTVY LQMTSLKPED TAVYYCAADS NVWSPPICGK TWYGPPPGGM   120
DYWGKGTQVT VSSAAAYPYD VPDYGSHHHH HH                                 152

SEQ ID NO: 613          moltype = AA   length = 140
FEATURE                 Location/Qualifiers
REGION                  1..140
                        note = Synthetic polymer
source                  1..140
                        mol_type = protein
                        organism = synthetic construct
SEQUENCE: 613
QVQLQESGGG LVQAGDSLRL SCAGSEGTLS SYGIGWFRQA PGKEREFVGG INWSGDSTDY    60
ADSVKGRFTI SRDSAKNTVY LQMNSLKPED TAVYYCAAGE SGVWVGGLDY WGQGTQVTVS   120
SAAAYPYDVP DYGSHHHHHH                                               140

SEQ ID NO: 614          moltype = AA   length = 152
FEATURE                 Location/Qualifiers
REGION                  1..152
                        note = Synthetic polymer
source                  1..152
                        mol_type = protein
                        organism = synthetic construct
SEQUENCE: 614
QVQLQESGGG LVQAGGSLRL SCAASGFSSD DYTIAWFRRA PGKEREGISC FSSSDGSAGY    60
ADSVKGRFTV SSDNAKNTVY LQMNSLKPED TAVYYCAADS NVWSPPICGS TWYGPPPGGM   120
AYWGKGTQVT VSSAAAYPYD VPDYGSHHHH HH                                 152

SEQ ID NO: 615          moltype = AA   length = 150
FEATURE                 Location/Qualifiers
REGION                  1..150
                        note = Synthetic polymer
source                  1..150
                        mol_type = protein
                        organism = synthetic construct
SEQUENCE: 615
QVQLQESGGG LVQAGGSLRL SCATSGFTFD DYAIAWFRQA PGKEREGVSC ISNTDSSTYY    60
ADSVKGRFTI SSDNAKNTVY LQMSSLKPED TAVYYCAADG NVWSPPICGS AGPPPGGMDY   120
WGKGTQVTVS SAAAYPYDVP DYGSHHHHHH                                    150

SEQ ID NO: 616          moltype = AA   length = 152
FEATURE                 Location/Qualifiers
REGION                  1..152
                        note = Synthetic polymer
source                  1..152
                        mol_type = protein
```

```
                       organism = synthetic construct
SEQUENCE: 616
QVQLQESGGG LVQAGGSLRL SCEVSGLSSD DYTIGWFRQA PGKEREGFSC FSTRDGNAGY    60
ADSVKGRFTI SSDNAKNTVY LQMNNLKPED TAVYYCAADF NVWSPPICGS RWYGPPPGGM   120
DYWGKGTQVT VSSAAAYPYD VPDYGSHHHH HH                                 152

SEQ ID NO: 617         moltype = AA   length = 152
FEATURE                Location/Qualifiers
REGION                 1..152
                       note = Synthetic polymer
source                 1..152
                       mol_type = protein
                       organism = synthetic construct
SEQUENCE: 617
QVQLQESGGG LVQAGGSLRL SCEVSGLSSD DYTIGWFRQA PGKKREGFSC FSSRDGSTGY    60
ADSVKGRFTI SSDNAKNTVY LQMNSLKPED TAVYYCAADF NVWSPPICGS RWYGPPPGGM   120
DYWGKGTQVT VSSAAAYPYD VPDYGSHHHH HH                                 152

SEQ ID NO: 618         moltype = AA   length = 152
FEATURE                Location/Qualifiers
REGION                 1..152
                       note = Synthetic polymer
source                 1..152
                       mol_type = protein
                       organism = synthetic construct
SEQUENCE: 618
QVQLQESGGG LVQAGGSLRL SCAASGFSSD DYTIGWFRQA PGKEREGFSC FSSRDGSTGY    60
ADSVKGRFTI SSDNAKNTVY LQMNSLKPED TAVYYCAADF NVWSPPICGS RWYGPPPGGM   120
DYWGKGTQVT VSSAAAYPYD VPDYGSHHHH HH                                 152

SEQ ID NO: 619         moltype = AA   length = 151
FEATURE                Location/Qualifiers
REGION                 1..151
                       note = Synthetic polymer
source                 1..151
                       mol_type = protein
                       organism = synthetic construct
SEQUENCE: 619
QVQLQESGGG LVQAGGSLRL SCAASGFSFD DYTIGWFRQV PGKEREGISC ISSDGSTGYA    60
DSVKGRFTIS SDNAKNTVYL QINSLKPEDT AVYYCAADFN VWSPPICGSI WYGPPPGGMD   120
YWGKGTQVTV SSAAAYPYDV PDYGSHHHHH H                                  151

SEQ ID NO: 620         moltype = AA   length = 150
FEATURE                Location/Qualifiers
REGION                 1..150
                       note = Synthetic polymer
source                 1..150
                       mol_type = protein
                       organism = synthetic construct
SEQUENCE: 620
QVQLQESGGG LVQAGGSLRL SCATFGFTFD DYAIAWFRQA PGKEREGISC ISNTDSSTYY    60
ADSVKGRFTI SSDNAKNTVH LQMSSLKPED TAVYYCAADG NVWSPPICGS AGPPPGGMDY   120
WGKGTQVTVS SAAAYPYDVP DYGSHHHHHH                                    150

SEQ ID NO: 621         moltype = AA   length = 150
FEATURE                Location/Qualifiers
REGION                 1..150
                       note = Synthetic polymer
SITE                   19
                       note = misc_feature - Xaa can be any naturally occurring
                        amino acid
source                 1..150
                       mol_type = protein
                       organism = synthetic construct
SEQUENCE: 621
QVQLQESGGG LVQAGGSLXL SCAASGFTFD DYAIGWFRQA PGKEREGVSC ISSPDGSTYY    60
ADSVKGRFTI SSDNAKNTVY LQMNSLKPED TAVYYCAADF NVWSPPICGS VGPPPGGMDY   120
WGKGTQVTVS SAAAYPYDVP DYGSHHHHHH                                    150

SEQ ID NO: 622         moltype = AA   length = 152
FEATURE                Location/Qualifiers
REGION                 1..152
                       note = Synthetic polymer
source                 1..152
                       mol_type = protein
                       organism = synthetic construct
SEQUENCE: 622
QVQLQESGGG LVQAGASLRL SCKASGFTFG DYTIGWFRQA PGKEREGISC YSSSDGNTGY    60
ADSVKGRFTI SSDNAKNTVY LQMNSLRPED TAVYYCAADF NVWSPPICGS SWYGPPPGGM   120
```

```
AYWGKGTQVT VSSAAAYPYD VPDYGSHHHH HH                                       152

SEQ ID NO: 623          moltype = AA   length = 140
FEATURE                 Location/Qualifiers
REGION                  1..140
                        note = Synthetic polymer
source                  1..140
                        mol_type = protein
                        organism = synthetic construct
SEQUENCE: 623
QVQLQESGGG LVQAGDSLRL SCAGSEGTFS SYGIGWFRQA PGKEREFVGG INWSGDSTDY          60
ADSVKGRFTI SRDNAKNTVY LQMNSLKPED TAVYYCAAGE SGVWVGGLDY WGQGTQVTVS         120
SAAAYPYDVP DYGSHHHHHH                                                     140

SEQ ID NO: 624          moltype = AA   length = 152
FEATURE                 Location/Qualifiers
REGION                  1..152
                        note = Synthetic polymer
source                  1..152
                        mol_type = protein
                        organism = synthetic construct
SEQUENCE: 624
QVQLQESGGG LVQAGGSLRL SCAASGFSSD DYTIGWFRQA PGKEREGISC FSSSDGSTGF          60
ADSVKGRFTI SSDNATNTVY LQMNSLKPED TAVYYCAADF NVWSPPICGS SWYGPPPGGM         120
EYWGKGTQVT VSSAAAYPYD VPDYGSHHHH HH                                       152

SEQ ID NO: 625          moltype = AA   length = 150
FEATURE                 Location/Qualifiers
REGION                  1..150
                        note = Synthetic polymer
source                  1..150
                        mol_type = protein
                        organism = synthetic construct
SEQUENCE: 625
QVQLQESGGG LVQAGDSLRL SCTASGVSIG DYNIGWFRQA PGKEREGVSC ISSGDGTTYY          60
TDSVKGRFTI STDNAKNTVY LQMNSLKPED TAVYYCAADG NVWSPPICGS AGPPPGGMDY         120
WGKGTQVTVS SAAAYPYDVP DYGSHHHHHH                                          150

SEQ ID NO: 626          moltype = AA   length = 152
FEATURE                 Location/Qualifiers
REGION                  1..152
                        note = Synthetic polymer
source                  1..152
                        mol_type = protein
                        organism = synthetic construct
SEQUENCE: 626
QVQLQESGGG LVQAGGSLRL SCAASGFTFD DYTIAWFRQA PGGKEREGIS CISSDGSTGY          60
ADSVKGRFTI SSDNAKNMVY LQMNSLKPED TALYYCAADF NVWSPPICSS NWYGPPPRGM         120
DYWGKGTQVT VSSAAAYPYD VPDYGSHHHH HH                                       152

SEQ ID NO: 627          moltype = AA   length = 151
FEATURE                 Location/Qualifiers
REGION                  1..151
                        note = Synthetic polymer
source                  1..151
                        mol_type = protein
                        organism = synthetic construct
SEQUENCE: 627
QVQLQESGGG LVQAGGSLRL SCAASGFTFD DYTIAWFRQA PGKEREGISC ISSDGSTGYA          60
DSVRGRFTIS SDNAKNTVYL QMNSLKPEDT AVYYCAADFN VWSPPICGSI WYGPPPRGMD         120
YWGKGTQVTV SSAAAYPYDV PDYGSHHHHH H                                        151

SEQ ID NO: 628          moltype = AA   length = 118
FEATURE                 Location/Qualifiers
REGION                  1..118
                        note = Synthetic polymer
source                  1..118
                        mol_type = protein
                        organism = synthetic construct
SEQUENCE: 628
EVQLVESGGG LVQPGGSLRL SCAASGFNIK DTYIHWVRQA PGKGLEWVAR IDPANDNTLY          60
ASKFQGRATI SADTSKNTAY LQMNSLRAED TAVYYCGRGY GYYVFDHWGQ GTLVTVSS           118

SEQ ID NO: 629          moltype = AA   length = 118
FEATURE                 Location/Qualifiers
REGION                  1..118
                        note = Synthetic polymer
source                  1..118
                        mol_type = protein
```

```
                        organism = synthetic construct
SEQUENCE: 629
QVQLVQSGAE VKKPGATVKI SCKVSGFNIK DTYIHWVQQA PGKGLEWMGR IDPANDNTLY     60
ASKFQGRVTI TADTSTDTAY MELSSLRSED TAVYYCARGY GYYVFDHWGQ GTLVTVSS      118

SEQ ID NO: 630          moltype = AA   length = 107
FEATURE                 Location/Qualifiers
REGION                  1..107
                        note = Synthetic polymer
source                  1..107
                        mol_type = protein
                        organism = synthetic construct
SEQUENCE: 630
DVQITQSPSS LSASVGDRVT ITCRTSRSIS QYLAWYQQKP GKVPKLLIYS GSTLQSGVPS     60
RFSGSGSGTD FTLTISSLQP EDVATYYCQQ HNENPLTFGG GTKVEIK                  107

SEQ ID NO: 631          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 631
GSISSINVMG                                                            10

SEQ ID NO: 632          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 632
GSFSSINVMG                                                            10

SEQ ID NO: 633          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 633
GSISSINIMG                                                            10

SEQ ID NO: 634          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 634
GSISSINIMG                                                            10

SEQ ID NO: 635          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 635
VSIFSINAMG                                                            10

SEQ ID NO: 636          moltype = AA   length = 10
FEATURE                 Location/Qualifiers
REGION                  1..10
                        note = Synthetic polymer
source                  1..10
                        mol_type = protein
                        organism = synthetic construct
SEQUENCE: 636
GSIFSLNAMG                                                            10

SEQ ID NO: 637          moltype = AA   length = 10
FEATURE                 Location/Qualifiers
REGION                  1..10
```

```
                           note = Synthetic polymer
source                     1..10
                           mol_type = protein
                           organism = synthetic construct
SEQUENCE: 637
GRTISNYDMA                                                              10

SEQ ID NO: 638             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 638
GRTFTTSLMQ                                                              10

SEQ ID NO: 639             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 639
ERNLRIYDMA                                                              10

SEQ ID NO: 640             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 640
ERNLRSYDMA                                                              10

SEQ ID NO: 641             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 641
GLTFSNYHMG                                                              10

SEQ ID NO: 642             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 642
GLTFSSYHMG                                                              10

SEQ ID NO: 643             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 643
GLTFSRYHMG                                                              10

SEQ ID NO: 644             moltype = AA  length = 10
FEATURE                    Location/Qualifiers
REGION                     1..10
                           note = Synthetic polymer
source                     1..10
                           mol_type = protein
                           organism = synthetic construct
SEQUENCE: 644
GLTLSSYYIA                                                              10

SEQ ID NO: 645             moltype = AA  length = 10
FEATURE                    Location/Qualifiers
```

```
REGION                    1..10
                          note = Synthetic polymer
source                    1..10
                          mol_type = protein
                          organism = synthetic construct
SEQUENCE: 645
GLTFSSYYTG                                                              10

SEQ ID NO: 646            moltype = AA  length = 10
FEATURE                   Location/Qualifiers
REGION                    1..10
                          note = Synthetic polymer
source                    1..10
                          mol_type = protein
                          organism = synthetic construct
SEQUENCE: 646
GLTLSSYHMG                                                              10

SEQ ID NO: 647            moltype = AA  length = 10
FEATURE                   Location/Qualifiers
REGION                    1..10
                          note = Synthetic polymer
source                    1..10
                          mol_type = protein
                          organism = synthetic construct
SEQUENCE: 647
GRTSSPYVTG                                                              10

SEQ ID NO: 648            moltype = AA  length = 10
FEATURE                   Location/Qualifiers
REGION                    1..10
                          note = Synthetic polymer
source                    1..10
                          mol_type = protein
                          organism = synthetic construct
SEQUENCE: 648
GFTFSGYVMS                                                              10

SEQ ID NO: 649            moltype = AA  length = 10
FEATURE                   Location/Qualifiers
REGION                    1..10
                          note = Synthetic polymer
source                    1..10
                          mol_type = protein
                          organism = synthetic construct
SEQUENCE: 649
GFTFSGYVMT                                                              10

SEQ ID NO: 650            moltype = AA  length = 10
FEATURE                   Location/Qualifiers
REGION                    1..10
                          note = Synthetic polymer
source                    1..10
                          mol_type = protein
                          organism = synthetic construct
SEQUENCE: 650
GFTFSGYLMS                                                              10

SEQ ID NO: 651            moltype = AA  length = 16
FEATURE                   Location/Qualifiers
REGION                    1..16
                          note = Synthetic polymer
source                    1..16
                          mol_type = protein
                          organism = synthetic construct
SEQUENCE: 651
RITNLGLPNY ADWLKD                                                       16

SEQ ID NO: 652            moltype = AA  length = 16
FEATURE                   Location/Qualifiers
REGION                    1..16
                          note = Synthetic polymer
source                    1..16
                          mol_type = protein
                          organism = synthetic construct
SEQUENCE: 652
RITNLGLPNY ADSVTG                                                       16

SEQ ID NO: 653            moltype = AA  length = 16
```

```
FEATURE                 Location/Qualifiers
REGION                  1..16
                        note = Synthetic polymer
source                  1..16
                        mol_type = protein
                        organism = synthetic construct
SEQUENCE: 653
RITNIGLPNY ADSVKG                                                      16

SEQ ID NO: 654          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 654
RITNLGLPNY ADSVEG                                                      16

SEQ ID NO: 655          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 655
AITSGGRVVY SDSVKG                                                      16

SEQ ID NO: 656          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 656
AITSGGRTAY ADSVKG                                                      16

SEQ ID NO: 657          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 657
HITSDGRIVY ADPVKG                                                      16

SEQ ID NO: 658          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 658
RISGSGDRTD YADSVKG                                                     17

SEQ ID NO: 659          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 659
SITWSTGNTH YADSVKG                                                     17

SEQ ID NO: 660          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 660
VISSSGDSTH YSDFVKG                                                     17
```

| | | |
|---|---|---|
| SEQ ID NO: 661<br>FEATURE<br>REGION<br><br>source<br><br><br><br>SEQUENCE: 661<br>VITSSGDSTH YSDFVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 662<br>FEATURE<br>REGION<br><br>source<br><br><br><br>SEQUENCE: 662<br>QITWSDASIY YAGSVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 663<br>FEATURE<br>REGION<br><br>source<br><br><br><br>SEQUENCE: 663<br>QITWSDTSIY YAGSVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 664<br>FEATURE<br>REGION<br><br>source<br><br><br><br>SEQUENCE: 664<br>QITWSDGTTY YPGSVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 665<br>FEATURE<br>REGION<br><br>source<br><br><br><br>SEQUENCE: 665<br>QIRWSDDSTY YPGSVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 666<br>FEATURE<br>REGION<br><br>source<br><br><br><br>SEQUENCE: 666<br>QISWSDDSTY YADSVKG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |
| SEQ ID NO: 667<br>FEATURE<br>REGION<br><br>source<br><br><br><br>SEQUENCE: 667<br>TVSWGGVTYY ADSVKG | moltype = AA  length = 16<br>Location/Qualifiers<br>1..16<br>note = Synthetic polymer<br>1..16<br>mol_type = protein<br>organism = synthetic construct | <br><br><br><br><br><br><br><br><br>16 |
| SEQ ID NO: 668<br>FEATURE<br>REGION<br><br>source<br><br><br><br>SEQUENCE: 668<br>SIGSGGGYPS YTDSVEG | moltype = AA  length = 17<br>Location/Qualifiers<br>1..17<br>note = Synthetic polymer<br>1..17<br>mol_type = protein<br>organism = synthetic construct | <br><br><br><br><br><br><br><br><br>17 |

```
SEQ ID NO: 669          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 669
SIGSGGGYPS YTGSVEG                                                          17

SEQ ID NO: 670          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 670
HIGSGGGYPS YTDSVQG                                                          17

SEQ ID NO: 671          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 671
HIGSGGGHAT YTDSVEG                                                          17

SEQ ID NO: 672          moltype = AA   length = 17
FEATURE                 Location/Qualifiers
REGION                  1..17
                        note = Synthetic polymer
source                  1..17
                        mol_type = protein
                        organism = synthetic construct
SEQUENCE: 672
TIGSGGGITS YADSVKG                                                          17

SEQ ID NO: 673          moltype = AA   length = 7
FEATURE                 Location/Qualifiers
REGION                  1..7
                        note = Synthetic polymer
source                  1..7
                        mol_type = protein
                        organism = synthetic construct
SEQUENCE: 673
VALSAEY                                                                      7

SEQ ID NO: 674          moltype = AA   length = 7
FEATURE                 Location/Qualifiers
REGION                  1..7
                        note = Synthetic polymer
source                  1..7
                        mol_type = protein
                        organism = synthetic construct
SEQUENCE: 674
VALKAEY                                                                      7

SEQ ID NO: 675          moltype = AA   length = 7
FEATURE                 Location/Qualifiers
REGION                  1..7
                        note = Synthetic polymer
source                  1..7
                        mol_type = protein
                        organism = synthetic construct
SEQUENCE: 675
VGLKAEY                                                                      7

SEQ ID NO: 676          moltype = AA   length = 13
FEATURE                 Location/Qualifiers
REGION                  1..13
                        note = Synthetic polymer
source                  1..13
                        mol_type = protein
                        organism = synthetic construct
SEQUENCE: 676
```

KTKSAVLFGG MDY                                                                    13

SEQ ID NO: 677         moltype = AA   length = 7
FEATURE                Location/Qualifiers
REGION                 1..7
                       note = Synthetic polymer
source                 1..7
                       mol_type = protein
                       organism = synthetic construct
SEQUENCE: 677
YIRGEDY                                                                            7

SEQ ID NO: 678         moltype = AA   length = 7
FEATURE                Location/Qualifiers
REGION                 1..7
                       note = Synthetic polymer
source                 1..7
                       mol_type = protein
                       organism = synthetic construct
SEQUENCE: 678
KHYASNY                                                                            7

SEQ ID NO: 679         moltype = AA   length = 8
FEATURE                Location/Qualifiers
REGION                 1..8
                       note = Synthetic polymer
source                 1..8
                       mol_type = protein
                       organism = synthetic construct
SEQUENCE: 679
QDFGSPSF                                                                           8

SEQ ID NO: 680         moltype = AA   length = 8
FEATURE                Location/Qualifiers
REGION                 1..8
                       note = Synthetic polymer
source                 1..8
                       mol_type = protein
                       organism = synthetic construct
SEQUENCE: 680
QDFRSPDF                                                                           8

SEQ ID NO: 681         moltype = AA   length = 8
FEATURE                Location/Qualifiers
REGION                 1..8
                       note = Synthetic polymer
source                 1..8
                       mol_type = protein
                       organism = synthetic construct
SEQUENCE: 681
QIFGSPNF                                                                           8

SEQ ID NO: 682         moltype = AA   length = 7
FEATURE                Location/Qualifiers
REGION                 1..7
                       note = Synthetic polymer
source                 1..7
                       mol_type = protein
                       organism = synthetic construct
SEQUENCE: 682
LAIHGDY                                                                            7

SEQ ID NO: 683         moltype = AA   length = 7
FEATURE                Location/Qualifiers
REGION                 1..7
                       note = Synthetic polymer
source                 1..7
                       mol_type = protein
                       organism = synthetic construct
SEQUENCE: 683
NQIRQWP                                                                            7

SEQ ID NO: 684         moltype = AA   length = 7
FEATURE                Location/Qualifiers
REGION                 1..7
                       note = Synthetic polymer
source                 1..7
                       mol_type = protein
                       organism = synthetic construct -continued

```
SEQUENCE: 684
NSIRQWP                                                                      7

SEQ ID NO: 685         moltype = AA  length = 7
FEATURE                Location/Qualifiers
REGION                 1..7
                       note = Synthetic polymer
source                 1..7
                       mol_type = protein
                       organism = synthetic construct
SEQUENCE: 685
NAIRQWP                                                                      7

SEQ ID NO: 686         moltype = AA  length = 8
FEATURE                Location/Qualifiers
REGION                 1..8
                       note = Synthetic polymer
source                 1..8
                       mol_type = protein
                       organism = synthetic construct
SEQUENCE: 686
RKVGGPDY                                                                     8

SEQ ID NO: 687         moltype = AA  length = 7
FEATURE                Location/Qualifiers
REGION                 1..7
                       note = Synthetic polymer
source                 1..7
                       mol_type = protein
                       organism = synthetic construct
SEQUENCE: 687
NTFGNVY                                                                      7

SEQ ID NO: 688         moltype = AA  length = 115
FEATURE                Location/Qualifiers
REGION                 1..115
                       note = Synthetic polymer
source                 1..115
                       mol_type = protein
                       organism = synthetic construct
SEQUENCE: 688
QVQLVESGGG LVHPGGSLRL SCAASGSISS INVMGWYRQA PGKERELVAR ITNLGLPNYA            60
DWLKDRFTIS RDNAKNTVYL QMNSLKPEDT AVYYCYLVAL SAEYWGQGTQ VTVSS                115

SEQ ID NO: 689         moltype = AA  length = 115
FEATURE                Location/Qualifiers
REGION                 1..115
                       note = Synthetic polymer
source                 1..115
                       mol_type = protein
                       organism = synthetic construct
SEQUENCE: 689
QVQLVESGGG LVHPGGSLRL SCAASGSFSS INVMGWYRQA PGKERELVAR ITNLGLPNYA            60
DSVTGRFTIS RDNAKNTVYL QMNSLKPEDT AVYYCYLVAL KAEYWGQGTQ VTVSS                115

SEQ ID NO: 690         moltype = AA  length = 115
FEATURE                Location/Qualifiers
REGION                 1..115
                       note = Synthetic polymer
source                 1..115
                       mol_type = protein
                       organism = synthetic construct
SEQUENCE: 690
QVQLVESGGG LVHRGGSLRL SCAASGSISS INIMGWYRQA PGKERELVAR ITNIGLPNYA            60
DSVKGRFTIS RDNAKSTVYL QMNSLNAEDT AVYYCYLVAL KAEYWGQGTQ VTVSS                115

SEQ ID NO: 691         moltype = AA  length = 115
FEATURE                Location/Qualifiers
REGION                 1..115
                       note = Synthetic polymer
source                 1..115
                       mol_type = protein
                       organism = synthetic construct
SEQUENCE: 691
QVQLVESGGG LVQPGGSLRL SCAASGSISS INVMGWYRQA PGKERELVAR ITNLGLPNYA            60
DSVEGRFTIS RDKDENTVYL EMNTLKPEDT AVYYCYLVGL KAEYWGQGTQ VTVSS                115

SEQ ID NO: 692         moltype = AA  length = 121
FEATURE                Location/Qualifiers
```

```
REGION                   1..121
                         note = Synthetic polymer
source                   1..121
                         mol_type = protein
                         organism = synthetic construct
SEQUENCE: 692
QVQLVESGGG LVQPGGSLRL SCAASGSSDS INAMGWYRQA PGKERELVAA ITSGGRVVYS    60
DSVKGRGTIS RDNAKNTVYL QIASLKPEDT AVYYCNVKTK SAVLFGGMDY WGKGTQVTVS   120
S                                                                  121

SEQ ID NO: 693           moltype = AA   length = 115
FEATURE                  Location/Qualifiers
REGION                   1..115
                         note = Synthetic polymer
source                   1..115
                         mol_type = protein
                         organism = synthetic construct
SEQUENCE: 693
QVQLVESGGG LVQPGGSLRL SCAASVSIFS INAMGWYRQA PGKERELVAA ITSGGRTAYA    60
DSVKGRFTIS RDNSKNTVYL QMDSLKPEDT DVYYCKAYIR GEDYWGKGTQ VTVSS        115

SEQ ID NO: 694           moltype = AA   length = 115
FEATURE                  Location/Qualifiers
REGION                   1..115
                         note = Synthetic polymer
source                   1..115
                         mol_type = protein
                         organism = synthetic construct
SEQUENCE: 694
DVQLVESGGG LVQPGGSLRL SCAASGSIFS LNAMGWYRQA PGKERELVAH ITSDGRIVYA    60
DPVKGRFTIS RVDGKNMVTL QMNSLKPEDT AVYYCNAKHY ASNYWGQGTQ VTVSS        115

SEQ ID NO: 695           moltype = AA   length = 117
FEATURE                  Location/Qualifiers
REGION                   1..117
                         note = Synthetic polymer
source                   1..117
                         mol_type = protein
                         organism = synthetic construct
SEQUENCE: 695
QVQLVESGGG SVQAGGSLRL SCAASGRTIS NYDMAWSRQA PGKEREFVAR ISGSGDRTDY    60
ADSVKGRFTI SRDNAKNTVY LQMNSLKPED TAIYYCQIQD FGSPSFSGQG TQVTVSS      117

SEQ ID NO: 696           moltype = AA   length = 117
FEATURE                  Location/Qualifiers
REGION                   1..117
                         note = Synthetic polymer
source                   1..117
                         mol_type = protein
                         organism = synthetic construct
SEQUENCE: 696
DVQLVESGGG SVQAGGSLRL SCAASGRTIS NYDMAWSRQA PGKEREFVAR ISGSGDRTDY    60
ADSVKGRFTI SRDNAKNTVY LQMNSLKPED TAIYYCQIQD FRSPDFWSQG TQVTVSS      117

SEQ ID NO: 697           moltype = AA   length = 117
FEATURE                  Location/Qualifiers
REGION                   1..117
                         note = Synthetic polymer
source                   1..117
                         mol_type = protein
                         organism = synthetic construct
SEQUENCE: 697
QVQLVESGGE SVQAGGSLRL SCAASGRTIS NYDMAWSRQA PGKEREFVAR ISGSGDRTDY    60
ADSVKGRFTI SRDNAKNTVY LQMNSLKPED TAIYNCQTQI FGSPNFSGQG TQVTVSS      117

SEQ ID NO: 698           moltype = AA   length = 116
FEATURE                  Location/Qualifiers
REGION                   1..116
                         note = Synthetic polymer
source                   1..116
                         mol_type = protein
                         organism = synthetic construct
SEQUENCE: 698
QVQLVESGGG LVQAGDSLRL SCAASGRTFT TSLMQWHRQA PGKEREFVAS ITWSTGNTHY    60
ADSVKGRFTI SRDNARNTVY LQMNSLKPED TAIYTCRVLA IHGDYWGQGT QVTVSS       116

SEQ ID NO: 699           moltype = AA   length = 116
FEATURE                  Location/Qualifiers
REGION                   1..116
```

```
                            note = Synthetic polymer
source                      1..116
                            mol_type = protein
                            organism = synthetic construct
SEQUENCE: 699
DVQLVESGGG LVQAGDSLRL SCAASERNLR IYDMAWYRQA PGKEREYVAV ISSSGDSTHY    60
SDFVKGRFTI SRDNAKNTVS LQMDSLKPED TAFYYCNVNQ IRQWPWGQGT QVTVSS       116

SEQ ID NO: 700              moltype = AA  length = 116
FEATURE                     Location/Qualifiers
REGION                      1..116
                            note = Synthetic polymer
source                      1..116
                            mol_type = protein
                            organism = synthetic construct
SEQUENCE: 700
QVQLVESGGG LVQAGDSLRL SCAASERNLR IYDMAWYRQA PGKEREYVAV ISSSGDSTHY    60
SDFVKGRFTI SRDNAKNTVS LQMDSLKPED TAFYYCNVNS IRQWPWGQGT QVTVSS       116

SEQ ID NO: 701              moltype = AA  length = 116
FEATURE                     Location/Qualifiers
REGION                      1..116
                            note = Synthetic polymer
source                      1..116
                            mol_type = protein
                            organism = synthetic construct
SEQUENCE: 701
QVQLVESGGG LVQAGDSLRL SCTASERNLR SYDMAWWRQA PGKEREYVAV ITSSGDSTHY    60
SDFVKGRFTI SRDNAKNTVS LQMDSLKPED TASYYCNVNA IRQWPWGQGT QVTVSS       116

SEQ ID NO: 702              moltype = AA  length = 117
FEATURE                     Location/Qualifiers
REGION                      1..117
                            note = Synthetic polymer
source                      1..117
                            mol_type = protein
                            organism = synthetic construct
SEQUENCE: 702
DVQLVESGGG SVQAGGSLRL SCAISGLTFS NYHMGWYRQA PGREREFVAQ ITWSDASIYY    60
AGSVKGRFTI SRDNVKNIVY LQIDNLKPED TAIYYCDARK VGGPDYWGQG TQVTVSS      117

SEQ ID NO: 703              moltype = AA  length = 117
FEATURE                     Location/Qualifiers
REGION                      1..117
                            note = Synthetic polymer
source                      1..117
                            mol_type = protein
                            organism = synthetic construct
SEQUENCE: 703
QVQLVESGGG LVQAGGSLTL SCAISGLTFS SYHMGWYRQA PGREREFVAQ ITWSDTSIYY    60
AGSVKGRFTI SRDNVKNIVY LQIDNLKPED TAIYYCDARK VGGPDYWGQG TQVTVSS      117

SEQ ID NO: 704              moltype = AA  length = 117
FEATURE                     Location/Qualifiers
REGION                      1..117
                            note = Synthetic polymer
source                      1..117
                            mol_type = protein
                            organism = synthetic construct
SEQUENCE: 704
DVQLVESGGG LVQAGGSLRL SCAISGLTFS RYHMGWYRQA PGREREFVAQ ITWSDGTTYY    60
PGSVKGRFTI SRDNARNTVY LQIDNLKPED TAIYYCDARK VGGPDYWGQG TQVTVSS      117

SEQ ID NO: 705              moltype = AA  length = 117
FEATURE                     Location/Qualifiers
REGION                      1..117
                            note = Synthetic polymer
source                      1..117
                            mol_type = protein
                            organism = synthetic construct
SEQUENCE: 705
QVQLVESGGG LVQAGGSLRL SCATSGLTLS SYYIAWYRQA PGREREFVAQ IRWSDDSTYY    60
PGSVKGRFTI SRDNARNTVY LRMDNLKPED TARYYCDARK VGGPDYWGQG TQVTVSS      117

SEQ ID NO: 706              moltype = AA  length = 117
FEATURE                     Location/Qualifiers
REGION                      1..117
                            note = Synthetic polymer
source                      1..117
```

```
                            mol_type = protein
                            organism = synthetic construct
SEQUENCE: 706
DVQLVESGGG LVQAGGSLRL SCATSGLTFS SYYTGWYRQA PGREREFVAQ ISWSDDSTYY    60
ADSVKGRFTI SRDNARNTVY LQMNNLKPGD TAIYYCDARK VGGPDYWGQG TQVTVSS      117

SEQ ID NO: 707              moltype = AA   length = 117
FEATURE                     Location/Qualifiers
REGION                      1..117
                            note = Synthetic polymer
source                      1..117
                            mol_type = protein
                            organism = synthetic construct
SEQUENCE: 707
DVQLVESGGG LVQAGGSLRL SCATSGLTLS SYHMGWYRQA PGREREFVAQ ISWSDDSTYY    60
ADSVKGRFTI SRDNARNTVY LQMNNLKPED TAIYYCDARK VGGPDYWGQG TQVTVSS      117

SEQ ID NO: 708              moltype = AA   length = 115
FEATURE                     Location/Qualifiers
REGION                      1..115
                            note = Synthetic polymer
source                      1..115
                            mol_type = protein
                            organism = synthetic construct
SEQUENCE: 708
DVQLVESGGG LVQAGGSLRL SCAASGRTSS PYVTGWYRQT PGKEREPVAT VSWGGVTYYA    60
DSVKGRFTIS RDNAKNTVYL QMNALKPEDT AIYYCNVNTF GNVYWGQGTQ VTVSS        115

SEQ ID NO: 709              moltype = AA   length = 112
FEATURE                     Location/Qualifiers
REGION                      1..112
                            note = Synthetic polymer
source                      1..112
                            mol_type = protein
                            organism = synthetic construct
SEQUENCE: 709
QVQLVESGGG LVQPGGSLRL SCAASGFTFS GYVMSWVRQA PGKGLEWVAS IGSGGGYPSY    60
TDSVEGRFTI SRDNAKNTLY LLMDNLKPDD TAVYYCEMLG RRGQGTQVTV SS           112

SEQ ID NO: 710              moltype = AA   length = 112
FEATURE                     Location/Qualifiers
REGION                      1..112
                            note = Synthetic polymer
source                      1..112
                            mol_type = protein
                            organism = synthetic construct
SEQUENCE: 710
QVQLVESGGG LVQPGGSLRL SCAASGFTFS GYVMSWVRQA PGKGLEWVAS IGSGGGYPSY    60
TDSVEGRFTI SRDNAKNTLY LQMNNLKPDD TAVYYCEMLG RRGQGTQVTV SS           112

SEQ ID NO: 711              moltype = AA   length = 112
FEATURE                     Location/Qualifiers
REGION                      1..112
                            note = Synthetic polymer
source                      1..112
                            mol_type = protein
                            organism = synthetic construct
SEQUENCE: 711
QVQLVESGGG LVQPGGSLRL SCAASGFTFS GYVMSWVRQA PGKGLEWVAS IGSGGGYPSY    60
TGSVEGRFTI SRDNAKNTLY LLMNNLKPDD TAVYYCEMLG RRGQGTQVTV SS           112

SEQ ID NO: 712              moltype = AA   length = 112
FEATURE                     Location/Qualifiers
REGION                      1..112
                            note = Synthetic polymer
source                      1..112
                            mol_type = protein
                            organism = synthetic construct
SEQUENCE: 712
QVQLVESGGG LVQPGGSLRL SCAASGFTFS GYVMSWVRQA PGKGLEWVAH IGSGGGYPSY    60
TDSVQGRFTI SRDNAKNTLY LQMNNLKPED TAVYYCEMLG RRGQGTQVTV SS           112

SEQ ID NO: 713              moltype = AA   length = 112
FEATURE                     Location/Qualifiers
REGION                      1..112
                            note = Synthetic polymer
source                      1..112
                            mol_type = protein
                            organism = synthetic construct
```

-continued

```
SEQUENCE: 713
QVQLVESGGG LVQPGGSLRL SCAASGFTFS GYVMTWVRQA PGKGLEWVAH IGSGGGHATY    60
TDSVEGRFTI SRDNAKNTLY LQMNNLKAED TAVYYCEFLG RRGQGTQVTV SS           112

SEQ ID NO: 714          moltype = AA  length = 112
FEATURE                 Location/Qualifiers
REGION                  1..112
                        note = Synthetic polymer
source                  1..112
                        mol_type = protein
                        organism = synthetic construct
SEQUENCE: 714
QVQLVESGGG LVQPGGSLRL SCAASGFTFS GYLMSWVRQA PGKGLEWVAT IGSGGGITSY    60
ADSVKGRFTI SRDNAKNTLY LQMNNLKHED TAVYYCETVI KRGQGTQVTV SS           112

SEQ ID NO: 715          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 715
GRISSINSMG                                                           10

SEQ ID NO: 716          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 716
GSITSINAMG                                                           10

SEQ ID NO: 717          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 717
GRFFRVNAMG                                                           10

SEQ ID NO: 718          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 718
GSSDSINAMG                                                           10

SEQ ID NO: 719          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 719
GSVFSINAWG                                                           10

SEQ ID NO: 720          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 720
GSILSINSMG                                                           10

SEQ ID NO: 721          moltype = AA  length = 10
FEATURE                 Location/Qualifiers
REGION                  1..10
                        note = Synthetic polymer
```

```
source                   1..10
                         mol_type = protein
                         organism = synthetic construct
SEQUENCE: 721
VSISSINSMG                                                                        10

SEQ ID NO: 722           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 722
GRVFSINAMG                                                                        10

SEQ ID NO: 723           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 723
VNIDTLNSMA                                                                        10

SEQ ID NO: 724           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 724
GGISSINSMG                                                                        10

SEQ ID NO: 725           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 725
GSMHSVNSMA                                                                        10

SEQ ID NO: 726           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 726
GDISSINAMG                                                                        10

SEQ ID NO: 727           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 727
GSIFSIDAMG                                                                        10

SEQ ID NO: 728           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 728
GSIFSINAMG                                                                        10

SEQ ID NO: 729           moltype = AA  length = 10
FEATURE                  Location/Qualifiers
REGION                   1..10
```

|  |  |  |
|---|---|---|
| | note = Synthetic polymer | |
| source | 1..10 | |
| | mol_type = protein | |
| | organism = synthetic construct | |
| SEQUENCE: 729 | | |
| GSIFSIAAMG | | 10 |
| | | |
| SEQ ID NO: 730 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 730 | | |
| GNIASITAMG | | 10 |
| | | |
| SEQ ID NO: 731 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 731 | | |
| GFTFDDYAIG | | 10 |
| | | |
| SEQ ID NO: 732 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 732 | | |
| GSISSINAMG | | 10 |
| | | |
| SEQ ID NO: 733 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 733 | | |
| VSIFRSYFMG | | 10 |
| | | |
| SEQ ID NO: 734 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 734 | | |
| GSIVSINAIG | | 10 |
| | | |
| SEQ ID NO: 735 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 735 | | |
| GSIFSINAMG | | 10 |
| | | |
| SEQ ID NO: 736 | moltype = AA   length = 10 | |
| FEATURE | Location/Qualifiers | |
| REGION | 1..10 | |
| | note = Synthetic polymer | |
| source | 1..10 | |
| | mol_type = protein | |
| | organism = synthetic construct | |
| SEQUENCE: 736 | | |
| RSFSSFNAMG | | 10 |
| | | |
| SEQ ID NO: 737 | moltype = AA   length = 10 | |
| FEATURE | Location/Qualifiers | |

```
REGION                   1..10
                         note = Synthetic polymer
source                   1..10
                         mol_type = protein
                         organism = synthetic construct
SEQUENCE: 737
GSFSSINAMG                                                                    10

SEQ ID NO: 738           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 738
GTSFSINGMA                                                                    10

SEQ ID NO: 739           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 739
GRTFSTYAMG                                                                    10

SEQ ID NO: 740           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 740
GSIFSINAMG                                                                    10

SEQ ID NO: 741           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 741
GRIFDINAMG                                                                    10

SEQ ID NO: 742           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 742
GTLFSINGMA                                                                    10

SEQ ID NO: 743           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 743
GSIDSINAMG                                                                    10

SEQ ID NO: 744           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 744
GRAFSTNSMG                                                                    10

SEQ ID NO: 745           moltype = AA  length = 10
```

```
FEATURE                 Location/Qualifiers
REGION                  1..10
                        note = Synthetic polymer
source                  1..10
                        mol_type = protein
                        organism = synthetic construct
SEQUENCE: 745
GSIISINSMG                                                                    10

SEQ ID NO: 746          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 746
RNFFSINAMG                                                                    10

SEQ ID NO: 747          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 747
GRFFRVNAMG                                                                    10

SEQ ID NO: 748          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 748
GSIVSINSMG                                                                    10

SEQ ID NO: 749          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 749
GSIFSINAMG                                                                    10

SEQ ID NO: 750          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 750
GSIIGINSMG                                                                    10

SEQ ID NO: 751          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 751
GRTFPGYVMA                                                                    10

SEQ ID NO: 752          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 752
GSIFSINAMG                                                                    10
```

| | | |
|---|---|---|
| SEQ ID NO: 753<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 753<br>GRTFSINAMG | | 10 |
| SEQ ID NO: 754<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 754<br>GRTLSSYTIG | | 10 |
| SEQ ID NO: 755<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 755<br>GSFFSINAMG | | 10 |
| SEQ ID NO: 756<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 756<br>GSIFSINSMG | | 10 |
| SEQ ID NO: 757<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 757<br>GSIFSFNAMG | | 10 |
| SEQ ID NO: 758<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 758<br>GSIFSINAMG | | 10 |
| SEQ ID NO: 759<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 759<br>GRTFSTYAMA | | 10 |
| SEQ ID NO: 760<br>FEATURE<br>REGION<br><br>source | moltype = AA   length = 10<br>Location/Qualifiers<br>1..10<br>note = Synthetic polymer<br>1..10<br>mol_type = protein<br>organism = synthetic construct | |
| SEQUENCE: 760<br>GSFFSINAMG | | 10 |

```
SEQ ID NO: 761          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 761
VNIGSLNSMV                                                                    10

SEQ ID NO: 762          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 762
GRTLSNYAVG                                                                    10

SEQ ID NO: 763          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 763
GSISSINAMG                                                                    10

SEQ ID NO: 764          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 764
GRFFRVNAMG                                                                    10

SEQ ID NO: 765          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 765
GSVFSINAMG                                                                    10

SEQ ID NO: 766          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 766
GSIFEINSIG                                                                    10

SEQ ID NO: 767          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 767
GSIFNINSMG                                                                    10

SEQ ID NO: 768          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 768
```

```
VNIGTLNSMA                                                               10

SEQ ID NO: 769         moltype = AA   length = 10
FEATURE                Location/Qualifiers
REGION                 1..10
                       note = Synthetic polymer
source                 1..10
                       mol_type = protein
                       organism = synthetic construct
SEQUENCE: 769
GSIFSINSMG                                                               10

SEQ ID NO: 770         moltype = AA   length = 10
FEATURE                Location/Qualifiers
REGION                 1..10
                       note = Synthetic polymer
source                 1..10
                       mol_type = protein
                       organism = synthetic construct
SEQUENCE: 770
GRIGSINSMG                                                               10

SEQ ID NO: 771         moltype = AA   length = 10
FEATURE                Location/Qualifiers
REGION                 1..10
                       note = Synthetic polymer
source                 1..10
                       mol_type = protein
                       organism = synthetic construct
SEQUENCE: 771
GSIFSFNAMG                                                               10

SEQ ID NO: 772         moltype = AA   length = 10
FEATURE                Location/Qualifiers
REGION                 1..10
                       note = Synthetic polymer
source                 1..10
                       mol_type = protein
                       organism = synthetic construct
SEQUENCE: 772
GRISSINSMG                                                               10

SEQ ID NO: 773         moltype = AA   length = 10
FEATURE                Location/Qualifiers
REGION                 1..10
                       note = Synthetic polymer
source                 1..10
                       mol_type = protein
                       organism = synthetic construct
SEQUENCE: 773
GRTLSNYAVA                                                               10

SEQ ID NO: 774         moltype = AA   length = 10
FEATURE                Location/Qualifiers
REGION                 1..10
                       note = Synthetic polymer
source                 1..10
                       mol_type = protein
                       organism = synthetic construct
SEQUENCE: 774
GRIGSINSMG                                                               10

SEQ ID NO: 775         moltype = AA   length = 10
FEATURE                Location/Qualifiers
REGION                 1..10
                       note = Synthetic polymer
source                 1..10
                       mol_type = protein
                       organism = synthetic construct
SEQUENCE: 775
RSFFSFNAMG                                                               10

SEQ ID NO: 776         moltype = AA   length = 10
FEATURE                Location/Qualifiers
REGION                 1..10
                       note = Synthetic polymer
source                 1..10
                       mol_type = protein
                       organism = synthetic construct
```

```
SEQUENCE: 776
GRFFRVNAMG                                                                      10

SEQ ID NO: 777          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 777
GIIFSINAMG                                                                      10

SEQ ID NO: 778          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 778
GRTLSNYAVA                                                                      10

SEQ ID NO: 779          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 779
GRIFSVNAMG                                                                      10

SEQ ID NO: 780          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 780
GRTFSSYAMA                                                                      10

SEQ ID NO: 781          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 781
AITNGGAKTY ADSVKG                                                               16

SEQ ID NO: 782          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 782
AITSGGRLSY ADSVKG                                                               16

SEQ ID NO: 783          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 783
AITNGGQTAY ADSVKG                                                               16

SEQ ID NO: 784          moltype = AA  length = 16
FEATURE                 Location/Qualifiers
REGION                  1..16
                        note = Synthetic polymer
source                  1..16
                        mol_type = protein
```

```
                                 organism = synthetic construct
SEQUENCE: 784
AITSGGRSTY IDSAKG                                                              16

SEQ ID NO: 785           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 785
AITNQGRIAY APSVNG                                                              16

SEQ ID NO: 786           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 786
AITNDGRTTY VDSVKG                                                              16

SEQ ID NO: 787           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 787
AVTVGGRYAY ADSAKN                                                              16

SEQ ID NO: 788           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 788
AITNQGATTY ADSVKG                                                              16

SEQ ID NO: 789           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 789
GITGSGQITY ANSVRG                                                              16

SEQ ID NO: 790           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 790
AITNGGRTVY GDSVKG                                                              16

SEQ ID NO: 791           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 791
AITSGGRLAY APSVNG                                                              16

SEQ ID NO: 792           moltype = AA  length = 16
FEATURE                  Location/Qualifiers
REGION                   1..16
                         note = Synthetic polymer
source                   1..16
```

```
SEQUENCE: 792
AITNGGRTTY VDSVKG                                                    16

SEQ ID NO: 793        moltype = AA  length = 16
FEATURE               Location/Qualifiers
REGION                1..16
                      note = Synthetic polymer
source                1..16
                      mol_type = protein
                      organism = synthetic construct
SEQUENCE: 793
AITTGGRTTY VDSVKG                                                    16

SEQ ID NO: 794        moltype = AA  length = 16
FEATURE               Location/Qualifiers
REGION                1..16
                      note = Synthetic polymer
source                1..16
                      mol_type = protein
                      organism = synthetic construct
SEQUENCE: 794
AITNQGRLTY ADSVKG                                                    16

SEQ ID NO: 795        moltype = AA  length = 16
FEATURE               Location/Qualifiers
REGION                1..16
                      note = Synthetic polymer
source                1..16
                      mol_type = protein
                      organism = synthetic construct
SEQUENCE: 795
AITSGGRRAY ADSVKG                                                    16

SEQ ID NO: 796        moltype = AA  length = 18
FEATURE               Location/Qualifiers
REGION                1..18
                      note = Synthetic polymer
source                1..18
                      mol_type = protein
                      organism = synthetic construct
SEQUENCE: 796
AITSASASRT TYADSVKG                                                  18

SEQ ID NO: 797        moltype = AA  length = 17
FEATURE               Location/Qualifiers
REGION                1..17
                      note = Synthetic polymer
source                1..17
                      mol_type = protein
                      organism = synthetic construct
SEQUENCE: 797
CISRSDGSTY YDDSVKG                                                   17

SEQ ID NO: 798        moltype = AA  length = 16
FEATURE               Location/Qualifiers
REGION                1..16
                      note = Synthetic polymer
source                1..16
                      mol_type = protein
                      organism = synthetic construct
SEQUENCE: 798
AITNQGRVTY ADSVKG                                                    16

SEQ ID NO: 799        moltype = AA  length = 16
FEATURE               Location/Qualifiers
REGION                1..16
                      note = Synthetic polymer
source                1..16
                      mol_type = protein
                      organism = synthetic construct
SEQUENCE: 799
AITDGGRLAY ADSAKG                                                    16

SEQ ID NO: 800        moltype = AA  length = 16
FEATURE               Location/Qualifiers
REGION                1..16
                      note = Synthetic polymer
```

```
source                    1..16
                          mol_type = protein
                          organism = synthetic construct
SEQUENCE: 800
SITNQGIRNY STSVMG                                                        16

SEQ ID NO: 801            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 801
AITNQGRTTY ADSVKG                                                        16

SEQ ID NO: 802            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 802
AITNGGRIAY GIAVNG                                                        16

SEQ ID NO: 803            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 803
AITNGGRIAY SDSAKG                                                        16

SEQ ID NO: 804            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 804
GITSDGSTGY ADSVKG                                                        16

SEQ ID NO: 805            moltype = AA   length = 17
FEATURE                   Location/Qualifiers
REGION                    1..17
                          note = Synthetic polymer
source                    1..17
                          mol_type = protein
                          organism = synthetic construct
SEQUENCE: 805
AISWSGGSTY YADSVKG                                                       17

SEQ ID NO: 806            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 806
AITDQGRLAY ADSAKG                                                        16

SEQ ID NO: 807            moltype = AA   length = 16
FEATURE                   Location/Qualifiers
REGION                    1..16
                          note = Synthetic polymer
source                    1..16
                          mol_type = protein
                          organism = synthetic construct
SEQUENCE: 807
AITNGGQTTY ADSVKG                                                        16

SEQ ID NO: 808            moltype = AA   length = 16
FEATURE                   Location/Qualifiers
REGION                    1..16
```

```
                        note = Synthetic polymer
source                  1..16
                        mol_type = protein
                        organism = synthetic construct
SEQUENCE: 808
GITSDGSTGY ADSVKG                                                          16

SEQ ID NO: 809          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 809
AITTGGRTAY VDSVKG                                                          16

SEQ ID NO: 810          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 810
AITSQGRITL ADSVKG                                                          16

SEQ ID NO: 811          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 811
AITVDGRLAY ADSAKH                                                          16

SEQ ID NO: 812          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 812
AITNGGRIAY GTSVMG                                                          16

SEQ ID NO: 813          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 813
AITNGGQIAY ADSVKG                                                          16

SEQ ID NO: 814          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 814
AITDQGRTTY ADSVKG                                                          16

SEQ ID NO: 815          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 815
GITTQGRITY GNSVRG                                                          16

SEQ ID NO: 816          moltype = AA  length = 16
FEATURE                 Location/Qualifiers
```

```
REGION                  1..16
                        note = Synthetic polymer
source                  1..16
                        mol_type = protein
                        organism = synthetic construct
SEQUENCE: 816
AITSGGRTTY VDSVKG                                                          16

SEQ ID NO: 817          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 817
AINWRGGDTY YADSVKG                                                         17

SEQ ID NO: 818          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 818
AITDGGAKTY ADSVKG                                                          16

SEQ ID NO: 819          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 819
AITNQGRLSY VDSVKG                                                          16

SEQ ID NO: 820          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 820
AITNQGRRTY ADSVKG                                                          16

SEQ ID NO: 821          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 821
AITNGGRIAY TDSVKG                                                          16

SEQ ID NO: 822          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 822
AITNGGRTTY ADSVKG                                                          16

SEQ ID NO: 823          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 823
AITDGGRLTY ADSAKG                                                          16

SEQ ID NO: 824          moltype = AA  length = 16
```

```
FEATURE                 Location/Qualifiers
REGION                  1..16
                        note = Synthetic polymer
source                  1..16
                        mol_type = protein
                        organism = synthetic construct
SEQUENCE: 824
AITTGGRTTY VDSVKG                                                          16

SEQ ID NO: 825          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 825
AISWSGGSTE YHDSVKG                                                         17

SEQ ID NO: 826          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 826
AITNQGRIAY ADSVKG                                                          16

SEQ ID NO: 827          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 827
GITGSGQITY ANSVRG                                                          16

SEQ ID NO: 828          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 828
AINWSSGGIS YSNSAKG                                                         17

SEQ ID NO: 829          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 829
AITGQGRTTY ADSVKG                                                          16

SEQ ID NO: 830          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 830
AITNGGQIVY ADSVKG                                                          16

SEQ ID NO: 831          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 831
AITTQGRTTY EDSVKG                                                          16
```

```
SEQ ID NO: 832          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 832
AITSGGITNY ANSVQG                                                        16

SEQ ID NO: 833          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 833
AITVGGRLAY ADSAKG                                                        16

SEQ ID NO: 834          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 834
GITGGGQITY ANSVRG                                                        16

SEQ ID NO: 835          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 835
AITSQGRSTY ADSAKG                                                        16

SEQ ID NO: 836          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 836
AITNGGATVY ADSVKG                                                        16

SEQ ID NO: 837          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 837
AITDGGRLTY ADSAKN                                                        16

SEQ ID NO: 838          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 838
AITNGGAKTY ADSVKG                                                        16

SEQ ID NO: 839          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 839
AINWSSGGIS YSNAAKG                                                       17
```

```
SEQ ID NO: 840           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 840
AITNGGATVY ADSVKG                                                            16

SEQ ID NO: 841           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 841
AITNGGRIAY GTSVMG                                                            16

SEQ ID NO: 842           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 842
AITNGGQTAY ADSVKG                                                            16

SEQ ID NO: 843           moltype = AA  length = 16
FEATURE                  Location/Qualifiers
REGION                   1..16
                         note = Synthetic polymer
SITE                     5
                         note = misc_feature - Xaa can be any naturally occurring
                          amino acid
source                   1..16
                         mol_type = protein
                         organism = synthetic construct
SEQUENCE: 843
AITNXGRTTY ADSVKG                                                            16

SEQ ID NO: 844           moltype = AA  length = 17
FEATURE                  Location/Qualifiers
REGION                   1..17
                         note = Synthetic polymer
source                   1..17
                         mol_type = protein
                         organism = synthetic construct
SEQUENCE: 844
AIWWASGGIS YANSAKG                                                           17

SEQ ID NO: 845           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 845
AITNQGAPTY ADSVKG                                                            16

SEQ ID NO: 846           moltype = AA  length = 17
FEATURE                  Location/Qualifiers
REGION                   1..17
                         note = Synthetic polymer
source                   1..17
                         mol_type = protein
                         organism = synthetic construct
SEQUENCE: 846
AISWSGGSTY YADSVKG                                                           17

SEQ ID NO: 847           moltype = AA  length = 7
FEATURE                  Location/Qualifiers
REGION                   1..7
                         note = Synthetic polymer
source                   1..7
```

```
                              mol_type = protein
                              organism = synthetic construct
SEQUENCE: 847
FTRRDDY                                                                  7

SEQ ID NO: 848               moltype = AA   length = 7
FEATURE                      Location/Qualifiers
REGION                       1..7
                             note = Synthetic polymer
source                       1..7
                             mol_type = protein
                             organism = synthetic construct
SEQUENCE: 848
FQSSGID                                                                  7

SEQ ID NO: 849               moltype = AA   length = 8
FEATURE                      Location/Qualifiers
REGION                       1..8
                             note = Synthetic polymer
source                       1..8
                             mol_type = protein
                             organism = synthetic construct
SEQUENCE: 849
WAADYQQY                                                                 8

SEQ ID NO: 850               moltype = AA   length = 8
FEATURE                      Location/Qualifiers
REGION                       1..8
                             note = Synthetic polymer
source                       1..8
                             mol_type = protein
                             organism = synthetic construct
SEQUENCE: 850
WNRDRQQY                                                                 8

SEQ ID NO: 851               moltype = AA   length = 13
FEATURE                      Location/Qualifiers
REGION                       1..13
                             note = Synthetic polymer
source                       1..13
                             mol_type = protein
                             organism = synthetic construct
SEQUENCE: 851
KPTPVYGSTV GDY                                                          13

SEQ ID NO: 852               moltype = AA   length = 7
FEATURE                      Location/Qualifiers
REGION                       1..7
                             note = Synthetic polymer
source                       1..7
                             mol_type = protein
                             organism = synthetic construct
SEQUENCE: 852
FTRDKDY                                                                  7

SEQ ID NO: 853               moltype = AA   length = 8
FEATURE                      Location/Qualifiers
REGION                       1..8
                             note = Synthetic polymer
source                       1..8
                             mol_type = protein
                             organism = synthetic construct
SEQUENCE: 853
WDRDRQQY                                                                 8

SEQ ID NO: 854               moltype = AA   length = 7
FEATURE                      Location/Qualifiers
REGION                       1..7
                             note = Synthetic polymer
source                       1..7
                             mol_type = protein
                             organism = synthetic construct
SEQUENCE: 854
FTRTDDY                                                                  7

SEQ ID NO: 855               moltype = AA   length = 8
FEATURE                      Location/Qualifiers
REGION                       1..8
                             note = Synthetic polymer
```

```
source                  1..8
                        mol_type = protein
                        organism = synthetic construct
SEQUENCE: 855
YDRSSTPY                                                                8

SEQ ID NO: 856          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 856
FTRGDDY                                                                 7

SEQ ID NO: 857          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 857
LNSATTY                                                                 7

SEQ ID NO: 858          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 858
YTRDEDY                                                                 7

SEQ ID NO: 859          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 859
FTRDEDY                                                                 7

SEQ ID NO: 860          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 860
KWYDPLVIEY YDN                                                         13

SEQ ID NO: 861          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 861
KADHNDY                                                                 7

SEQ ID NO: 862          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 862
FRSGADDY                                                                8

SEQ ID NO: 863          moltype = AA  length = 15
FEATURE                 Location/Qualifiers
REGION                  1..15
```

```
                          note = Synthetic polymer
source                    1..15
                          mol_type = protein
                          organism = synthetic construct
SEQUENCE: 863
EVPSTYSCSG FREDY                                                    15

SEQ ID NO: 864            moltype = AA   length = 8
FEATURE                   Location/Qualifiers
REGION                    1..8
                          note = Synthetic polymer
source                    1..8
                          mol_type = protein
                          organism = synthetic construct
SEQUENCE: 864
FAASGMEY                                                             8

SEQ ID NO: 865            moltype = AA   length = 8
FEATURE                   Location/Qualifiers
REGION                    1..8
                          note = Synthetic polymer
source                    1..8
                          mol_type = protein
                          organism = synthetic construct
SEQUENCE: 865
WTTDRQQY                                                             8

SEQ ID NO: 866            moltype = AA   length = 9
FEATURE                   Location/Qualifiers
REGION                    1..9
                          note = Synthetic polymer
source                    1..9
                          mol_type = protein
                          organism = synthetic construct
SEQUENCE: 866
FAGWGKEDY                                                            9

SEQ ID NO: 867            moltype = AA   length = 7
FEATURE                   Location/Qualifiers
REGION                    1..7
                          note = Synthetic polymer
source                    1..7
                          mol_type = protein
                          organism = synthetic construct
SEQUENCE: 867
FSPTGDY                                                              7

SEQ ID NO: 868            moltype = AA   length = 13
FEATURE                   Location/Qualifiers
REGION                    1..13
                          note = Synthetic polymer
source                    1..13
                          mol_type = protein
                          organism = synthetic construct
SEQUENCE: 868
KPTPVYGSTV GDY                                                      13

SEQ ID NO: 869            moltype = AA   length = 13
FEATURE                   Location/Qualifiers
REGION                    1..13
                          note = Synthetic polymer
source                    1..13
                          mol_type = protein
                          organism = synthetic construct
SEQUENCE: 869
KASPVYGSTV EDY                                                      13

SEQ ID NO: 870            moltype = AA   length = 8
FEATURE                   Location/Qualifiers
REGION                    1..8
                          note = Synthetic polymer
source                    1..8
                          mol_type = protein
                          organism = synthetic construct
SEQUENCE: 870
STPRGDSY                                                             8

SEQ ID NO: 871            moltype = AA   length = 15
FEATURE                   Location/Qualifiers
```

```
REGION                     1..15
                           note = Synthetic polymer
source                     1..15
                           mol_type = protein
                           organism = synthetic construct
SEQUENCE: 871
EAEGSGREGN FYERS                                                            15

SEQ ID NO: 872             moltype = AA  length = 8
FEATURE                    Location/Qualifiers
REGION                     1..8
                           note = Synthetic polymer
source                     1..8
                           mol_type = protein
                           organism = synthetic construct
SEQUENCE: 872
WDRDRQQY                                                                     8

SEQ ID NO: 873             moltype = AA  length = 7
FEATURE                    Location/Qualifiers
REGION                     1..7
                           note = Synthetic polymer
source                     1..7
                           mol_type = protein
                           organism = synthetic construct
SEQUENCE: 873
FTRSDDY                                                                      7

SEQ ID NO: 874             moltype = AA  length = 8
FEATURE                    Location/Qualifiers
REGION                     1..8
                           note = Synthetic polymer
source                     1..8
                           mol_type = protein
                           organism = synthetic construct
SEQUENCE: 874
STPRGDSY                                                                     8

SEQ ID NO: 875             moltype = AA  length = 7
FEATURE                    Location/Qualifiers
REGION                     1..7
                           note = Synthetic polymer
source                     1..7
                           mol_type = protein
                           organism = synthetic construct
SEQUENCE: 875
FTRDTDY                                                                      7

SEQ ID NO: 876             moltype = AA  length = 7
FEATURE                    Location/Qualifiers
REGION                     1..7
                           note = Synthetic polymer
source                     1..7
                           mol_type = protein
                           organism = synthetic construct
SEQUENCE: 876
WTTLGTF                                                                      7

SEQ ID NO: 877             moltype = AA  length = 8
FEATURE                    Location/Qualifiers
REGION                     1..8
                           note = Synthetic polymer
source                     1..8
                           mol_type = protein
                           organism = synthetic construct
SEQUENCE: 877
WVRDGQQY                                                                     8

SEQ ID NO: 878             moltype = AA  length = 13
FEATURE                    Location/Qualifiers
REGION                     1..13
                           note = Synthetic polymer
source                     1..13
                           mol_type = protein
                           organism = synthetic construct
SEQUENCE: 878
KAIPVYGSTV EDY                                                              13

SEQ ID NO: 879             moltype = AA  length = 13
```

```
FEATURE              Location/Qualifiers
REGION               1..13
                     note = Synthetic polymer
source               1..13
                     mol_type = protein
                     organism = synthetic construct
SEQUENCE: 879
KAAATHLSTV ADY                                                          13

SEQ ID NO: 880       moltype = AA  length = 7
FEATURE              Location/Qualifiers
REGION               1..7
                     note = Synthetic polymer
source               1..7
                     mol_type = protein
                     organism = synthetic construct
SEQUENCE: 880
FGRFDDY                                                                 7

SEQ ID NO: 881       moltype = AA  length = 14
FEATURE              Location/Qualifiers
REGION               1..14
                     note = Synthetic polymer
source               1..14
                     mol_type = protein
                     organism = synthetic construct
SEQUENCE: 881
WGVKTGPESG SGTL                                                         14

SEQ ID NO: 882       moltype = AA  length = 7
FEATURE              Location/Qualifiers
REGION               1..7
                     note = Synthetic polymer
source               1..7
                     mol_type = protein
                     organism = synthetic construct
SEQUENCE: 882
FTRDEDY                                                                 7

SEQ ID NO: 883       moltype = AA  length = 10
FEATURE              Location/Qualifiers
REGION               1..10
                     note = Synthetic polymer
source               1..10
                     mol_type = protein
                     organism = synthetic construct
SEQUENCE: 883
RLTTEYDYAY                                                              10

SEQ ID NO: 884       moltype = AA  length = 7
FEATURE              Location/Qualifiers
REGION               1..7
                     note = Synthetic polymer
source               1..7
                     mol_type = protein
                     organism = synthetic construct
SEQUENCE: 884
FTRGNDY                                                                 7

SEQ ID NO: 885       moltype = AA  length = 7
FEATURE              Location/Qualifiers
REGION               1..7
                     note = Synthetic polymer
source               1..7
                     mol_type = protein
                     organism = synthetic construct
SEQUENCE: 885
FQSSGID                                                                 7

SEQ ID NO: 886       moltype = AA  length = 7
FEATURE              Location/Qualifiers
REGION               1..7
                     note = Synthetic polymer
source               1..7
                     mol_type = protein
                     organism = synthetic construct
SEQUENCE: 886
FSPTDDF                                                                 7
```

```
SEQ ID NO: 887           moltype = AA  length = 13
FEATURE                  Location/Qualifiers
REGION                   1..13
                         note = Synthetic polymer
source                   1..13
                         mol_type = protein
                         organism = synthetic construct
SEQUENCE: 887
KAIPIYGSTA EDY                                                          13

SEQ ID NO: 888           moltype = AA  length = 7
FEATURE                  Location/Qualifiers
REGION                   1..7
                         note = Synthetic polymer
source                   1..7
                         mol_type = protein
                         organism = synthetic construct
SEQUENCE: 888
FSLTDDY                                                                  7

SEQ ID NO: 889           moltype = AA  length = 8
FEATURE                  Location/Qualifiers
REGION                   1..8
                         note = Synthetic polymer
source                   1..8
                         mol_type = protein
                         organism = synthetic construct
SEQUENCE: 889
WTRDRQQY                                                                 8

SEQ ID NO: 890           moltype = AA  length = 7
FEATURE                  Location/Qualifiers
REGION                   1..7
                         note = Synthetic polymer
source                   1..7
                         mol_type = protein
                         organism = synthetic construct
SEQUENCE: 890
FTRDEDF                                                                  7

SEQ ID NO: 891           moltype = AA  length = 14
FEATURE                  Location/Qualifiers
REGION                   1..14
                         note = Synthetic polymer
source                   1..14
                         mol_type = protein
                         organism = synthetic construct
SEQUENCE: 891
EVEGSGREGN FYGA                                                         14

SEQ ID NO: 892           moltype = AA  length = 5
FEATURE                  Location/Qualifiers
REGION                   1..5
                         note = Synthetic polymer
source                   1..5
                         mol_type = protein
                         organism = synthetic construct
SEQUENCE: 892
PGWDY                                                                    5

SEQ ID NO: 893           moltype = AA  length = 8
FEATURE                  Location/Qualifiers
REGION                   1..8
                         note = Synthetic polymer
source                   1..8
                         mol_type = protein
                         organism = synthetic construct
SEQUENCE: 893
YDRSATAY                                                                 8

SEQ ID NO: 894           moltype = AA  length = 11
FEATURE                  Location/Qualifiers
REGION                   1..11
                         note = Synthetic polymer
source                   1..11
                         mol_type = protein
                         organism = synthetic construct
SEQUENCE: 894
ASSVLSGTVD Y                                                            11
```

```
SEQ ID NO: 895         moltype = AA  length = 8
FEATURE                Location/Qualifiers
REGION                 1..8
                       note = Synthetic polymer
source                 1..8
                       mol_type = protein
                       organism = synthetic construct
SEQUENCE: 895
FAADGMEY                                                                  8

SEQ ID NO: 896         moltype = AA  length = 13
FEATURE                Location/Qualifiers
REGION                 1..13
                       note = Synthetic polymer
source                 1..13
                       mol_type = protein
                       organism = synthetic construct
SEQUENCE: 896
KAAASYVSTV ADY                                                           13

SEQ ID NO: 897         moltype = AA  length = 6
FEATURE                Location/Qualifiers
REGION                 1..6
                       note = Synthetic polymer
source                 1..6
                       mol_type = protein
                       organism = synthetic construct
SEQUENCE: 897
TAKDDY                                                                    6

SEQ ID NO: 898         moltype = AA  length = 9
FEATURE                Location/Qualifiers
REGION                 1..9
                       note = Synthetic polymer
source                 1..9
                       mol_type = protein
                       organism = synthetic construct
SEQUENCE: 898
FTGWGKEDY                                                                 9

SEQ ID NO: 899         moltype = AA  length = 8
FEATURE                Location/Qualifiers
REGION                 1..8
                       note = Synthetic polymer
source                 1..8
                       mol_type = protein
                       organism = synthetic construct
SEQUENCE: 899
WAADYQQY                                                                  8

SEQ ID NO: 900         moltype = AA  length = 8
FEATURE                Location/Qualifiers
REGION                 1..8
                       note = Synthetic polymer
source                 1..8
                       mol_type = protein
                       organism = synthetic construct
SEQUENCE: 900
YDRSATPY                                                                  8

SEQ ID NO: 901         moltype = AA  length = 8
FEATURE                Location/Qualifiers
REGION                 1..8
                       note = Synthetic polymer
source                 1..8
                       mol_type = protein
                       organism = synthetic construct
SEQUENCE: 901
WARDRQQY                                                                  8

SEQ ID NO: 902         moltype = AA  length = 7
FEATURE                Location/Qualifiers
REGION                 1..7
                       note = Synthetic polymer
source                 1..7
                       mol_type = protein
                       organism = synthetic construct
SEQUENCE: 902
```

```
FTRGDDY                                                                          7

SEQ ID NO: 903          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 903
WTKDRQQY                                                                         8

SEQ ID NO: 904          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 904
FTRTYDY                                                                          7

SEQ ID NO: 905          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 905
ASSILSGTVD Y                                                                    11

SEQ ID NO: 906          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 906
WAADYQQY                                                                         8

SEQ ID NO: 907          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 907
KPAPVYGSTV GDY                                                                  13

SEQ ID NO: 908          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 908
FAADGMEY                                                                         8

SEQ ID NO: 909          moltype = AA  length = 6
FEATURE                 Location/Qualifiers
REGION                  1..6
                        note = Synthetic polymer
source                  1..6
                        mol_type = protein
                        organism = synthetic construct
SEQUENCE: 909
FGSGGG                                                                           6

SEQ ID NO: 910          moltype = AA  length = 11
FEATURE                 Location/Qualifiers
REGION                  1..11
                        note = Synthetic polymer
source                  1..11
                        mol_type = protein
                        organism = synthetic construct
```

```
SEQUENCE: 910
ASSVLSGTAD Y                                                                    11

SEQ ID NO: 911          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 911
FTRGDDY                                                                         7

SEQ ID NO: 912          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 912
EAEGSGREGN FYERS                                                                15

SEQ ID NO: 913          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 913
QVQLQESGGG LVQPGGSLRL SCAASGRISS INSMGWYRQA PGNQRELVAA ITNGGAKTYA               60
DSVKGRFTIS TDNAGNTVYL QMDSLRPEDT AVYYCKAFTR RDDYWGQGTQ ITVSSAAAYP              120
YDVPDYGSHH HHHH                                                               134

SEQ ID NO: 914          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 914
QVQLQESGGG LVQAGGSLRL SCAASGSITS INAMGWYRQA PGKQRELVAA ITSGGRLSYA               60
DSVKGRFTIS RDNAESTVAL QMNSLKPEDT AVYSCAAFQS SGIDWGQGTQ VTVSSAAAYP              120
YDVPDYGSHH HHHH                                                               134

SEQ ID NO: 915          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 915
QVQLQESGGG LVQPGGSLRL SCAASGRFFR VNAMGWYRQA PGKQRELVAA ITNGGQTAYA               60
DSVKGRFTIS KESARNTVHL QMSSLKPEDT AVYYCTIWAA DYQQYWGQGT QVTVSSAAAY              120
PYDVPDYGSH HHHH                                                               135

SEQ ID NO: 916          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 916
QVQLQESGGG LVQAGESLRL SCAASGSSDS INAMGWYRQA PGKQRELVAA ITSGGRSTYI               60
DSAKGRATIS RDNARNTAYL QMSSLKAEDT AVYYCTIWNR DRQQYWGQGT QVTVSSAAAY              120
PYDVPDYGSH HHHH                                                               135

SEQ ID NO: 917          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 917
```

```
                                  -continued

QVQLQESGGG LVQSGGSLRL SCAASGSVFS INAWGWYRQA PGKQRELVAA ITNQGRIAYA    60
PSVNGRFTIS RDSAKNTVYL QMNSLKPEDT AVYYCNAKPT PVYGSTVGDY WGQGTQVTVS   120
SAAAYPYDVP DYGSHHHHHH                                              140

SEQ ID NO: 918          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 918
QVQLQESGGG LVQAGGSLRL SCAASGSILS INSMGWYRPA LGNQRELVAA ITNDGRTTYV    60
DSVKGRFTIS RDNAKNTVYL QMNSLKPEDT AVYWCKAFTR DKDYWGQGTQ VTVSSAAAYP   120
YDVPDYGSHH HHHH                                                    134

SEQ ID NO: 919          moltype = AA  length = 135
FEATURE                 Location/Qualifiers
REGION                  1..135
                        note = Synthetic polymer
SITE                    108
                        note = misc_feature - Xaa can be any naturally occurring
                         amino acid
source                  1..135
                        mol_type = protein
                        organism = synthetic construct
SEQUENCE: 919
QVQLQESGGG LVQTGGSLRL SCAASVSISS INSMGWYRQA PGKERELVAA VTGGRYAYA     60
DSAKNRFTIS RDDAQNTVHL QMSSLRAEDT AVYYCTIWDR DRQQYWGXGT QVTVSSAAAY   120
PYDVPDYGSH HHHH                                                    135

SEQ ID NO: 920          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 920
QVQLQESGGG LVQPGGSLRL SCAASGRVFS INAMGWYRQA PGKQRELVAA ITNQGATTYA    60
DSVKGRFTIS RDTAGNTVYL QMNSLRPEDT AVHYCKAFTR TDDYWGQGTQ VTVSSAAAYP   120
YDVPDYGSHH HHHH                                                    134

SEQ ID NO: 921          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 921
QVQLQESGGG LVQAGGSLRL SCAASVNIDT LNSMAWYRQA PGKQRELVAG ITGSGQITYA    60
NSVRGRFTVS RDNAKSTVYL QMNTLQPEDT AVYYCAAYDR SSTPYWGQGT QVTVSSAAAY   120
PYDVPDYGSH HHHH                                                    135

SEQ ID NO: 922          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 922
QVQLQESGGG LVQPGGSLRL SCAASGGISS INSMGWYRQA PGNQRELVAA ITNGGRTVYG    60
DSVKGRFTIS RDSAGNTVHL QMDSLRPEDT GVYYCKAFTR GDDYWGQGTQ VTVSSAAAYP   120
YDVPDYGSHH HHHH                                                    134

SEQ ID NO: 923          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 923
QVQLQESGGG LVQPGGFLSL SCAASGSMHS VNSMAWYRQV PGKQRELVAA ITSGGRLAYA    60
PSVNGRFTIS RDYAKNTIHL QMNSLEPEDT AVYYCAALNS ATTYWGQGTQ VTVSSAAAYP   120
YDVPDYGSHH HHHH                                                    134
```

```
SEQ ID NO: 924              moltype = AA  length = 134
FEATURE                     Location/Qualifiers
REGION                      1..134
                            note = Synthetic polymer
source                      1..134
                            mol_type = protein
                            organism = synthetic construct
SEQUENCE: 924
QVQLQESGGG LVQAGGSLRL SCAATGDISS INAMGWHRPA RGNERELVAA ITNGGRTTYV    60
DSVKGRFTIS RDNAKNTVYL QMNSLKPEDT AVYFCKAYTR DEDYWGQGTQ VTVSSAAAYP   120
YDVPDYGSHH HHHH                                                     134

SEQ ID NO: 925              moltype = AA  length = 134
FEATURE                     Location/Qualifiers
REGION                      1..134
                            note = Synthetic polymer
source                      1..134
                            mol_type = protein
                            organism = synthetic construct
SEQUENCE: 925
QVQLQESGGG LVRAGGSLRL SCAASGSIFS IDAMGWYRPA HGEQRELVAA ITTGGRTTYV    60
DSVKGRFTIS RDNAKNTVYL QMNSLKPEDT AVYFCKAFTR DEDYWGQGTQ VTVSSAAAYP   120
YDVPDYGSHH HHHH                                                     134

SEQ ID NO: 926              moltype = AA  length = 140
FEATURE                     Location/Qualifiers
REGION                      1..140
                            note = Synthetic polymer
source                      1..140
                            mol_type = protein
                            organism = synthetic construct
SEQUENCE: 926
QVQLQESGGG LVQPGGSLRL SCAASGSIFS INAMGWYRQA PGKQRELVAA ITNQGRLTYA    60
DSVKGRFTIS RDNAKNTVFL QMDSLKPEDT AVYYCNAKWY DPLVIEYYDN WGQGTQVTVS   120
SAAAYPYDVP DYGSHHHHHH                                               140

SEQ ID NO: 927              moltype = AA  length = 134
FEATURE                     Location/Qualifiers
REGION                      1..134
                            note = Synthetic polymer
source                      1..134
                            mol_type = protein
                            organism = synthetic construct
SEQUENCE: 927
QVQLQESGGG LVQPGGSLRL SCAASGSIFS IAAMGWYRQA PGKQRELVAA ITSGGRRAYA    60
DSVKGRFTIS RDNDENTVAL QMNSLKPEDT DVYYCNAKAD HNDYWGQGTQ ITVSSAAAYP   120
YDVPDYGSHH HHHH                                                     134

SEQ ID NO: 928              moltype = AA  length = 137
FEATURE                     Location/Qualifiers
REGION                      1..137
                            note = Synthetic polymer
source                      1..137
                            mol_type = protein
                            organism = synthetic construct
SEQUENCE: 928
QVQLQESGGG LVQPGGSLRL SCAAIGNIAS ITAMGWYRQA PGKQRELVAA ITSASASRTT    60
YADSVKGRFT ISRDNAKNTV YLQMNSLQPE DTAVYYCKGF RSGADDYWGQ GTQVTVSSAA   120
AYPYDVPDYG SHHHHHH                                                  137

SEQ ID NO: 929              moltype = AA  length = 143
FEATURE                     Location/Qualifiers
REGION                      1..143
                            note = Synthetic polymer
source                      1..143
                            mol_type = protein
                            organism = synthetic construct
SEQUENCE: 929
QVQLQESGGG LVQPGGSLRL SCAASGFTFD DYAIGWFRQA PGKEHEGVSC ISRSDGSTYY    60
DDSVKGRFTI SSDNAKNTVY LQMNSLKPED TAVYYCAAEV PSTYSCSGFR EDYKGKGTQV   120
TVSSAAAYPY DVPDYGSHHH HHH                                           143

SEQ ID NO: 930              moltype = AA  length = 135
FEATURE                     Location/Qualifiers
REGION                      1..135
                            note = Synthetic polymer
source                      1..135
                            mol_type = protein
                            organism = synthetic construct
```

```
SEQUENCE: 930
QVQLQESGGG LVQPGGSLRL SCAASGSISS INAMGWYRQA PGNQRELVAA ITNQGRVTYA   60
DSVKGRFTIS RDGAKNTVYL QMNSLKPEDT AVYYCKVFAA SGMEYWGKGT QVTVSSAAAY  120
PYDVPDYGSH HHHHH                                                  135

SEQ ID NO: 931          moltype = AA   length = 135
FEATURE                 Location/Qualifiers
REGION                  1..135
                        note = Synthetic polymer
source                  1..135
                        mol_type = protein
                        organism = synthetic construct
SEQUENCE: 931
QVQLQESGGG LVQAGESLRL SCAASVSIFR SYFMGWYRQA PGKQRELVAA ITDGGRLAYA   60
DSAKGRFTIS REDTRNTVHL QMSSLKAEDT AVYYCTIWTT DRQQYWGQGT QVTVSSAAAY  120
PYDVPDYGSH HHHH                                                   135

SEQ ID NO: 932          moltype = AA   length = 136
FEATURE                 Location/Qualifiers
REGION                  1..136
                        note = Synthetic polymer
source                  1..136
                        mol_type = protein
                        organism = synthetic construct
SEQUENCE: 932
QVQLQESGGG WVQPGGSLRL SCAATGSIVS INAIGWYRQA PGKQRELVAS ITNQGIRNYS   60
TSVMGRFTIS RDDVKNTVSL QMNSLKPEDS AVYYCKGFAG WGKEDYWGQG TQVTVSSAAA  120
YPYDVPDYGS HHHHHH                                                 136

SEQ ID NO: 933          moltype = AA   length = 134
FEATURE                 Location/Qualifiers
REGION                  1..134
                        note = Synthetic polymer
source                  1..134
                        mol_type = protein
                        organism = synthetic construct
SEQUENCE: 933
QVQLQESGGG LVQAGASLRL SCAASGSIFS INAMGWYRQA PGKQRELVAA ITNQGRTTYA   60
DSVKGRFTIS RDNAKNTVYL QMDSLEPEDT AIYYCKGFSP TGDYWGQGTQ VTVSSAAAYP  120
YDVPDYGSHH HHHH                                                   134

SEQ ID NO: 934          moltype = AA   length = 140
FEATURE                 Location/Qualifiers
REGION                  1..140
                        note = Synthetic polymer
source                  1..140
                        mol_type = protein
                        organism = synthetic construct
SEQUENCE: 934
QVQLQESGGG LVQPGGSLRL SCLASRSFSS FNAMGWYRQA PGKERELVAA ITNGGRIAYG   60
IAVNGRFTIS RDNAKNTVYL QMNSLKPEDT AVYYCNAKPT PVYGSTVGDY WGQGTQVTVS  120
SAAAYPYDVP DYGSHHHHHH                                             140

SEQ ID NO: 935          moltype = AA   length = 140
FEATURE                 Location/Qualifiers
REGION                  1..140
                        note = Synthetic polymer
source                  1..140
                        mol_type = protein
                        organism = synthetic construct
SEQUENCE: 935
QVQLQESGGG LVQAGGSLTL SCAASGSFSS INAMGYYRQA PGKQRELVAA ITNGGRIAYS   60
DSAKGRFTIS RDSAKNTMYL QMNSLKPEDT DVYYCNAKAS PVYGSTVEDY WGQGTQVTVS  120
SAAAYPYDVP DYGSHHHHHH                                             140

SEQ ID NO: 936          moltype = AA   length = 135
FEATURE                 Location/Qualifiers
REGION                  1..135
                        note = Synthetic polymer
source                  1..135
                        mol_type = protein
                        organism = synthetic construct
SEQUENCE: 936
QVQLQESGGG LVQPGGSLRL SCAASGTSFS INGMAWYRQA PGGQRELVGG ITSDGSTGYA   60
DSVKGRFTVS RDNAKNTVYL QMNRLKPEDT AVYYCGTSTP RGDSYWGQGT QVTVSSAAAY  120
PYDVPDYGSH HHHH                                                   135

SEQ ID NO: 937          moltype = AA   length = 145
FEATURE                 Location/Qualifiers
```

```
REGION                          1..145
                                note = Synthetic polymer
source                          1..145
                                mol_type = protein
                                organism = synthetic construct
SEQUENCE: 937
QVQLQESGGG LVQAGGSLRL SCAASGRTFS TYAMGWFRQA PGKERGLVAA ISWSGGSTYY    60
ADSVKGRFTI FRDNAENTVY LQMNSLKPED TAVYYCAAEA EGSGREGNFY ERSWYQGQGT   120
QVTVSSAAAY PYDVPDYGSH HHHHH                                        145

SEQ ID NO: 938                  moltype = AA  length = 135
FEATURE                         Location/Qualifiers
REGION                          1..135
                                note = Synthetic polymer
source                          1..135
                                mol_type = protein
                                organism = synthetic construct
SEQUENCE: 938
QVQLQESGGG LVETGGSLRL SCAASGSIFS INAMGWYRQA PGKQRELVAA ITDQGRLAYA    60
DSAKGRFTIS RENARNTLHL QMSSLKAEDT AVYYCTIWDR DRQQYWGQGT QVTVSSAAAY   120
PYDVPDYGSH HHHH                                                    135

SEQ ID NO: 939                  moltype = AA  length = 134
FEATURE                         Location/Qualifiers
REGION                          1..134
                                note = Synthetic polymer
source                          1..134
                                mol_type = protein
                                organism = synthetic construct
SEQUENCE: 939
QVQLQESGGG LVQPGGSLRL SCAASGRIFD INAMGWYRQA PGKQRELVAA ITNGGQTTYA    60
DSVKGRFTIS RDNAGNTVYL QMNSLRPEDT AVYYCKAFTR SDDYWGQGTQ VTVSSAAAYP   120
YDVPDYGSHH HHHH                                                    134

SEQ ID NO: 940                  moltype = AA  length = 135
FEATURE                         Location/Qualifiers
REGION                          1..135
                                note = Synthetic polymer
source                          1..135
                                mol_type = protein
                                organism = synthetic construct
SEQUENCE: 940
QVQLQESGGG LVQAGGSLRL SCAASGTLFS INGMAWYRQA PGKRRELVGG ITSDGSTGYA    60
DSVKGRFTIS RDNAKNTAYL QMNSLKPEDT AVYYCGTSTP RGDSYWGQGT QVTVSSAAAY   120
PYDVPDYGSH HHHH                                                    135

SEQ ID NO: 941                  moltype = AA  length = 134
FEATURE                         Location/Qualifiers
REGION                          1..134
                                note = Synthetic polymer
source                          1..134
                                mol_type = protein
                                organism = synthetic construct
SEQUENCE: 941
QVQLQESGGG LVQAGGSLRL SCAASGSIDS INAMGWYRPA LGEQRELVAA ITTGGRTAYV    60
DSVKGRFTIS RDAAKNTVYL QMNSLKPEDT AVYSCKAFTR DTDYWGQGTQ VTVSSAAAYP   120
YDVPDYGSHH HHHH                                                    134

SEQ ID NO: 942                  moltype = AA  length = 134
FEATURE                         Location/Qualifiers
REGION                          1..134
                                note = Synthetic polymer
source                          1..134
                                mol_type = protein
                                organism = synthetic construct
SEQUENCE: 942
QVQLQESGGG LAQPGGSLQL SCAASGRAFS TNSMGWYRQA SGKQRELVAA ITSQGRITLA    60
DSVKGRFTIS SDNTKNTVFL QMNSLKPEDT AVYYCNAWTT LGTFGGQGTQ VTVSSAAAYP   120
YDVPDYGSHH HHHH                                                    134

SEQ ID NO: 943                  moltype = AA  length = 136
FEATURE                         Location/Qualifiers
REGION                          1..136
                                note = Synthetic polymer
source                          1..136
                                mol_type = protein
                                organism = synthetic construct
SEQUENCE: 943
QVQLQESGGG LVQTGESLSL SCAVASGSII SINSMGWYRQ APEKQRELVA AITVDGRLAY    60
```

```
ADSAKHRFTI SKESARNTVH LHMSSLKPED TAVYYCTIWV RDGQQYWGQG TQVTVSSAAA    120
YPYDVPDYGS HHHHHH                                                   136

SEQ ID NO: 944          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 944
QVQLQESGGG LVQPGGSLRL SCAVSRNFFS INAMGWYRQA PGKQRELVAA ITNGGRIAYG    60
TSVMGRFTIS RDDAKNTVDL QMNSLRPEDT AVYYCNAKAI PVYGSTVEDY WGQGTQVTVS    120
SAAAYPYDVP DYGSHHHHHH                                                140

SEQ ID NO: 945          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 945
QVQLQESGGG LVQPGGSLRL SCAASGRFFR VNAMGWYRQV PGKQRELVAA ITNGGQIAYA    60
DSVKGRFTIS RDSAKNTVYL QMNSLKSEDT DVYYCNAKAA ATHLSTVADY WGQGTQVTVS    120
SAAAYPYDVP DYGSHHHHHH                                                140

SEQ ID NO: 946          moltype = AA  length = 136
FEATURE                 Location/Qualifiers
REGION                  1..136
                        note = Synthetic polymer
source                  1..136
                        mol_type = protein
                        organism = synthetic construct
SEQUENCE: 946
QVQLQESGGG LVQPGGSLRL SCAASGSIVS INSMGWYRQA PGKQRELVAA ITDQGRTTYA    60
DSVKGRFTIS RDDAKNKNTV YLQMNSLKAE DTAVYACKAF GRFDDYWGQG TQVTVSSAAA    120
YPYDVPDYGS HHHHHH                                                   136

SEQ ID NO: 947          moltype = AA  length = 141
FEATURE                 Location/Qualifiers
REGION                  1..141
                        note = Synthetic polymer
source                  1..141
                        mol_type = protein
                        organism = synthetic construct
SEQUENCE: 947
QVQLQESGGG LVQPGGSLRL SCAAYGSIFS INAMGWYRQA PGKERELVAG ITTQGRITYG    60
NSVRGRFTIS GDNAKNTVYL QMKSLKPEDT AVYYCSAWGV KTGPESGSGT LEGQGTQVTV    120
SSAAAYPYDV PDYGSHHHHH H                                              141

SEQ ID NO: 948          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 948
QVQLQESGGG LVQAGGSLRL SCAASGSIIG INSMGYYRTA PGKQRELVAA ITSGGRTTYV    60
DSVKGRFTIS RDNAKNTVYL QMNSLKPEDT AVYFCKAFTR DEDYWGQGTQ VTVSSAAAYP    120
YDVPDYGSHH HHHH                                                      134

SEQ ID NO: 949          moltype = AA  length = 138
FEATURE                 Location/Qualifiers
REGION                  1..138
                        note = Synthetic polymer
source                  1..138
                        mol_type = protein
                        organism = synthetic construct
SEQUENCE: 949
QVQLQESGGG LVQAGGSLRL SCAASGRTFP GYVMAWFRQS PGQEREFAAA INWRGGDTYY    60
ADSVKGRFTI SRDNVKNTVF LQMNSLKPED TAVYFCAARL TTEYDYAYWG QGTQVTVSSA    120
AAYPYDVPDY GSHHHHHH                                                  138

SEQ ID NO: 950          moltype = AA  length = 134
FEATURE                 Location/Qualifiers
REGION                  1..134
                        note = Synthetic polymer
```

```
source                  1..134
                        mol_type = protein
                        organism = synthetic construct
SEQUENCE: 950
QVQLQESGGG LVQPGESLRL SCAASGSIFS INAMGWYRQA PGKQRELVAA ITDGGAKTYA     60
DSVKGRFTIS TDNAGNTVYL QMDSLRPEDT AVYYCKAFTR GNDYWGQGTQ VTVSSAAAYP   120
YDVPDYGSHH HHHH                                                     134

SEQ ID NO: 951          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 951
QVQLQESGGG LVQAGESLRL SCVVSGRTFS INAMGWYRQA PGKQRELVAA ITNQGRLSYV     60
DSVKGRFTIS RDNAANTVYL QMNSLKPEDT AVYYCAAFQS SGIDWGQGTQ VTVSSAAAYP   120
YDVPDYGSHH HHHH                                                     134

SEQ ID NO: 952          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 952
QVQLQESGGG LVQAGGSLRL SCAASGRTLS SYTIGWYRQA PGKQRELVAA ITNQGRRTYA     60
DSVKGRFTIS RDNAKNTVYL QMDSLKSEDT AVYYCKGFSP TDDFWGQGTQ VTVSSAAAYP   120
YDVPDYGSHH HHHH                                                     134

SEQ ID NO: 953          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 953
QVQLQESGGG LVQPGGSLRL SCTASGSFFS INAMGWYRQA PGNQRELVAA ITNGGRIAYT     60
DSVKGRFTIS NDNAKNTVYL QMNSLKPEDT DVYYCNAKAI PIYGSTAEDY WGQGTQVTVS   120
SAAAYPYDVP DYGSHHHHHH                                               140

SEQ ID NO: 954          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 954
QVQLQESGGG LVQAGGSLRL SCAASGSIFS INSMGWYRQA PGKQRELVAA ITNGGRTTYA     60
DSVKGRFTIS RDNAKNTVYL QMDSLKPEDT AVYYCKGFSL TDDYWGQGTQ VTVSSAAAYP   120
YDVPDYGSHH HHHH                                                     134

SEQ ID NO: 955          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 955
QVQLQESGGG LVQTGGSLRL SCAASGSIFS FNAMGWYRQA PGKQRELVAA ITDGGRLTYA     60
DSAKGRFTIS RENTRNTVHL QMSSLKAEDT ADYYCTIWTR DRQQYWGQGT QVTVSSAAAY   120
PYDVPDYGSH HHHH                                                     135

SEQ ID NO: 956          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 956
QVQLQESGGG LVQAGGSLRL SCAASGSIFS INAMGWYRPA LGEQRELVAA ITTGGRTTYV     60
DSVKGRFSIS RDNAKNTVYL QMNSLKPEDT AVYFCKAFTR DEDFWGQGTQ VTVSSAAAYP   120
YDVPDYGSHH HHHH                                                     134
```

```
SEQ ID NO: 957          moltype = AA   length = 145
FEATURE                 Location/Qualifiers
REGION                  1..145
                        note = Synthetic polymer
source                  1..145
                        mol_type = protein
                        organism = synthetic construct
SEQUENCE: 957
QVQLQESGGG LVQAGGSLRL SCEASGRTFS TYAMAWFRQA PGKERDLVAA ISWSGGSTEY   60
HDSVKGRFTI SRDNTKNTVY LQMNSLKAED TAVYYCAAEV EGSGREGNFY GASWYPGQGT  120
QVTVSSAAAY PYDVPDYGSH HHHHH                                       145

SEQ ID NO: 958          moltype = AA   length = 132
FEATURE                 Location/Qualifiers
REGION                  1..132
                        note = Synthetic polymer
source                  1..132
                        mol_type = protein
                        organism = synthetic construct
SEQUENCE: 958
QVQLQESGGG LVQPGGSLRL SCAASGSFFS INAMGWYRQA PGKQRELVAA ITNQGRIAYA   60
DSVKGRFTIS RDNAKNTVYL QMNSLKPEDT AVYYCGRPGW DYWGQGTQVT VSSAAAYPYD  120
VPDYGSHHHH HH                                                     132

SEQ ID NO: 959          moltype = AA   length = 135
FEATURE                 Location/Qualifiers
REGION                  1..135
                        note = Synthetic polymer
source                  1..135
                        mol_type = protein
                        organism = synthetic construct
SEQUENCE: 959
QVQLQESGGG LVQAGGSLRL SCVASVNIGS LNSMVWYRQS PGKQRELVAG ITGSGQITYA   60
NSVRGRFTVS RDIAKSTAYL QMNTLKPEDT AVYYCAAYDR SATAYWGQGT QVTVSSAAAY  120
PYDVPDYGSH HHHH                                                   135

SEQ ID NO: 960          moltype = AA   length = 139
FEATURE                 Location/Qualifiers
REGION                  1..139
                        note = Synthetic polymer
source                  1..139
                        mol_type = protein
                        organism = synthetic construct
SEQUENCE: 960
QVQLQESGGG LVQAGGSLRV SCAASGRTLS NYAVGWWRQA PGKQREFVAA INWSSGGISY   60
SNSAKGRFAL SRDNAKNTVY LQMDSLKPED TAVYYCAAAS SVLSGTVDYW GQGTQVTVSS  120
AAAYPYDVPD YGSHHHHHH                                              139

SEQ ID NO: 961          moltype = AA   length = 135
FEATURE                 Location/Qualifiers
REGION                  1..135
                        note = Synthetic polymer
source                  1..135
                        mol_type = protein
                        organism = synthetic construct
SEQUENCE: 961
QVQLQESGGG LVQPGGSLRL SCAASGSISS INAMGWYRQA PGKQRELVAA ITGQGRTTYA   60
DSVKGRFTIS RDGAKNTVYL QMNSLKPEDT AVYYCKVFAA DGMEYWGKGT QVTVSSAAAY  120
PYDVPDYGSH HHHH                                                   135

SEQ ID NO: 962          moltype = AA   length = 140
FEATURE                 Location/Qualifiers
REGION                  1..140
                        note = Synthetic polymer
source                  1..140
                        mol_type = protein
                        organism = synthetic construct
SEQUENCE: 962
QVQLQESGGG LVQPGGSLRL SCAASGRFFR VNAMGWYRQA PGKQRELVAA ITNGGQIVYA   60
DSVKGRFTIS RDSAKNTVYL QMNSLKSEDT AVYYCNAKAA ASYVSTVADY WGQGTQVTVS  120
SAAAYPYDVP DYGSHHHHHH                                             140

SEQ ID NO: 963          moltype = AA   length = 134
FEATURE                 Location/Qualifiers
REGION                  1..134
                        note = Synthetic polymer
source                  1..134
                        mol_type = protein
```

```
                              -continued
                           organism = synthetic construct
SEQUENCE: 963
QVQLQESGGG LVQAGGSLRL SCAASGSVFS INAMGWYRQA PEKQRELVAA ITTQGRTTYE    60
DSVKGRFTIS RDGAQNTVYL QMDSLKPEDT AVYYCKAWTA KDDYWGKGTQ VTVSSAAAYP   120
YDVPDYGSHH HHHH                                                    134

SEQ ID NO: 964             moltype = AA   length = 136
FEATURE                    Location/Qualifiers
REGION                     1..136
                           note = Synthetic polymer
source                     1..136
                           mol_type = protein
                           organism = synthetic construct
SEQUENCE: 964
QVQLQESGGG RVQPGGSLRL SCAAIGSIFE INSIGWYRQA PGKQRELVAA ITSGGITNYA    60
NSVQGRSTIS RDNVNNTVYL QMNSLKPEDS AVYYCKGFTG WGKEDYWGQG TQVTVSSAAA   120
YPYDVPDYGS HHHHHH                                                  136

SEQ ID NO: 965             moltype = AA   length = 135
FEATURE                    Location/Qualifiers
REGION                     1..135
                           note = Synthetic polymer
source                     1..135
                           mol_type = protein
                           organism = synthetic construct
SEQUENCE: 965
QVQLQESGGG LVQTGGSLRL SCAASGSIFN INSMGWYRQA PGKQRELVAA ITVGGRLAYA    60
DSAKGRFTIS KESARNTVHL QMSSLKPEDT AVYYCTIWAA DYQQYWGQGT QVTVSSAAAY   120
PYDVPDYGSH HHHH                                                    135

SEQ ID NO: 966             moltype = AA   length = 135
FEATURE                    Location/Qualifiers
REGION                     1..135
                           note = Synthetic polymer
source                     1..135
                           mol_type = protein
                           organism = synthetic construct
SEQUENCE: 966
QVQLQESGGG LVQAGGSLRL SCAASVNIGT LNSMAWYREA PGKQRELVAG ITGGGQITYA    60
NSVRGRFTVS RDIAKSTAYL QMNTLKPEDT AVYYCAAYDR SATPYWGQGT QVTVSSAAAY   120
PYDVPDYGSH HHHH                                                    135

SEQ ID NO: 967             moltype = AA   length = 135
FEATURE                    Location/Qualifiers
REGION                     1..135
                           note = Synthetic polymer
source                     1..135
                           mol_type = protein
                           organism = synthetic construct
SEQUENCE: 967
QVQLQESGGG LVQTGGSLRL SCAASGSIFS INSMGWYRQA PGKQRELVAA ITSQGRSTYA    60
DSAKGRFTIS LGNARNTVNL QMSSLKTEDT AVYYCTIWAR DRQQYWGQGT QVTVSSAAAY   120
PYDVPDYGSH HHHH                                                    135

SEQ ID NO: 968             moltype = AA   length = 134
FEATURE                    Location/Qualifiers
REGION                     1..134
                           note = Synthetic polymer
source                     1..134
                           mol_type = protein
                           organism = synthetic construct
SEQUENCE: 968
QVQLQESGGG LVQPGGSLRL SCAASGRIGS INSMGWYRQA PGKQREMVAA ITNGGATVYA    60
DSVKGRFTIS RDNAGNTVDL HMNSLRPEDS AVYYCKAFTR GDDYWGQGTQ VTVSSAAAYP   120
YDVPDYGSHH HHHH                                                    134

SEQ ID NO: 969             moltype = AA   length = 135
FEATURE                    Location/Qualifiers
REGION                     1..135
                           note = Synthetic polymer
source                     1..135
                           mol_type = protein
                           organism = synthetic construct
SEQUENCE: 969
QVQLQESGGG LVQPGGSLKL SCAASGSIFS FNAMGWYRQA PGKQRELVAA ITDGGRLTYA    60
DSAKNRFTIS RENTRNTVHL QMSSLKAEDT AVYYCTIWTK DRQQYWGQGT QVTVSSAAAY   120
PYDVPDYGSH HHHH                                                    135

SEQ ID NO: 970             moltype = AA   length = 134
```

```
FEATURE            Location/Qualifiers
REGION             1..134
                   note = Synthetic polymer
source             1..134
                   mol_type = protein
                   organism = synthetic construct
SEQUENCE: 970
QVQLQESGGG LVQPGGSLRL SCAASGRISS INSMGWYRQA PGKQRELVAA ITNGGAKTYA    60
DSVKGRFTIS RDGAGNTVYL QMDNLRPEDT AVYYCKAFTR TYDYWGQGTQ VTVSSAAAYP   120
YDVPDYGSHH HHHH                                                    134

SEQ ID NO: 971           moltype = AA  length = 139
FEATURE            Location/Qualifiers
REGION             1..139
                   note = Synthetic polymer
source             1..139
                   mol_type = protein
                   organism = synthetic construct
SEQUENCE: 971
QVQLQESGGG LVQAGGSLRV SCAASGRTLS NYAVAWFRQA PGKQREFVAA INWSSGGISY    60
SNAAKGRFAL SRDNAKNTVY LQMDSLKPED TAVYYCAAAS SILSGTVDYW GQGTQVTVSS   120
AAAYPYDVPD YGSHHHHHH                                               139

SEQ ID NO: 972           moltype = AA  length = 135
FEATURE            Location/Qualifiers
REGION             1..135
                   note = Synthetic polymer
source             1..135
                   mol_type = protein
                   organism = synthetic construct
SEQUENCE: 972
QVQLQESGGG LVQPGGSLRL SCAASGRIGS INSMGWYRQA PGKQREMVAA ITNGGATVYA    60
DSVKGRFTIS RDNAGNTVDL HMNSLRPEDS AVYYCTIWAA DYQQYWGQGT QVTVSSAAAY   120
PYDVPDYGSH HHHH                                                    135

SEQ ID NO: 973           moltype = AA  length = 140
FEATURE            Location/Qualifiers
REGION             1..140
                   note = Synthetic polymer
source             1..140
                   mol_type = protein
                   organism = synthetic construct
SEQUENCE: 973
QVQLQESGGG LVQPGGSLRL SCAASRSFFS FNAMGWYRQA PGKQRELVAA ITNGGRIAYG    60
TSVMGRFTIS RDNAKNTVYL QMDSLKPEDT AVYYCNAKPA PVYGSTVGDY WGQGTQVTVS   120
SAAAYPYDVP DYGSHHHHHH                                              140

SEQ ID NO: 974           moltype = AA  length = 135
FEATURE            Location/Qualifiers
REGION             1..135
                   note = Synthetic polymer
source             1..135
                   mol_type = protein
                   organism = synthetic construct
SEQUENCE: 974
QVQLQESGGG LVQPGGSPRL SCAASGRFFR VNAMGWYRQA PGKQRELVAA ITNGGQTAYA    60
DSVKGRFTIS RDSAKNTVYL QMNSLKSEDT AVYYCKVFAA DGMEYWGKGT QVTVSSAAAY   120
PYDVPDYGSH HHHH                                                    135

SEQ ID NO: 975           moltype = AA  length = 133
FEATURE            Location/Qualifiers
REGION             1..133
                   note = Synthetic polymer
SITE               54
                   note = misc_feature - Xaa can be any naturally occurring
                    amino acid
source             1..133
                   mol_type = protein
                   organism = synthetic construct
SEQUENCE: 975
QVQLQESGGG LVQPGESLRL SCAASGIIFS INAMGWYRQA PGKQRELVAA ITNXGRTTYA    60
DSVKGRFTIS RDNAKNTVTL QMNSLKPEDT AVYYCNAFGS GGGVGQGTQV TVSSAAAYPY   120
DVPDYGSHHH HHH                                                     133

SEQ ID NO: 976           moltype = AA  length = 139
FEATURE            Location/Qualifiers
REGION             1..139
                   note = Synthetic polymer
source             1..139
```

```
                            mol_type = protein
                            organism = synthetic construct
SEQUENCE: 976
QVQLQESGGG LVQAGGSLRL SCAASGRTLS NYAVAWFRQA PGKQRELVAA IWWASGGISY    60
ANSAKGRFVL SRDNAKNTVY LQMDSLKPED TAVYYCAAAS SVLSGTADYW GQGTQVTVSS   120
AAAYPYDVPD YGSHHHHHH                                                139

SEQ ID NO: 977              moltype = AA   length = 134
FEATURE                     Location/Qualifiers
REGION                      1..134
                            note = Synthetic polymer
source                      1..134
                            mol_type = protein
                            organism = synthetic construct
SEQUENCE: 977
QVQLQESGGG LVQPGGSLRL SCAASGRIFS VNAMGWYRQA PGKQRELVAA ITNQGAPTYA    60
DSVKGRFTIS RDNAGNTVYL QMNSLRPEDT AVYYCKAFTR GDDYWGQGTQ VTVSSAAAYP   120
YDVPDYGSHH HHHH                                                     134

SEQ ID NO: 978              moltype = AA   length = 145
FEATURE                     Location/Qualifiers
REGION                      1..145
                            note = Synthetic polymer
source                      1..145
                            mol_type = protein
                            organism = synthetic construct
SEQUENCE: 978
QVQLQESGGG SVQAGGSLRL SCAASGRTFS SYAMAWFRQA PGMERELVAA ISWSGGSTYY    60
ADSVKGRFTI SRDNAENTVY LQMNSLKPED TAVYYCAAEA EGSGREGNFY ERSWYQGQGT   120
QVTVSSAAAY PYDVPDYGSH HHHHH                                         145

SEQ ID NO: 979              moltype = AA   length = 447
FEATURE                     Location/Qualifiers
REGION                      1..447
                            note = Synthetic polymer
source                      1..447
                            mol_type = protein
                            organism = synthetic construct
SEQUENCE: 979
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                       447

SEQ ID NO: 980              moltype = AA   length = 218
FEATURE                     Location/Qualifiers
REGION                      1..218
                            note = Synthetic polymer
source                      1..218
                            mol_type = protein
                            organism = synthetic construct
SEQUENCE: 980
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 981              moltype = AA   length = 440
FEATURE                     Location/Qualifiers
REGION                      1..440
                            note = Synthetic polymer
source                      1..440
                            mol_type = protein
                            organism = synthetic construct
SEQUENCE: 981
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP APEFLGGPSV FLFPPKPKDT   240
LMISRTPEVT CVVVDVSQED PEVQFNWYVD GVEVHNAKTK PREEQFNSTY RVVSVLTVLH   300
QDWLNGKEYK CKVSNKGLPS SIEKTISKAK GQPREPQVYT LPPSQEEMTK NQVSLTCLVK   360
GFYPSDIAVE WESNGQPENN YKTTPPVLDS DGSFFLYSRL TVDKSRWQEG NVFSCSVMHE   420
ALHNHYTQKS LSLSLGK                                                  440

SEQ ID NO: 982              moltype = AA   length = 214
```

```
FEATURE              Location/Qualifiers
REGION               1..214
                     note = Synthetic polymer
source               1..214
                     mol_type = protein
                     organism = synthetic construct
SEQUENCE: 982
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 983       moltype = AA   length = 106
FEATURE              Location/Qualifiers
REGION               1..106
                     note = Synthetic polymer
source               1..106
                     mol_type = protein
                     organism = synthetic construct
SEQUENCE: 983
EIVLTQSPSS LSASVGDRVT ITCSARSSVS YMHWYQQKPG KAPKLLIYRT SNLASGVPSR    60
FSGSGSGTDF TLTINSLQPE DFATYYCQQR SSFPLTFGGG TKLEIK                  106

SEQ ID NO: 984       moltype = AA   length = 106
FEATURE              Location/Qualifiers
REGION               1..106
                     note = Synthetic polymer
source               1..106
                     mol_type = protein
                     organism = synthetic construct
SEQUENCE: 984
EIVLTQSPSS LSASVGDRVT ITCSARSSVS YMHWFQQKPG KAPKLWIYRT SNLASGVPSR    60
FSGSGSGTDY TLTINSLQPE DFATYYCQQR SSFPLTFGGG TKLEIK                  106

SEQ ID NO: 985       moltype = AA   length = 106
FEATURE              Location/Qualifiers
REGION               1..106
                     note = Synthetic polymer
source               1..106
                     mol_type = protein
                     organism = synthetic construct
SEQUENCE: 985
EIVLTQSPSS LSASVGDRVT ITCSARSSVS YMHWFQQKPG KAPKLWIYRT SNLASGVPSR    60
FSGSGSGTDY CLTINSLQPE DFATYYCQQR SSFPLTFGGG TKLEIK                  106

SEQ ID NO: 986       moltype = AA   length = 106
FEATURE              Location/Qualifiers
REGION               1..106
                     note = Synthetic polymer
source               1..106
                     mol_type = protein
                     organism = synthetic construct
SEQUENCE: 986
EIVLTQSPSS LSASVGDRVT ITCSARSSVS YMHWFQQKPG KAPKLWIYRT SNLASGVPSR    60
FSGSGSGTSY CLTINSLQPE DFATYYCQQR SSFPLTFGGG TKLEIK                  106

SEQ ID NO: 987       moltype = AA   length = 117
FEATURE              Location/Qualifiers
REGION               1..117
                     note = Synthetic polymer
source               1..117
                     mol_type = protein
                     organism = synthetic construct
SEQUENCE: 987
QVQLVQSGSE LKKPGASVKI SCKASGYSFS NYGMNWVRQA PGQGLQWMGW INTDSGESTY    60
AEEFKGRFVF SLDTSVSTAY LQITSLTAED TGMYFCAKVG YDALDYWGQG TLVTVSS      117

SEQ ID NO: 988       moltype = AA   length = 117
FEATURE              Location/Qualifiers
REGION               1..117
                     note = Synthetic polymer
source               1..117
                     mol_type = protein
                     organism = synthetic construct
SEQUENCE: 988
QVQLVQSGSE LKKPGASVKI SCKASGYTFT NYGMNWVRQA PGQGLQWMGW INTDSGESTY    60
AEEFKGRFVF SLDTSVSTAY LQITSLTAED TGMYFCAKVG YDALDYWGQG TLVTVSS      117

SEQ ID NO: 989       moltype = AA   length = 117
```

```
FEATURE                 Location/Qualifiers
REGION                  1..117
                        note = Synthetic polymer
source                  1..117
                        mol_type = protein
                        organism = synthetic construct
SEQUENCE: 989
QVQLVQSGSE LKKPGASVKI SCKASGYTFT NYGMNWVRQA PGQGLQWMGW INTDSGESTY    60
AEEFKGRFVF SLDTSVNTAY LQITSLTAED TGMYFCVRVG YDALDYWGQG TLVTVSS     117

SEQ ID NO: 990          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 990
QIQLVQSGSE LKKPGASVKI SCKASGYTFT NYGMNWVRQA PGQGLQWMGW INTDSGESTY    60
AEEFKGRFVF SLDTSVNTAY LQITSLTAED TGMYFCVRVG YDALDYWGQG TLVTVSS     117

SEQ ID NO: 991          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 991
QIQLVQSGSE LKKPGASVKI SCKASGYTFT NYGMNWVKQA PGQGLKWMGW INTDSGESTY    60
AEEFKGRFAF SLDTSVNTAY LQITSLNAED TGMYFCVRVG YDALDYWGQG TLVTVSS     117

SEQ ID NO: 992          moltype = AA  length = 254
FEATURE                 Location/Qualifiers
REGION                  1..254
                        note = Synthetic polymer
source                  1..254
                        mol_type = protein
                        organism = synthetic construct
SEQUENCE: 992
LFTVTVPKEL YIIEHGSNVT LECNFDTGSH VNLGAITASL QKVENDTSPH RERATLLEEQ    60
LPLGKASFHI PQVQVRDEGQ YQCIIIYGVA WDYKYLTLKV KASYRKINTH ILKVPETDEV   120
ELTCQATGYP LAEVSWPNVS VPANTSHSRT PEGLYQVTSV LRLKPPPGRN FSCVFWNTHV   180
RELTLASIDL QSQMEPRTHP TWLLHIFIPF CIIAFIFIAT VIALRKQLCQ KLYSSKDTTK   240
RPVTTTKREV NSAI                                                    254

SEQ ID NO: 993          moltype = AA  length = 453
FEATURE                 Location/Qualifiers
REGION                  1..453
                        note = Synthetic polymer
source                  1..453
                        mol_type = protein
                        organism = synthetic construct
SEQUENCE: 993
MIFLLLMLSL ELQLHQIAAL FTVTVPKELY IIEHGSNVTL ECNFDTGSHV NLGAITASLQ    60
KVENDTSPHR ERATLLEEQL PLGKASFHIP QVQVRDEGQY QCIIIYGVAW DYKYLTLKVK   120
ASYRKINTHI LKVPETDEVE LTCQATGYPL AEVSWPNVSV PANTSHSRTP EGLYQVTSVL   180
RLKPPPGRNF SCVFWNTHVR ELTLASIDLQ SQMEPRTHPT WEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                               453

SEQ ID NO: 994          moltype = AA  length = 29
FEATURE                 Location/Qualifiers
REGION                  1..29
                        note = Synthetic polymer
source                  1..29
                        mol_type = protein
                        organism = synthetic construct
SEQUENCE: 994
SNTSESFKSN TSESFFRVTQ LAPKAQIKE                                     29

SEQ ID NO: 995          moltype = AA  length = 119
FEATURE                 Location/Qualifiers
REGION                  1..119
                        note = Synthetic polymer
source                  1..119
                        mol_type = protein
```

```
                     organism = synthetic construct
SEQUENCE: 995
EVQLQQSGPV LVKPGASVKM SCKASGYTFT DYYMNWVKQS HGKSLEWIGN INPYNGGTTY    60
NQKFKGKATL TVDKSSRTAY MEINSLTSED SAVYYCARGR IYDGSLDYWG QGTALTVSS    119

SEQ ID NO: 996          moltype = AA   length = 106
FEATURE                 Location/Qualifiers
REGION                  1..106
                        note = Synthetic polymer
source                  1..106
                        mol_type = protein
                        organism = synthetic construct
SEQUENCE: 996
DIQMTQFPSS LCASQGGKVT VTCKASQDIN NYMAWYQHKP GKGPRLLIHY TSTLLSGIPS    60
RFSGSGSGRD YSFSISNLEP EDIATYYCLQ YDNLWTFGGG TKLEIK                 106

SEQ ID NO: 997          moltype = AA   length = 116
FEATURE                 Location/Qualifiers
REGION                  1..116
                        note = Synthetic polymer
source                  1..116
                        mol_type = protein
                        organism = synthetic construct
SEQUENCE: 997
QVQLQQSGAE LAKPGASVRL SCKASGYTFT NYWMHWVKQR PGQGLEWIGH INPSSGFTTY    60
NQNFKDKATL TADKSSNTAY MQLSSLTYED SAVYFCARED YDVDYWGQGT TLTVSS      116

SEQ ID NO: 998          moltype = AA   length = 107
FEATURE                 Location/Qualifiers
REGION                  1..107
                        note = Synthetic polymer
source                  1..107
                        mol_type = protein
                        organism = synthetic construct
SEQUENCE: 998
DIVMTQSQKF MSTSVGDRVS VTCKASQSVD TNVAWYQQKP GQSPKALIFS ASYRYSGVPD    60
RFTGSGSGTD FTLTINSVQS EDLAEYFCQQ YNSYPYTFGS GTKLEIK                107

SEQ ID NO: 999          moltype = AA   length = 122
FEATURE                 Location/Qualifiers
REGION                  1..122
                        note = Synthetic polymer
source                  1..122
                        mol_type = protein
                        organism = synthetic construct
SEQUENCE: 999
EVQLVESGGG LVKPGGSLKL SCAASGFTFS DYGMHWVRQA PEKGLEWVAY ISSGSYTIYY    60
TDTVKGRFTI SRDNAKNTLF LQMTSLRSED TAMYYCARRG YGSFYEYYFD YWGQGTTLTV  120
SS                                                                 122

SEQ ID NO: 1000         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1000
QIVLTQSPAL MSASPGEKVT MTCSASSSVS YMYWYQQKPR SSPKPWIYLT SNLASGVPAR    60
FSGSGSGTSY SLTISSMEAE DAATYYCQQW SSNPFTFGSG TKLEIK                 106

SEQ ID NO: 1001         moltype = AA   length = 119
FEATURE                 Location/Qualifiers
REGION                  1..119
                        note = Synthetic polymer
source                  1..119
                        mol_type = protein
                        organism = synthetic construct
SEQUENCE: 1001
EVQLVESGGG LVQAGKSLRL SCAASGSIFS IHAMGWFRQA PGKEREFVAA ITWSGGITYY    60
EDSVKGRFTI SRDNAKNTVY LQMNSLKPED TAIYYCAADR AESSWYDYWG QGTQVTVSS   119

SEQ ID NO: 1002         moltype = AA   length = 119
FEATURE                 Location/Qualifiers
REGION                  1..119
                        note = Synthetic polymer
source                  1..119
                        mol_type = protein
                        organism = synthetic construct
```

```
SEQUENCE: 1002
EVQLVESGGG LVQAGGSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTQVTVSS    119

SEQ ID NO: 1003         moltype = AA   length = 119
FEATURE                 Location/Qualifiers
REGION                  1..119
                        note = Synthetic polymer
source                  1..119
                        mol_type = protein
                        organism = synthetic construct
SEQUENCE: 1003
EVQLVESGGG LVQAGGSLRL SCAASGSISS IHAMGWFRQA PGKEREFVAA ITWSGGITYY    60
ADSLKGRFTI SRDNAKNTGY LQMNSLKPED TAIYYCAADR AQSSWYDYWG QGTQVTVSS    119

SEQ ID NO: 1004         moltype = AA   length = 119
FEATURE                 Location/Qualifiers
REGION                  1..119
                        note = Synthetic polymer
source                  1..119
                        mol_type = protein
                        organism = synthetic construct
SEQUENCE: 1004
EVQLVESGGG LVQAGGSLGL SCAASGSIFS INAMAWFRQA PGKEREFVAL ISWSGGSTYY    60
EDSVKGRFTI SRDNAKNTVY LQMNSLKPED TAIYYCAADR VDSNWYDYWG QGTQVTVSS    119

SEQ ID NO: 1005         moltype = AA   length = 120
FEATURE                 Location/Qualifiers
REGION                  1..120
                        note = Synthetic polymer
source                  1..120
                        mol_type = protein
                        organism = synthetic construct
SEQUENCE: 1005
EVQLVESGGG LVQAGGSLRL SCAASGRAFS SGTMGWFRRA PGKEREFVAS IPWSGGRIYY    60
ADSVKGRFTI SRDNAQNTVY LQMNSLKPED TAVYYCAVKE RSTGWDFASW GQCTQVTVSS   120

SEQ ID NO: 1006         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1006
QVQLVQSGAE LKQPGASVKM SCKASGYSFT SSWIHWVKQA PGQGLEWIGY IYPSTGFTEY    60
NQKFKDRATL TADKSTSTAY MELSSLRSED SAVYYCARWR DSSGYHAMDY WGQGTSVTVS   120
S                                                                  121

SEQ ID NO: 1007         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1007
QVQLVQSGAE VKQPGASVKM SCKASGYSFT SSWIHWVKQA PGQGLEWIGY IYPSTGFTEY    60
NQKFKDRATL TADKSTSTAY MELSSLRSED TAVYYCARWR DSSGYHAMDY WGQGTSVTVS   120
S                                                                  121

SEQ ID NO: 1008         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1008
QVQLVQSGHE VKQPGASVKM SCKASGYSFT SSWIHWVKQA PGQGLEWIGY IYPSTGFTEY    60
NQKFKDRATL TADKSTSTAY MELSSLRSED TAVYYCARWR DSSGYHAMDY WGQGTLVTVS   120
S                                                                  121

SEQ ID NO: 1009         moltype = AA   length = 121
FEATURE                 Location/Qualifiers
REGION                  1..121
                        note = Synthetic polymer
source                  1..121
                        mol_type = protein
```

```
                    organism = synthetic construct
SEQUENCE: 1009
QVQLVQSGHE VKQPGASVKM SCKASGYSFT SSWIHWVRQA PGQGLEWIGY IYPSTGFTEY      60
NQKFKDRATL TADKSTSTAY MELSSLRSED TAVYYCARWR DSSGYHAMDY WGQGTLVTVS     120
S                                                                    121

SEQ ID NO: 1010        moltype = AA   length = 121
FEATURE                Location/Qualifiers
REGION                 1..121
                       note = Synthetic polymer
source                 1..121
                       mol_type = protein
                       organism = synthetic construct
SEQUENCE: 1010
QVQLVQSGHE VKQPGASVKV SCKASGYSFT SSWIHWVRQA PGQGLEWIGY IYPSTGFTEY      60
NQKFKDRATI TADKSTSTAY MELSSLRSED TAVYYCARWR DSSGYHAMDY WGQGTLVTVS     120
S                                                                    121

SEQ ID NO: 1011        moltype = AA   length = 111
FEATURE                Location/Qualifiers
REGION                 1..111
                       note = Synthetic polymer
source                 1..111
                       mol_type = protein
                       organism = synthetic construct
SEQUENCE: 1011
DIVLTQSPAS LTLSPGQRLT ISCRASQSVS TSGYSYMHWY QQKPDQSPKL LIKFGSNLES      60
GIPARFSGSG SGTDFTLTIS SLEEEDFATY YCQHSWEIPY TFGQGTKLEI K              111

SEQ ID NO: 1012        moltype = AA   length = 111
FEATURE                Location/Qualifiers
REGION                 1..111
                       note = Synthetic polymer
source                 1..111
                       mol_type = protein
                       organism = synthetic construct
SEQUENCE: 1012
DIVLTQSPAT LSLSPGQRLT ISCRASQSVS TSGYSYMHWY QQKPDQSPKL LIKFGSNLES      60
GIPARFSGSG SGTDFTLTIS SLEPEDFATY YCQHSWEIPY TFGQGTKLEI K              111

SEQ ID NO: 1013        moltype = AA   length = 111
FEATURE                Location/Qualifiers
REGION                 1..111
                       note = Synthetic polymer
source                 1..111
                       mol_type = protein
                       organism = synthetic construct
SEQUENCE: 1013
EIVLTQSPAT LSLSPGQRLT ISCRASQSVS TSGYSYMHWY QQKPDQSPKL LIKFGSNLES      60
GIPARFSGSG SGTDFTLTIS SLEPEDFATY YCQHSWEIPY TFGQGTKLEI K              111

SEQ ID NO: 1014        moltype = AA   length = 111
FEATURE                Location/Qualifiers
REGION                 1..111
                       note = Synthetic polymer
source                 1..111
                       mol_type = protein
                       organism = synthetic construct
SEQUENCE: 1014
DIVLTQSPAT LSLSPGQRLT ISCRASQSVS TSGYSYMHWY QQKPDQSPKL LIKFGSNLES      60
GIPARFSGSG SGTDFTLTIS SLEPEDFAVY YCQHSWEIPY TFGQGTKLEI K              111

SEQ ID NO: 1015        moltype = AA   length = 451
FEATURE                Location/Qualifiers
REGION                 1..451
                       note = Synthetic polymer
source                 1..451
                       mol_type = protein
                       organism = synthetic construct
SEQUENCE: 1015
EVQLVESGGG LVQPGGSLRL SCAASGFTFS RYWMSWVRQA PGKGLEWVAN IKQDGSEKYY      60
VDSVKGRFTI SRDNAKNSLY LQMNSLRAED TAVYYCAREG GWFGELAFDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKRVE PKSCDKTHTC PPCPAPEFEG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPASIEKTI SKAKGQPREP QVYTLPPSRE     360
EMTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                    451
```

```
SEQ ID NO: 1016            moltype = AA   length = 215
FEATURE                    Location/Qualifiers
REGION                     1..215
                           note = Synthetic polymer
source                     1..215
                           mol_type = protein
                           organism = synthetic construct
SEQUENCE: 1016
EIVLTQSPGT LSLSPGERAT LSCRASQRVS SSYLAWYQQK PGQAPRLLIY DASSRATGIP    60
DRFSGSGSGT DFTLTISRLE PEDFAVYYCQ QYGSLPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 1017            moltype = AA   length = 121
FEATURE                    Location/Qualifiers
REGION                     1..121
                           note = Synthetic polymer
source                     1..121
                           mol_type = protein
                           organism = synthetic construct
SEQUENCE: 1017
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
S                                                                  121

SEQ ID NO: 1018            moltype = AA   length = 108
FEATURE                    Location/Qualifiers
REGION                     1..108
                           note = Synthetic polymer
source                     1..108
                           mol_type = protein
                           organism = synthetic construct
SEQUENCE: 1018
EIVLTQSPGT LSLSPGERAT LSCRASQRVS SSYLAWYQQK PGQAPRLLIY DASSRATGIP    60
DRFSGSGSGT DFTLTISRLE PEDFAVYYCQ QYGSLPWTFG QGTKVEIK               108

SEQ ID NO: 1019            moltype = AA   length = 448
FEATURE                    Location/Qualifiers
REGION                     1..448
                           note = Synthetic polymer
source                     1..448
                           mol_type = protein
                           organism = synthetic construct
SEQUENCE: 1019
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 1020            moltype = AA   length = 214
FEATURE                    Location/Qualifiers
REGION                     1..214
                           note = Synthetic polymer
source                     1..214
                           mol_type = protein
                           organism = synthetic construct
SEQUENCE: 1020
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 1021            moltype = AA   length = 450
FEATURE                    Location/Qualifiers
REGION                     1..450
                           note = Synthetic polymer
source                     1..450
                           mol_type = protein
                           organism = synthetic construct
SEQUENCE: 1021
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
```

```
STYRVVSVLT VLHQDWLNGK EYKCKVSNKA LPAPIEKTIS KAKGQPREPQ VYTLPPSRDE      360
LTKNQVSLTC LVKGFYPSDI AVEWESNGQP ENNYKTTPPV LDSDGSFFLY SKLTVDKSRW      420
QQGNVFSCSV MHEALHNHYT QKSLSLSPGK                                      450

SEQ ID NO: 1022              moltype = AA   length = 216
FEATURE                      Location/Qualifiers
REGION                       1..216
                             note = Synthetic polymer
source                       1..216
                             mol_type = protein
                             organism = synthetic construct
SEQUENCE: 1022
QSALTQPASV SGSPGQSITI SCTGTSSDVG GYNYVSWYQQ HPGKAPKLMI YDVSNRPSGV       60
SNRFSGSKSG NTASLTISGL QAEDEADYYC SSYTSSSTRV FGTGTKVTVL GQPKANPTVT      120
LFPPSSEELQ ANKATLVCLI SDFYPGAVTV AWKADGSPVK AGVETTKPSK QSNNKYAASS      180
YLSLTPEQWK SHRSYSCQVT HEGSTVEKTV APTECS                               216

SEQ ID NO: 1023              moltype = AA   length = 123
FEATURE                      Location/Qualifiers
REGION                       1..123
                             note = Synthetic polymer
source                       1..123
                             mol_type = protein
                             organism = synthetic construct
SEQUENCE: 1023
QVQLVQSGAE VKKPGSSVKV SCKTSGDTFS TYAISWVRQA PGQGLEWMGG IIPIFGKAHY       60
AQKFQGRVTI TADESTSTAY MELSSLRSED TAVYFCARKF HFVSGSPFGM DVWGQGTTVT      120
VSS                                                                   123

SEQ ID NO: 1024              moltype = AA   length = 106
FEATURE                      Location/Qualifiers
REGION                       1..106
                             note = Synthetic polymer
source                       1..106
                             mol_type = protein
                             organism = synthetic construct
SEQUENCE: 1024
EIVLTQSPAT LSLSPGERAT LSCRASQSVS SYLAWYQQKP GQAPRLLIYD ASNRATGIPA       60
RFSGSGSGTD FTLTISSLEP EDFAVYYCQQ RSNWPTFGQG TKVEIK                    106

SEQ ID NO: 1025              moltype = AA   length = 117
FEATURE                      Location/Qualifiers
REGION                       1..117
                             note = Synthetic polymer
source                       1..117
                             mol_type = protein
                             organism = synthetic construct
SEQUENCE: 1025
QVQLVQSGAE VKKPGASVKV SCKASGYTFT DYGFSWVRQA PGQGLEWMGW ITAYNGNTNY       60
AQKLQGRVTM TTDTSTSTVY MELRSLRSDD TAVYYCARDY FYGMDVWGQG TTVTVSS         117

SEQ ID NO: 1026              moltype = AA   length = 107
FEATURE                      Location/Qualifiers
REGION                       1..107
                             note = Synthetic polymer
source                       1..107
                             mol_type = protein
                             organism = synthetic construct
SEQUENCE: 1026
EIVLTQSPAT LSLSPGERAT LSCRASQSVS SYLVWYQQKP GQAPRLLIYD ASNRATGIPA       60
RFSGSGSGTD FTLTISSLEP EDFAVYYCQQ RSNWPRTFGQ GTKVEIK                   107

SEQ ID NO: 1027              moltype = AA   length = 118
FEATURE                      Location/Qualifiers
REGION                       1..118
                             note = Synthetic polymer
source                       1..118
                             mol_type = protein
                             organism = synthetic construct
SEQUENCE: 1027
QVQLVQSGAE VKKPGASVKV SCKASGYTFT SYDVHWVRQA PGQRLEWMGW LHADTGITKF       60
SQKFQGRVTI TRDTSASTAY MELSSLRSED TAVYYCARER IQLWFDYWGQ GTLVTVSS       118

SEQ ID NO: 1028              moltype = AA   length = 107
FEATURE                      Location/Qualifiers
REGION                       1..107
                             note = Synthetic polymer
source                       1..107
                             mol_type = protein
```

```
                        organism = synthetic construct
SEQUENCE: 1028
DIQMTQSPSS LSASVGDRVT ITCRASQGIS SWLAWYQQKP EKAPKSLIYA ASSLQSGVPS      60
RFSGSGSGTD FTLTISSLQP EDFATYYCQQ YNSYPYTFGQ GTKLEIK                  107

SEQ ID NO: 1029         moltype = AA   length = 120
FEATURE                 Location/Qualifiers
REGION                  1..120
                        note = Synthetic polymer
source                  1..120
                        mol_type = protein
                        organism = synthetic construct
SEQUENCE: 1029
QVQLVQSGAE VKKPGSSVKV SCKVSGGIFS TYAINWVRQA PGQGLEWMGG IIPIFGTANH      60
AQKFQGRVTI TADESTSTAY MELSSLRSED TAVYYCARDQ GIAAALFDYW GQGTLVTVSS     120

SEQ ID NO: 1030         moltype = AA   length = 108
FEATURE                 Location/Qualifiers
REGION                  1..108
                        note = Synthetic polymer
source                  1..108
                        mol_type = protein
                        organism = synthetic construct
SEQUENCE: 1030
EIVLTQSPGT LSLSPGERAT LSCRASQSVS SSYLAWYQQK PGQAPRLLIY GASSRATGIP      60
DRFSGSGSGT DFTLTISRLE PEDFAVYYCQ QYGSSPWTFG QGTKVEIK                 108

SEQ ID NO: 1031         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1031
EVQLVESGGG LVQPGRSLRL SCAVSGFTFD DYVVHWVRQA PGKGLEWVSG ISGNSGNIGY      60
ADSVKGRFTI SRDNAKNSLY LQMNSLRAED TALYYCAVPF DYWGQGTLVT VSS           113

SEQ ID NO: 1032         moltype = AA   length = 107
FEATURE                 Location/Qualifiers
REGION                  1..107
                        note = Synthetic polymer
source                  1..107
                        mol_type = protein
                        organism = synthetic construct
SEQUENCE: 1032
DIQMTQSPSS LSASVGDRVT ITCRASQGIS SWLAWYQQKP EKAPKSLIYA ASSLQSGVPS      60
RFSGSGSGTD FTLTISSLQP EDFATYYCQQ YNSYPYTFGQ GTKLEIK                  107

SEQ ID NO: 1033         moltype = AA   length = 123
FEATURE                 Location/Qualifiers
REGION                  1..123
                        note = Synthetic polymer
source                  1..123
                        mol_type = protein
                        organism = synthetic construct
SEQUENCE: 1033
QVQLVQSGAE VKKPGSSVKV SCKTSGDTFS SYAISWVRQA PGQGLEWMGG IIPIFGRAHY      60
AQKFQGRVTI TADESTSTAY MELSSLRSED TAVYFCARKF HFVSGSPFGM DVWGQGTTVT    120
VSS                                                                 123

SEQ ID NO: 1034         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1034
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPTFGQG TKVEIK                   106

SEQ ID NO: 1035         moltype = AA   length = 123
FEATURE                 Location/Qualifiers
REGION                  1..123
                        note = Synthetic polymer
source                  1..123
                        mol_type = protein
                        organism = synthetic construct
```

```
SEQUENCE: 1035
QVQLVQSGAE VKKPGSSVKV SCKTSGGTFS SYAISWVRQA PGQGLEWMGG IIPIFGKAHY    60
AQKFQGRVTI TADESTTTAY MELSSLRSED TAVYYCARKY DYVSGSPFGM DVWGQGTTVT   120
VSS                                                                 123

SEQ ID NO: 1036         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1036
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIK                  106

SEQ ID NO: 1037         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1037
QVQLVQSGAE VKKPGSSVKV SCKASGGTFS SYAINWVRQA PGQGLEWMGG IIPIFGSANY    60
AQKFQDRVTI TADESTSAAY MELSSLRSED TAVYYCARDS SGWSRYYMDV WGQGTTVTVS   120
S                                                                   121

SEQ ID NO: 1038         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1038
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPFGGG TKVEIK                  106

SEQ ID NO: 1039         moltype = AA   length = 123
FEATURE                 Location/Qualifiers
REGION                  1..123
                        note = Synthetic polymer
source                  1..123
                        mol_type = protein
                        organism = synthetic construct
SEQUENCE: 1039
QVQLVQSGAE VKEPGSSVKV SCKASGGTFN SYAISWVRQA PGQGLEWMGG IIPLFGIAHY    60
AQKFQGRVTI TADESTNTAY MDLSSLRSED TAVYYCARKY SYVSGSPFGM DVWGQGTTVT   120
VSS                                                                 123

SEQ ID NO: 1040         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1040
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TRLEIK                  106

SEQ ID NO: 1041         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1041
EVQLVESGGG LVQPGRSLRL SCAASGITFD DYGMHWVRQA PGKGLEWVSG ISWNRGRIEY    60
ADSVKGRFTI SRDNAKNSLY LQMNSLRAED TALYYCAKGR FRYFDWFLDY WGQGTLVTVS   120
S                                                                   121

SEQ ID NO: 1042         moltype = AA   length = 107
FEATURE                 Location/Qualifiers
REGION                  1..107
                        note = Synthetic polymer
source                  1..107
```

```
                        mol_type = protein
                        organism = synthetic construct
SEQUENCE: 1042
AIQLTQSPSS LSASVGDRVT ITCRASQGIS SALAWYQQKP GKAPKLLIYD ASSLESGVPS      60
RFSGSGSGTD FTLTISSLQP EDFATYYCQQ FNSYPFTFGP GTKVDIK                   107

SEQ ID NO: 1043         moltype = AA   length = 118
FEATURE                 Location/Qualifiers
REGION                  1..118
                        note = Synthetic polymer
source                  1..118
                        mol_type = protein
                        organism = synthetic construct
SEQUENCE: 1043
EVKLQESGPS LVKPSQTLSL TCSVTGYSIT SDYWNWIRKF PGNKLEYVGY ISYTGSTYYN      60
PSLKSRISIT RDTSKNQYYL QLNSVTSEDT ATYYCARYGG WLSPFDYWGQ GTTLTVSS       118

SEQ ID NO: 1044         moltype = AA   length = 107
FEATURE                 Location/Qualifiers
REGION                  1..107
                        note = Synthetic polymer
source                  1..107
                        mol_type = protein
                        organism = synthetic construct
SEQUENCE: 1044
DIVMTQSHKL MSTSVGDRVS ITCKASQDVG TAVAWYQQKP GQSPKLLIYW ASTRHTGVPD      60
RFTGSGSGTD FTLTISNVQS EDLADYFCQQ DSSYPLTFGA GTKVELK                   107

SEQ ID NO: 1045         moltype = AA   length = 120
FEATURE                 Location/Qualifiers
REGION                  1..120
                        note = Synthetic polymer
source                  1..120
                        mol_type = protein
                        organism = synthetic construct
SEQUENCE: 1045
EVQLQESGPG LVAPSQSLSI TCTVSGFSLT TYSINWIRQP PGKGLEWLGV MWAGGGTNSN      60
SVLKSRLIIS KDNSKSQVFL KMNSLQTDDT ARYYCARYYG NSPYYAIDYW GQGTSVTVSS    120

SEQ ID NO: 1046         moltype = AA   length = 107
FEATURE                 Location/Qualifiers
REGION                  1..107
                        note = Synthetic polymer
source                  1..107
                        mol_type = protein
                        organism = synthetic construct
SEQUENCE: 1046
DIVTTQSHKL MSTSVGDRVS ITCKASQDVG TAVAWYQQKP GQSPKLLIYW ASTRHTGVPD      60
RFTGSGSGTD FTLTISNVQS EDLADYFCQQ DSSYPLTFGA GTKVELK                   107

SEQ ID NO: 1047         moltype = AA   length = 118
FEATURE                 Location/Qualifiers
REGION                  1..118
                        note = Synthetic polymer
source                  1..118
                        mol_type = protein
                        organism = synthetic construct
SEQUENCE: 1047
EVKLQESGPS LVKPSQTLSL TCSVTGYSII SDYWNWIRKF PGNKLEYLGY ISYTGSTYYN      60
PSLKSRISIT RDTSKNQYYL QLNSVTTEDT ATYYCARRGG WLLPFDYWGQ GTTLTVSS      118

SEQ ID NO: 1048         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1048
DIVMTQSPSS LAVSVGEKVS MGCKSSQSLL YSSNQKNSLA WYQQKPGQSP KLLIDWASTR      60
ESGVPDRFTG SGSGTDFTLT ISSVKAEDLA VYYCQQYYGY PLTFGAGTKL ELK           113

SEQ ID NO: 1049         moltype = AA   length = 118
FEATURE                 Location/Qualifiers
REGION                  1..118
                        note = Synthetic polymer
source                  1..118
                        mol_type = protein
                        organism = synthetic construct
```

```
SEQUENCE: 1049
EVKLQESGPS LVKPGASVKL SCKASGYTFT SYDINWVKQR PGQGLEWIGW IFPRDNNTKY  60
NENFKGKATL TVDTSSTTAY MELHSLTSED SAVYFCTKEN WVGDFDYWGQ GTTLTLSS   118

SEQ ID NO: 1050         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1050
DIVMTQSPAI MSASPGEKVT MTCSASSSIR YMHWYQQKPG TSPKRWISDT SKLTSGVPAR  60
FSGSGSGTSY ALTISSMEAE DAATYYCHQR SSYPWTFGGG TKLEIK                106

SEQ ID NO: 1051         moltype = AA   length = 114
FEATURE                 Location/Qualifiers
REGION                  1..114
                        note = Synthetic polymer
source                  1..114
                        mol_type = protein
                        organism = synthetic construct
SEQUENCE: 1051
EVQLQQSGPD LVTPGASVRI SCQASGYTFP DYYMNWVKQS HGKSLEWIGD IDPNYGGTTY  60
NQKFKGKAIL TVDRSSSTAY MELRSLTSED SAVYYCARGA LTDWGQGTSL TVSS        114

SEQ ID NO: 1052         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1052
QIVLSQSPAI LSASPGEKVT MTCRASSSVS YIYWFQQKPG SSPKPWIYAT FNLASGVPAR  60
FSGSGSGTSY SLTISRVETE DAATYYCQQW SNNPLTFGAG TKLELK                106

SEQ ID NO: 1053         moltype = AA   length = 115
FEATURE                 Location/Qualifiers
REGION                  1..115
                        note = Synthetic polymer
source                  1..115
                        mol_type = protein
                        organism = synthetic construct
SEQUENCE: 1053
EVQLVQSGPE LKKPGASVKM SCKASGYTFT SYVMHWVKQA PGQRLEWIGY VNPFNDGTKY  60
NEMFKGRATL TSDKSTSTAY MELSSLRSED SAVYYCARQA WGYPWGQGTL VTVSS       115

SEQ ID NO: 1054         moltype = AA   length = 115
FEATURE                 Location/Qualifiers
REGION                  1..115
                        note = Synthetic polymer
source                  1..115
                        mol_type = protein
                        organism = synthetic construct
SEQUENCE: 1054
EVQLVQSGAE VKKPGASVKM SCKASGYTFT SYVMHWVKQA PGQRLEWIGY VNPFNDGTKY  60
NEMFKGRATL TSDKSTSTAY MELSSLRSED TAVYYCARQA WGYPWGQGTL VTVSS       115

SEQ ID NO: 1055         moltype = AA   length = 115
FEATURE                 Location/Qualifiers
REGION                  1..115
                        note = Synthetic polymer
source                  1..115
                        mol_type = protein
                        organism = synthetic construct
SEQUENCE: 1055
EVQLVQSGAE VKKPGASVKM SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 1056         moltype = AA   length = 115
FEATURE                 Location/Qualifiers
REGION                  1..115
                        note = Synthetic polymer
source                  1..115
                        mol_type = protein
                        organism = synthetic construct
SEQUENCE: 1056
EVQLVQSGAE VKKPGASVKV SCKASGYTFT SYVMHWVRQA PGQRLEWIGY VNPFNDGTKY  60
```

```
NEMFKGRATL TSDKSTSTAY MELSSLRSED TAVYYCARQA WGYPWGQGTL VTVSS         115

SEQ ID NO: 1057          moltype = AA   length = 115
FEATURE                  Location/Qualifiers
REGION                   1..115
                         note = Synthetic polymer
source                   1..115
                         mol_type = protein
                         organism = synthetic construct
SEQUENCE: 1057
EVQLVQSGAE VKKPGASVKV SCKASGYTFT SYVMHWVRQA PGQRLEWIGY VNPFNDGTKY    60
NEMFKGRATI TSDKSTSTAY MELSSLRSED TAVYYCARQA WGYPWGQGTL VTVSS         115

SEQ ID NO: 1058          moltype = AA   length = 111
FEATURE                  Location/Qualifiers
REGION                   1..111
                         note = Synthetic polymer
source                   1..111
                         mol_type = protein
                         organism = synthetic construct
SEQUENCE: 1058
DIVLTQSPAS LALSPGERAT LSCRATESVE YYGTSLVQWY QQKPGQPPKL LIYAASSVDS    60
GVPSRFSGSG SGTDFTLTIN SLEEEDAAMY FCQQSRRVPY TFGQGTKLEI K            111

SEQ ID NO: 1059          moltype = AA   length = 111
FEATURE                  Location/Qualifiers
REGION                   1..111
                         note = Synthetic polymer
source                   1..111
                         mol_type = protein
                         organism = synthetic construct
SEQUENCE: 1059
DIVLTQSPAT LSLSPGERAT LSCRATESVE YYGTSLVQWY QQKPGQPPKL LIYAASSVDS    60
GVPSRFSGSG SGTDFTLTIN SLEAEDAAMY FCQQSRRVPY TFGQGTKLEI K            111

SEQ ID NO: 1060          moltype = AA   length = 111
FEATURE                  Location/Qualifiers
REGION                   1..111
                         note = Synthetic polymer
source                   1..111
                         mol_type = protein
                         organism = synthetic construct
SEQUENCE: 1060
EIVLTQSPAT LSLSPGERAT LSCRATESVE YYGTSLVQWY QQKPGQPPKL LIYAASSVDS    60
GVPSRFSGSG SGTDFTLTIN SLEAEDAAMY FCQQSRRVPY TFGQGTKLEI K            111

SEQ ID NO: 1061          moltype = AA   length = 111
FEATURE                  Location/Qualifiers
REGION                   1..111
                         note = Synthetic polymer
source                   1..111
                         mol_type = protein
                         organism = synthetic construct
SEQUENCE: 1061
DIVLTQSPAT LSLSPGERAT LSCRATESVE YYGTSLVQWY QQKPGQPPKL LIYAASSVDS    60
GVPSRFSGSG SGTDFTLTIN SLEAEDAATY FCQQSRRVPY TFGQGTKLEI K            111

SEQ ID NO: 1062          moltype = AA   length = 120
FEATURE                  Location/Qualifiers
REGION                   1..120
                         note = Synthetic polymer
source                   1..120
                         mol_type = protein
                         organism = synthetic construct
SEQUENCE: 1062
EVQLVESGGG LVKPGGSLRL SCAASGFTFS TYSMNWVRQA PGKGLEWVSS ISSSGDYIYY    60
ADSVKGRFTI SRDNAKNSLF LQMNSLKAED TAVYYCARDL VTSMVAFDYW GQGTLVTVSS   120

SEQ ID NO: 1063          moltype = AA   length = 108
FEATURE                  Location/Qualifiers
REGION                   1..108
                         note = Synthetic polymer
source                   1..108
                         mol_type = protein
                         organism = synthetic construct
SEQUENCE: 1063
SYELTQPPSV SVSPGQAARI TCSGDALPQK YVFWYQQKSG QAPVLVIYED SKRPSGIPER    60
FSGSSSGTMA TLTISGAQVE DEADYYCYST DRSGNHRVFG GGTRLTVL                108
```

```
SEQ ID NO: 1064         moltype = AA   length = 120
FEATURE                 Location/Qualifiers
REGION                  1..120
                        note = Synthetic polymer
source                  1..120
                        mol_type = protein
                        organism = synthetic construct
SEQUENCE: 1064
EVQLVESGGG LVQPGGSLRL SCAASGFTFS SYWMSWVRQA PGKGLEWVAN IKQDGGEQYY    60
VDSVKGRFTI SRDNAKNSLY LQMNSLRAED TAVYYCARDW NYGYYDMDVW GQGTTVTVSS   120

SEQ ID NO: 1065         moltype = AA   length = 108
FEATURE                 Location/Qualifiers
REGION                  1..108
                        note = Synthetic polymer
source                  1..108
                        mol_type = protein
                        organism = synthetic construct
SEQUENCE: 1065
EIVLTQSPGT LSLSPGERAT LSCRASQSVS SNYLAWFQQK PGQAPRLLIF GTSSRATGIP    60
DRFSGSGSGT DFTLTISRLE PEDFAVYYCQ QYGSSIFTFG PGTKVDIK                108

SEQ ID NO: 1066         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1066
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
S                                                                   121

SEQ ID NO: 1067         moltype = AA   length = 108
FEATURE                 Location/Qualifiers
REGION                  1..108
                        note = Synthetic polymer
source                  1..108
                        mol_type = protein
                        organism = synthetic construct
SEQUENCE: 1067
EIVLTQSPGT LSLSPGERAT LSCRASQRVS SSYLAWYQQK PGQAPRLLIY DASSRATGIP    60
DRFSGSGSGT DFTLTISRLE PEDFAVYYCQ QYGSLPWTFG QGTEVEIK                108

SEQ ID NO: 1068         moltype = AA   length = 121
FEATURE                 Location/Qualifiers
REGION                  1..121
                        note = Synthetic polymer
source                  1..121
                        mol_type = protein
                        organism = synthetic construct
SEQUENCE: 1068
EVQLLESGGG LVQPGGSLRL SCAASGFTFS NYAMSWVRQA PGKGLEWVSA IRGSGGSTYY    60
ADSVKGRFTI SRDNSKNTLY LQMNSLRAED TAVYYCAKDL HYDSSGYLDY WGQGTLVTVS   120
S                                                                   121

SEQ ID NO: 1069         moltype = AA   length = 107
FEATURE                 Location/Qualifiers
REGION                  1..107
                        note = Synthetic polymer
source                  1..107
                        mol_type = protein
                        organism = synthetic construct
SEQUENCE: 1069
DIQMTQSPSS VSASVGDRVT ITCRASQGIR SWLAWYQQKP GKAPKLLIYA ISRLQSGVPS    60
RFSGSGSGTD FTLTISSLQP EDFATYYCQQ ANSFPLTFGG GTKVEIK                 107

SEQ ID NO: 1070         moltype = AA   length = 119
FEATURE                 Location/Qualifiers
REGION                  1..119
                        note = Synthetic polymer
source                  1..119
                        mol_type = protein
                        organism = synthetic construct
SEQUENCE: 1070
EVQLVESGGG LVQPGGSLRL SCAASGFTFS SYWMSWVRQA PGKGLEWVAN IKQDGGEKYY    60
VDSVKGRFTI SRDNAKNSLF LQMNSLRAED TAVYYCARVQ LYSDYFDYWG QGTLVTVSS    119
```

```
SEQ ID NO: 1071          moltype = AA   length = 107
FEATURE                  Location/Qualifiers
REGION                   1..107
                         note = Synthetic polymer
source                   1..107
                         mol_type = protein
                         organism = synthetic construct
SEQUENCE: 1071
DIQMTQSPSS VSASVGDRVT ITCRASQGIS SWLAWYQQKS GKAPKLLIYA ASGLQSGVPS      60
RFSGSGSGTD FTLTISSLQP EDLATYYCQQ SHSLPPTFGQ GTKVEIK                   107

SEQ ID NO: 1072          moltype = AA   length = 121
FEATURE                  Location/Qualifiers
REGION                   1..121
                         note = Synthetic polymer
source                   1..121
                         mol_type = protein
                         organism = synthetic construct
SEQUENCE: 1072
EVQLLESGGD LVQPGGSLRL SCAASGFTFN SYAMSWVRQA PGKGLEWVST ISGSGGFTFS      60
ADSVKGRFTI SRDNSKNTLF LQMNSLRVED SAVYSCAKVL VGFNNGCWDY WGQGTLVTVS     120
S                                                                    121

SEQ ID NO: 1073          moltype = AA   length = 108
FEATURE                  Location/Qualifiers
REGION                   1..108
                         note = Synthetic polymer
source                   1..108
                         mol_type = protein
                         organism = synthetic construct
SEQUENCE: 1073
SYVLTQPPSV SVAPGQTARI TCGGNNIGSK SVHWYQQKPG QAPVLVVYDD SDRPSGIPER      60
FSGSNSGNTA TLTISRVEAG DEADYYCQVW DSSNDHVVFG GGTKLTVL                  108

SEQ ID NO: 1074          moltype = AA   length = 120
FEATURE                  Location/Qualifiers
REGION                   1..120
                         note = Synthetic polymer
source                   1..120
                         mol_type = protein
                         organism = synthetic construct
SEQUENCE: 1074
EVQLVESGGG LVKPGGSLRL SCAASGFTFS TYSMNWVRQA PGKGLEWVSS ISSSGDYIYY      60
ADSVKGRFTI SRDNAKNSLY LQMNSLRAED TAVYYCARDL VTSMVAFDYW GQGTLVTVSS    120

SEQ ID NO: 1075          moltype = AA   length = 108
FEATURE                  Location/Qualifiers
REGION                   1..108
                         note = Synthetic polymer
source                   1..108
                         mol_type = protein
                         organism = synthetic construct
SEQUENCE: 1075
SYELTQPPSV SVSPGQTARI TCSGDALPQK YVFWYQQKSG QAPVLVIYED SKRPSGIPER      60
FSGSSSGTMA TLTISGAQVE DEADYYCYST DRSGNHRVFG GGTKLTVL                  108

SEQ ID NO: 1076          moltype = AA   length = 121
FEATURE                  Location/Qualifiers
REGION                   1..121
                         note = Synthetic polymer
source                   1..121
                         mol_type = protein
                         organism = synthetic construct
SEQUENCE: 1076
EVQLVESGGG LVQPGGSLRL SCAASGFTFS RYWMSWVRQA PGKGLEWVAN IKQDGSEKYY      60
VDSVKGRFTI SRDNAKNSLY LQMNSLRAED TAVYYCAREG GWFGELAFDY WGQGTLVTVS     120
S                                                                    121

SEQ ID NO: 1077          moltype = AA   length = 108
FEATURE                  Location/Qualifiers
REGION                   1..108
                         note = Synthetic polymer
source                   1..108
                         mol_type = protein
                         organism = synthetic construct
SEQUENCE: 1077
EIVLTQSPGT LSLSPGERAT LSCRASQRVS SSYLAWYQQK PGQAPRLLIY DASSRATGIP      60
DRFSGSGSGT DFTLTISRLE PEDFAVYYCQ QYGSLPWTFG QGTKVEIK                  108
```

```
SEQ ID NO: 1078        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1078
QVQLVQSGAE VKKPGASVKV SCKASGYTFT SYWMYWVRQA TGQGLEWMGR IDPNSGSTKY   60
NEKFKNRFTI SRDDSKNTAY LQMNSLKTED TAVYYCARDY RKGLYAMDYW GQGTTVTVSS  120

SEQ ID NO: 1079        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1079
EVQLVQSGAE VKKPGATVKI SCKVSGYTFT SYWMYWVRQA TGQGLEWMGR IDPNSGSTKY   60
NEKFKNRVTI TADKSTSTAY MELSSLRSED TAVYYCARDY RKGLYAMDYW GQGTTVTVSS  120

SEQ ID NO: 1080        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1080
EVQLVQSGAE VKKPGESLRI SCKGSGYTFT SYWMYWVRQA PGQGLEWMGR IDPNSGSTKY   60
NEKFKNRVTI SVDTSKNQFS LKLSSVTAAD TAVYYCARDY RKGLYAMDYW GQGTTVTVSS  120

SEQ ID NO: 1081        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1081
EVQLVQSGAE VKKPGATVKI SCKVSGYTFT SYWMYWIRQS PSRGLEWLGR IDPNSGSTKY   60
NEKFKNRLTI SKDTSKNQVV LTMTNMDPVD TATYYCARDY RKGLYAMDYW GQGTTVTVSS  120

SEQ ID NO: 1082        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1082
EVQLVQSGAE VKKPGESLRI SCKGSGYTFT SYWMYWIRQP PGKGLEWIGR IDPNSGSTKY   60
NEKFKNRVTI TADKSTSTAY MELSSLRSED TAVYYCARDY RKGLYAMDYW GQGTTVTVSS  120

SEQ ID NO: 1083        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1083
QVQLVQSGAE VKKPGASVKV SCKASGYTFT SYWMYWIRQS PSRGLEWLGR IDPNSGSTKY   60
NEKFKNRFTI SRDDSKNTAY LQMNSLKTED TAVYYCARDY RKGLYAMDYW GQGTTVTVSS  120

SEQ ID NO: 1084        moltype = AA  length = 120
FEATURE                Location/Qualifiers
REGION                 1..120
                       note = Synthetic polymer
source                 1..120
                       mol_type = protein
                       organism = synthetic construct
SEQUENCE: 1084
EVQLVQSGAE VKKPGESLRI SCKGSGYTFT SYWMYWVRQA RGQRLEWIGR IDPNSGSTKY   60
NEKFKNRLTI SKDTSKNQVV LTMTNMDPVD TATYYCARDY RKGLYAMDYW GQGTTVTVSS  120

SEQ ID NO: 1085        moltype = AA  length = 120
FEATURE                Location/Qualifiers
```

```
REGION                    1..120
                          note = Synthetic polymer
source                    1..120
                          mol_type = protein
                          organism = synthetic construct
SEQUENCE: 1085
QITLKESGPT LVKPTQTLTL TCTFSGYTFT SYWMYWVRQA PGKGLEWVSR IDPNSGSTKY    60
NEKFKNRVTI TADKSTSTAY MELSSLRSED TAVYYCARDY RKGLYAMDYW GQGTTVTVSS   120

SEQ ID NO: 1086           moltype = AA  length = 120
FEATURE                   Location/Qualifiers
REGION                    1..120
                          note = Synthetic polymer
source                    1..120
                          mol_type = protein
                          organism = synthetic construct
SEQUENCE: 1086
EVQLVQSGAE VKKPGATVKI SCKVSGYTFT SYWMYWVRQA RGQRLEWIGR IDPNSGSTKY    60
NEKFKNRFTI SRDNSKNTLY LQMNSLRAED TAVYYCARDY RKGLYAMDYW GQGTTVTVSS   120

SEQ ID NO: 1087           moltype = AA  length = 107
FEATURE                   Location/Qualifiers
REGION                    1..107
                          note = Synthetic polymer
source                    1..107
                          mol_type = protein
                          organism = synthetic construct
SEQUENCE: 1087
DIVMTQTPLS LPVTPGEPAS ISCKASQDVG TAVAWYLQKP GQSPQLLIYW ASTRHTGIPA    60
RFSGSGSGTE FTLTISSLQS EDFAVYYCQQ YNSYPLTFGQ GTKVEIK                107

SEQ ID NO: 1088           moltype = AA  length = 107
FEATURE                   Location/Qualifiers
REGION                    1..107
                          note = Synthetic polymer
source                    1..107
                          mol_type = protein
                          organism = synthetic construct
SEQUENCE: 1088
DIQMTQSPSS LSASVGDRVT ITCKASQDVG TAVAWYLQKP GQSPQLLIYW ASTRHTGVPS    60
RFSGSGSGTD FTLTISSLQP EDFATYYCQQ YNSYPLTFGQ GTKVEIK                107

SEQ ID NO: 1089           moltype = AA  length = 107
FEATURE                   Location/Qualifiers
REGION                    1..107
                          note = Synthetic polymer
source                    1..107
                          mol_type = protein
                          organism = synthetic construct
SEQUENCE: 1089
EIVLTQSPDF QSVTPKEKVT ITCKASQDVG TAVAWYLQKP GQSPQLLIYW ASTRHTGVPD    60
RFSGSGSGTD FTLKISRVEA EDVGVYYCQQ YNSYPLTFGQ GTKVEIK                107

SEQ ID NO: 1090           moltype = AA  length = 107
FEATURE                   Location/Qualifiers
REGION                    1..107
                          note = Synthetic polymer
source                    1..107
                          mol_type = protein
                          organism = synthetic construct
SEQUENCE: 1090
EIVLTQSPDF QSVTPKEKVT ITCKASQDVG TAVAWYLQKP GQSPQLLIYW ASTRHTGVPS    60
RFSGSGSGTD FTFTISSLQP EDIATYYCQQ YNSYPLTFGQ GTKVEIK                107

SEQ ID NO: 1091           moltype = AA  length = 107
FEATURE                   Location/Qualifiers
REGION                    1..107
                          note = Synthetic polymer
source                    1..107
                          mol_type = protein
                          organism = synthetic construct
SEQUENCE: 1091
EIVLTQSPAT LSLSPGERAT LSCKASQDVG TAVAWYLQKP GQSPQLLIYW ASTRHTGIPP    60
RFSGSGYGTD FTLTINNIES EDAAYYFCQQ YNSYPLTFGQ GTKVEIK                107

SEQ ID NO: 1092           moltype = AA  length = 107
FEATURE                   Location/Qualifiers
REGION                    1..107
                          note = Synthetic polymer
```

```
source                     1..107
                           mol_type = protein
                           organism = synthetic construct
SEQUENCE: 1092
DVVMTQSPLS LPVTLGQPAS ISCKASQDVG TAVAWYQQKP GQAPRLLIYW ASTRHTGVPS    60
RFSGSGSGTE FTLTISSLQP DDFATYYCQQ YNSYPLTFGQ GTKVEIK                 107

SEQ ID NO: 1093            moltype = AA   length = 107
FEATURE                    Location/Qualifiers
REGION                     1..107
                           note = Synthetic polymer
source                     1..107
                           mol_type = protein
                           organism = synthetic construct
SEQUENCE: 1093
DIQMTQSPSS LSASVGDRVT ITCKASQDVG TAVAWYQQKP GQAPRLLIYW ASTRHTGVPS    60
RFSGSGSGTD FTFTISSLQP EDIATYYCQQ YNSYPLTFGQ GTKVEIK                 107

SEQ ID NO: 1094            moltype = AA   length = 107
FEATURE                    Location/Qualifiers
REGION                     1..107
                           note = Synthetic polymer
source                     1..107
                           mol_type = protein
                           organism = synthetic construct
SEQUENCE: 1094
AIQLTQSPSS LSASVGDRVT ITCKASQDVG TAVAWYLQKP GQSPQLLIYW ASTRHTGVPS    60
RFSGSGSGTD FTFTISSLEA EDAATYYCQQ YNSYPLTFGQ GTKVEIK                 107

SEQ ID NO: 1095            moltype = AA   length = 107
FEATURE                    Location/Qualifiers
REGION                     1..107
                           note = Synthetic polymer
source                     1..107
                           mol_type = protein
                           organism = synthetic construct
SEQUENCE: 1095
EIVLTQSPDF QSVTPKEKVT ITCKASQDVG TAVAWYQQKP GQAPRLLIYW ASTRHTGVPS    60
RFSGSGSGTE FTLTISSLQP DDFATYYCQQ YNSYPLTFGQ GTKVEIK                 107

SEQ ID NO: 1096            moltype = AA   length = 116
FEATURE                    Location/Qualifiers
REGION                     1..116
                           note = Synthetic polymer
source                     1..116
                           mol_type = protein
                           organism = synthetic construct
SEQUENCE: 1096
EVKLVESGGG LVKPGGSLKL SCAASGFIFR SYGMSWVRQT PEKRLEWVAS ISSGGSTYYP    60
DSVKGRFTIS RDNARNILYL QMSSLRSEDT AMYDCARGYD SGFAYWGQGT LVTVSE       116

SEQ ID NO: 1097            moltype = AA   length = 116
FEATURE                    Location/Qualifiers
REGION                     1..116
                           note = Synthetic polymer
source                     1..116
                           mol_type = protein
                           organism = synthetic construct
SEQUENCE: 1097
EVKLVESGGG LVKPGGSLKL SCAASGFTFR SYGMSWVRQT PEKRLEWVAS ISSGGTTYYP    60
DSVKGRFIIS RDNARNILYL QMSSLRSEDT AMYYCAKGYD SGFAYWGQGT LVIVSA       116

SEQ ID NO: 1098            moltype = AA   length = 116
FEATURE                    Location/Qualifiers
REGION                     1..116
                           note = Synthetic polymer
source                     1..116
                           mol_type = protein
                           organism = synthetic construct
SEQUENCE: 1098
QVQLKQSGPG LVQPSQSLSI TCTVSGFSLT TYGVHWVRQS PGKGLEWLGV IWRGVTTDYN    60
AAFMSRLTIT KDNSKSQVFF KMNSLQANDT AIYYCARLGF YAMDYWGQGT SVTVSS       116

SEQ ID NO: 1099            moltype = AA   length = 116
FEATURE                    Location/Qualifiers
REGION                     1..116
                           note = Synthetic polymer
source                     1..116
                           mol_type = protein
```

-continued

```
                              organism = synthetic construct
SEQUENCE: 1099
QVQLKQSGPG LVQPSQSLSI TCTVSGFSLT SYGVHWVRQS PGKGLEWLGV IWSGGVTDYN    60
AAFISRLSIS KDNSKSQVFF KMNSLQANDT AIYYCARLGF YAMDYWGQGT SVTVSS        116

SEQ ID NO: 1100           moltype = AA  length = 119
FEATURE                   Location/Qualifiers
REGION                    1..119
                          note = Synthetic polymer
source                    1..119
                          mol_type = protein
                          organism = synthetic construct
SEQUENCE: 1100
EVKLFESGGG LVQPGGSLKL SCVASGFDFS TYWMHWVRQA PGQGLEWIGQ INPDSTTINY    60
APSLKDRFII SRDNAKNTLF LQMSKVRSED TALYYCAKPG DYGYDFDCWG QGTTLTVSS     119

SEQ ID NO: 1101           moltype = AA  length = 119
FEATURE                   Location/Qualifiers
REGION                    1..119
                          note = Synthetic polymer
source                    1..119
                          mol_type = protein
                          organism = synthetic construct
SEQUENCE: 1101
EVQLQESGPS LVKPSQTLSL TCSVTGDSIT SGYWNWIRKF PGNKLEYMGY ISYSGSTYYN    60
PSLKSRISIT RDTSKNQYYL QLNSVTTEDT ATYYCARSLL WFSTGFAYWG QGTLVTVSA     119

SEQ ID NO: 1102           moltype = AA  length = 116
FEATURE                   Location/Qualifiers
REGION                    1..116
                          note = Synthetic polymer
source                    1..116
                          mol_type = protein
                          organism = synthetic construct
SEQUENCE: 1102
QVQLKQSGPG LVQPSQSLSI TCTVSGFSLT SYGVHWVRQS PGKGLEWLGV IWSGGITDYN    60
AAFKSRLSIS KDNSKSQVFF KMNSLQANDT AIYFCARLGF YAMDYWGQGT SVTVSS        116

SEQ ID NO: 1103           moltype = AA  length = 116
FEATURE                   Location/Qualifiers
REGION                    1..116
                          note = Synthetic polymer
source                    1..116
                          mol_type = protein
                          organism = synthetic construct
SEQUENCE: 1103
EVKLVESGGG LVKPGGSLKL SCAASGFTFR SYGMSWARQI PEKRLEWVAS ISSGGTTYYL    60
GSVQGRFTIS RDNARNILYL QMSSLRSEDT AMYYCARGYD AGFAYWGQGT LVSVSE        116

SEQ ID NO: 1104           moltype = AA  length = 117
FEATURE                   Location/Qualifiers
REGION                    1..117
                          note = Synthetic polymer
source                    1..117
                          mol_type = protein
                          organism = synthetic construct
SEQUENCE: 1104
EVQLQESGPS LVKPSQTLSL TCSVTGDSIT SGYWTWIRKF PGNKLEYMGY ISYTGSTYYN    60
PSLKSRISIS RDTSKSQYYL QLNSVTTEDT ATYYCARQRD WLGFAYWGQG TLVTVSA       117

SEQ ID NO: 1105           moltype = AA  length = 116
FEATURE                   Location/Qualifiers
REGION                    1..116
                          note = Synthetic polymer
source                    1..116
                          mol_type = protein
                          organism = synthetic construct
SEQUENCE: 1105
EEKLVESGGG LVKPGGSLKL SCAASGFSFS SYGMSWVRQT PEKRLEWVAS ISSGGSIYYP    60
DSVKGRFTIS RDNARNILYL QMSSLRSEDT AMYYCARGYD AGFAFWGQGT LVTASA        116

SEQ ID NO: 1106           moltype = AA  length = 116
FEATURE                   Location/Qualifiers
REGION                    1..116
                          note = Synthetic polymer
source                    1..116
                          mol_type = protein
                          organism = synthetic construct
SEQUENCE: 1106
```

```
QITLKESGPT LVKPTQTLTL TCTVSGFSLS TYGVHWIRQP PGKALEWLGV IWRGVTTDYN    60
AAFMSRLTIT KDNSKNQVVL TMNNMDPVDT ATYYCARLGF YAMDYWGQGT LVTVSS       116

SEQ ID NO: 1107          moltype = AA  length = 116
FEATURE                  Location/Qualifiers
REGION                   1..116
                         note = Synthetic polymer
source                   1..116
                         mol_type = protein
                         organism = synthetic construct
SEQUENCE: 1107
EVQLVESGGG LVKPGGSLRL SCAASGFIFR SYGMSWVRQA PGKGLEWVAS ISSGGSTYYP    60
DSVKGRFTIS RDNAKNSLYL QMNSLRAEDT AVYDCARGYD SGFAYWGQGT LVTVSS       116

SEQ ID NO: 1108          moltype = AA  length = 112
FEATURE                  Location/Qualifiers
REGION                   1..112
                         note = Synthetic polymer
source                   1..112
                         mol_type = protein
                         organism = synthetic construct
SEQUENCE: 1108
DIVLTQSPAS LAVSLGQRAT ISCRASQSVS TSSSSFMHWY QQKPGQPPKL LIKYASNLES    60
GVPARFSGSG SGTDFTLNIH PVEEEDTATY YCQHSWEIPY TFGGGTKLEI KR           112

SEQ ID NO: 1109          moltype = AA  length = 111
FEATURE                  Location/Qualifiers
REGION                   1..111
                         note = Synthetic polymer
source                   1..111
                         mol_type = protein
                         organism = synthetic construct
SEQUENCE: 1109
DIVLTQSPPS LAVSLGQRAT ISCRASQSVS TSSSSYMHWY QQKPGQPPKL LIKYASNLES    60
GVPARFSGSG SGTDFTLNIH PVEEEDTATY YCQHSWEIPY TFGGGTKLEI K            111

SEQ ID NO: 1110          moltype = AA  length = 107
FEATURE                  Location/Qualifiers
REGION                   1..107
                         note = Synthetic polymer
source                   1..107
                         mol_type = protein
                         organism = synthetic construct
SEQUENCE: 1110
SIVMTQTPKF LLVSAGDRVT ITCKASQSVS NDVAWYQQKP GQSPKLLIYY AANRYTGVPD    60
RFTGSGYGTD FTFTISIVQA EDLAVYFCQQ DYTSPYTFGG GTKLEIK                 107

SEQ ID NO: 1111          moltype = AA  length = 107
FEATURE                  Location/Qualifiers
REGION                   1..107
                         note = Synthetic polymer
source                   1..107
                         mol_type = protein
                         organism = synthetic construct
SEQUENCE: 1111
SIVMTQTPKF LLVSAGDRVT ITCKASQSVS NDVGWYQQKP GQSPKLLIYY ASNRYSGVPD    60
RFTGSGYGTD FTFTISTVQA EDLAVYFCQQ DYTSPYTFGG GTKLEIK                 107

SEQ ID NO: 1112          moltype = AA  length = 112
FEATURE                  Location/Qualifiers
REGION                   1..112
                         note = Synthetic polymer
source                   1..112
                         mol_type = protein
                         organism = synthetic construct
SEQUENCE: 1112
DVLMTQTPLY LPVSLGDQAS ISCRSSQIIV HSNANTYLEW FLQKPGQSPK LLIYKVSNRF    60
SGVPDRFSGS GSGTDFTLKI SRVEAEDLGV YYCFQGSHVP YTFGGGTKLE IK           112

SEQ ID NO: 1113          moltype = AA  length = 108
FEATURE                  Location/Qualifiers
REGION                   1..108
                         note = Synthetic polymer
source                   1..108
                         mol_type = protein
                         organism = synthetic construct
SEQUENCE: 1113
QIVLTQSPAI MSASPGEKVT LTCSASSSVS SSYLYWNQQK PGSSPKVWIY NTSNLASGVP    60
ARFSGSGSGT SYSLTISSME AEDAASYFCH QWRSYPPTLG AGTKLELK                108
```

```
SEQ ID NO: 1114         moltype = AA   length = 106
FEATURE                 Location/Qualifiers
REGION                  1..106
                        note = Synthetic polymer
source                  1..106
                        mol_type = protein
                        organism = synthetic construct
SEQUENCE: 1114
QIVLTQSPAI MSASPGEKVT MTCSANSSVS YMHWYQQKSG TSPKRWIYDT SKLASGVPAR    60
FSGSGSGTSY SLTISSMGAE DAATYYCQQW SSNPWTFGGG TKLEIK                  106

SEQ ID NO: 1115         moltype = AA   length = 111
FEATURE                 Location/Qualifiers
REGION                  1..111
                        note = Synthetic polymer
source                  1..111
                        mol_type = protein
                        organism = synthetic construct
SEQUENCE: 1115
DIVLTQSPAS LAVSLGQRAT ISCRASQSVS TSSYSYMHWY QQKPGQPPKL LIKYASNLES    60
GVPARFSGSG SGTDFTLNIH PVEEEDTATY YCQNSWEIPY TFGGGTKLEI K             111

SEQ ID NO: 1116         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1116
DIVMTQTPSS LAVSLGEKVT MSCKSSQSLL YSSNQKNSLA WYQQKPGQSP KLLIYWASNR    60
ESGVPDRFTG SSSGTDFTLT ISSVKAEDLA VYYCQQYYSY PLTFGAGTKL ELK           113

SEQ ID NO: 1117         moltype = AA   length = 111
FEATURE                 Location/Qualifiers
REGION                  1..111
                        note = Synthetic polymer
source                  1..111
                        mol_type = protein
                        organism = synthetic construct
SEQUENCE: 1117
DIVLTQSPAS LAVSLGQRAT ISCRASQSVS TSSYSYVHWY QQKPGQPPKL LIKYASNLES    60
GVPARFSGSG SGTDFTLNIH PVEEEDTATY YCQHSWEIPY TFGGGTKLEI K             111

SEQ ID NO: 1118         moltype = AA   length = 107
FEATURE                 Location/Qualifiers
REGION                  1..107
                        note = Synthetic polymer
source                  1..107
                        mol_type = protein
                        organism = synthetic construct
SEQUENCE: 1118
DIQMTQSPSS LSASVGDRVT ITCKASQSVS NDVAWYQQKP GKAPKLLIYY AANRYTGVPD    60
RFSGSGYGTD FTFTISSLQP EDIATYFCQQ DYTSPYTFGQ GTKLEIK                  107

SEQ ID NO: 1119         moltype = AA   length = 111
FEATURE                 Location/Qualifiers
REGION                  1..111
                        note = Synthetic polymer
source                  1..111
                        mol_type = protein
                        organism = synthetic construct
SEQUENCE: 1119
DIVLTQSPAS LAVSPGQRAT ITCRASQSVS TSSSSFMHWY QQKPGQPPKL LIKYASNLES    60
GVPARFSGSG SGTDFTLTIN PVEANDTANY YCQHSWEIPY TFGQGTKLEI K             111

SEQ ID NO: 1120         moltype = AA   length = 117
FEATURE                 Location/Qualifiers
REGION                  1..117
                        note = Synthetic polymer
source                  1..117
                        mol_type = protein
                        organism = synthetic construct
SEQUENCE: 1120
EVQLVQSGAE VKKPGESLRI SCKGSGYTFT TYWMHWVRQA TGQGLEWMGN IYPGTGGSNF    60
DEKFKNRVTI TADKSTSTAY MELSSLRSED TAVYYCTRWT TGTGAYWGQG TTVTVSS       117

SEQ ID NO: 1121         moltype = AA   length = 117
```

```
FEATURE            Location/Qualifiers
REGION             1..117
                   note = Synthetic polymer
source             1..117
                   mol_type = protein
                   organism = synthetic construct
SEQUENCE: 1121
EVQLVQSGAE VKKPGESLRI SCKGSGYTFT TYWMHWIRQS PSRGLEWLGN IYPGTGGSNF    60
DEKFKNRFTI SRDNSKNTLY LQMNSLRAED TAVYYCTRWT TGTGAYWGQG TTVTVSS      117

SEQ ID NO: 1122    moltype = AA  length = 117
FEATURE            Location/Qualifiers
REGION             1..117
                   note = Synthetic polymer
source             1..117
                   mol_type = protein
                   organism = synthetic construct
SEQUENCE: 1122
QVQLVQSGAE VKKPGASVKV SCKASGYTFT TYWMHWIRQS PSRGLEWLGN IYPGTGGSNF    60
DEKFKNRFTI SRDNSKNTLY LQMNSLRAED TAVYYCTRWT TGTGAYWGQG TTVTVSS      117

SEQ ID NO: 1123    moltype = AA  length = 117
FEATURE            Location/Qualifiers
REGION             1..117
                   note = Synthetic polymer
source             1..117
                   mol_type = protein
                   organism = synthetic construct
SEQUENCE: 1123
EVQLVQSGAE VKKPGESLRI SCKGSGYTFT TYWMHWVRQA PGQGLEWMGN IYPGTGGSNF    60
DEKFKNRFTI SRDNSKNTLY LQMNSLRAED TAVYYCTRWT TGTGAYWGQG TTVTVSS      117

SEQ ID NO: 1124    moltype = AA  length = 113
FEATURE            Location/Qualifiers
REGION             1..113
                   note = Synthetic polymer
source             1..113
                   mol_type = protein
                   organism = synthetic construct
SEQUENCE: 1124
EIVLTQSPAT LSLSPGERAT LSCKSSQSLL DSGNQKNFLT WYQQKPGQAP RLLIYWASTR    60
ESGVPSRFSG SGSGTEFTLT ISSLQPDDFA TYYCQNDYSY PYTFGQGTKV EIK          113

SEQ ID NO: 1125    moltype = AA  length = 113
FEATURE            Location/Qualifiers
REGION             1..113
                   note = Synthetic polymer
source             1..113
                   mol_type = protein
                   organism = synthetic construct
SEQUENCE: 1125
DIQMTQSPSS LSASVGDRVT ITCKSSQSLL DSGNQKNFLT WYQQKPGQAP RLLIYWASTR    60
ESGIPPRFSG SGYGTDFTLT INNIESEDAA YYFCQNDYSY PYTFGQGTKV EIK          113

SEQ ID NO: 1126    moltype = AA  length = 113
FEATURE            Location/Qualifiers
REGION             1..113
                   note = Synthetic polymer
source             1..113
                   mol_type = protein
                   organism = synthetic construct
SEQUENCE: 1126
EIVLTQSPAT LSLSPGERAT LSCKSSQSLL DSGNQKNFLT WYQQKPGKAP KLLIYWASTR    60
ESGVPSRFSG SGSGTDFTFT ISSLQPEDIA TYYCQNDYSY PYTFGQGTKV EIK          113

SEQ ID NO: 1127    moltype = AA  length = 113
FEATURE            Location/Qualifiers
REGION             1..113
                   note = Synthetic polymer
source             1..113
                   mol_type = protein
                   organism = synthetic construct
SEQUENCE: 1127
DIVMTQTPLS LPVTPGEPAS ISCKSSQSLL DSGNQKNFLT WYQQKPGQAP RLLIYWASTR    60
ESGVPSRFSG SGSGTDFTFT ISSLEAEDAA TYYCQNDYSY PYTFGQGTKV EIK          113

SEQ ID NO: 1128    moltype = AA  length = 113
FEATURE            Location/Qualifiers
REGION             1..113
```

```
                        note = Synthetic polymer
source                  1..113
                        mol_type = protein
                        organism = synthetic construct
SEQUENCE: 1128
EIVLTQSPAT LSLSPGERAT LSCKSSQSLL DSGNQKNFLT WYQQKPGKAP KLLIYWASTR    60
ESGVPSRFSG SGSGTDFTFT ISSLEAEDAA TYYCQNDYSY PYTFGQGTKV EIK           113

SEQ ID NO: 1129         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1129
EIVLTQSPDF QSVTPKEKVT ITCKSSQSLL DSGNQKNFLT WYQQKPGQAP RLLIYWASTR    60
ESGVPSRFSG SGSGTDFTFT ISSLEAEDAA TYYCQNDYSY PYTFGQGTKV EIK           113

SEQ ID NO: 1130         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1130
EIVLTQSPAT LSLSPGERAT LSCKSSQSLL DSGNQKNFLT WYQQKPGQAP RLLIYWASTR    60
ESGVPSRFSG SGSGTDFTFT ISSLEAEDAA TYYCQNDYSY PYTFGQGTKV EIK           113

SEQ ID NO: 1131         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1131
DIQMTQSPSS LSASVGDRVT ITCKSSQSLL DSGNQKNFLT WYLQKPGQSP QLLIYWASTR    60
ESGVPSRFSG SGSGTDFTFT ISSLEAEDAA TYYCQNDYSY PYTFGQGTKV EIK           113

SEQ ID NO: 1132         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1132
DVVMTQSPLS LPVTLGQPAS ISCKSSQSLL DSGNQKNFLT WYQQKPGKAP KLLIYWASTR    60
ESGVPSRFSG SGSGTDFTFT ISSLEAEDAA TYYCQNDYSY PYTFGQGTKV EIK           113

SEQ ID NO: 1133         moltype = AA  length = 118
FEATURE                 Location/Qualifiers
REGION                  1..118
                        note = Synthetic polymer
source                  1..118
                        mol_type = protein
                        organism = synthetic construct
SEQUENCE: 1133
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSA     118

SEQ ID NO: 1134         moltype = AA  length = 108
FEATURE                 Location/Qualifiers
REGION                  1..108
                        note = Synthetic polymer
source                  1..108
                        mol_type = protein
                        organism = synthetic construct
SEQUENCE: 1134
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKR                108

SEQ ID NO: 1135         moltype = AA  length = 126
FEATURE                 Location/Qualifiers
REGION                  1..126
                        note = Synthetic polymer
source                  1..126
```

```
                            mol_type = protein
                            organism = synthetic construct
SEQUENCE: 1135
EVQLVESGGG LVQPGGSLRL SCAASGFTLD YYAIGWFRQA PGKEREWASS ISSSDGSTYY    60
ADSVKGRFTI SRDNAKNTVF LQMNSLKPED TAVYSCAASQ APITIATMMK PFYDYWGQGT   120
QVTVSS                                                              126

SEQ ID NO: 1136             moltype = AA  length = 123
FEATURE                     Location/Qualifiers
REGION                      1..123
                            note = Synthetic polymer
source                      1..123
                            mol_type = protein
                            organism = synthetic construct
SEQUENCE: 1136
EVQLVESGGG LVQPGGSLRL SCAASGFTLD YYAKCWFRQA PGKEREWVSC ISSSDGSTYY    60
ADSVKGRFTI SRDNAKNTVY LQMNSLKPED TAVYFCAARH GGPLTVEYFF DYWGQGTQVT   120
VSS                                                                 123

SEQ ID NO: 1137             moltype = AA  length = 124
FEATURE                     Location/Qualifiers
REGION                      1..124
                            note = Synthetic polymer
source                      1..124
                            mol_type = protein
                            organism = synthetic construct
SEQUENCE: 1137
EVQLVESGGG LVQPGGSLRL SCAASGFTFD YYAIGWFRQA PGKAREGVSC ISGGDNSTYY    60
ADSVKGRFTI SRDNAKNTVY LQMNSLKPED TAVYYCATGG WKYCSGYDPE YIYWGQGTQV   120
TVSS                                                                124

SEQ ID NO: 1138             moltype = AA  length = 115
FEATURE                     Location/Qualifiers
REGION                      1..115
                            note = Synthetic polymer
source                      1..115
                            mol_type = protein
                            organism = synthetic construct
SEQUENCE: 1138
EVQLVESGGG LVQAGGSLRL SCAASGSTFS QYDVGWYRQA PGKQRELVAF SSSGGRTIYP    60
DSVKGRFTFS RDNTKNTVYL QMTSLKPEDT AVYYCKIDWY LNSYWGQGTQ VTVSS        115

SEQ ID NO: 1139             moltype = AA  length = 114
FEATURE                     Location/Qualifiers
REGION                      1..114
                            note = Synthetic polymer
source                      1..114
                            mol_type = protein
                            organism = synthetic construct
SEQUENCE: 1139
EVQLVESGGG LVQAGGSLRL SCAASGVDAS NSAMGWYRQA PGKQREWVAR ITGGGLIAYT    60
DSVKGRFTIS RDNAKSTVYL QMNSLEPEDT AVYYCNTINS RDGWGQGTQV TVSS         114

SEQ ID NO: 1140             moltype = AA  length = 111
FEATURE                     Location/Qualifiers
REGION                      1..111
                            note = Synthetic polymer
source                      1..111
                            mol_type = protein
                            organism = synthetic construct
SEQUENCE: 1140
EVQLVESGGG LVQAGGSLTI SCAASGITFS DSIVSWYRRA RGKQREWVAG ISNGGTTKYA    60
ESVLGRFTIS RDNAKNNVYL QMNGLNPEDT AVYLCKVRQY WGQGTQVTVS S            111

SEQ ID NO: 1141             moltype = AA  length = 130
FEATURE                     Location/Qualifiers
REGION                      1..130
                            note = Synthetic polymer
source                      1..130
                            mol_type = protein
                            organism = synthetic construct
SEQUENCE: 1141
EVQLVESGGG LVQAGGSLRL SCAASESTVL INAMGWYRQA PGKQRELVAS ISSGGSTNYA    60
DSVKGRFTIS RDNAKNTVYL QMNSLKPEDT AVYYCNADVY PQDYGLGYVE GKVYYGHDYW   120
GTGTLVTVSS                                                          130

SEQ ID NO: 1142             moltype = AA  length = 119
FEATURE                     Location/Qualifiers
REGION                      1..119
```

```
                        note       = Synthetic polymer
source                  1..119
                        mol_type   = protein
                        organism   = synthetic construct
SEQUENCE: 1142
EVQLVESGGG LVQAGGSLRL SCAASGSTFS NYVSNYAMGW GRQAPGTQRE LVASISNGDT    60
TNYADSVKGR FTISRDNAKN TVYLQMNSLK PEDTAVYYCF EHQVAGLTWG QGTQVTVSS    119

SEQ ID NO: 1143         moltype = AA   length = 118
FEATURE                 Location/Qualifiers
REGION                  1..118
                        note       = Synthetic polymer
SITE                    27
                        note       = misc_feature - Xaa can be any naturally occurring
                                     amino acid
SITE                    32
                        note       = misc_feature - Xaa can be any naturally occurring
                                     amino acid
SITE                    75
                        note       = misc_feature - Xaa can be any naturally occurring
                                     amino acid
source                  1..118
                        mol_type   = protein
                        organism   = synthetic construct
SEQUENCE: 1143
EVQLVESGGG LVQAGGSLRL SCVASGXALK IXVMGWYRQA PGKQRELVAA ITSGGRTNYS    60
DSVKGRFTIS GDNAXNTVYL QMNSLKSEDT AVYYCREWNS GYPPVDYWGQ GTQVTVSS    118

SEQ ID NO: 1144         moltype = AA   length = 120
FEATURE                 Location/Qualifiers
REGION                  1..120
                        note       = Synthetic polymer
source                  1..120
                        mol_type   = protein
                        organism   = synthetic construct
SEQUENCE: 1144
EVQLVESGGG LVQAGGSLRL SCAASGRTFS SGTMGWFRRA PGKEREFVAS IPWSGGRTYY    60
ADSVKDRFTI SRDNAQNTVF LQMNSLKPED TAVYYCAFKE RSTGWDFASW GQGIQVTVSS   120

SEQ ID NO: 1145         moltype = AA   length = 127
FEATURE                 Location/Qualifiers
REGION                  1..127
                        note       = Synthetic polymer
source                  1..127
                        mol_type   = protein
                        organism   = synthetic construct
SEQUENCE: 1145
EVQLVESGGG LVQTGGSLRL SCAASGFTLD YYGIGWFRQA PGKEREGVSF ISGSDGSTYY    60
AESVKGRFTI SRDKAKNTVY LQMNSLKPED TAVYYCAADP WGPPSIATMT SYEYKHWGQG   120
TQVTVSS                                                             127

SEQ ID NO: 1146         moltype = AA   length = 113
FEATURE                 Location/Qualifiers
REGION                  1..113
                        note       = Synthetic polymer
source                  1..113
                        mol_type   = protein
                        organism   = synthetic construct
SEQUENCE: 1146
EVQLVESGGG LVQPGGSLRL SCAASGFTFS TYTMIWLRRA PGKGFEWVST IDKDGNTNYV    60
DSVKGRFAVS RDNTKNTLYL QMNSLKPEDT AMYYCTKHGS SARGQGTRVT VSS          113

SEQ ID NO: 1147         moltype = AA   length = 114
FEATURE                 Location/Qualifiers
REGION                  1..114
                        note       = Synthetic polymer
source                  1..114
                        mol_type   = protein
                        organism   = synthetic construct
SEQUENCE: 1147
EVQLVESGGG LVEPGGSLRL SCVASGFTFS SYDMSWVRQA PGKGLEWVST INSGGGITYR    60
GSVKGRFTIS RDNAKNTLYL QMNSLKPEDT AVYYCENGGS SYRRGQGTQV TVSS         114

SEQ ID NO: 1148         moltype = AA   length = 5
FEATURE                 Location/Qualifiers
REGION                  1..5
                        note       = Synthetic polymer
source                  1..5
                        mol_type   = protein
```

```
                    organism = synthetic construct
SEQUENCE: 1148
INAMG                                                                           5

SEQ ID NO: 1149         moltype = AA   length = 9
FEATURE                 Location/Qualifiers
REGION                  1..9
                        note = Synthetic polymer
source                  1..9
                        mol_type = protein
                        organism = synthetic construct
SEQUENCE: 1149
NYVSNYAMG                                                                       9

SEQ ID NO: 1150         moltype = AA   length = 5
FEATURE                 Location/Qualifiers
REGION                  1..5
                        note = Synthetic polymer
SITE                    2
                        note = misc_feature - Xaa can be any naturally occurring
                         amino acid
source                  1..5
                        mol_type = protein
                        organism = synthetic construct
SEQUENCE: 1150
IXVMG                                                                           5

SEQ ID NO: 1151         moltype = AA   length = 5
FEATURE                 Location/Qualifiers
REGION                  1..5
                        note = Synthetic polymer
source                  1..5
                        mol_type = protein
                        organism = synthetic construct
SEQUENCE: 1151
SGTMG                                                                           5

SEQ ID NO: 1152         moltype = AA   length = 5
FEATURE                 Location/Qualifiers
REGION                  1..5
                        note = Synthetic polymer
source                  1..5
                        mol_type = protein
                        organism = synthetic construct
SEQUENCE: 1152
YYGIG                                                                           5

SEQ ID NO: 1153         moltype = AA   length = 5
FEATURE                 Location/Qualifiers
REGION                  1..5
                        note = Synthetic polymer
source                  1..5
                        mol_type = protein
                        organism = synthetic construct
SEQUENCE: 1153
TYTMI                                                                           5

SEQ ID NO: 1154         moltype = AA   length = 5
FEATURE                 Location/Qualifiers
REGION                  1..5
                        note = Synthetic polymer
source                  1..5
                        mol_type = protein
                        organism = synthetic construct
SEQUENCE: 1154
SYDMS                                                                           5

SEQ ID NO: 1155         moltype = AA   length = 16
FEATURE                 Location/Qualifiers
REGION                  1..16
                        note = Synthetic polymer
source                  1..16
                        mol_type = protein
                        organism = synthetic construct
SEQUENCE: 1155
SISSGGSTNY ADSVKG                                                              16

SEQ ID NO: 1156         moltype = AA   length = 16
FEATURE                 Location/Qualifiers
```

```
REGION                  1..16
                        note = Synthetic polymer
source                  1..16
                        mol_type = protein
                        organism = synthetic construct
SEQUENCE: 1156
SISNGDTINY ADSVKG                                                         16

SEQ ID NO: 1157         moltype = AA  length = 16
FEATURE                 Location/Qualifiers
REGION                  1..16
                        note = Synthetic polymer
source                  1..16
                        mol_type = protein
                        organism = synthetic construct
SEQUENCE: 1157
AITSGGRTNY SDSVKG                                                         16

SEQ ID NO: 1158         moltype = AA  length = 17
FEATURE                 Location/Qualifiers
REGION                  1..17
                        note = Synthetic polymer
source                  1..17
                        mol_type = protein
                        organism = synthetic construct
SEQUENCE: 1158
SIPWSGGRTY YADSVKD                                                        17

SEQ ID NO: 1159         moltype = AA  length = 17
FEATURE                 Location/Qualifiers
REGION                  1..17
                        note = Synthetic polymer
source                  1..17
                        mol_type = protein
                        organism = synthetic construct
SEQUENCE: 1159
FISGSDGSTY YAESVKG                                                        17

SEQ ID NO: 1160         moltype = AA  length = 16
FEATURE                 Location/Qualifiers
REGION                  1..16
                        note = Synthetic polymer
source                  1..16
                        mol_type = protein
                        organism = synthetic construct
SEQUENCE: 1160
TIDKDGNTNY VDSVKG                                                         16

SEQ ID NO: 1161         moltype = AA  length = 16
FEATURE                 Location/Qualifiers
REGION                  1..16
                        note = Synthetic polymer
source                  1..16
                        mol_type = protein
                        organism = synthetic construct
SEQUENCE: 1161
TINSGGGITY RGSVKG                                                         16

SEQ ID NO: 1162         moltype = AA  length = 22
FEATURE                 Location/Qualifiers
REGION                  1..22
                        note = Synthetic polymer
source                  1..22
                        mol_type = protein
                        organism = synthetic construct
SEQUENCE: 1162
DVYPQDYGLG YVEGKVYYGM DY                                                  22

SEQ ID NO: 1163         moltype = AA  length = 7
FEATURE                 Location/Qualifiers
REGION                  1..7
                        note = Synthetic polymer
source                  1..7
                        mol_type = protein
                        organism = synthetic construct
SEQUENCE: 1163
HQVAGLT                                                                    7

SEQ ID NO: 1164         moltype = AA  length = 10
```

```
FEATURE                 Location/Qualifiers
REGION                  1..10
                        note = Synthetic polymer
source                  1..10
                        mol_type = protein
                        organism = synthetic construct
SEQUENCE: 1164
WNSGYPPVDY                                                              10

SEQ ID NO: 1165         moltype = AA  length = 11
FEATURE                 Location/Qualifiers
REGION                  1..11
                        note = Synthetic polymer
source                  1..11
                        mol_type = protein
                        organism = synthetic construct
SEQUENCE: 1165
KERSTGWDFA S                                                            11

SEQ ID NO: 1166         moltype = AA  length = 18
FEATURE                 Location/Qualifiers
REGION                  1..18
                        note = Synthetic polymer
source                  1..18
                        mol_type = protein
                        organism = synthetic construct
SEQUENCE: 1166
DPWGPPSIAT MTSYEYKH                                                     18

SEQ ID NO: 1167         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1167
HGSSA                                                                   5

SEQ ID NO: 1168         moltype = AA  length = 6
FEATURE                 Location/Qualifiers
REGION                  1..6
                        note = Synthetic polymer
source                  1..6
                        mol_type = protein
                        organism = synthetic construct
SEQUENCE: 1168
GGSSYR                                                                  6

SEQ ID NO: 1169         moltype = AA  length = 114
FEATURE                 Location/Qualifiers
REGION                  1..114
                        note = Synthetic polymer
source                  1..114
                        mol_type = protein
                        organism = synthetic construct
SEQUENCE: 1169
QVQLVQSGAE LKKPGASVKM SCKASGYTFT GYTMHWVKQA PGQGLEWIGY INPRSGYTEY        60
NQKFKDRTTL TADKSTSTAY MELSSLRSED SAVYYCARPW FAYWGQGTLV TVSS              114

SEQ ID NO: 1170         moltype = AA  length = 114
FEATURE                 Location/Qualifiers
REGION                  1..114
                        note = Synthetic polymer
source                  1..114
                        mol_type = protein
                        organism = synthetic construct
SEQUENCE: 1170
QVQLVQSGAE VKKPGASVKM SCKASGYTFT GYTMHWVKQA PGQGLEWIGY INPRSGYTEY        60
NQKFKDRTTL TADKSTSTAY MELSSLRSED TAVYYCARPW FAYWGQGTLV TVSS              114

SEQ ID NO: 1171         moltype = AA  length = 114
FEATURE                 Location/Qualifiers
REGION                  1..114
                        note = Synthetic polymer
source                  1..114
                        mol_type = protein
                        organism = synthetic construct
SEQUENCE: 1171
```

```
QVQLVQSGAE VKKPGASVKM SCKASGYTFT GYTMHWVRQA PGQGLEWIGY INPRSGYTEY    60
NQKFKDRTTL TADKSTSTAY MELSSLRSED TAVYYCARPW FAYWGQGTLV TVSS         114

SEQ ID NO: 1172         moltype = AA   length = 114
FEATURE                 Location/Qualifiers
REGION                  1..114
                        note = Synthetic polymer
source                  1..114
                        mol_type = protein
                        organism = synthetic construct
SEQUENCE: 1172
QVQLVQSGAE VKKPGASVKV SCKASGYTFT GYTMHWVRQA PGQGLEWIGY INPRSGYTEY    60
NQKFKDRTTL TADKSTSTAY MELSSLRSED TAVYYCARPW FAYWGQGTLV TVSS         114

SEQ ID NO: 1173         moltype = AA   length = 114
FEATURE                 Location/Qualifiers
REGION                  1..114
                        note = Synthetic polymer
source                  1..114
                        mol_type = protein
                        organism = synthetic construct
SEQUENCE: 1173
QVQLVQSGAE VKKPGASVKV SCKASGYTFT GYTMHWVRQA PGQGLEWIGY INPRSGYTEY    60
NQKFKDRTTI TADKSTSTAY MELSSLRSED TAVYYCARPW FAYWGQGTLV TVSS         114

SEQ ID NO: 1174         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1174
DIVMTQSPAS LTVTPGEKVT ITCKSSQSLL NSGNQKNYLT WYQQKPGQPP KLLIYWASTR    60
ESGVPDRFTG SGSGTDFTLT ISSLQAEDVA VYYCQNDYSY PLTFGQGTKL EIK          113

SEQ ID NO: 1175         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1175
DIVMTQSPAS LSVTPGEKVT ITCKSSQSLL NSGNQKNYLT WYQQKPGQPP KLLIYWASTR    60
ESGVPDRFTG SGSGTDFTLT ISSLQAEDVA VYYCQNDYSY PLTFGQGTKL EIK          113

SEQ ID NO: 1176         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1176
DIVMTQSPAF LSVTPGEKVT ITCKSSQSLL NSGNQKNYLT WYQQKPGQPP KLLIYWASTR    60
ESGVPDRFTG SGSGTDFTLT ISSLQAEDVA VYYCQNDYSY PLTFGQGTKL EIK          113

SEQ ID NO: 1177         moltype = AA   length = 113
FEATURE                 Location/Qualifiers
REGION                  1..113
                        note = Synthetic polymer
source                  1..113
                        mol_type = protein
                        organism = synthetic construct
SEQUENCE: 1177
DIVMTQSPAF LSVTPGEKVT ITCKSSQSLL NSGNQKNYLT WYQQKPGQPP KLLIYWASTR    60
ESGVPDRFSG SGSGTDFTLT ISSLQAEDVA VYYCQNDYSY PLTFGQGTKL EIK          113

SEQ ID NO: 1178         moltype = AA   length = 504
FEATURE                 Location/Qualifiers
REGION                  1..504
                        note = Synthetic polymer
source                  1..504
                        mol_type = protein
                        organism = synthetic construct
SEQUENCE: 1178
MEPAGPAPGR LGPLLCLLLA ASCAWSGVAG EEELQVIQPD KSVLVAAGET ATLRCTATSL    60
IPVGPIQWFR GAGPGRELIY NQKEGHFPRV TTVSDLTKRN NMDFSIRIGN ITPADAGTYY   120
```

```
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
AAENTGSNER NIYIVVGVVC TLLVALLMAA LYLVRIRQKK AQGSTSSTRL HEPEKNAREI    420
TQDTNDITYA DLNLPKGKKP APQAAEPNNH TEYASIQTSP QPASEDTLTY ADLDMVHLNR    480
TPKQPAPKPE PSFSEYASVQ VPRK                                          504

SEQ ID NO: 1179        moltype = AA   length = 474
FEATURE                Location/Qualifiers
REGION                 1..474
                       note = Synthetic polymer
source                 1..474
                       mol_type = protein
                       organism = synthetic construct
SEQUENCE: 1179
EEELQVIQPD KSVLVAAGET ATLRCTATSL IPVGPIQWFR GAGPGRELIY NQKEGHFPRV     60
TTVSDLTKRN NMDFSIRIGN ITPADAGTYY CVKFRKGSPD DVEFKSGAGT ELSVRAKPSA    120
PVVSGPAARA TPQHTVSFTC ESHGFSPRDI TLKWFKNGNE LSDFQTNVDP VGESVSYSIH    180
STAKVVLTRE DVHSQVICEV AHVTLQGDPL RGTANLSETI RVPPTLEVTQ QPVRAENQVN    240
VTCQVRKFYP QRLQLTWLEN GNVSRTETAS TVTENKDGTY NWMSWLLVNV SAHRDDVKLT    300
CQVEHDGQPA VSKSHDLKVS AHPKEQGSNT AAENTGSNER NIYIVVGVVC TLLVALLMAA    360
LYLVRIRQKK AQGSTSSTRL HEPEKNAREI TQDTNDITYA DLNLPKGKKP APQAAEPNNH    420
TEYASIQTSP QPASEDTLTY ADLDMVHLNR TPKQPAPKPE PSFSEYASVQ VPRK          474

SEQ ID NO: 1180        moltype = AA   length = 508
FEATURE                Location/Qualifiers
REGION                 1..508
                       note = Synthetic polymer
source                 1..508
                       mol_type = protein
                       organism = synthetic construct
SEQUENCE: 1180
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
AAENTGSNER NIYIVVGVVC TLLVALLMAA LYLVRIRQKK AQGSTSSTRL HEPEKNAREI    420
TQVQSLDTND ITYADLNLPK GKKPAPQAAE PNNHTEYASI QTSPQPASED TLTYADLDMV    480
HLNRTPKQPA PKPEPSFSEY ASVQVPRK                                      508

SEQ ID NO: 1181        moltype = AA   length = 503
FEATURE                Location/Qualifiers
REGION                 1..503
                       note = Synthetic polymer
source                 1..503
                       mol_type = protein
                       organism = synthetic construct
SEQUENCE: 1181
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD VEFKSGAGTE LSVRAKPSAP VVSGPAARAT PQHTVSFTCE SHGFSPRDIT    180
LKWFKNGNEL SDFQTNVDPV GESVSYSIHS TAKVVLTRED VHSQVICEVA HVTLQGDPLR    240
GTANLSETIR VPPTLEVTQQ PVRAENQVNV TCQVRKFYPQ RLQLTWLENG NVSRTETAST    300
VTENKDGTYN WMSWLLVNVS AHRDDVKLTC QVEHDGQPAV SKSHDLKVSA HPKEQGSNTA    360
AENTGSNERN IYIVVGVVCT LLVALLMAAL YLVRIRQKKA QGSTSSTRLH EPEKNAREIT    420
QDTNDITYAD LNLPKGKKPA PQAAEPNNHT EYASIQTSPQ PASEDTLTYA DLDMVHLNRT    480
PKQPAPKPEP SFSEYASVQV PRK                                           503

SEQ ID NO: 1182        moltype = AA   length = 5
FEATURE                Location/Qualifiers
REGION                 1..5
                       note = Synthetic polymer
source                 1..5
                       mol_type = protein
                       organism = synthetic construct
SEQUENCE: 1182
GGGGS                                                                 5

SEQ ID NO: 1183        moltype = AA   length = 10
FEATURE                Location/Qualifiers
REGION                 1..10
                       note = Synthetic polymer
source                 1..10
                       mol_type = protein
                       organism = synthetic construct
SEQUENCE: 1183
```

```
GGGGSGGGGS                                                                    10

SEQ ID NO: 1184          moltype = AA   length = 15
FEATURE                  Location/Qualifiers
REGION                   1..15
                         note = Synthetic polymer
source                   1..15
                         mol_type = protein
                         organism = synthetic construct
SEQUENCE: 1184
GGGGSGGGGS GGGGS                                                              15

SEQ ID NO: 1185          moltype = AA   length = 20
FEATURE                  Location/Qualifiers
REGION                   1..20
                         note = Synthetic polymer
source                   1..20
                         mol_type = protein
                         organism = synthetic construct
SEQUENCE: 1185
GGGGSGGGGS GGGGSGGGGS                                                         20

SEQ ID NO: 1186          moltype = AA   length = 25
FEATURE                  Location/Qualifiers
REGION                   1..25
                         note = Synthetic polymer
source                   1..25
                         mol_type = protein
                         organism = synthetic construct
SEQUENCE: 1186
GGGGSGGGGS GGGGSGGGGS GGGGS                                                   25

SEQ ID NO: 1187          moltype = AA   length = 30
FEATURE                  Location/Qualifiers
REGION                   1..30
                         note = Synthetic polymer
source                   1..30
                         mol_type = protein
                         organism = synthetic construct
SEQUENCE: 1187
GGGGSGGGGS GGGGSGGGGS GGGGSGGGGS                                              30

SEQ ID NO: 1188          moltype = AA   length = 35
FEATURE                  Location/Qualifiers
REGION                   1..35
                         note = Synthetic polymer
source                   1..35
                         mol_type = protein
                         organism = synthetic construct
SEQUENCE: 1188
GGGGSGGGGS GGGGSGGGGS GGGGSGGGGS GGGGS                                        35

SEQ ID NO: 1189          moltype = AA   length = 40
FEATURE                  Location/Qualifiers
REGION                   1..40
                         note = Synthetic polymer
source                   1..40
                         mol_type = protein
                         organism = synthetic construct
SEQUENCE: 1189
GGGGSGGGGS GGGGSGGGGS GGGGSGGGGS GGGGSGGGGS                                   40

SEQ ID NO: 1190          moltype = AA   length = 16
FEATURE                  Location/Qualifiers
REGION                   1..16
                         note = Synthetic polymer
source                   1..16
                         mol_type = protein
                         organism = synthetic construct
SEQUENCE: 1190
GGSGGSGGGG SGGGGS                                                             16

SEQ ID NO: 1191          moltype = AA   length = 8
FEATURE                  Location/Qualifiers
REGION                   1..8
                         note = Synthetic polymer
source                   1..8
                         mol_type = protein
                         organism = synthetic construct
```

```
SEQUENCE: 1191
GGGGGGGG                                                                        8

SEQ ID NO: 1192         moltype = AA  length = 6
FEATURE                 Location/Qualifiers
REGION                  1..6
                        note = Synthetic polymer
source                  1..6
                        mol_type = protein
                        organism = synthetic construct
SEQUENCE: 1192
GGGGGG                                                                          6

SEQ ID NO: 1193         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1193
EAAAK                                                                           5

SEQ ID NO: 1194         moltype = AA  length = 10
FEATURE                 Location/Qualifiers
REGION                  1..10
                        note = Synthetic polymer
source                  1..10
                        mol_type = protein
                        organism = synthetic construct
SEQUENCE: 1194
EAAAKEAAAK                                                                     10

SEQ ID NO: 1195         moltype = AA  length = 15
FEATURE                 Location/Qualifiers
REGION                  1..15
                        note = Synthetic polymer
source                  1..15
                        mol_type = protein
                        organism = synthetic construct
SEQUENCE: 1195
EAAAKEAAAK EAAAK                                                               15

SEQ ID NO: 1196         moltype = AA  length = 12
FEATURE                 Location/Qualifiers
REGION                  1..12
                        note = Synthetic polymer
source                  1..12
                        mol_type = protein
                        organism = synthetic construct
SEQUENCE: 1196
AEAAAKEAAA KA                                                                  12

SEQ ID NO: 1197         moltype = AA  length = 17
FEATURE                 Location/Qualifiers
REGION                  1..17
                        note = Synthetic polymer
source                  1..17
                        mol_type = protein
                        organism = synthetic construct
SEQUENCE: 1197
AEAAAKEAAA KEAAAKA                                                             17

SEQ ID NO: 1198         moltype = AA  length = 22
FEATURE                 Location/Qualifiers
REGION                  1..22
                        note = Synthetic polymer
source                  1..22
                        mol_type = protein
                        organism = synthetic construct
SEQUENCE: 1198
AEAAAKEAAA KEAAAKEAAA KA                                                       22

SEQ ID NO: 1199         moltype = AA  length = 27
FEATURE                 Location/Qualifiers
REGION                  1..27
                        note = Synthetic polymer
source                  1..27
                        mol_type = protein
```

```
                        organism = synthetic construct
SEQUENCE: 1199
AEAAAKEAAA KEAAAKEAAA KEAAAKA                                       27

SEQ ID NO: 1200         moltype = AA   length = 46
FEATURE                 Location/Qualifiers
REGION                  1..46
                        note = Synthetic polymer
source                  1..46
                        mol_type = protein
                        organism = synthetic construct
SEQUENCE: 1200
AEAAAKEAAA KEAAAKEAAA KALEAEAAAK EAAAKEAAAK EAAAKA                  46

SEQ ID NO: 1201         moltype = AA   length = 5
FEATURE                 Location/Qualifiers
REGION                  1..5
                        note = Synthetic polymer
source                  1..5
                        mol_type = protein
                        organism = synthetic construct
SEQUENCE: 1201
PAPAP                                                                5

SEQ ID NO: 1202         moltype = AA   length = 18
FEATURE                 Location/Qualifiers
REGION                  1..18
                        note = Synthetic polymer
source                  1..18
                        mol_type = protein
                        organism = synthetic construct
SEQUENCE: 1202
KESGSVSSEQ LAQFRSLD                                                 18

SEQ ID NO: 1203         moltype = AA   length = 14
FEATURE                 Location/Qualifiers
REGION                  1..14
                        note = Synthetic polymer
source                  1..14
                        mol_type = protein
                        organism = synthetic construct
SEQUENCE: 1203
EGKSSGSGSE SKST                                                     14

SEQ ID NO: 1204         moltype = AA   length = 12
FEATURE                 Location/Qualifiers
REGION                  1..12
                        note = Synthetic polymer
source                  1..12
                        mol_type = protein
                        organism = synthetic construct
SEQUENCE: 1204
GSAGSAAGSG EF                                                       12

SEQ ID NO: 1205         moltype =    length =
SEQUENCE: 1205
000

SEQ ID NO: 1206         moltype = AA   length = 6
FEATURE                 Location/Qualifiers
REGION                  1..6
                        note = Synthetic polymer
source                  1..6
                        mol_type = protein
                        organism = synthetic construct
SEQUENCE: 1206
GGSGGS                                                               6

SEQ ID NO: 1207         moltype = AA   length = 9
FEATURE                 Location/Qualifiers
REGION                  1..9
                        note = Synthetic polymer
source                  1..9
                        mol_type = protein
                        organism = synthetic construct
SEQUENCE: 1207
GGSGGSGGS                                                            9

SEQ ID NO: 1208         moltype = AA   length = 12
```

```
FEATURE              Location/Qualifiers
REGION               1..12
                     note = Synthetic polymer
source               1..12
                     mol_type = protein
                     organism = synthetic construct
SEQUENCE: 1208
GGSGGSGGSG GS                                                              12

SEQ ID NO: 1209      moltype = AA  length = 15
FEATURE              Location/Qualifiers
REGION               1..15
                     note = Synthetic polymer
source               1..15
                     mol_type = protein
                     organism = synthetic construct
SEQUENCE: 1209
GGSGGSGGSG GSGGS                                                           15

SEQ ID NO: 1210      moltype = AA  length = 18
FEATURE              Location/Qualifiers
REGION               1..18
                     note = Synthetic polymer
source               1..18
                     mol_type = protein
                     organism = synthetic construct
SEQUENCE: 1210
GGSGGSGGSG GSGGSGGS                                                        18

SEQ ID NO: 1211      moltype = AA  length = 21
FEATURE              Location/Qualifiers
REGION               1..21
                     note = Synthetic polymer
source               1..21
                     mol_type = protein
                     organism = synthetic construct
SEQUENCE: 1211
GGSGGSGGSG GSGGSGGSGG S                                                    21

SEQ ID NO: 1212      moltype = AA  length = 24
FEATURE              Location/Qualifiers
REGION               1..24
                     note = Synthetic polymer
source               1..24
                     mol_type = protein
                     organism = synthetic construct
SEQUENCE: 1212
GGSGGSGGSG GSGGSGGSGG SGGS                                                 24

SEQ ID NO: 1213      moltype = AA  length = 27
FEATURE              Location/Qualifiers
REGION               1..27
                     note = Synthetic polymer
source               1..27
                     mol_type = protein
                     organism = synthetic construct
SEQUENCE: 1213
GGSGGSGGSG GSGGSGGSGG SGGSGGS                                              27

SEQ ID NO: 1214      moltype = AA  length = 30
FEATURE              Location/Qualifiers
REGION               1..30
                     note = Synthetic polymer
source               1..30
                     mol_type = protein
                     organism = synthetic construct
SEQUENCE: 1214
GGSGGSGGSG GSGGSGGSGG SGGSGGSGGS                                           30

SEQ ID NO: 1215      moltype = AA  length = 33
FEATURE              Location/Qualifiers
REGION               1..33
                     note = Synthetic polymer
source               1..33
                     mol_type = protein
                     organism = synthetic construct
SEQUENCE: 1215
GGSGGSGGSG GSGGSGGSGG SGGSGGSGGS GGS                                       33
```

```
SEQ ID NO: 1216          moltype = AA   length = 36
FEATURE                  Location/Qualifiers
REGION                   1..36
                         note = Synthetic polymer
source                   1..36
                         mol_type = protein
                         organism = synthetic construct
SEQUENCE: 1216
GGSGGSGGSG GSGGSGGSGG SGGSGGSGGS GGSGGS                                    36

SEQ ID NO: 1217          moltype = AA   length = 39
FEATURE                  Location/Qualifiers
REGION                   1..39
                         note = Synthetic polymer
source                   1..39
                         mol_type = protein
                         organism = synthetic construct
SEQUENCE: 1217
GGSGGSGGSG GSGGSGGSGG SGGSGGSGGS GGSGGSGGS                                 39

SEQ ID NO: 1218          moltype = AA   length = 42
FEATURE                  Location/Qualifiers
REGION                   1..42
                         note = Synthetic polymer
source                   1..42
                         mol_type = protein
                         organism = synthetic construct
SEQUENCE: 1218
GGSGGSGGSG GSGGSGGSGG SGGSGGSGGS GGSGGSGGSG GS                             42

SEQ ID NO: 1219          moltype = AA   length = 45
FEATURE                  Location/Qualifiers
REGION                   1..45
                         note = Synthetic polymer
source                   1..45
                         mol_type = protein
                         organism = synthetic construct
SEQUENCE: 1219
GGSGGSGGSG GSGGSGGSGG SGGSGGSGGS GGSGGSGGSG GSGGS                          45

SEQ ID NO: 1220          moltype = AA   length = 48
FEATURE                  Location/Qualifiers
REGION                   1..48
                         note = Synthetic polymer
source                   1..48
                         mol_type = protein
                         organism = synthetic construct
SEQUENCE: 1220
GGSGGSGGSG GSGGSGGSGG SGGSGGSGGS GGSGGSGGSG GSGGSGGS                       48

SEQ ID NO: 1221          moltype = AA   length = 51
FEATURE                  Location/Qualifiers
REGION                   1..51
                         note = Synthetic polymer
source                   1..51
                         mol_type = protein
                         organism = synthetic construct
SEQUENCE: 1221
GGSGGSGGSG GSGGSGGSGG SGGSGGSGGS GGSGGSGGSG GSGGSGGSGG S                   51

SEQ ID NO: 1222          moltype = AA   length = 54
FEATURE                  Location/Qualifiers
REGION                   1..54
                         note = Synthetic polymer
source                   1..54
                         mol_type = protein
                         organism = synthetic construct
SEQUENCE: 1222
GGSGGSGGSG GSGGSGGSGG SGGSGGSGGS GGSGGSGGSG GSGGSGGSGG SGGS                54

SEQ ID NO: 1223          moltype = AA   length = 57
FEATURE                  Location/Qualifiers
REGION                   1..57
                         note = Synthetic polymer
source                   1..57
                         mol_type = protein
                         organism = synthetic construct
SEQUENCE: 1223
GGSGGSGGSG GSGGSGGSGG SGGSGGSGGS GGSGGSGGSG GSGGSGGSGG SGGSGGS             57
```

```
SEQ ID NO: 1224          moltype = AA  length = 60
FEATURE                  Location/Qualifiers
REGION                   1..60
                         note = Synthetic polymer
source                   1..60
                         mol_type = protein
                         organism = synthetic construct
SEQUENCE: 1224
GGSGGSGGSG GSGGSGGSGG SGGSGGSGGS GGSGGSGGSG GSGGSGGSGG SGGSGGSGGS    60

SEQ ID NO: 1225          moltype = AA  length = 45
FEATURE                  Location/Qualifiers
REGION                   1..45
                         note = Synthetic polymer
source                   1..45
                         mol_type = protein
                         organism = synthetic construct
SEQUENCE: 1225
GGGGSGGGGS GGGGSGGGGS GGGGSGGGGS GGGGSGGGGS GGGGS                    45

SEQ ID NO: 1226          moltype = AA  length = 50
FEATURE                  Location/Qualifiers
REGION                   1..50
                         note = Synthetic polymer
source                   1..50
                         mol_type = protein
                         organism = synthetic construct
SEQUENCE: 1226
GGGGSGGGGS GGGGSGGGGS GGGGSGGGGS GGGGSGGGGS GGGGSGGGGS                50

SEQ ID NO: 1227          moltype = AA  length = 55
FEATURE                  Location/Qualifiers
REGION                   1..55
                         note = Synthetic polymer
source                   1..55
                         mol_type = protein
                         organism = synthetic construct
SEQUENCE: 1227
GGGGSGGGGS GGGGSGGGGS GGGGSGGGGS GGGGSGGGGS GGGGSGGGGS GGGGS          55

SEQ ID NO: 1228          moltype = AA  length = 60
FEATURE                  Location/Qualifiers
REGION                   1..60
                         note = Synthetic polymer
source                   1..60
                         mol_type = protein
                         organism = synthetic construct
SEQUENCE: 1228
GGGGSGGGGS GGGGSGGGGS GGGGSGGGGS GGGGSGGGGS GGGGSGGGGS GGGGSGGGGS    60

SEQ ID NO: 1229          moltype = AA  length = 65
FEATURE                  Location/Qualifiers
REGION                   1..65
                         note = Synthetic polymer
source                   1..65
                         mol_type = protein
                         organism = synthetic construct
SEQUENCE: 1229
GGGGSGGGGS GGGGSGGGGS GGGGSGGGGS GGGGSGGGGS GGGGSGGGGS GGGGSGGGGS    60
GGGGS                                                                65

SEQ ID NO: 1230          moltype = AA  length = 70
FEATURE                  Location/Qualifiers
REGION                   1..70
                         note = Synthetic polymer
source                   1..70
                         mol_type = protein
                         organism = synthetic construct
SEQUENCE: 1230
GGGGSGGGGS GGGGSGGGGS GGGGSGGGGS GGGGSGGGGS GGGGSGGGGS GGGGSGGGGS    60
GGGGSGGGGS                                                           70

SEQ ID NO: 1231          moltype = AA  length = 75
FEATURE                  Location/Qualifiers
REGION                   1..75
                         note = Synthetic polymer
source                   1..75
                         mol_type = protein
```

```
                              organism = synthetic construct
SEQUENCE: 1231
GGGGSGGGGS GGGGSGGGGS GGGGSGGGGS GGGGSGGGGS GGGGSGGGGS GGGGSGGGGS   60
GGGGSGGGGS GGGGS                                                    75

SEQ ID NO: 1232        moltype = AA   length = 80
FEATURE                Location/Qualifiers
REGION                 1..80
                       note = Synthetic polymer
source                 1..80
                       mol_type = protein
                       organism = synthetic construct
SEQUENCE: 1232
GGGGSGGGGS GGGGSGGGGS GGGGSGGGGS GGGGSGGGGS GGGGSGGGGS GGGGSGGGGS   60
GGGGSGGGGS GGGGSGGGGS                                               80

SEQ ID NO: 1233        moltype = AA   length = 85
FEATURE                Location/Qualifiers
REGION                 1..85
                       note = Synthetic polymer
source                 1..85
                       mol_type = protein
                       organism = synthetic construct
SEQUENCE: 1233
GGGGSGGGGS GGGGSGGGGS GGGGSGGGGS GGGGSGGGGS GGGGSGGGGS GGGGSGGGGS   60
GGGGSGGGGS GGGGSGGGGS GGGGS                                         85

SEQ ID NO: 1234        moltype = AA   length = 90
FEATURE                Location/Qualifiers
REGION                 1..90
                       note = Synthetic polymer
source                 1..90
                       mol_type = protein
                       organism = synthetic construct
SEQUENCE: 1234
GGGGSGGGGS GGGGSGGGGS GGGGSGGGGS GGGGSGGGGS GGGGSGGGGS GGGGSGGGGS   60
GGGGSGGGGS GGGGSGGGGS GGGGSGGGGS                                    90

SEQ ID NO: 1235        moltype = AA   length = 95
FEATURE                Location/Qualifiers
REGION                 1..95
                       note = Synthetic polymer
source                 1..95
                       mol_type = protein
                       organism = synthetic construct
SEQUENCE: 1235
GGGGSGGGGS GGGGSGGGGS GGGGSGGGGS GGGGSGGGGS GGGGSGGGGS GGGGSGGGGS   60
GGGGSGGGGS GGGGSGGGGS GGGGSGGGGS GGGGS                              95

SEQ ID NO: 1236        moltype = AA   length = 100
FEATURE                Location/Qualifiers
REGION                 1..100
                       note = Synthetic polymer
source                 1..100
                       mol_type = protein
                       organism = synthetic construct
SEQUENCE: 1236
GGGGSGGGGS GGGGSGGGGS GGGGSGGGGS GGGGSGGGGS GGGGSGGGGS GGGGSGGGGS   60
GGGGSGGGGS GGGGSGGGGS GGGGSGGGGS GGGGSGGGGS                         100

SEQ ID NO: 1237        moltype = AA   length = 5
FEATURE                Location/Qualifiers
REGION                 1..5
                       note = Synthetic polymer
source                 1..5
                       mol_type = protein
                       organism = synthetic construct
SEQUENCE: 1237
GGGSE                                                               5

SEQ ID NO: 1238        moltype = AA   length = 5
FEATURE                Location/Qualifiers
REGION                 1..5
                       note = Synthetic polymer
source                 1..5
                       mol_type = protein
                       organism = synthetic construct
SEQUENCE: 1238
GSESG                                                               5
```

```
SEQ ID NO: 1239         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1239
GSEGS                                                                      5

SEQ ID NO: 1240         moltype = AA  length = 35
FEATURE                 Location/Qualifiers
REGION                  1..35
                        note = Synthetic polymer
source                  1..35
                        mol_type = protein
                        organism = synthetic construct
SEQUENCE: 1240
GEGGSGEGSS GEGSSSEGGG SEGGGSEGGG SEGGS                                     35

SEQ ID NO: 1241         moltype = AA  length = 4
FEATURE                 Location/Qualifiers
REGION                  1..4
                        note = Synthetic polymer
source                  1..4
                        mol_type = protein
                        organism = synthetic construct
SEQUENCE: 1241
CPPC                                                                       4

SEQ ID NO: 1242         moltype = AA  length = 123
FEATURE                 Location/Qualifiers
REGION                  1..123
                        note = Synthetic polymer
source                  1..123
                        mol_type = protein
                        organism = synthetic construct
SEQUENCE: 1242
QVQLVQSGAE VKKPGSSVKV SCKTSGDTFS TYAISWVRQA PGQGLEWMGG IIPIFGKAHY          60
AQKFQGRVTI TADESTSTAY MELSSLRSED TAVYFCARKF HFVSGSPFGM DVWGQGTTVT         120
VSS                                                                      123

SEQ ID NO: 1243         moltype = AA  length = 106
FEATURE                 Location/Qualifiers
REGION                  1..106
                        note = Synthetic polymer
source                  1..106
                        mol_type = protein
                        organism = synthetic construct
SEQUENCE: 1243
EIVLTQSPAT LSLSPGERAT LSCRASQSVS SYLAWYQQKP GQAPRLLIYD ASNRATGIPA          60
RFSGSGSGTD FTLTISSLEP EDFAVYYCQQ RSNWPTFGQG TKVEIK                       106

SEQ ID NO: 1244         moltype = AA  length = 453
FEATURE                 Location/Qualifiers
REGION                  1..453
                        note = Synthetic polymer
source                  1..453
                        mol_type = protein
                        organism = synthetic construct
SEQUENCE: 1244
QVQLVQSGAE VKKPGSSVKV SCKTSGDTFS TYAISWVRQA PGQGLEWMGG IIPIFGKAHY          60
AQKFQGRVTI TADESTSTAY MELSSLRSED TAVYFCARKF HFVSGSPFGM DVWGQGTTVT         120
VSSASTKGPS VFPLAPSSKS TSGGTAALGC LVKDYFPEPV TVSWNSGALT SGVHTFPAVL         180
QSSGLYSLSS VVTVPSSSLG TQTYICNVNH KPSNTKVDKK VEPKSCDKTH TCPPCPAPEL         240
LGGPSVFLFP PKPKDTLMIS RTPEVTCVVV DVSHEDPEVK FNWYVDGVEV HNAKTKPREE         300
QYNSTYRVVS VLTVLHQDWL NGKEYKCKVS NKALPAPIEK TISKAKGQPR EPQVYTLPPS         360
RDELTKNQVS LTCLVKGFYP SDIAVEWESN GQPENNYKTT PPVLDSDGSF FLYSKLTVDK         420
SRWQQGNVFS CSVMHEALHN HYTQKSLSLS PGK                                     453

SEQ ID NO: 1245         moltype = AA  length = 213
FEATURE                 Location/Qualifiers
REGION                  1..213
                        note = Synthetic polymer
source                  1..213
                        mol_type = protein
                        organism = synthetic construct
SEQUENCE: 1245
```

```
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 1246         moltype = AA  length = 119
FEATURE                 Location/Qualifiers
REGION                  1..119
                        note = Synthetic polymer
source                  1..119
                        mol_type = protein
                        organism = synthetic construct
SEQUENCE: 1246
QVQLQESGGG LVQAGKSLRL SCAASGSIFS IHAMGWFRQA PGKEREFVAA ITWSGGITYY    60
EDSVKGRFTI SRDNAKNTVY LQMNSLKPED TAIYYCAADR AESSWYDYWG QGTQVTVSS    119

SEQ ID NO: 1247         moltype = AA  length = 119
FEATURE                 Location/Qualifiers
REGION                  1..119
                        note = Synthetic polymer.
source                  1..119
                        mol_type = protein
                        organism = synthetic construct
SEQUENCE: 1247
QVQLQESGGG LVQAGKSLRL SCAASGSIAS IHAMGWFRQA PGKEREFVAV ITWSGGITYY    60
ADSVKGRFTI SRDNAKNTVY LQMNSLKPED TAIYYCAGDK HQSSWYDYWG QGTQVTVSS    119
```